US010300140B2

(12) United States Patent
Bhatt et al.

(10) Patent No.: US 10,300,140 B2
(45) Date of Patent: May 28, 2019

(54) SUR-BINDING PROTEINS AGAINST ERBB3

(75) Inventors: Ramesh R. Bhatt, Belmont, CA (US); Pamela K. Foreman, Los Altos, CA (US); Lawrence C. Horowitz, Atherton, CA (US); Michael Horowitz, Los Altos, CA (US); Medini Gore, Los Altos, CA (US); Phil Kobel, San Jose, CA (US)

(73) Assignee: I2 PHARMACEUTICALS, INC., Boulder, CO (US)

( * ) Notice: Subject to any disclaimer, the term of this patent is extended or adjusted under 35 U.S.C. 154(b) by 166 days.

(21) Appl. No.: 14/235,431

(22) PCT Filed: Jul. 27, 2012

(86) PCT No.: PCT/US2012/048730
§ 371 (c)(1),
(2), (4) Date: Jul. 3, 2014

(87) PCT Pub. No.: WO2013/016714
PCT Pub. Date: Jan. 31, 2013

(65) Prior Publication Data
US 2014/0308287 A1 Oct. 16, 2014

(51) Int. Cl.
*A61K 39/395* (2006.01)
*C07K 16/30* (2006.01)
*C07K 16/32* (2006.01)
*A61K 39/00* (2006.01)

(52) U.S. Cl.
CPC ........ *A61K 39/39558* (2013.01); *C07K 16/32* (2013.01); *A61K 2039/505* (2013.01); *C07K 2317/30* (2013.01); *C07K 2317/51* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,256,746 A | 3/1981 | Miyashita et al. |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,439,196 A | 3/1984 | Higuchi |
| 4,447,224 A | 5/1984 | De Cant et al. |
| 4,447,233 A | 5/1984 | Mayfield |
| 4,450,254 A | 5/1984 | Isley et al. |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,563,304 A | 1/1986 | Carlsson et al. |
| 4,596,556 A | 6/1986 | Morrow et al. |
| 4,683,192 A | 7/1987 | Nishiyama |
| 4,683,202 A | 7/1987 | Mullis |
| 4,790,824 A | 12/1988 | Morrow et al. |
| 4,800,159 A | 1/1989 | Mullis et al. |
| 4,816,567 A | 3/1989 | Cabilly et al. |
| 4,941,880 A | 7/1990 | Burns |
| 4,965,188 A | 10/1990 | Mullis et al. |
| 5,064,413 A | 11/1991 | McKinnon et al. |
| 5,182,205 A | 1/1993 | Bauer et al. |
| 5,208,020 A | 5/1993 | Chari et al. |
| 5,312,335 A | 5/1994 | McKinnon, Jr. et al. |
| 5,374,548 A | 12/1994 | Caras |
| 5,399,163 A | 3/1995 | Peterson et al. |
| 5,399,331 A | 3/1995 | Loughrey et al. |
| 5,416,016 A | 5/1995 | Low et al. |
| 5,416,064 A | 5/1995 | Chari et al. |
| 5,383,851 A | 6/1995 | McKinnon, Jr. et al. |
| 5,427,908 A | 6/1995 | Dower et al. |
| 5,474,765 A | 12/1995 | Thorpe |
| 5,475,982 A | 12/1995 | Laude-Bousquet |
| 5,480,968 A | 1/1996 | Kraus et al. |
| 5,585,499 A | 12/1996 | Chari et al. |
| 5,622,929 A | 4/1997 | Willner et al. |
| 5,641,869 A | 6/1997 | Vandlen et al. |
| 5,762,918 A | 6/1998 | Thorpe |
| 5,824,805 A | 10/1998 | King et al. |
| 5,846,545 A | 12/1998 | Chari et al. |
| 6,333,410 B1 | 12/2001 | Chari et al. |

(Continued)

FOREIGN PATENT DOCUMENTS

| EP | 0 269 127 | 2/1994 |
|---|---|---|
| EP | 1396500 A1 | 3/2004 |

(Continued)

OTHER PUBLICATIONS

Xu (Journal of Molecular Biology, vol. 397, p. 352-360, 2010).*
Paul, Fundamental Immunology, 3rd Edition, 1993, pp. 292-295.*
Rudikoff et al. (Proceedings of the National Academy of Sciences USA, vol. 79, p. 1979-1983, 1982).*
Johnson and Wu (Methods in Molecular Biology, Antibody Engineering: Methods and Protocols, vol. 248, p. 11-25, 2004).*
Ewert (Methods, vol. 34, p. 184-199, 2004) (Year: 2004).*
U.S. Appl. No. 14/979,114, filed Dec. 22, 2015, Sea Lane Biotechnologies, LLC.
Foreman et al., "ErbB3 Inhibitor Surrobodies inhibit Tumor Cell Proliferation In Vitro and In Vivo", Molecular Cancer Therapeutics, vol. 11, No. 7, Jul. 1, 2012 (Jul. 1, 2012), pp. 1411-1420, XP55042173, ISSN: 1535-7163, DOI: 10.1159/1535-7163. MCT-12-0068.

(Continued)

*Primary Examiner* — Michael Allen
(74) *Attorney, Agent, or Firm* — Cooley LLP

(57) ABSTRACT

Embodiments concern constructs comprising surrogate light chain sequences. In particular, embodiments concern constructs that can bind to ErbB3 and aspects relating to such constructs.

7 Claims, 81 Drawing Sheets
Specification includes a Sequence Listing.

(56) References Cited

U.S. PATENT DOCUMENTS

| | | |
|---|---|---|
| 6,337,070 B1 | 1/2002 | Yoshinobu et al. |
| 6,441,163 B1 | 8/2002 | Chari et al. |
| 6,716,821 B2 | 4/2004 | Zhao et al. |
| 6,720,409 B2 | 4/2004 | Okuno et al. |
| 7,276,497 B2 | 10/2007 | Chari et al. |
| 7,473,796 B2 | 1/2009 | Chari et al. |
| 7,612,181 B2 | 11/2009 | Wu et al. |
| 8,114,967 B2 | 2/2012 | Bhatt et al. |
| 8,198,417 B2 | 6/2012 | Steeves et al. |
| 9,169,318 B2 | 10/2015 | Howowitz et al. |
| 2002/0054882 A1 | 5/2002 | Yoshinobu et al. |
| 2003/0198637 A1 | 10/2003 | Tong et al. |
| 2003/0215453 A1 | 11/2003 | Dedera et al. |
| 2005/0169933 A1 | 8/2005 | Steeves et al. |
| 2005/0238649 A1 | 10/2005 | Doronina et al. |
| 2006/0024317 A1 | 2/2006 | Boyd et al. |
| 2006/0074008 A1 | 4/2006 | Senter et al. |
| 2006/0147997 A1 | 7/2006 | Ramakrishnan |
| 2007/0004909 A1 | 1/2007 | Johnson et al. |
| 2007/0191314 A1 | 8/2007 | Klucker et al. |
| 2008/0014205 A1 | 1/2008 | Horowitz et al. |
| 2008/0124345 A1* | 5/2008 | Rothe ............... C07K 16/2863 424/174.1 |
| 2009/0082213 A1 | 3/2009 | Horowitz et al. |
| 2009/0098164 A1* | 4/2009 | Bhatt ............... A61K 47/48776 424/246.1 |
| 2009/0226455 A1* | 9/2009 | Filvaroff ............... C07K 16/32 424/139.1 |
| 2009/0274713 A1 | 11/2009 | Chari et al. |
| 2010/0004139 A1 | 1/2010 | Bhatt et al. |
| 2010/0040635 A1 | 2/2010 | Horowitz et al. |
| 2010/0062950 A1 | 3/2010 | Bhatt et al. |
| 2010/0210034 A1* | 8/2010 | Bates ............... C07K 16/32 436/501 |
| 2010/0255010 A1* | 10/2010 | Fuh ............... C07K 16/2863 424/174.1 |
| 2010/0297174 A1 | 11/2010 | Garcia-Sastre et al. |
| 2011/0256154 A1* | 10/2011 | Vincent ............... C07K 16/32 424/174.1 |
| 2012/0123098 A1 | 5/2012 | Bhatt et al. |
| 2012/0128671 A1 | 5/2012 | Howowitz et al. |
| 2012/0156217 A1 | 6/2012 | Setiady et al. |
| 2012/0202713 A1 | 8/2012 | Bhatt et al. |
| 2012/0294853 A1 | 11/2012 | McDonagh et al. |
| 2014/0228544 A1 | 8/2014 | Bhatt et al. |
| 2015/0004162 A1 | 1/2015 | Kashyap et al. |
| 2015/0011736 A1 | 1/2015 | Horowitz et al. |
| 2015/0045540 A1 | 2/2015 | Howowitz et al. |
| 2016/0096882 A1 | 4/2016 | Howowitz et al. |

FOREIGN PATENT DOCUMENTS

| | | |
|---|---|---|
| JP | 2011-516423 A | 5/2011 |
| WO | WO 1984/000687 A1 | 3/1984 |
| WO | WO 1997/016208 A1 | 5/1997 |
| WO | WO 2000/073349 A1 | 12/2000 |
| WO | WO 2001/035993 A2 | 5/2001 |
| WO | WO 2001/060402 A2 | 8/2001 |
| WO | WO 2002/030463 A2 | 4/2002 |
| WO | WO 2002/096457 A2 | 12/2002 |
| WO | WO 2004/003019 A2 | 1/2004 |
| WO | WO 2004/010957 A2 | 2/2004 |
| WO | WO 2007/077028 | 7/2007 |
| WO | WO 2007/134327 A2 | 11/2007 |
| WO | WO 2008/028946 A2 | 3/2008 |
| WO | WO 2008/089073 A2 | 7/2008 |
| WO | WO 2008/100624 A2 | 8/2008 |
| WO | WO 2008/118970 | 10/2008 |
| WO | WO 2008/153236 A1 | 12/2008 |
| WO | WO 2009/021754 A2 | 2/2009 |
| WO | WO 2009/079259 A2 | 6/2009 |
| WO | WO 2009/121004 A2 | 10/2009 |
| WO | WO 2009/134976 A1 | 11/2009 |
| WO | WO 2010/006286 A2 | 1/2010 |
| WO | WO 2010/132604 A2 | 11/2010 |
| WO | WO 2010/151808 A1 | 12/2010 |
| WO | WO 2011/071957 A1 | 6/2011 |
| WO | WO 2011/112955 A1 | 9/2011 |
| WO | WO 2011/143307 A1 | 11/2011 |
| WO | WO 2011/153431 A2 | 12/2011 |
| WO | WO 2013/003652 A1 | 1/2013 |
| WO | WO 2013/016714 A1 | 1/2013 |
| WO | WO 2013/096828 A1 | 6/2013 |
| WO | WO 2013/109994 A1 | 7/2013 |

OTHER PUBLICATIONS

Friedman et al., "Engineering and characterization of bi-specific HER2 x EGFR-binding affibody molecule", Biotechnology and Applied Biochemistry, Academic Press, US, vol. 54, No. 2, Oct. 1, 2009, pp. 121-131, XP002679895, ISSN: 0885-4513, DOI: 10.1042/BA20090096 Retrieved from the Internet: URL: http://onlinelibrary.wiley.com/doi/10. [retrieved on Dec. 23, 2010] the whole document.

International Search Report and the Written Opinion, International Application No. PCT/US2012/048730 dated Nov. 6, 2012, 15 pages.

Office Action dated Nov. 13, 2015 in European Patent App. No. 12746432.9.

Robinson et al., "Targeting ErbB2 and ErbB3 with a bispecific single-chain Fv enhances targeting selectivity and induces a therapeutic effect in vitro", British Journal of Cancer, Harcourt Publishers, vol. 99, No. 9, 28 Oct. 28, 2008, pp. 1415-1425, XP009115294, ISSN: 0007-0920, DOI: 10.1038/SJ.BJC.6604700 [retrieved on Oct. 7, 2008] the whole document.

Xu et al., "Combinatorial surrobody libraries", Proceedings of the National Academy of Sciences, National Academy of Sciences, US, vol. 105, No. 31, Aug. 5, 2008, pp. 10756-10761, XP002498064, ISSN: 0027-8424, DOI: 10.1073/PNAS.085293105 the whole document.

Yuste, L., "Activation of ErbB2 by Overexpression or by Transmembrane Neuregulin Results in Differential Signaling and Sensitivity to Herceptin", Cancer Research, vol. 65, No. 15, Aug. 1, 2005, pp. 6801-6810, XP55042216, ISSN: 0008-5472, DOI: 10.1158/008-5472. CAN-04-4023 the whole document.

Database UniProt (online) Immunoglobulin lambda-like polypeptide 1, XP002498605 (1990), 3 pages.

Graduate School of Infection Control Diseases, et al. "Analysis on epitopes of neutralizing antibodies against a highly pathogenic avian influenza H5N1 and preparation of scFv." BMB2007 (30th Meeting of the Molecular Biology Society of Japan/80th Meeting of the Japanese Biochemical Society Joint Meeting) Lecture Abstracts, 2007, p. 851, #4P-1098 (and English translation), 3 pages.

Hagiwara, S. "Transgenic expression of VpreB-3 under the control of the immunoglobulin heavy chain enhancer and SV40 promoter", The Kobe Journal of Medical Sciences (1996); 42(1): 43-59.

Kudo et al. (PIR database, 1987 accession No. A26166, accessed on Jul. 19, 2010 Score Alignment , 4 pages.

Milutinovic, Snezana, et al. "Dual Agonist Surrobody Simultaneously Activates Death Receptors DR4 and DR5 to Induce Cancer Cell Death." Molecular Cancer Therapeutics (2016); 15.1: 114-124, 11 pages.

Ada, G.L. and Jones, P.D. "The Immune response to influenza infection", Current topics in Microbiology and Immunology (1986); 128: 1-54.

Adams, Camellia W., et al. "Humanization of a recombinant monoclonal antibody to produce a therapeutic HER dimerization inhibitor, pertuzumab." Cancer Immunology, Immunotherapy (2006); 55.6: 717-727.

Bowie, James U., et al. "Deciphering the message in protein sequences: tolerance to amino acid substitutions." Science (1990); 247.4948: 1306-1310.

Brummell, David A., et al. "Probing the combining site of an anti-carbohydrate antibody by saturation-mutagenesis: role of the heavy-chain CDR3 residues." Biochemistry (1993); 32.4: 1180-1187.

(56) References Cited

OTHER PUBLICATIONS

Carlsson et al., "Protein Thiolation and Reversible Protein-Protein Conjugation", Biochem. J., 173:723-737 (1978).

Chumsae, et al: "Comparison of methionine oxidation in thermal stability and chemically stressed samples of a fully human monoclonal antibody", Journal of Chromatography (2007); 850: 285-294.

Colman, "Effects of amino acid sequence changes on antibody-antigen interactions", Research in Immunol. (1994); 145: 33-36.

Colman et al., "Structure of the catalytic and antigenic sites in influenza virus neuraminidase", Nature (1983); 303: 41-44.

Couch and Kasel, "Immunity to influenza in man", Annual Reviews in Microbiology (1983); 37.1: 529-549.

Daniel, Claude, et al. "Mapping of linear antigenic sites on the S glycoprotein of a neurotropic murine coronavirus with synthetic peptides: a combination of nine prediction algorithms fails to identify relevant epitopes and peptide immunogenicity is drastically influenced by the nature of the protein carrier." Virology (1994); 202.2: 540-549.

Davies and Riechmann, "Affinity improvement of single antibody VH domains: residues in all three hyper variable regions affect antigen binding", Immunotechnology (1996); 2.3: 169-179.

Dubowchik and Walker, "Receptor-mediated and enzyme-dependent targeting of cytotoxic anticancer drugs", Pharm. Therapeutics 83:67-123 (1999).

Goudsmit, Japp, "Discovery of a unique set of human monoclonal antibodies active against H5N1." Presentation at 5th International Bird Flu Summit, Sep. 27, 2007, URL link http://investors.crucell.com/C/132631/present 2007 v2.html, 35 pages.

Goudsmit, Japp, "New Directions in Fighting Flu." Presentation at Symposium for 10th Anniversary of Inflexal V, Apr. 26, 2007, 38 pages.

Güssow and Seemann. "[5] Humanization of monoclonal antibodies." Methods in Enzymology (1991); 203: 99-121.

Hashida et al., "More Useful Maleimide Compounds for the Conjugation of Fab' to Horseradish Peroxidase through Thiol Groups in the Hinge", J. Applied Biochem., 56-63 (1984).

Hirabayashi et al. "Kinetic analysis of the interactions of recombinant human VpreBand Ig V domain." Journal of Immunology (1995); 155(3): 1218-1228.

Hollis et al. PIR database, 1996, accession No. A33911, accessed on Sep. 12, 2012, Score Alignment 3 pages.

Holm et al. "Functional mapping and single chain construction of the anti-cytokeratin 8 monoclonal antibody TSI." Molecular Immunology (2007); 44.6: 1075-1084.

Horváth, et al. "A Hemagglutinin-Based Multipeptide Construct Elicits Enhanced Protective Immune Response in Mice Against Influenza A Virus Infection", Immunology Letters (1998); 60.2: 127-136.

Jang et al, "The structural basis for DNA binding by an anti-DNA autoantibody", Molecular immunology (1998); 35.18: 1207-1217.

Johnson et al., "Anti-Tumor Activity of CC49-Doxorubicin Immunoconjugates", Anticancer Res. 15:1387-93 (1995).

Kaneko et al., "New Hydrazone Derivatives of Adriamycin and Their Immunoconjugates—a Correlation between Acid Stability and Cytotoxicity", Bioconjugate Chem. 2:133-41 (1991).

Karasuyama et al. "Surrogate light chain in B cell development", Advances in Immunology (1996); 63: 1-41.

Lanig et al. "Three dimensional modeling of a pre B-cell receptor", Molecular Immunology (2004); 40(17): 1263-1272.

Lau et al., "Conjugation of Doxorubicin to Monoclonal Anti-carcinoembryonic Antigen Antibody via Novel Thiol-directed Cross-linking Reagents", Bioorg-Med-Chem. 3(10):1299-1304 (1995).

Lau et al., "Novel Doxorubicin-Monoclonal Anti-carcinoembryonic Antigen Antibody Immunoconjugate Activity in vitro", Bioorg-Med-Chem. 3(10): 1305-12 (1995).

Law, et al., "Broadly neutralizing antibodies protect against hepatitis C virus quasispecies challenge", Nature Medicine (2008); 14(1): 25-27.

Lee, et al. "Generation of Bivalent and Bispecific Kringle Single Domains by Loop Grafting as Potent Agonists against Death Receptors 4 and 5." Journal of Molecular Biology (2011); 411(1): 201-219.

Lee, et al., High-affinity human antibodies from phage-displayed synthetic Fab libraries with a single framework scaffold, J. Mol. Biol., 340: 1073-1093, (2004).

Lerner, et al., "Manufacturing immunity to disease in a test tube: the magic bullet realized", Angewandte Chemie International Edition (2006); 45.48: 8106-8125.

Lerner, et. al., "Rare antibodies from combinatorial libraries suggests an S.O.S. component of the human immunological repertoire", Molecular BioSystems (2011); 7.4: 1004-1012.

Lippincott-Schwartz. "Antibodies as Cell Biological Tools." Current Protocols in Cell Biology (2002); 16.0.1-16.0.2.

Liu et al., "New Procedures for Preparation and Isolation of Conjugates of Proteins and a Synthetic Copolymer of D-Amino Acids and Immunochemical Characterization of Such Conjugatest", Biochem., 18:690-697 (1979).

Luke, et al., "Meta-analysis: Convalescent blood products for Spanish influenza pneumonia: A future H5N1 treatment", Annals of Internal Medicine (2006); 145.8: 599-609.

McKeller, Morgan R., and Martinez-Valdez, Hector. "The κ-like pre-B receptor: Surplus biology or a missing link?." Seminars in Immunology (2006); 18(1): 40-43.

Melchers et al. "The surrogate light chain in B-cell development", Immunology Today (1993); 14.2: 60-68.

Morris, Glenn E. "Epitope Mapping of Protein Antigens by Competition ELISA" In: "The Protein Protocols Handbook", Jan. 1, 1996, (Jan. 1, 1996), Humana Press, Totowa, NJ, XP055007939, ISBN: 978-1-60-327259-9, pp. 595-600, DOI: 10.1007/978-1-60327-259-9_96.

Milutinovic, Snezana, et al. "Development of a novel SurrobodyTM that simultaneously activates both death receptors DR4 and DR5 and induces cancer cell death with high potency." Cancer Research (2013); 73.8 Supplement: 4318-4318.

Neville, Jr. et al., "Enhancement of Immunotoxin Efficacy by Acid-cleavable Cross-linking Agents Utilizing Diphtheria Toxin and Toxin Mutants", Biol. Chem. 264:14653-14661 (1989).

Ohnishi and Melchers. "The nonimmunoglobulin portion of λ5 mediates cell-autonomous pre-B cell receptor signaling." Nature Immunology (2003); 4.9: 849-856.

Palese, P. and Shaw, M.L. "Orthomyxoviridae: The viruses and their replication", Fields Virology (2007); 2: 1647-1689.

Portolano, Stefano, et al. "Lack of promiscuity in autoantigen-specific H and L chain combinations as revealed by human H and L chain"roulette"." The Journal of Immunology (1993); 150.3: 880-887.

Smith-Gill et al, "Contributions of immunoglobulin heavy and light chains to antibody specificity for lysozyme and two haptens", The Journal of Immunology (1987); 139.12: 4135-4144.

Song et al. "Light chain of natural antibody plays a dominant role in protein antigen binding", Biochemical and Biophysical Research Communications (2000); 268.2: 390-394.

Thorpe et al., "New Coupling Agents for the Synthesis of Immunotoxins Containing a Hindered Disulfide Bond with Improved Stability in Vivo", Cancer Res. 47:5924-5931 (1987).

Vajdos et al. "Comprehensive functional maps of the antigen-binding site of an Anti-ErbB2 antibody obtained with shotam scanning mutagenesis", Journal of Molecular Biology (2002); 320. 2: 415-428.

Ward et al, "Binding activities of a repertoire of single immunoglobulin variable domains secreted from *Escherichia coli*", Nature (1989); 341.6242: 544-546.

Wawrzynczak et al., "In Immunoconjugates: Antibody Conjugates in Radioimagery and Therapy of Cancer," (C.W. Vogel ed., Oxford U. Press (1987).

Wiley and Skehel. "The structure and function of the hemagglutinin membrane glycoprotein of influenza virus." Ann. Rev. Biochem. (1987); 56:365-394.

Wu et al. "Humanization of a Murine monoclonal antibody by simultaneous optimization of framework and CDR residues", Journal of Molecular Biology (1999); 294.1: 151-162.

(56) References Cited

OTHER PUBLICATIONS

Yoshitake et al., "Conjugation of Glucose Oxidase from Aspergillus niger and Rabbit Antibodies Using N-Hydroxysuccinimide Ester of N-(4-Carboxycyclohexylmethyl)-Maleimide", Eur. J. Biochem., 101:395-399 (1979).
Ashkenazi, A., "Directing cancer cells to self-destruct with pro-apoptotic receptor agonists." Nat. Rev. Drug Discov. (2008); 7:1001-1012.
Bankovich et al. "Structural insight into pre-B cell receptor function." Science (2007); 316: 291-294.
Bendig, Mary M. "Humanization of Rodent Monoclonal Antibodies by CDR grafting." Methods: Companion to Methods in Enzymology (1995); 8.2: 83-93.
Burks et al, "In vitro scanning saturation mutagenesis of an antibody binding pocket." PNAS 94: 412-417, (1997).
Casset et al. "A peptide mimetic of an anti-CD4 monoclonal antibody by rational design." Biochemical and Biophysical Research Communications (2003); 307: 198-205.
Chen et al. "Selection and analysis of an optimized anti-VEGF antibody: Crystal structure of an affinity-matured Fabin complex with Antigen." Journal of Molecular Biology (1999); 293: 865-881.
Collins et al. "A genome annotation-driven approach to cloning the human ORFeome." Genome Biology (2004); 5(10): R84, Epub Sep. 30, 2004.
De Pascalis et al. "Grafting of "Abbreviated" complementarity-determining regions containing specificity-determining residues essential for ligand contact to engineer a less immunogenic humanized monoclonal antibody." The Journal of Immunology (2002); 169: 3076-3084.
Extended European Search Report for European Application No. EP 13177665.0, dated Jan. 16, 2014, 14 pages.
Francés et al. "A surrogate 15 kDa JC kappa protein is expressed in combination with mu heavy chain by human B cell precursors." EMBO Journal (1994); 13: 5937-5943.
Franklin, Matthew C., et al. "Insights into ErbB signaling from the structure of the ErbB2-pertuzumab complex." Cancer Cell (2004); 5.4: 317-328.
Gauthier et al. "U-surrogate light chain physicochemical interactions of the human preB cell receptor: implications for VH repertoire selection and cell signaling at the preB cell stage." Journal of Immunology (1999); 162: 41-50.
Gocník, et al. "Antibodies specific to the HA2 glycopolypeptide of influenza. A virus haemagglutinin with fusion-inhibition activity contribute to the protection of mice against lethal infection." Journal of General Virology (2007); 88(Part 3): 951-955.
Govorkova, et al. "Immunization with reverse-genetics-produced H5N1 influenza vaccine protects ferrets against homologous and heterologous challenge." Journal of Infectious Diseases (2006); 194.2: 159-167.
Greenspan and Di Cera "Defining epitopes: It's not as easy as it seems." Nature Biotechnology (1999); 17(10): 936-937.
Hanson, et al. "Passive immunoprophylaxis and therapy with humanized monoclonal antibody specific for influenza A H5 hemagglutinin in mice." Respiratory Research (2006); 7: 126, pp. 1-10.
Hollis, Gregory F., et al. "Immunoglobulin lambda light-chain-related genes 14.1 and 16.1 are expressed in pre-B cells and may encode the human immunoglobulin omega light-chain protein." Proceedings of the National Academy of Sciences (1989); 86.14: 5552-5556.
Holt, et al. "Domain antibodies: proteins for therapy." Trends in Biotechnology (2003); 21.11: 484-490.
International Search Report and Written Opinion for International Application No. PCT/US2008/058283, dated Oct. 30, 2008, 11 pages.
International Preliminary Report on Patentability for International Application No. PCT/US2008/058283, dated Sep. 29, 2009, 7 pages.
International Search Report and Written Opinion for International Application No. PCT/US2009/038636, dated Feb. 8, 2010, 21 pages.
International Preliminary Report on Patentability for International Application No. PCT/US2009/038636, dated Sep. 28, 2010, 13 pages.
International Search Report and Written Opinion for International Application No. PCT/US2010/034604, dated Jan. 26, 2011, 21 pages.
International Preliminary Report on Patentability for International Application No. PCT/US2010/034604, dated Nov. 15, 2011, 13 pages.
International Search Report and Written Opinion for International Application No. PCT/US2012/044746, dated Dec. 4, 2012, 10 pages.
International Preliminary Report on Patentability for International Application No. PCT/US2012/044746, dated Jan. 7, 2014, 6 pages.
International Preliminary Report on Patentability for International Application No. PCT/US2012/048730, dated Jan. 28, 2014, 7 pages.
International Search Report and the Written Opinion for International Application No. PCT/US2012/071352, dated May 14, 2013, 15 pages.
International Preliminary Report on Patentability for International Application No. PCT/US2012/071352, dated Jun. 24, 2014, 9 pages.
International Search Report and the Written Opinion for International Application No. PCT/US2013/022308, dated Mar. 8, 2013, 9 pages.
International Preliminary Report on Patentability for International Application No. PCT/US2013/022308, dated Jul. 22, 2014, 5 pages.
Karasuyama et al. "The proteins encoded by the VpreB and _5 pre-B cell-specific genes can associate with each other and with heavy chain." The Journal of Experimental Medicine (1990); 172.3: 969-972.
Kashap, et al. "Combinatorial,antibody libraries from survivors of the Turkish HSNI avian influenza outbreak reveal virus neutralization strategies." Proceedings of the National Academy of Sciences (2008); 105(16): 5986-5991.
Kobayashi et al. "Tryptophan H33 plays an important role in pyrimidine (6-4) pyrimidone photoproduct binding by a high-affinity antibody." Protein Engineering (1999); 12.10: 879-884.
Kong, et al., "Successful treatment of avian influenza with convalescent plasma." Hong Kong Med. Journal (2006); 12(6): 489.
Kumar et al. "Molecular Cloning and Expression of the Fabs of Human Autoantibodies in Escherichia coli. Determination of the heavy or light chain contribution to the anti-DNA/-Cardiolipin activity of the Fab." J. Biol. Chem. (2000); 275: 35129-35136.
Lamminmaki and Kankare. "Expanding the conformational diversity by random insertions to CDRH2 results in improved anti-estradiol antibodies." J. Mol. Biol., 291: 589-602, (1999).
Lu, et al. "Passive immunotherapy for influenza A H5NI virus infection with equine hyperimmune globulin F(ab')2 in mice." Respiratory Research (2006); 7: 43, pp. 1-7.
MacCallum, et al. "Antibody-antigen interactions: contact analysis and binding site topography." Journal of Molecular Biology (1996); 262.5: 732-745.
Mariuzza, et al. "The structural basis of antigen-antibody recognition." Annual Review of Biophysics and Biophysical Chemistry (1987); 16.1: 139-159.
Mårtensson, Inga-Lill, et al. "The pre-B cell receptor checkpoint." FEBS Letters (2010); 584.12: 2572-2579.
Mateu, et al. "Non-additive effects of multiple amino acid substitutions on antigen-antibody recognition." European Journal of Immunology (1992); 22: 1385-1389.
Melchers et al. "Fit for life in the immune system? Surrogate L chain tests H chains that test L chains." Proc. Natl. Acad. Sci. USA (1999); 96: 2571-2573.
Minegishi et al., "Novel mechanisms control the folding and assembly of 5/14.1 and VpreB to produce an intact surrogate light chain." Proceedings of the National Academy of Sciences (1999); 96.6: 3041-3046.
Okuno, et al. "A common neutralizing epitope conserved between the hemagglutinins of influenza A virus H1 and H2 strains." Journal of Virology (1993); 67.5: 2552-2558.

(56) References Cited

OTHER PUBLICATIONS

Oner, et al. "Avian influenza A (H5N1) infection in eastern Turkey in 2006." New England Journal of Medicine (2006); 355.21: 2179-2185.

Pan, et al. "Methionine oxidation in human IgG2 Fc decreases binding affinities to protein A and FcRn." Protein Science (2009); 18.2: 424-433.

Rangel et al. "Assembly of the kappa preB receptor requires a V kappa-like protein encoded by a germline transcript." Journal of Biological Chemistry (2005); 280.18: 17807-17814.

Rudikoff et al. "Single amino acid substitution altering antigen-binding specificity." Proceedings of the National Academy of Sciences (1982); 79.6: 1979-1983.

Simmons, et al. "Prophylactic and therapeutic efficacy of human monoclonal antibodies against H5NI influenza." PLOS Medicine (2007); 4(5): 928-936.

Smirnov, et al. "Prevention and treatment of bronchopneumonia in mice caused by mouse-adapted variant of avian H5N2 influenza A virus using monoclonal antibody against conserved epitope in the HA stem region." Archives of Virology (2000); 145.8: 1733-1741.

Smirnov, et al. "An epitope shared by the hemagglutinins ofHI, H2, H5 and H6 subtypes of influenza A virus." Acta Virologica (1999); 43.4: 237-244.
Thompson et al. "A pro-B-cell stage characterized by germline Ig transcription without surrogate light chain expression." Immunogenetics (1998); 48(5): 305-311.
Throsby, et al. "Heterosubtypic neutralizing monoclonal antibodies cross-protective against H5NI recovered from human IgM memory B cells." PLoS ONE (2008); 3.12:: e3942, pp. 1-15.
Vermot-Desroches, C. et al. "Characterization of monoclonal antibodies directed against trail or trail receptors." Cellular Immunology (2005); 236.1: 86-91.
Zhou, et al. "Treatment with convalescent plasma for influenza A (H5NI) infection." New England Journal of Medicine (2007); 357.14: 1450-1451.

* cited by examiner

FIG. 1A

Sequence of human ErbB3 accession number P21860.

```
MetArgAlaAsnAspAlaLeuGlnValLeuGlyLeuLeuPheSerLeuAlaArgGlySer
GluValGlyAsnSerGlnAlaValCysProGlyThrLeuAsnGlyLeuSerValThrGly
AspAlaGluAsnGlnTyrGlnThrLeuTyrLysLeuTyrGluArgCysGluValValMet
GlyAsnLeuGluIleValLeuThrGlyHisAsnAlaAspLeuSerPheLeuGlnTrpIle
ArgGluValThrGlyTyrValLeuValAlaMetAsnGluPheSerThrLeuProLeuPro
AsnLeuArgValValArgGlyThrGlnValTyrAspGlyLysPheAlaIlePheValMet
LeuAsnTyrAsnThrAsnSerSerHisAlaLeuArgGlnLeuArgLeuThrGlnLeuThr
GluIleLeuSerGlyGlyValTyrIleGluLysAsnAspLysLeuCysHisMetAspThr
IleAspTrpArgAspIleValArgAspArgAspAlaGluIleValValLysAspAsnGly
ArgSerCysProProCysHisGluValCysLysGlyArgCysTrpGlyProGlySerGlu
AspCysGlnThrLeuThrLysThrIleCysAlaProGlnCysAsnGlyHisCysPheGly
ProAsnProAsnGlnCysCysHisAspGluCysAlaGlyGlyCysSerGlyProGlnAsp
ThrAspCysPheAlaCysArgHisPheAsnAspSerGlyAlaCysValProArgCysPro
GlnProLeuValTyrAsnLysLeuThrPheGlnLeuGluProAsnProHisThrLysTyr
GlnTyrGlyGlyValCysValAlaSerCysProHisAsnPheValValAspGlnThrSer
CysValArgAlaCysProProAspLysMetGluValAspLysAsnGlyLeuLysMetCys
GluProCysGlyGlyLeuCysProLysAlaCysGluGlyThrGlySerGlySerArgPhe
GlnThrValAspSerSerAsnIleAspGlyPheValAsnCysThrLysIleLeuGlyAsn
LeuAspPheLeuIleThrGlyLeuAsnGlyAspProTrpHisLysIleProAlaLeuAsp
ProGluLysLeuAsnValPheArgThrValArgGluIleThrGlyTyrLeuAsnIleGln
SerTrpProProHisMetHisAsnPheSerValPheSerAsnLeuThrThrIleGlyGly
ArgSerLeuTyrAsnArgGlyPheSerLeuLeuIleMetLysAsnLeuAsnValThrSer
LeuGlyPheArgSerLeuLysGluIleSerAlaGlyArgIleTyrIleSerAlaAsnArg
GlnLeuCysTyrHisHisSerLeuAsnTrpThrLysValLeuArgGlyProThrGluGlu
ArgLeuAspIleLysHisAsnArgProArgArgAspCysValAlaGluGlyLysValCys
AspProLeuCysSerSerGlyGlyCysTrpGlyProGlyProGlyGlnCysLeuSerCys
ArgAsnTyrSerArgGlyGlyValCysValThrHisCysAsnPheLeuAsnGlyGluPro
ArgGluPheAlaHisGluAlaGluCysPheSerCysHisProGluCysGlnProMetGlu
GlyThrAlaThrCysAsnGlySerGlySerAspThrCysAlaGlnCysAlaHisPheArg
AspGlyProHisCysValSerSerCysProHisGlyValLeuGlyAlaLysGlyProIle
TyrLysTyrProAspValGlnAsnGluCysArgProCysHisGluAsnCysThrGlnGly
CysLysGlyProGluLeuGlnAspCysLeuGlyGlnThrLeuValLeuIleGlyLysThr
HisLeuThrMetAlaLeuThrValIleAlaGlyLeuValValIlePheMetMetLeuGly
GlyThrPheLeuTyrTrpArgGlyArgArgIleGlnAsnLysArgAlaMetArgArgTyr
LeuGluArgGlyGluSerIleGluProLeuAspProSerGluLysAlaAsnLysValLeu
AlaArgIlePheLysGluThrGluLeuArgLysLeuLysValLeuGlySerGlyValPhe
GlyThrValHisLysGlyValTrpIleProGluGlyGluSerIleLysIleProValCys
IleLysValIleGluAspLysSerGlyArgGlnSerPheGlnAlaValThrAspHisMet
LeuAlaIleGlySerLeuAspHisAlaHisIleValArgLeuLeuGlyLeuCysProGly
SerSerLeuGlnLeuValThrGlnTyrLeuProLeuGlySerLeuLeuAspHisValArg
GlnHisArgGlyAlaLeuGlyProGlnLeuLeuLeuAsnTrpGlyValGlnIleAlaLys
GlyMetTyrTyrLeuGluGluHisGlyMetValHisArgAsnLeuAlaAlaArgAsnVal
LeuLeuLysSerProSerGlnValGlnValAlaAspPheGlyValAlaAspLeuLeuPro
ProAspAspLysGlnLeuLeuTyrSerGluAlaLysThrProIleLysTrpMetAlaLeu
GluSerIleHisPheGlyLysTyrThrHisGlnSerAspValTrpSerTyrGlyValThr
ValTrpGluLeuMetThrPheGlyAlaGluProTyrAlaGlyLeuArgLeuAlaGluVal
ProAspLeuLeuGluLysGlyGluArgLeuAlaGlnProGlnIleCysThrIleAspVal
TyrMetValMetValLysCysTrpMetIleAspGluAsnIleArgProThrPheLysGlu
LeuAlaAsnGluPheThrArgMetAlaArgAspProProArgTyrLeuValIleLysArg
GluSerGlyProGlyIleAlaProGlyProGluProHisGlyLeuThrAsnLysLysLeu
GluGluValGluLeuGluProGluLeuAspLeuAspLeuGluAlaGluGluAsp
AsnLeuAlaThrThrThrLeuGlySerAlaLeuSerLeuProValGlyThrLeuAsnArg
```

FIG. 1A (continued)

```
ProArgGlySerGlnSerLeuLeuSerProSerSerGlyTyrMetProMetAsnGlnGly
AsnLeuGlyGluSerCysGlnGluSerAlaValSerGlySerSerGluArgCysProArg
ProValSerLeuHisProMetProArgGlyCysLeuAlaSerGluSerSerGluGlyHis
ValThrGlySerGluAlaGluLeuGlnGluLysValSerMetCysArgSerArgSerArg
SerArgSerProArgProArgGlyAspSerAlaTyrHisSerGlnArgHisSerLeuLeu
ThrProValThrProLeuSerProProGlyLeuGluGluGluAspValAsnGlyTyrVal
MetProAspThrHisLeuLysGlyThrProSerSerArgGluGlyThrLeuSerSerVal
GlyLeuSerSerValLeuGlyThrGluGluGluAspGluAspGluGluTyrGluTyrMet
AsnArgArgArgArgHisSerProProHisProProArgProSerSerLeuGluGluLeu
GlyTyrGluTyrMetAspValGlySerAspLeuSerAlaSerLeuGlySerThrGlnSer
CysProLeuHisProValProIleMetProThrAlaGlyThrThrProAspGluAspTyr
GluTyrMetAsnArgGlnArgAspGlyGlyGlyProGlyGlyAspTyrAlaAlaMetGly
AlaCysProAlaSerGluGlnGlyTyrGluGluMetArgAlaPheGlnGlyProGlyHis
GlnAlaProHisValHisTyrAlaArgLeuLysThrLeuArgSerLeuGluAlaThrAsp
SerAlaPheAspAsnProAspTyrTrpHisSerArgLeuPheProLysAlaAsnAlaGln
ArgThr
```

(SEQ ID NO: 36)

FIG. 1B

Sequence of murine ErbB3 accession Q61526

MetSerAlaIleGlyThrLeuGlnValLeuGlyPheLeuLeuSerLeuAlaArgGlySer
GluMetGlyAsnSerGlnAlaValCysProGlyThrLeuAsnGlyLeuSerValThrGly
AspAlaAspAsnGlnTyrGlnThrLeuTyrLysLeuTyrGluCysGluValValMet
GlyAsnLeuGluIleValLeuThrGlyHisAsnAlaAspLeuSerPheLeuGlnTrpIle
ArgGluValThrGlyTyrValLeuValAlaMetAsnGluPheSerValLeuProLeuPro
AsnLeuArgValValArgGlyThrGlnValTyrAspGlyLysPheAlaIlePheValMet
LeuAsnTyrAsnThrAsnSerSerHisAlaLeuArgGlnLeuArgPheThrGlnLeuThr
GluIleLeuLeuGlyGlyValTyrIleGluLysAsnAspLysLeuCysHisMetAspThr
IleAspTrpArgAspIleValArgValProAspAlaGluIleValValLysAsnAsnGly
GlyAsnCysProProCysHisGluValCysLysGlyArgCysTrpGlyProGlyProGlu
AspCysGlnIleLeuThrLysThrIleCysAlaProGlnCysAsnGlyArgCysPheGly
ProAsnProAsnGlnCysCysHisAspGluCysAlaGlyGlyCysSerGlyProGlnAsp
ThrAspCysPheAlaCysArgHisPheAsnAspSerGlyAlaCysValProArgCysPro
AlaProLeuValTyrAsnLysLeuThrPheGlnLeuGluProAsnProHisIleLysTyr
GlnTyrGlyGlyValCysValAlaSerCysProHisAsnPheValValAspGlnThrPhe
CysValArgAlaCysProAlaAspLysMetGluValAspLysAsnGlyLeuLysMetCys
GluProCysArgGlyLeuCysProLysAlaCysGluGlyThrGlySerGlySerArgTyr
GlnThrValAspSerSerAsnIleAspGlyPheValAsnCysThrLysIleLeuGlyAsn
LeuAspPheLeuIleThrGlyLeuAsnGlyAspProTrpHisLysIleProAlaLeuAsp
ProGluLysLeuAsnValPheArgThrValArgGluIleThrGlyTyrLeuAsnIleGln
SerTrpProProHisMetHisAsnPheSerValPheSerAsnLeuThrThrIleGlyGly
ArgSerLeuTyrAsnArgGlyPheSerLeuLeuIleMetLysAsnLeuAsnValThrSer
LeuGlyPheArgSerLeuLysGluIleSerAlaGlyArgValTyrIleSerAlaAsnGln
GlnLeuCysTyrHisHisSerLeuAsnTrpThrArgLeuLeuArgGlyProAlaGluGlu
ArgLeuAspIleLysTyrAsnArgProLeuGlyGluCysValAlaGluGlyLysValCys
AspProLeuCysSerSerGlyGlyCysTrpGlyProGlyProGlnCysLeuSerCys
ArgAsnTyrSerArgGluCysValCysValThrHisCysAsnValLeuGlnGlyGluPro
ArgGluPheValHisGluAlaHisCysPheSerCysHisProGluCysGlnProMetGlu
GlyThrSerThrCysAsnGlySerGlySerAspAlaCysAlaArgCysAlaHisPheArg
AspGlyProHisCysValAsnSerCysProHisGlyIleLeuGlyAlaLysGlyProIle
TyrLysTyrProAspAlaGlnAsnGluCysArgProCysHisGluAsnCysThrGlnGly
CysLysGlyProGluLeuGlnAspCysLeuGlyGlnAlaGluValLeuMetSerLysPro
HisLeuValIleAlaValThrValGlyLeuThrValIlePheLeuIleLeuGlyGlySer
PheLeuTyrTrpArgGlyArgArgIleGlnAsnLysArgAlaMetArgArgTyrLeuGlu
ArgGlyGluSerIleGluProLeuAspProSerGluLysAlaAsnLysValLeuAlaArg
IlePheLysGluThrGluLeuArgLysLeuLysValLeuGlySerGlyValPheGlyThr
ValHisLysGlyIleTrpIleProGluGlyGluSerIleLysIleProValCysIleLys
ValIleGluAspLysSerGlyArgGlnSerPheGlnAlaValThrAspHisMetLeuAla
ValGlySerLeuAspHisAlaHisIleValArgLeuLeuGlyLeuCysProGlySerSer
LeuGlnLeuValThrGlnTyrLeuProLeuGlySerLeuLeuAspHisValArgGlnHis
ArgGluThrLeuGlyProGlnLeuLeuLeuAsnTrpGlyValGlnIleAlaLysGlyMet
TyrTyrLeuGluGluHisSerMetValHisArgAspLeuAlaLeuArgAsnValMetLeu
LysSerProSerGlnValGlnValAlaAspPheGlyValAlaAspLeuLeuProProAsp
AspLysGlnLeuLeuHisSerGluAlaLysThrProIleLysTrpMetAlaLeuGluSer
IleHisPheGlyLysTyrThrHisGlnSerAspValTrpSerTyrGlyValThrValTrp
GluLeuMetThrPheGlyAlaGluProTyrAlaGlyLeuArgLeuAlaGluIleProAsp
LeuLeuGluLysGlyGluArgLeuAlaGlnProGlnIleCysThrIleAspValTyrMet
ValMetValLysCysTrpMetIleAspGluAsnIleArgProThrPheLysGluLeuAla
AsnGluPheThrArgMetAlaArgAspProProArgTyrLeuValIleLysArgAlaSer
GlyProGlyIleProProAlaAlaGluProSerAlaLeuSerThrLysGluLeuGlnAsp
AlaGluLeuGluProAspLeuAspLeuAspLeuAspValGluValGluGluGluGlyLeu
AlaThrThrLeuGlySerAlaLeuSerLeuProThrGlyThrLeuThrArgProArgGly
SerGlnSerLeuLeuSerProSerSerGlyTyrMetProMetAsnGlnSerAsnLeuGly
GluAlaCysLeuAspSerAlaValLeuGlyGlyArgGluGlnPheSerArgProIleSer
LeuHisProIleProArgGlyArgGlnThrSerGluSerSerGluGlyHisValThrGly

FIG. 1B (continued)

```
SerGluAlaGluLeuGlnGluArgValSerMetCysArgSerArgSerArgSerArgSer
ProArgProArgGlyAspSerAlaTyrHisSerGlnArgHisSerLeuLeuThrProVal
ThrProLeuSerProProGlyLeuGluGluGluAspGlyAsnGlyTyrValMetProAsp
ThrHisLeuArgGlyThrSerSerSerArgGluGlyThrLeuSerSerValGlyLeuSer
SerValLeuGlyThrGluGluGluAspGluAspGluGluTyrGluTyrMetAsnArgLys
ArgArgGlySerProAlaArgProProArgProGlySerLeuGluGluLeuGlyTyrGlu
TyrMetAspValGlySerAspLeuSerAlaSerLeuGlySerThrGlnSerCysProLeu
HisProMetAlaIleValProSerAlaGlyThrThrProAspGluAspTyrGluTyrMet
AsnArgArgArgGlyAlaGlyGlySerGlyGlyAspTyrAlaAlaMetGlyAlaCysPro
AlaAlaGluGlnGlyTyrGluGluMetArgAlaPheGlnGlyProGlyHisGlnAlaPro
HisValArgTyrAlaArgLeuLysThrLeuArgSerLeuGluAlaThrAspSerAlaPhe
AspAsnProAspTyrTrpHisSerArgLeuPheProLysAlaAsnAlaGlnArgIle
```

(SEQ ID NO: 37)

FIG. 2A

2716-F05
GluValGlnLeuLeuGluSerGlyGlyGlyLeuValGlnProGlyGlySerLeuArgLeu
SerCysAlaAlaSerGlyPheThrPheSerAsnTyrTrpMetHisTrpValArgGlnAla
ProGlyLysGlyLeuGluTrpValAlaLeuIleSerGlyGlyGlyAsnThrTyrTyr
AlaAspSerValLysGlyArgPheThrIleSerArgAspAsnSerLysAsnThrLeuTyr
LeuGlnMetAsnSerLeuArgAlaGluAspThrAlaValTyrTyrCysAlaLysAspAsn
GluLysAsnLeuTyrThrTrpLeuAspTyrTrpGlyGlnGlyThrLeuValThrValSer
Ser     (SEQ ID NO: 38)

2716-F05
SerAsnTyrTrpMetHis     (SEQ ID NO: 39)   TrpValAlaLeuIleSerGlyGlyGlyGlyAsnThrTyr
       (SEQ ID NO: 40) AlaLysAspAsnGluLysAsnLeuTyrThrTrpLeuAsp (SEQ ID NO: 41)

2817-C01
GluValGlnLeuLeuGluSerGlyGlyGlyLeuValGlnProGlyGlySerLeuArgLeu
SerCysAlaAlaSerGlyPheThrPheSerThrTyrAlaMetAsnTrpValArgGlnAla
ProGlyLysGlyLeuGluTrpValAlaLeuIleSerSerGlyGlySerTyrTyrLysTyrTyr
AlaAspSerValLysGlyArgPheThrIleSerArgAspAsnSerLysAsnThrLeuTyr
LeuGlnMetAsnSerLeuArgAlaGluAspThrAlaValTyrTyrCysAlaLysAspAsn
PheIleLeuLeuAsnSerTrpPheAspTyrTrpGlyGlnGlyThrLeuValThrValSer
Ser     (SEQ ID NO: 42)

2817-C01
SerThrTyrAlaMetAsn(SEQ ID NO: 43)     TrpValAlaLeuIleSerSerGlyGlySerTyrLysTyr(SEQ ID NO: 44)
       AlaLysAspAsnPheIleLeuLeuAsnSerTrpPheAsp     (SEQ ID NO: 45)

2816-D12
GlnValGlnLeuValGlnSerGlyAlaGluValLysLysProGlySerSerValLysVal
SerCysLysAlaSerGlyGlyThrPheSerSerTyrAlaIleSerTrpValArgGlnAla
ProGlyGlnGlyLeuGluTrpMetGlyGlyIleThrValTyrThrGlyThrThrAsnTyr
AlaGlnLysPheGlnGlyArgValThrIleThrAlaAspLysSerThrSerThrAlaTyr
MetGluLeuSerSerLeuArgSerGluAspThrAlaValTyrTyrCysAlaArgAlaAsn
AlaIleThrValAsnArgSerLeuAspTyrTrpGlyGlnGlyThrLeuValThrValSer
Ser     (SEQ ID NO: 46)

FIG. 2A (cont'd)

2816-D12
SerSerTyrAlaIleSer(SEQ ID NO: 47) TrpMetGlyGlyIleThrValTyrThrGlyThrThrAsn(SEQ ID NO: 48)
AlaArgAlaAsnAlaIleThrValAsnArgSerLeuAsp (SEQ ID NO: 49)

2890-A03
GluValGlnLeuValGluSerGlyGlyGlyLeuValLysProGlyGlySerLeuArgLeu
SerCysAlaAlaSerGlyPheThrPheArgAsnTyrSerMetSerTrpValArgGlnAla
ProGlyLysGlyLeuGluTrpValAlaAlaIleSerTyrGlyGlyAlaTyrLysTyrTyr
AlaAspSerValLysGlyArgPheThrIleSerArgAspAsnAlaLysAsnSerLeuTyr
LeuGlnMetAsnSerLeuArgAlaGluAspThrAlaValTyrTyrCysAlaArgGluVal
GlyLeuAspTyrAlaMetAspTyrTrpGlyGlnGlyThrLeuValThrValSerSer
(SEQ ID NO: 50)

FIG. 2B

2890-A03
ArgAsnTyrSerMetSer(SEQ ID NO: 51) TrpValAlaAlaIleSerTyrGlyGlyAlaTyrLysTyr (SEQ ID NO: 52)
AlaArgGluValGlyLeuAspTyrAlaMetAsp(SEQ ID NO: 53)

2900-B11
GluValGlnLeuValGluSerGlyGlyGlyLeuValLysProGlyGlySerLeuArgLeu
SerCysAlaAlaSerGlyPheThrPheSerAsnTyrSerMetSerTrpValArgGlnAla
ProGlyLysGlyLeuGluTrpValAlaAsnIleSerAlaGlyAlaTyrAlaTyrLysTyrTyr
AlaAspSerValLysGlyArgPheThrIleSerArgAspAsnAlaLysAsnSerLeuTyr
LeuGlnMetAsnSerLeuArgAlaGluAspThrAlaValTyrTyrCysAlaArgAspArg
PheLysTyrLeuTrpSerTrpPheAspTyrTrpGlyGlnGlyThrLeuValThrValSer
 (SEQ ID NO: 54)

2900-B11
SerAsnTyrSerMetSer(SEQ ID NO: 55)   TrpValAlaAsnIleSerAlaGlyAlaTyrLysTyr(SEQ ID NO: 56)
AlaArgAspArgPheLysTyrLeuTrpSerTrpPheAsp(SEQ ID NO: 57)

2900-A07
GluValGlnLeuLeuGluSerGlyGlyGlyLeuValGlnProGlyGlySerLeuArgLeu
SerCysAlaAlaSerGlyPheThrPheSerSerTyrTrpMetHisTrpValArgGlnAla
ProGlyLysGlyLeuGluTrpValAlaValIleSerAsnGlyGlyAlaTyrLysTyrTyr
AlaAspSerValLysGlyArgPheThrIleSerArgAspAsnSerLysAsnThrLeuTyr
LeuGlnMetAsnSerLeuArgAlaGluAspThrAlaValTyrTyrCysAlaArgAspAsn
AlaIleTrpLeuTrpAlaIleTrpLeuTrpAlaTrpPheAsp
Ser  (SEQ ID NO: 58)

2900-A07
SerSerTyrTrpMetHis(SEQ ID NO: 59) TrpValAlaValIleSerAsnGlyGlyAlaTyrLysTyr(SEQ ID NO: 60)
AlaArgAspAsnAlaIleTrpLeuTrpAlaTrpPheAsp  (SEQ ID NO: 61)

2815-B08
GluValGlnLeuValGluSerGlyGlyGlyLeuValLysProGlyGlySerLeuArgLeu
SerCysAlaAlaSerGlyPheThrPheSerAsnTyrGluMetSerTrpValArgGlnAla
ProGlyLysGlyLeuGluTrpValAlaThrIleSerArgTyrAspGlyGlyTyrTyrLysTyrTyr
AlaAspSerValLysGlyArgPheThrIleSerArgAspAsnAlaLysAsnSerLeuTyr
LeuGlnMetAsnSerLeuArgAlaGluAspThrAlaValTyrTyrCysAlaArgAspAsn
SerTyrLeuLeuTyrTyrTyrPheAspTyrTrpGlyGlnGlyThrLeuValThrValSer

FIG. 2B (continued)

Ser (SEQ ID NO: 62)

2815-B08
SerAsnTyrGluMetSer(SEQ ID NO: 63) TrpValAlaThrIleSerTyrAspGlyGlyTyrLysTyr(SEQ ID NO: 64)
AlaArgAspAsnSerTyrLeuLeuTyrTyrTrpPheAsp (SEQ ID NO: 65)

| SEQ ID No | | Similarities between 2817-C01 and 2716-F05 |
|---|---|---|
| 70 | 2817-C01 | EVQLLESGGGLVQPGGSLRLSCAASGFTFSTYAMNWVRQAPGKGLEWV |
| 71 | 2716-F05 | EVQLLESGGGLVQPGGSLRLSCAASGFTFSNYWMHWVRQAPGKGLEWV |
| | 2817-C01 | ALISSGGSYKYYADSVKGRFTISRDNSKNTLYLQMNSLRAEDTAVYYCAK |
| | 2716-F05 | ALISGGGNTYYADSVKGRFTISRDNSKNTLYLQMNSLRAEDTAVYYCAK |
| | 2817-C01 | DNFILLNSWFDYWGQGTLVTV |
| | 2716-F05 | DNEKNLYTWLDYWGQGTLVTV |

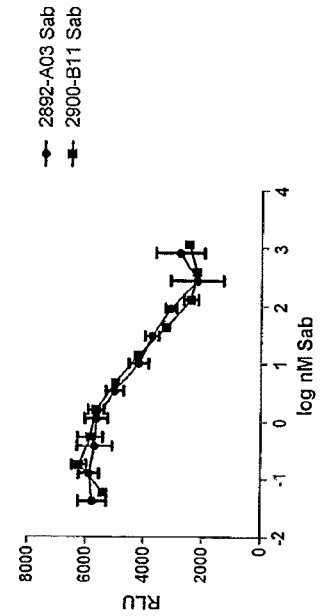
FIG. 3B
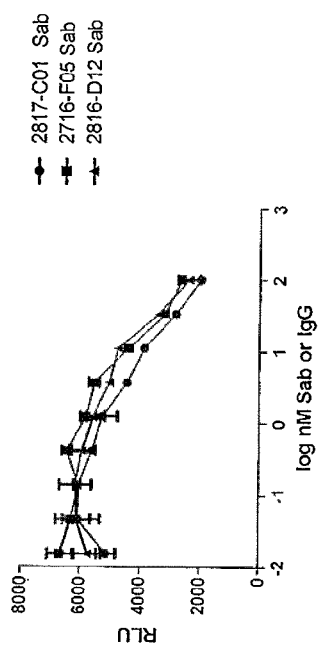
FIG. 3A
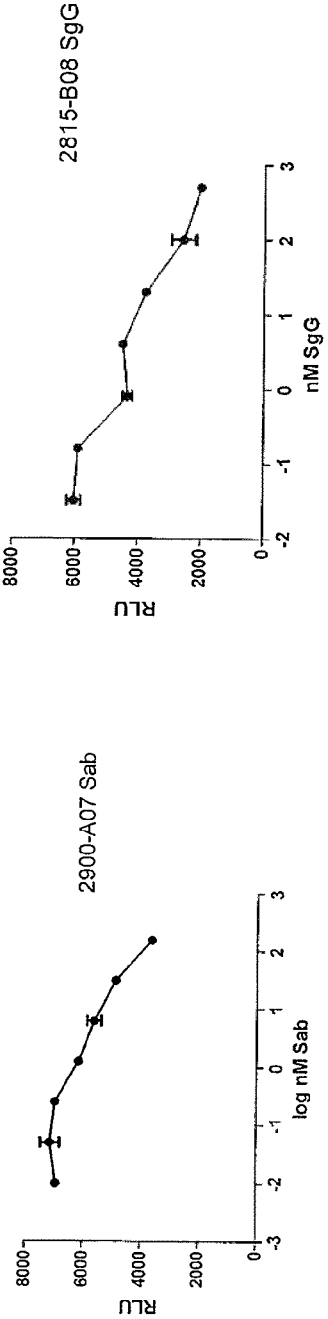
FIG. 3D
FIG. 3C

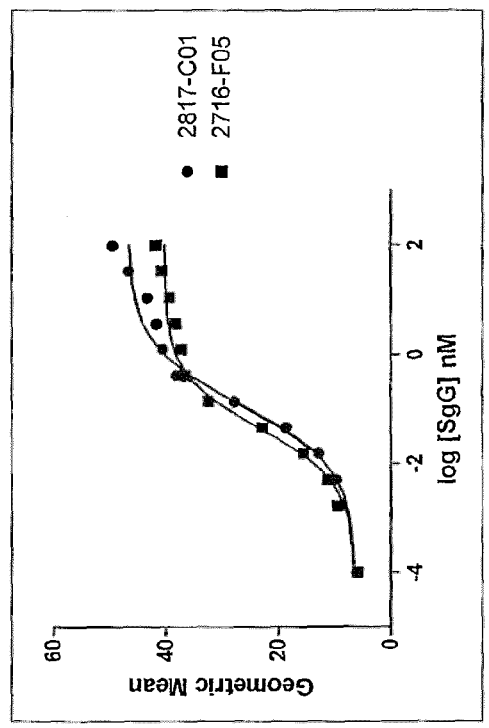
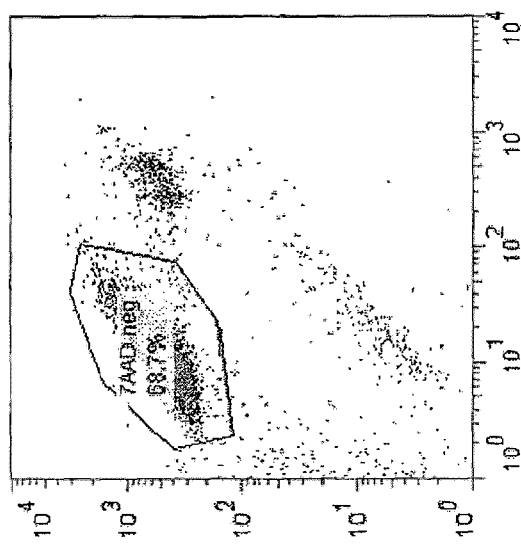
FIG. 4B
FIG. 4A

Fig. 7A 2-3-3-3
ThrGlnValCysThrGlyThrAspMetLysLeuArgLeuProAlaSerProGluThrHis
LeuAspMetLeuArgHisLeuTyrGlnGlyCysGlnValValGlnGlyAsnLeuGluLeu
ThrTyrLeuProThrAsnAlaSerLeuSerPheLeuGlnAspIleGlnGluValGlnGly
TyrValLeuIleAlaHisAsnGlnValArgGlnValProLeuGlnArgLeuArgIleVal
ArgGlyThrGlnLeuPheGluAspAsnTyrAlaLeuAlaValLeuAspAsnGlyAspPro
LeuAsnAsnThrThrProValThrGlyAlaSerProGlyGlyLeuArgGluLeuGlnLeu
ArgSerLeuThrGluIleLeuLysGlyGlyValLeuIleGlnArgAsnProGlnLeuCys
TyrGlnAspThrIleLeuTrpLysAspIlePheHisLysAsnAsnGlnLeuAlaLeuThr
LeuIleAspThrAsnArgSerArgSerCysProProCysHisGluValCysLysGlyArg
CysTrpGlyProGlySerGluAspCysGlnThrLeuThrLysThrIleCysAlaProGln
CysAsnGlyHisCysPheGlyProAsnProAsnGlnCysCysHisAspGluCysAlaGly
GlyCysSerGlyProGlnAspThrAspCysPheAlaCysArgHisPheAsnAspSerGly
AlaCysValProArgCysProGlnProLeuValTyrAsnLysLeuThrPheGlnLeuGlu
ProAsnProHisThrLysTyrGlnTyrGlyGlyValCysValAlaSerCysProHisAsn
PheValValAspGlnThrSerCysValArgAlaCysProProAspLysMetGluValAsp
LysAsnGlyLeuLysMetCysGluProCysGlyGlyLeuCysProLysAlaCysGluGly
ThrGlySerGlySerArgPheGlnThrValAspSerSerAsnIleAspGlyPheValAsn
CysThrLysIleLeuGlyAsnLeuAspPheLeuIleThrGlyLeuAsnGlyAspProTrp
HisLysIleProAlaLeuAspProGluLysLeuAsnValPheArgThrValArgGluIle
ThrGlyTyrLeuAsnIleGlnSerTrpProProHisMetHisAsnPheSerValPheSer
AsnLeuThrThrIleGlyGlyArgSerLeuTyrAsnArgGlyPheSerLeuLeuIleMet
LysAsnLeuAsnValThrSerLeuGlyPheArgSerLeuLysGluIleSerAlaGlyArg
IleTyrIleSerAlaAsnArgGlnLeuCysTyrHisHisSerLeuAsnTrpThrLysVal
LeuArgGlyProThrGluGluArgLeuAspIleLysHisAsnArgProArgArgAspCys
ValAlaGluGlyLysValCysAspProLeuCysSerSerGlyGlyCysTrpGlyProGly
ProGlyGlnCysLeuSerCysArgAsnTyrSerArgGlyGlyValCysValThrHisCys
AsnPheLeuAsnGlyGluProArgGluPheAlaHisGluAlaGluCysPheSerCysHis
ProGluCysGlnProMetGluGlyThrAlaThrCysAsnGlySerGlySerAspThrCys
AlaGlnCysAlaHisPheArgAspGlyProHisCysValSerSerCysProHisGlyVal
LeuGlyAlaLysGlyProIleTyrLysTyrProAspValGlnAsnGluCysArgProCys
HisGluAsnCysThrGlnGlyCysLysGlyProGluLeuGlnAspCysLeuGlyGlnThr
LeuValLeuIleGlyLysThrHisLeuThrIleGluGlyArgMetAspAspLysThrHis
ThrCysProProCysProAlaProGluLeuLeuGlyGlyProSerValPheLeuPhePro
ProLysProLysAspThrLeuMetIleSerArgThrProGluValThrCysValValVal
AspValSerHisGluAspProGluValLysPheAsnTrpTyrValAspGlyValGluVal
HisAsnAlaLysThrLysProArgGluGluGlnTyrAsnSerThrTyrArgValValSer
ValLeuThrValLeuHisGlnAspTrpLeuAsnGlyLysGluTyrLysCysLysValSer
AsnLysAlaLeuProAlaProIleGluLysThrIleSerLysAlaLysGlyGlnProArg
GluProGlnValTyrThrLeuProProSerArgAspGluLeuThrLysAsnGlnValSer
LeuThrCysLeuValLysGlyPheTyrProSerAspIleAlaValGluTrpGluSerAsn
GlyGlnProGluAsnAsnTyrLysThrThrProProValLeuAspSerAspGlySerPhe
PheLeuTyrSerLysLeuThrValAspLysSerArgTrpGlnGlnGlyAsnValPheSer
CysSerValMetHisGluAlaLeuHisAsnHisTyrThrGlnLysSerLeuSerLeuSer
ProGly (SEQ ID NO 81)

Fig. 7B
3-3-2-3

GlyAsnSerGlnAlaValCysProGlyThrLeuAsnGlyLeuSerValThr
GlyAspAlaGluAsnGlnTyrGlnThrLeuTyrLysLeuTyrGluArgCysGluValVal
MetGlyAsnLeuGluIleValLeuThrGlyHisAsnAlaAspLeuSerPheLeuGlnTrp
IleArgGluValThrGlyTyrValLeuValAlaMetAsnGluPheSerThrLeuProLeu
ProAsnLeuArgValValArgGlyThrGlnValTyrAspGlyLysPheAlaIlePheVal
MetLeuAsnTyrAsnThrAsnSerSerHisAlaLeuArgGlnLeuArgLeuThrGlnLeu
ThrGluIleLeuSerGlyGlyValTyrIleGluLysAsnAspLysLeuCysHisMetAsp
ThrIleAspTrpArgAspIleValArgAspArgAspAlaGluIleValValLysAspAsn
GlyArgSerCysProProCysHisGluValCysLysGlyArgCysTrpGlyProGlySer
GluAspCysGlnThrLeuThrLysThrIleCysAlaProGlnCysAsnGlyHisCysPhe
GlyProAsnProAsnGlnCysCysHisAspGluCysAlaGlyGlyCysSerGlyProGln
AspThrAspCysPheAlaCysArgHisPheAsnAspSerGlyAlaCysValProArgCys
ProGlnProLeuValTyrAsnLysLeuThrPheGlnLeuGluProAsnProHisThrLys
TyrGlnTyrGlyGlyValCysValAlaSerCysProHisAsnPheValValAspGlnThr
SerCysValArgAlaCysProProAspLysMetGluValAspLysAsnGlyLeuLysMet
CysGluProCysGlyGlyLeuCysProLysAlaCysTyrGlyLeuGlyMetGluHisLeu
ArgGluValArgAlaValThrSerAlaAsnIleGlnGluPheAlaGlyCysLysLysIle
PheGlySerLeuAlaPheLeuProGluSerPheAspGlyAspProAlaSerAsnThrAla
ProLeuGlnProGluGlnLeuGlnValPheGluThrLeuGluGluIleThrGlyTyrLeu
TyrIleSerAlaTrpProAspSerLeuProAspLeuSerValPheGlnAsnLeuGlnVal
IleArgGlyArgIleLeuHisAsnGlyAlaTyrSerLeuThrLeuGlnGlyLeuGlyIle
SerTrpLeuGlyLeuArgSerLeuArgGluLeuGlySerGlyLeuAlaLeuIleHisHis
AsnThrHisLeuCysPheValHisThrValProTrpAspGlnLeuPheArgAsnProHis
GlnAlaLeuLeuHisThrAlaAsnArgProGluAspGluCysValGlyGluGlyLysVal
CysAspProLeuCysSerSerGlyGlyCysTrpGlyProGlyProGlnCysLeuSer
CysArgAsnTyrSerArgGlyGlyValCysValThrHisCysAsnPheLeuAsnGlyGlu
ProArgGluPheAlaHisGluAlaGluCysPheSerCysHisProGluCysGlnProMet
GluGlyThrAlaThrCysAsnGlySerGlySerAspThrCysAlaGlnCysAlaHisPhe
ArgAspGlyProHisCysValSerSerCysProHisGlyValLeuGlyAlaLysGlyPro
IleTyrLysTyrProAspValGlnAsnGluCysArgProCysHisGluAsnCysThrGln
GlyCysLysGlyProGluLeuGlnAspCysLeuGlyGlnThrLeuValLeuIleGlyLys
ThrHisLeuThrIleGluGlyArgMetAspAspLysThrHisThrCysProProCysPro
AlaProGluLeuLeuGlyGlyProSerValPheLeuPheProProLysProLysAspThr
LeuMetIleSerArgThrProGluValThrCysValValValAspValSerHisGluAsp
ProGluValLysPheAsnTrpTyrValAspGlyValGluValHisAsnAlaLysThrLys
ProArgGluGluGlnTyrAsnSerThrTyrArgValValSerValLeuThrValLeuHis
GlnAspTrpLeuAsnGlyLysGluTyrLysCysLysValSerAsnLysAlaLeuProAla
ProIleGluLysThrIleSerLysAlaLysGlyGlnProArgGluProGlnValTyrThr
LeuProProSerArgAspGluLeuThrLysAsnGlnValSerLeuThrCysLeuValLys
GlyPheTyrProSerAspIleAlaValGluTrpGluSerAsnGlyGlnProGluAsnAsn
TyrLysThrThrProProValLeuAspSerAspGlySerPhePheLeuTyrSerLysLeu
ThrValAspLysSerArgTrpGlnGlnGlyAsnValPheSerCysSerValMetHisGlu
AlaLeuHisAsnHisTyrThrGlnLysSerLeuSerLeuSerProGly (SEQ ID NO 82)

Fig. 7C 3-3-3-2

GlyAsnSerGlnAlaValCysProGlyThrLeuAsnGlyLeuSerValThrGlyAspAla
GluAsnGlnTyrGlnThrLeuTyrLysLeuTyrGluArgCysGluValValMetGlyAsn
LeuGluIleValLeuThrGlyHisAsnAlaAspLeuSerPheLeuGlnTrpIleArgGlu
ValThrGlyTyrValLeuValAlaMetAsnGluPheSerThrLeuProLeuProAsnLeu
ArgValValArgGlyThrGlnValTyrAspGlyLysPheAlaIlePheValMetLeuAsn
TyrAsnThrAsnSerSerHisAlaLeuArgGlnLeuArgLeuThrGlnLeuThrGluIle
LeuSerGlyGlyValTyrIleGluLysAsnAspLysLeuCysHisMetAspThrIleAsp
TrpArgAspIleValArgAspArgAspAlaGluIleValValLysAspAsnGlyArgSer
CysProProCysHisGluValCysLysGlyArgCysTrpGlyProGlySerGluAspCys
GlnThrLeuThrLysThrIleCysAlaProGlnCysAsnGlyHisCysPheGlyProAsn
ProAsnGlnCysCysHisAspGluCysAlaGlyGlyCysSerGlyProGlnAspThrAsp
CysPheAlaCysArgHisPheAsnAspSerGlyAlaCysValProArgCysProGlnPro
LeuValTyrAsnLysLeuThrPheGlnLeuGluProAsnProHisThrLysTyrGlnTyr
GlyGlyValCysValAlaSerCysProHisAsnPheValValAspGlnThrSerCysVal
ArgAlaCysProProAspLysMetGluValAspLysAsnGlyLeuLysMetCysGluPro
CysGlyGlyLeuCysProLysAlaCysGluGlyThrGlySerGlySerArgPheGlnThr
ValAspSerSerAsnIleAspGlyPheValAsnCysThrLysIleLeuGlyAsnLeuAsp
PheLeuIleThrGlyLeuAsnGlyAspProTrpHisLysIleProAlaLeuAspProGlu
LysLeuAsnValPheArgThrValArgGluIleThrGlyTyrLeuAsnIleGlnSerTrp
ProProHisMetHisAsnPheSerValPheSerAsnLeuThrThrIleGlyGlyArgSer
LeuTyrAsnArgGlyPheSerLeuLeuIleMetLysAsnLeuAsnValThrSerLeuGly
PheArgSerLeuLysGluIleSerAlaGlyArgIleTyrIleSerAlaAsnArgGlnLeu
CysTyrHisHisSerLeuAsnTrpThrLysValLeuArgGlyProThrGluGluArgLeu
AspIleLysHisAsnArgProArgArgAspCysValAlaGluGlyLeuAlaCysHisGln
LeuCysAlaArgGlyHisCysTrpGlyProGlyProThrGlnCysValAsnCysSerGln
PheLeuArgGlyGlnGluCysValGluGluCysArgValLeuGlnGlyLeuProArgGlu
TyrValAsnAlaArgHisCysLeuProCysHisProGluCysGlnProGlnAsnGlySer
ValThrCysPheGlyProGluAlaAspGlnCysValAlaCysAlaHisTyrLysAspPro
ProPheCysValAlaArgCysProSerGlyValLysProAspLeuSerTyrMetProIle
TrpLysPheProAspGluGluGlyAlaCysGlnProCysProIleAsnCysThrHisSer
CysValAspLeuAspAspLysGlyCysProAlaGluGlnArgAlaSerProLeuThrIle
GluGlyArgMetAspAspLysThrHisThrCysProProCysProAlaProGluLeuLeu
GlyGlyProSerValPheLeuPheProProLysProLysAspThrLeuMetIleSerArg
ThrProGluValThrCysValValValAspValSerHisGluAspProGluValLysPhe
AsnTrpTyrValAspGlyValGluValHisAsnAlaLysThrLysProArgGluGluGln
TyrAsnSerThrTyrArgValValSerValLeuThrValLeuHisGlnAspTrpLeuAsn
GlyLysGluTyrLysCysLysValSerAsnLysAlaLeuProAlaProIleGluLysThr
IleSerLysAlaLysGlyGlnProArgGluProGlnValTyrThrLeuProProSerArg
AspGluLeuThrLysAsnGlnValSerLeuThrCysLeuValLysGlyPheTyrProSer
AspIleAlaValGluTrpGluSerAsnGlyGlnProGluAsnAsnTyrLysThrThrPro
ProValLeuAspSerAspGlySerPhePheLeuTyrSerLysLeuThrValAspLysSer
ArgTrpGlnGlnGlyAsnValPheSerCysSerValMetHisGluAlaLeuHisAsnHis
TyrThrGlnLysSerLeuSerLeuSerProGly (SEQ ID NO 83)

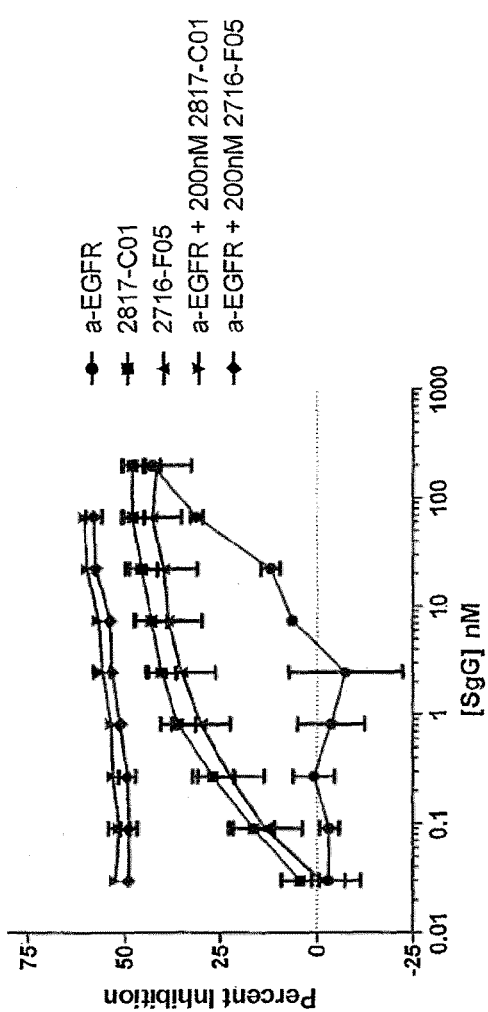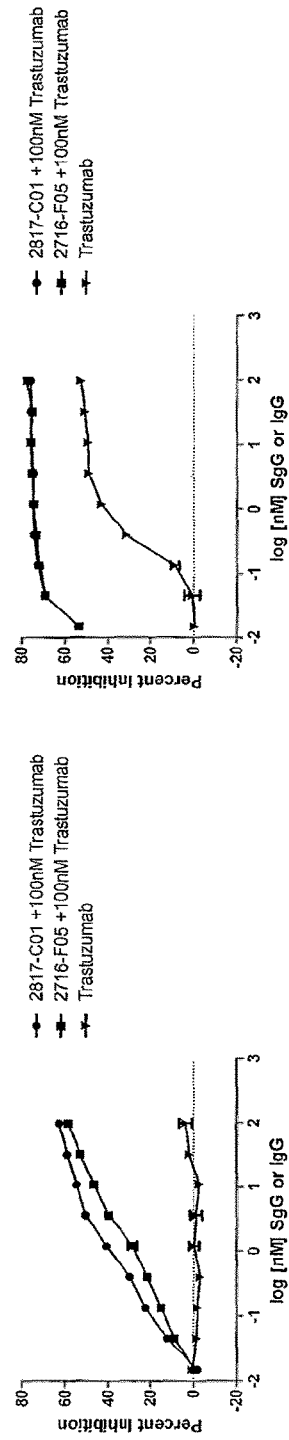
FIG. 12A
FIG. 12B
FIG. 12C

FIG. 18

Nucleic Acid sequences

2716-F05
GAAGTCCAGTTGTTGGAATCAGGCGGAGGTCTGGTACAGCCCGGAGGGAGCTTGC
GACTGTCGTGTGCGGCCTCCGGGTTCACCTTCTCGAATTACTGGATGCACTGGGTG
CGCCAAGCCCCAGGGAAGGGTCTTGAGTGGGTGGCCTTGATCTCAGGGGGAGGAG
GTAACACATACTACGCGGATTCCGTCAAAGGACGGTTTACAATTTCCAGAGACAA
CTCGAAGAACACGCTCTACCTCCAGATGAATAGCCTTAGGGCGGAGGACACGGCG
GTCTATTACTGCGCGAAAGATAACGAGAAGAATCTGTACACGTGGCTCGACTACT
GGGGACAGGGAACCCTCGTGACTGTATCGTCAGTTTGATTACTGGGGACAGGGTA
CACTCGTGACGGTGAGCAGC  (SEQ. ID NO: 84)

2817-C01
GAAGTCCAGTTGTTGGAATCAGGCGGAGGTCTGGTACAGCCCGGAGGGAGCTTGC
GACTGTCGTGTGCGGCCTCCGGGTTCACCTTCTCGACGTACGCGATGAATTGGGTG
CGCCAAGCCCCAGGGAAGGGTCTTGAGTGGGTGGCCCTCATTTCCTCGGGAGGGT
CATACAAGTATTACGCGGATTCCGTCAAAGGACGGTTTACAATTTCCAGAGACAA
CTCGAAGAACACGCTCTACCTCCAGATGAATAGCCTTAGGGCGGAGGACACGGCG
GTCTATTACTGCGCAAAAGACAACTTCATCTTGCTGAACAGCTGGTTTGATTACTG
GGGACAGGGAACCCTCGTGACTGTATCGTCA  (SEQ. ID NO: 85)

2816-D12
CAGGTCCAGCTTGTACAATCAGGAGCAGAGGTCAAGAAACCCGGATCGTCAGTCA
AAGTAAGCTGCAAGGCGTCCGGCGGTACCTTTAGCAGCTACGCGATCTCGTGGGT
GAGGCAGGCGCCAGGACAGGGTTTGGAATGGATGGGAGGGATCACGGTGTACAC
GGGGACTACAAACTATGCACAGAAGTTCCAAGGGCGGGTCACTATCACAGCTGAC
AAATCCACGTCAACAGCGTATATGGAGCTGTCGTCCTTGAGATCGGAAGATACCG
CCGTGTACTATTGTGCCCGAGCGAACGCAATTACGGTGAATCGCTCGCTCGATTAC
TGGGGACAGGGGACGCTCGTGACGGTGAGCTCG (SEQ. ID NO: 86)

2890-A03
GAGGTCCAGCTCGTGGAAAGCGGTGGGGGTTTGGTAAAGCCGGGAGGCTCGCTGC
GGCTTTCATGTGCGGCCTCCGGATTCACCTTTCGGAACTACTCCATGTCGTGGGTC
AGACAGGCTCCCGGTAAAGGGTTGGAATGGGTCGCGGCAATCTCATACGGGGGTG
CCTATAAGTACTACGCGGACTCAGTAAAGGGAAGGTTTACAATTTCGCGAGATAA
TGCCAAAAACTCCTTGTATCTCCAAATGAACTCACTGAGAGCAGAGGATACTGCC
GTGTACTATTGCGCGAGGGAGGTGGGACTCGATTATGCTATGGACTACTGGGGAC
AGGGTACACTCGTGACGGTGAGCAGC (SEQ. ID NO: 87)

2900-B11
GAGGTCCAGCTCGTGGAAAGCGGTGGGGGTTTGGTAAAGCCGGGAGGCTCGCTGC
GGCTTTCATGTGCGGCCTCCGGATTCACCTTTTCGAACTATTCAATGTCGTGGGTCA
GACAGGCTCCCGGTAAAGGGTTGGAATGGGTGGCAAACATCAGCGCGGGTGGAGC
CTACAAATACTACGCGGACTCAGTAAAGGGAAGGTTTACAATTTCGCGAGATAAT
GCCAAAAACTCCTTGTATCTCCAAATGAACTCACTGAGAGCAGAGGATACTGCCG

FIG. 18 (continued)

TGTACTATTGCGCTCGGGACAGGTTCAAGTATCTCTGGTCCTGGTTTGATTACTGG
GGACAGGGTACACTCGTGACGGTGAGCAGC  (SEQ. ID NO: 88)

2815-B08
GAGGTCCAGCTCGTGGAAAGCGGTGGGGGTTTGGTAAAGCCGGGAGGCTCGCTGC
GGCTTTCATGTGCGGCCTCCGGATTCACCTTTTCCAATTACGAGATGTCGTGGGTC
AGACAGGCTCCCGGTAAAGGGTTGGAATGGGTGGCCACGATCTCATATGATGGGG
GATACAAGTACTACGCGGACTCAGTAAAGGGAAGGTTTACAATTTCGCGAGATAA
TGCCAAAAACTCCTTGTATCTCCAAATGAACTCACTGAGAGCAGAGGATACTGCC
GTGTACTATTGCGCGAGAGACAACAGCTATCTCTTGTATTACTGGTTCGACTACTG
GGGACAGGGTACACTCGTGACGGTGAGCAGC  (SEQ. ID NO: 89)

SLC Alignment with VL5 genes

| SEQ ID No | | | |
|---|---|---|---|
| 90 | VPREB1_Lambda5_011507 | (1) | AQ_VLHQPPA_SALG_IRLTCTLRNDH_GVISW_QQK_GH |
| 91 | 5c | (1) | -QAVLTQPASLSASP_ASASLTCTLSS_NVG_IRYA_QQK_GS |
| 92 | 5b | (1) | -QPVHTQPSSHSASS_ASVRLTCMLSS_SVG_EWIRW_QQK_GN |
| 93 | 5e | (1) | -QPVHTQPSSASR_GERLTC_LPS_IVGSIN_QQK_GS |
| | VPREB1_Lambda5_011507 | (46) | PPE_IRYFIQSDKSG_PQVPPRESG_KDV_NRGYLSTSEI_PE |
| | 5c | (45) | PPQLLRYKSDSDKQG_SFSREGSKLASA_AGIIL_ISG_S |
| | 5b | (45) | PPR_LLKYMSDSNKGG_GVPSRESGSNDASA_GIIRLSG_PE |
| | 5e | (45) | PPR_ILKYVSDSDKGG_GVPSRFSGSKPASANT_GILLISG_LGS |
| | VPREB1_Lambda5_011507 | (91) | DE_MYCA_GARSS_EKERLPSKPQFWYVFGGTQLTILGQPKSDP |
| | 5c | (90) | DE_DYC_LMHRSA-------- |
| | 5b | (90) | DE_DYC_GTMERNSKT-------- |
| | 5e | (90) | DE_DYC_VLMPDNAS-------- |

VPreB1 shares only 56% - 62% (amino acids 2-97) to VL lambda5 germlines

FIG. 22

SLC Alignment with Constant Lambda

| SEQ ID No | | | | |
|---|---|---|---|---|
| 94 | Constant lambda | (1) | | 1                                                    50 |
| 95 | human lambda 5 | (1) | | MRPGTGQGGLEAPGEPGPNLRQRWPLLLLGLAVTHGLLRPTAASQSRAL |
| | | | | 51                                                  100 |
| | Constant lambda | (1) | | -------------------------------------------------- |
| | human lambda 5 | (51) | | GPGAPGGSSRSSLRSRWGRFLLQRGSWTGPRCWPRGFQSKHNSVTHVFGS |
| | | | | 101                                                 150 |
| | Constant lambda | (1) | | .K.TVA.R..KA.PSV.T.F.PSS.E.EL.QAM.KAT.Y.C.S.Y.....A |
| | human lambda 5 | (101) | | .Q....S.P..T.SV.T.F.PSS.PE..S..E..HLA....C.N.L..I.T |
| | | | | 151                                                 200 |
| | Constant lambda | (51) | | .KA.V.T....................T...Q..H.YS...T |
| | human lambda 5 | (151) | | .TQ..M....................R...Q..R....M.E |
| | | | | 201        213 |
| | Constant lambda | (101) | | ...K.WA..T.. |
| | human lambda 5 | (201) | | ...K.V....A.. |

- *Lambda 5 (amino acids 101-213) is 84% identical to Lambda constant region*

FIG. 23

SLC alignment with constant kappa

| SEQ ID No | | | |
|---|---|---|---|
| 96 | human lambda 5 | (1) | 1<br>MRPGTGQGGLEAPGEPGPNLRQRWPLLLLGLAVVTHGLLRPTAASQSRALGPGAPGGSSRSSLRS<br>65 |
| 97 | Constant kappa<br>human lambda 5 | (1)<br>(66) | 66<br>----------------------------------------------------------------RTV A  F  D Q  K GT<br>RWGRFLLQRGSWTGPRCWPRGFQSKHNSVTHVFGSGTQLTVLSQPKAT  S E Q NK<br>130<br>195 |
| | Constant kappa<br>human lambda 5 | (23)<br>(131) | 131<br>SV  N  V NALQ G SQ SV EQDSKDST L T  T  KAD EKH V A<br>D  T A GTPI - GV MT - PSKQSNNK A SY  PEQ RSR S<br>213 |
| | Constant kappa<br>human lambda 5 | (88)<br>(195) | 196<br>E T QI SP T K FNR -<br>Q M  S - - - E  VAP S |

Lambda 5 shares only 35% (amino acids 109-213) to a constant kappa region

FIG. 24

MSWAPVLLMLFVYCTGCGPQPVLHQPPAMSSALGTTIRLTCTLRNDHDIGVYSVYWYQQRPGHPPRF
LLRYFSQSDKSQGPQVPPRFSGSKDVARNRGYLSISELQPEDEAMYYCAMGARSSEKEEREREWEE
EMEPTAARTRVP
(Human VpreB1; CAG30495; 145 amino acids; SEQ ID NO:1)

MAWTSVLLMLLAHLTGCGPQPMVHQPPSASSSLGATIRLSCTLSNDHNIGIYSIYWYQ
QRPGHPPRFLLRYFSHSDKHQGPDIPPRFSGSKDTARNLGYLSISELQPEDEAVYYCAV
GLRSHEKKRMEREWEGEKSYTDLGS
(Mouse VpreB2; P13373; 142 amino acids; SEQ ID NO:2)

MAWTSVLLMLLAHLTGKGTLGVQGFLAPPVALLCPSDGHASIFSGCGPQPMVHQPPS
ASSSLGATIRLSCTLSNDHNIGIYSIYWYQQRPGHPPRFLLRYFSHSDKHQGPDIPPRFSG
SKDTARNLGYLSISELQPEDEAVYYCAVGLRSHEKKRMEREWEGEKSYTDLGS
(Mouse VpreB2 splice variant; CAA01964; 171 amino acids; SEQ ID NO:3)

MACRCLSFLLMGTFLSVSQTVLAQLDALLVFPGQVAQLSCTLSPQHVTIRDYGVSWY
QQRAGSAPRYLLYYRSEEDHHRPADIPDRFSAAKDEAHNACVLTISPVQPEDDADYYC
SVGYGFSP
(Human VpreB3 splice variant; CAG30496; 123 amino acids; SEQ ID NO:4)

MKLRVGQTLGTIPRQCEVLLLLLLLGLVDGVHHILSPSSAERSRAVGPGASVGSNRPSLWALPGRLLFQ
IIPRGAGPRCSPHRLPSKPQFWYVFGGGTQLTILGQPKSDPLVTLFLPSLKNLQPTRPHVVCLVSEFYP
GTLVVDWKVDGVPVTQGVETTQPSKQTNNKYMVSSYLTLISDQWMPHSRYSCRVTHEGNTVEKSVSP
AECS
(Mouse lambda 5; CAA01962; 209 amino acids; SEQ ID NO:5)

MRPGTGQGGLEAPGEPGPNLRQRWPLLLLGLAVVTHGLLRPTAASQSRALGPGAPGG
SSRSSLRSRWGRFLLQRGSWTGPRCWPRGFQSKHNSVTHVFGSGTQLTVLSQPKATPS
VTLFPPSSEELQANKATLVCLMNDFYPGILTVTWKADGTPITQGVEMTTPSKQSNNKY
AASSYLSLTPEQWRSRRSYSCQVMHEGSTVEKTVAPAECS
(Human lambda 5; NP_064455; 213 amino acids; SEQ ID NO:6)

MRPGTGQGGLEAPGEPGPNLRQRWPLLLLGLAVVTHGSVTHVFGSGTQLTVLSQPKATPSVTLFPPS
SEELQANKATLVCLMNDFYPGILTVTWKADGTPITQGVEMTTPSKQSNNKYAASSYLSLTPEQWRSRR
SYSCQVMHEGSTVEKTVAPAECS
(Human lambda 5dT; 158 amino acids; SEQ ID NO:7)

MSWAPVLLMLFVYCTGCGPQPVLHQPPAMSSALGTTIRLTCTLRNDHDIGVYSVYWY
QQRPGHPPRFLLRYFSQSDKSQGPQVPPRFSGSKDVARNRGYLSISELQPEDEAMYYC
AMGARSSVTHVFGSGTQLTVLSQPKATPSVTLFPPSSEELQANKATLVCLMNDFYPGI
LTVTWKADGTPITQGVEMTTPSKQSNNKYAASSYLSLTPEQWRSRRSYSCQVMHEGS
TVEKTVAPAECS
(VpreB1-Lambda5 (Fusion 1); 242 amino acids; SEQ ID NO:10)

FIG. 25

METDTLLLWVLLLWVPGSTGQPVLHQPPAMSSALGTTIRLTCTLRNDHDIGVYSVYW
YQQRPGHPPRFLLRYFSQSDKSQGPQVPPRFSGSKDVARNRGYLSISELQPEDEAMYY
CAMGARSSVTHVFGGGTKLTVLSQPKAAPSVTLFPPSSEELQANTATLVCLISDFYPGA
VTVAWKADSSPVKAGVETTTPSKQSNNKYAASSYLSLTPEQWKSHRSYSCQVTHEGS
TVEKTVAPTECS
(VpreB1- CL (Fusion 2); 242 amino acids; SEQ ID NO:11)

VKKLLLFAIPLVVPFYSHSAQPVLHQPPAMSSALGTTIRLTCTLRNDHDIGVYSVYWY
QQRPGHPPRFLLRYFSQSDKSQGPQVPPRFSGSKDVARNRGYLSISELQPEDEAMYYC
AMGARSSVTHVFGSGTQLTVLSQPKATPSVTLFPPSSEELQANKATLVCLMNDFYPGI
LTVTWKADGTPITQGVEMTTPSKQSNNKYAASSYLSLTPEQWRSRRSYSCQVMHEGS
TVEKTVAPAECSGAPVPYPDPLEPR
(geneIII VpreB1-Lambda5-E tag Fusion (Fusion 1); 256 amino acids; SEQ ID NO:12)

FIG. 25 Continued

Mature fusion sequence of fusion I

QPVLHQPPAMSSALGTTIRLTCTLRNDHDIGVYSVYWYQQRPGHPPRFLLRYFSQSDKSQGPQVPPRFSGSK
DVARNRGYLSISELQPEDEAMYYCAMGARSSVTHVFGSGTQLTVLSQPKATPSVTLFPPSSEELQANKATLVC
LMNDFYPGILTVTWKADGTPITQGVEMTTPSKQSNNKYAASSYLSLTPEQWRSRRSYSCQVMHEGSTVEKT
VAPAECS (SEQ ID NO: 276)

FIG. 25 continued (last page)

Surrogate Light Chain Alignment with Variable and Constant Lambda Light Chains

```
SEQ ID NO
 98  VpreB SLC        (1)   MSWAPVLLMLFVYCTGCGPQPVLHQPPAMSSALGTTIRLTCTLRNDH DIGVYSVYW QQRPGHPP
 99    VL1 1b         (1)   ---------GSQSVLTQPPSVSAAPGQKVTISCSGSSSN_IGNNYVSW YQQLPGTAP
100  Lambda 5         (1)   MRPSTGQGGLEAPGPNLRQRWPLLLLGLAVTHG----------------------------

LR2                                        LR3        130
     VpreB SLC       (66)   R FLLRYFSQSDKSQ PQVPPRFSGSKDVARNRGYLSISELQPEDEAMYYC AMGARSSEK ERERE
        VL1 1b       (48)   K LIYDNNK----R SGIPDRFSGSK--SGTSATLGITGLQTGDEADYYC GTWDSSLSA VFGGG
     Lambda 5        (38)   -LLRPTAASQSRALGPGAPGGSRSSLRSRWGRFLLQRGSWTGPRCWPRGFQSKHNSVTHVFGSG
     Constant Lambda  (1)   ------------------------------------------------------------G 131                                                        195
     VpreB SLC       (131)  WEEEMEPTAARTRVP-------------------------------------------------
        VL1 1b       (107)  TKLTVLRTASGAAAA-------------------------------------------------
     Lambda 5        (102)  TQLTVLSQPKATPSVTLFPPSSEELQANKATLVCLMNDFYPGILTVTWKADGTPITQGVEMTTPS
     Constant Lambda   (2)  TKLTVLRQPKAAPSVTLFPPSSEELQANKATLVCLISDFYPGAVTVAWKADGSPVKAGVETTPS 196                             242
     Lambda 5        (167)  KQSNNKYAASSYLSLTPEQWRSRRSYSCQVMHEGSTVEKTVAPAECS
     Constant Lambda  (67)  KOSNNKYAASSYLSLTPEOWKSHKSYSCOVTHEGSTVEKTVAPTECS
```

FIG. 27

Ab B light chain variable region:
QSALTQPASVSGSPGQSITISCTGTSSDVGSYNVVSWYQQHPGKAPKLIIYEVSQRPSG
VSNRFSGSKSGNTASLTISGLQTEDEADYYCCSYAGSSIFVIFGGGTKVTVL (SEQ ID NO 101)

Ab B heavy chain variable regions:
EVQLLESGGGLVQPGGSLRLSCAASGFTFSHYVMAWVRQAPGKGLEWVSSISSSGGWTL
YADSVKGRFTISRDNSKNTLYLQMNSLRAEDTAVYYCTRGLKMATIFDYWGQGTLVTVS
S (SEQ ID NO 102)

FIG. 28C

Ab A light chain variable region:
DIEMTQSPDSLAVSLGERATINCRSSQSVLYSSSNRNYLAWYQQNPGQPPKLLIYWAST
RESGVPDRFSGSGSGTDFTLTISSLQAEDVAVYYCQQYYSTPRTFGNGTKVEIK (SEQ ID NO 103)

Ab A heavy chain variable region:
QVQLQQWGAGLLKPSETLSLTCAVYGGSFSGYYWSWIRQPPGKGLEWIGEINHSGSTNY
NPSLKSRVTISVETSKNQFSLKLSSVTAADTAVYYCARDKWTWYFDLWGRGTLVTVSS
(SEQ ID NO 104)

| Exemplar | EC50 (pM) | Framework | SEQ ID No | CDR1 | SEQ ID No | CDR2 | SEQ ID No | CDR3 |
|---|---|---|---|---|---|---|---|---|
| 2817-C01 (Parent) | 55 | VH3-23 | 105 | S T Y A M N | 117 | W V A L I S S G G S Y K Y | 150 | AKDNFILLNSWFD |
| 2995-B06 | 10 | VH3-23 | 106 | S N Y G M H | 118 | W V A L I S S G G A Y T Y | 150 | AKDNFILLNSWFD |
| 2995-A12 | 10 | VH3-23 | 107 | S D Y W M N | 119 | W V A N I S S G G G Y T Y | 150 | AKDNFILLNSWFD |
| 2995-D03 | 15 | VH3-23 | 108 | S S Y A M H | 120 | W V A L I S S N G S G Y K Y | 130 | AKDNFILLNSWFD |
| 2995-C05 | 15 | VH3-23 | 109 | S D Y W M H | 121 | W V A A I S S G S S R Y T Y | 150 | AKDNFILLNSWFD |
| 2995-B02 | 16 | VH3-23 | 110 | S D Y W M H | 122 | W V A A I S S N N G A Y T Y | 150 | AKDNFILLNSWFD |
| 2995-A02 | 18 | VH3-23 | 111 | S S Y W M N | 123 | W V A A I S Z G G S I K Y | 150 | AKDNFILLNSWFD |
| 2995-C10 | 20 | VH3-23 | 112 | S S Y W M H | 124 | W V A V I S S N N G G Y T Y | 150 | AKDNFILLNSWFD |
| 2995-A08 | 20 | VH3-23 | 112 | S N Y W M H | 125 | W V A L I S S G G A Y T Y | 150 | AKDNFILLNSWFD |
| 2995-H09 | 20 | VH3-23 | 113 | S N Y W M H | 126 | W V A G I S S N G G R Y I Y | 150 | AKDNFILLNSWFD |
| 2995-B04 | 21 | VH3-23 | 113 | S D Y W M N | 127 | W V A S I S S N G T Y Y Y | 150 | AKDNFILLNSWFD |
| 2995-G10 | 22 | VH3-23 | 107 | S N Y W M H | 128 | W V A L I S S G G A Y T Y | 150 | AKDNFILLNSWFD |
| 2995-A05 | 22 | VH3-23 | 113 | S N Y W M H | 129 | W V A N I S S G G S Y I Y | 150 | AKDNFILLNSWFD |
| 2995-A07 | 22 | VH3-23 | 112 | S D Y W M H | 130 | W V A A I S S G G A Y K Y | 150 | AKDNFILLNSWFD |
| 2995-H07 | 25 | VH3-23 | 107 | S D Y W M N | 131 | W V A G I S S G G G R Y T Y | 150 | AKDNFILLNSWFD |
| 2995-H03 | 26 | VH3-23 | 109 | S S Y W M H | 132 | W V V I S S G G S Y T Y | 150 | AKDNFILLNSWFD |
| 2995-D11 | 27 | VH3-23 | 112 | S N Y W M N | 133 | W V A A I S S G G G R Y T Y | 150 | AKDNFILLNSWFD |
| 2995-C03 | 27 | VH3-23 | 112 | S S Y W M H | 134 | W V A N I S S G G G Y I Y | 150 | AKDNFILLNSWFD |
| 2995-C02 | 28 | VH3-23 | 114 | S S Y W M H | 135 | W V V I S S G G G Y K Y | 150 | AKDNFILLNSWFD |
| 2995-G11 | 29 | VH3-23 | 112 | S S Y W M H | 136 | W V A A I S S D G G A Y K Y | 150 | AKDNFILLNSWFD |
| 2995-A06 | 32 | VH3-23 | 112 | S N Y W M H | 137 | W V A A I S S G G G Y I Y | 150 | AKDNFILLNSWFD |
| 2995-B10 | 32 | VH3-23 | 112 | S S Y W M H | 138 | W V A L I S S G G G A Y T Y | 150 | AKDNFILLNSWFD |
| 2995-D07 | 33 | VH3-23 | 113 | S S Y W M S | 139 | W V A G I S Y G G S T Y Y | 150 | AKDNFILLNSWFD |
| 2995-D01 | 38 | VH3-23 | 115 | S S Y W M H | 140 | W V A L I S S G G T Y I Y | 150 | AKDNFILLNSWFD |
| 2995-E08 | 39 | VH3-23 | 112 | S N Y W M H | 141 | W V A G I S S G T Y Y | 150 | AKDNFILLNSWFD |
| 2995-E12 | 40 | VH3-23 | 113 | S N Y W M H | 142 | W V A L I S S G G R Y K Y | 150 | AKDNFILLNSWFD |
| 2995-A09 | 45 | VH3-23 | 112 | S D Y W M H | 143 | W V A G I S W G G R Y T Y | 150 | AKDNFILLNSWFD |
| 2995-B01 | 46 | VH3-23 | 116 | S D Y A M H | 144 | W V A A I S S G S T Y T Y | 150 | AKDNFILLNSWFD |
| 2995-D08 | 52 | VH3-23 | 109 | S S Y W M H | 145 | W V A A I S S W G G S Y T Y | 150 | AKDNFILLNSWFD |
| 2995-C07 | 56 | VH3-23 | 113 | S N Y W M H | 146 | W V A L I S S G T Y Y | 150 | AKDNFILLNSWLD |
| 2995-F08 | 59 | VH3-23 | 112 | S S Y W M H | 147 | W V S G I S N N G R Y K Y | 150 | AKDNFILLNSWFD |
| 2995-H11 | 63 | VH3-23 | 109 | S D Y W M H | 148 | W V S A I S S G G S G Y K Y | 150 | AKDNFILLNSWFD |
| 2995-A01 | 71 | VH3-23 | 112 | S S Y W M H | 149 | W V A A I S S S G T Y T Y | 150 | AKDNFILLNSWFD |

FIG. 34B

| Exemplar | EC50 (pM) | Framework | SEQ ID No | CDR1 | SEQ ID No | CDR2 | SEQ ID No | CDR3 |
|---|---|---|---|---|---|---|---|---|
| 2716-F05 (Parent) | 220 | VH3-23 | 151 | S N Y W M H | 157 | W V A L I S G G G N T Y | 177 | AKDNEKNLYTWLD |
| 3000-B09 | 70 | VH3-23 | 152 | S S D Y W M H | 158 | W V A L I S G G G Y K Y | 177 | AKDNEKNLYTWLD |
| 3000-A08 | 72 | VH3-23 | 153 | S S Y W M N | 159 | W V A L I S N G G G I K Y | 177 | AKDNEKNLYTWLD |
| 3000-A05 | 82 | VH3-23 | 152 | S S D Y W M H | 160 | W V A L I S A G G T Y K Y | 177 | AKDNEKNLYTWLD |
| 3000-B06 | 84 | VH3-23 | 154 | S S S Y W M H | 161 | W V A L I S N N G A Y I Y | 177 | AKDNEKNLYTWLD |
| 3000-A07 | 87 | VH3-23 | 152 | S S D Y W M H | 162 | W V A V I S G G G A Y K Y | 177 | AKDNEKNLYTWLD |
| 3000-C07 | 102 | VH3-23 | 155 | S S Y W M S | 163 | W V A L I S G G G S I K Y | 177 | AKDNEKNLYTWLD |
| 3000-E01 | 105 | VH3-23 | 154 | S S S Y W M H | 164 | W V A V I S N N G A Y T Y | 177 | AKDNEKNLYTWLD |
| 3000-E04 | 109 | VH3-23 | 152 | S S D Y W M H | 165 | W V A L I S W G G A Y K Y | 177 | AKDNEKNLYTWLD |
| 3000-H03 | 109 | VH3-23 | 152 | S S D Y W M H | 166 | W V S L I S G G G A Y T Y | 177 | AKDNEKNLYTWLD |
| 3000-B02 | 115 | VH3-23 | 154 | S S S Y W M H | 167 | W V A V I S G G G N Y I Y | 177 | AKDNEKNLYTWLD |
| 3000-F09 | 118 | VH3-23 | 154 | S S Y W M H | 168 | W V A L I S S G G G I T Y | 177 | AKDNEKNLYTWLD |
| 3000-E07 | 121 | VH3-23 | 156 | S N Y W M H | 169 | W V A L I S G G G N I Y | 177 | AKDNEKNLYTWLD |
| 3000-A04 | 127 | VH3-23 | 154 | S S S Y W M H | 170 | W V A L I S A G G T S K Y | 177 | AKDNEKNLYTWLD |
| 3000-A11 | 139 | VH3-23 | 154 | S S S Y W M H | 171 | W V A L I S W G G G T K Y | 177 | AKDNEKNLYTWLD |
| 3000-D07 | 152 | VH3-23 | 154 | S S S Y W M H | 172 | W V S L I S A S G G S I K Y | 177 | AKDNEKNLYTWLD |
| 3000-G09 | 158 | VH3-23 | 154 | S S S Y W M H | 173 | W V A L I S N G G G Y K Y | 177 | AKDNEKNLYTWLD |
| 3000-C03 | 164 | VH3-23 | 154 | S S S Y W M H | 174 | W V A L I S N N G T Y K Y | 177 | AKDNEKNLYTWLD |
| 3000-B03 | 179 | VH3-23 | 156 | S N Y W M H | 175 | W V A L I S N N G T Y T Y | 177 | AKDNEKNLYTWLD |
| 3000-C08 | 182 | VH3-23 | 154 | S S S Y W M H | 176 | W V A V I S N N G R Y K Y | 177 | AKDNEKNLYTWLD |

SEQ ID NO: 178

| S | $X_{101}$ | Y | $X_{102}$ | M | $X_{103}$ |
|---|---|---|---|---|---|
|   | T |   | A |   | N |
|   | N |   | G |   | H |
|   | D |   | W |   | S |
|   | S |   |   |   |   |

SEQ ID NO: 179

| W | V | $X_{104}$ | $X_{105}$ | I | S | $X_{106}$ | $X_{107}$ | $X_{108}$ | $X_{109}$ | $X_{104}$ | $X_{110}$ | $X_{111}$ |
|---|---|---|---|---|---|---|---|---|---|---|---|---|
|   |   | A | L |   |   | S | G | G | S | Y | K | Y |
|   |   | S | N |   |   | G | N | S | A | I | T | S |
|   |   |   | A |   |   | N | S |   | G |   | I |   |
|   |   |   | V |   |   | D |   |   | R |   |   |   |
|   |   |   | G |   |   | A |   |   | A |   |   |   |
|   |   |   | S |   |   | Y |   |   | T |   |   |   |
|   |   |   |   |   |   | W |   |   |   |   |   |   |

FIG. 34C

SEQ ID NO: 180

| S | $X_{201}$ | Y | W | M | $X_{202}$ |
|---|---|---|---|---|---|
|   | N |   |   |   | H |
|   | D |   |   |   | N |
|   | S |   |   |   | S |

SEQ ID NO: 181

| W | V | $X_{203}$ | $X_{204}$ | I | S | $X_{205}$ | $X_{206}$ | G | $X_{207}$ | $X_{208}$ | $X_{209}$ | Y |
|---|---|---|---|---|---|---|---|---|---|---|---|---|
|   |   | A | L |   |   | G | G |   | G | N | T |   |
|   |   | S | V |   |   | S | N |   | T | Y | I |   |
|   |   |   |   |   |   | N | S |   | A | I | K |   |
|   |   |   |   |   |   | A |   |   | S | S |   |   |
|   |   |   |   |   |   | W |   |   | N | T |   |   |
|   |   |   |   |   |   |   |   |   | R |   |   |   |

FIG. 34D

2995-B06
EVQLLESGGGLVQPGGSLRLSCAASGFTFSNYGMHWVRQAPGKGLEWVALISSGGAYT
YYADSVKGRFTISRDNSKNTLYLQMNSLRAEDTAVYYCAKDNFILLNSWFD (SEQ ID
NO: 193)

2995-A12
EVQLLESGGGLVQPGGSLRLSCAASGFTFSDYWMNWVRQAPGKGLEWVANISGGGGYI
YYADSVKGRFTISRDNSKNTLYLQMNSLRAEDTAVYYCAKDNFILLNSWFD (SEQ ID
NO: 194)

2995-D03
EVQLLESGGGLVQPGGSLRLSCAASGFTFSSYAMHWVRQAPGKGLEWVALISNGSGYK
YYADSVKGRFTISRDNSKNTLYLQMNSLRAEDTAVYYCAKDNFILLNSWFD (SEQ ID
NO: 195)

2995-C05
EVQLLESGGGLVQPGGSLRLSCAASGFTFSDYWMHWVRQAPGKGLEWVAAISSGSSYT
YYADSVKGRFTISRDNSKNTLYLQMNSLRAEDTAVYYCAKDNFILLNSWFD (SEQ ID
NO: 196)

2995-B02
EVQLLESGGGLVQPGGSLRLSCAASGFTFSDYWMHWVRQAPGKGLEWVAVISSNGRY
TYYADSVKGRFTISRDNSKNTLYLQMNSLRAEDTAVYYCAKDNFILLNSWFD (SEQ ID
NO: 197)

2995-A02
EVQLLESGGGLVQPGGSLRLSCAASGFTFSSYWMNWVRQAPGKGLEWVALISNGGGIK
YYADSVKGRFTISRDNSKNTLYLQMNSLRAEDTAVYYCAKDNFILLNSWFD (SEQ ID
NO: 198)

2995-C10
EVQLLESGGGLVQPGGSLRLSCAASGFTFSSYWMHWVRQAPGKGLEWVAGISGGGAY
TYYADSVKGRFTISRDNSKNTLYLQMNSLRAEDTAVYYCAKDNFILLNSWFD (SEQ ID
NO: 199)

2995-A08
EVQLLESGGGLVQPGGSLRLSCAASGFTFSSYWMHWVRQAPGKGLEWVAGISNGGSIY
YADSVKGRFTISRDNSKNTLYLQMNSLRAEDTAVYYCAKDNFILLNSWFD (SEQ ID
NO: 200)

2995-H09
EVQLLESGGGLVQPGGSLRLSCAASGFTFSNYWMHWVRQAPGKGLEWVASISNGGRYI
YYADSVKGRFTISRDNSKNTLYLQMNSLRAEDTAVYYCAKDNFILLNSWFD (SEQ ID
NO: 201)

FIG. 34E

2995-B04
EVQLLESGGGLVQPGGSLRLSCAASGFTFSNYWMHWVRQAPGKGLEWVALISNNGTY
TYYADSVKGRFTISRDNSKNTLYLQMNSLRAEDTAVYYCAKDNFILLNSWFD (SEQ ID
NO: 202)

2995-G10
EVQLLESGGGLVQPGGSLRLSCAASGFTFSDYWMNWVRQAPGKGLEWVANISNGGTYI
YYADSVKGRFTISRDNSKNTLYLQMNSLRAEDTAVYYCAKDNFILLNSWFD (SEQ ID
NO: 203)

2995-A05
EVQLLESGGGLVQPGGSLRLSCAASGFTFSNYWMHWVRQAPGKGLEWVAAISNGSSYT
YYADSVKGRFTISRDNSKNTLYLQMNSLRAEDTAVYYCAKDNFILLNSWFD (SEQ ID
NO: 204)

2995-A07
EVQLLESGGGLVQPGGSLRLSCAASGFTFSSYWMHWVRQAPGKGLEWVAGISSGGAYT
YYADSVKGRFTISRDNSKNTLYLQMNSLRAEDTAVYYCAKDNFILLNSWFD (SEQ ID
NO: 205)

2995-H07
EVQLLESGGGLVQPGGSLRLSCAASGFTFSDYWMNWVRQAPGKGLEWVALISNNGSYT
YYADSVKGRFTISRDNSKNTLYLQMNSLRAEDTAVYYCAKDNFILLNSWFD (SEQ ID
NO: 206)

2995-H03
EVQLLESGGGLVQPGGSLRLSCAASGFTFSDYWMHWVRQAPGKGLEWVAVISGGGAY
KYYADSVKGRFTISRDNSKNTLYLQMNSLRAEDTAVYYCAKDNFILLNSWFD (SEQ ID
NO: 207)

2995-D11
EVQLLESGGGLVQPGGSLRLSCAASGFTFSSYWMHWVRQAPGKGLEWVAVISNNGRY
KYYADSVKGRFTISRDNSKNTLYLQMNSLRAEDTAVYYCAKDNFILLNSWFD (SEQ ID
NO: 208)

2995-C03
EVQLLESGGGLVQPGGSLRLSCAASGFTFSSYWMHWVRQAPGKGLEWVAGISGGGRY
TYYADSVKGRFTISRDNSKNTLYLQMNSLRAEDTAVYYCAKDNFILLNSWFD (SEQ ID
NO: 209)

2995-C02
EVQLLESGGGLVQPGGSLRLSCAASGFTFSNYWMNWVRQAPGKGLEWVANISSGGSYT
YYADSVKGRFTISRDNSKNTLYLQMNSLRAEDTAVYYCAKDNFILLNSWFD (SEQ ID
NO: 210)

FIG. 34E continued

2995-G11
EVQLLESGGGLVQPGGSLRLSCAASGFTFSSYWMHWVRQAPGKGLEWVSAISSGGGYI
YYADSVKGRFTISRDNSKNTLYLQMNSLRAEDTAVYYCAKDNFILLNSWFD (SEQ ID NO: 211)

2995-A06
EVQLLESGGGLVQPGGSLRLSCAASGFTFSSYWMHWVRQAPGKGLEWVAGISDGGAY
TYYADSVKGRFTISRDNSKNTLYLQMNSLRAEDTAVYYCAKDNFILLNSWFD (SEQ ID NO: 212)

2995-B10
EVQLLESGGGLVQPGGSLRLSCAASGFTFSSYWMHWVRQAPGKGLEWVAAISAGSGYI
YYADSVKGRFTISRDNSKNTLYLQMNSLRAEDTAVYYCAKDNFILLNSWFD (SEQ ID NO: 213)

2995-D07
EVQLLESGGGLVQPGGSLRLSCAASGFTFSNYWMHWVRQAPGKGLEWVAAISNGGGY
KYYADSVKGRFTISRDNSKNTLYLQMNSLRAEDTAVYYCAKDNFILLNSWFD (SEQ ID NO: 214)

2995-D01
EVQLLESGGGLVQPGGSLRLSCAASGFTFSSYWMSWVRQAPGKGLEWVALISNGGSIK
YYADSVKGRFTISRDNSKNTLYLQMNSLRAEDTAVYYCAKDNFILLNSWFD (SEQ ID NO: 215)

2995-E08
EVQLLESGGGLVQPGGSLRLSCAASGFTFSSYWMHWVRQAPGKGLEWVAGISSGGSYK
YYADSVKGRFTISRDNSKNTLYLQMNSLRAEDTAVYYCAKDNFILLNSWFD (SEQ ID NO: 216)

2995-E12
EVQLLESGGGLVQPGGSLRLSCAASGFTFSNYWMHWVRQAPGKGLEWVALISSGSTYIS
YADSVKGRFTISRDNSKNTLYLQMNSLRAEDTAVYYCAKDNFILLNSWFD (SEQ ID NO: 217)

2995-A09
EVQLLESGGGLVQPGGSLRLSCAASGFTFSSYWMHWVRQAPGKGLEWVAGISYGGTYT
YYADSVKGRFTISRDNSKNTLYLQMNSLRAEDTAVYYCAKDNFILLNSWFD (SEQ ID NO: 218)

2995-B01
EVQLLESGGGLVQPGGSLRLSCAASGFTFSDYAMHWVRQAPGKGLEWVALISSGGRYK
YYADSVKGRFTISRDNSKNTLYLQMNSLRAEDTAVYYCAKDNFILLNSWFD (SEQ ID NO: 219)

FIG. 34E continued

2995-B05
EVQLLESGGGLVQPGGSLRLSCAASGFTFSSYWMHWVRQAPGKGLEWVAGISSGGSYK
YYADSVKGRFTISRDNSKNTLYLQMNSLRAEDTAVYYCAKDNFILLNSWFD  (SEQ ID
NO: 220)

2995-D08
EVQLLESGGGLVQPGGSLRLSCAASGFTFSDYWMHWVRQAPGKGLEWVAAISWGGSY
TYYADSVKGRFTISRDNSKNTLYLQMNSLRAEDTAVYYCAKDNFILLNSWFD  (SEQ ID
NO: 221)

2995-C07
EVQLLESGGGLVQPGGSLRLSCAASGFTFSNYWMHWVRQAPGKGLEWVALISSGSTYIS
YADSVKGRFTISRDNSKNTLYLQMNSLRAEDTAVYYCAKDNFILLNSWLD  (SEQ ID
NO: 222)

2995-F08
EVQLLESGGGLVQPGGSLRLSCAASGFTFSSYWMHWVRQAPGKGLEWVSGISNNGRYK
YYADSVKGRFTISRDNSKNTLYLQMNSLRAEDTAVYYCAKDNFILLNSWFD  (SEQ ID
NO: 223)

2995-H11
EVQLLESGGGLVQPGGSLRLSCAASGFTFSDYWMHWVRQAPGKGLEWVSAISSSGGYK
YYADSVKGRFTISRDNSKNTLYLQMNSLRAEDTAVYYCAKDNFILLNSWFD  (SEQ ID
NO: 224)

2995-A01
EVQLLESGGGLVQPGGSLRLSCAASGFTFSSYWMHWVRQAPGKGLEWVAAISSSGTYT
YYADSVKGRFTISRDNSKNTLYLQMNSLRAEDTAVYYCAKDNFILLNSWFD  (SEQ ID
NO: 225)

2995-A03
EVQLLESGGGLVQPGGSLRLSCAASGFTFSNYWMHWVRQAPGKGLEWVAAISNNSRY
KYYADSVKGRFTISRDNSKNTLYLQMNSLRAEDTAVYYCAKDNFILLNSWFD  (SEQ ID
NO: 226)

2995-G02
EVQLLESGGGLVQPGGSLRLSCAASGFTFSDYWMHWVRQAPGKGLEWVASISGGGGYI
YYADSVKGRFTISRDNSKNTLYLQMNSLRAEDTAVYYCAKDNFILLNSWFD  (SEQ ID
NO: 227)

2995-F11
EVQLLESGGGLVQPGGSLRLSCAASGFTFSNYEMHWVRQAPGKGLEWVALISNGGSYT
YYADSVKGRFTISRDNSKNTLYLQMNSLRAEDTAVYYCAKDNFILLNSWFD  (SEQ ID
NO: 228)

FIG. 34E continued

2995-F10
EVQLLESGGGLVQPGGSLRLSCAASGFTFSSYWMHWVRQAPGKGLEWVALISAGSATK
YYADSVKGRFTISRDNSKNTLYLQMNSLRAEDTAVYYCAKDNFILLNSWFD (SEQ ID NO: 229)

2995-E05
EVQLLESGGGLVQPGGSLRLSCAASGFTFSSYWMHWVRQAPGKGLEWVAVISSNSSYK
YYADSVKGRFTISRDNSKNTLYLQMNSLRAEDTAVYYCAKDNFILLNSWFD (SEQ ID NO: 230)

2995-B09
EVQLLESGGGLVQPGGSLRLSCAASGFTFSSYWMHWVRQAPGKGLEWVSAISNSGAYT
YYADSVKGRFTISRDNSKNTLYLQMNSLRAEDTAVYYCAKDNFILLNSWFD (SEQ ID NO: 231)

2995-A0412.64
EVQLLESGGGLVQPGGSLRLSCAASGFTFSDYSMHWVRQAPGKGLEWVALISYGGANT
YYADSVKGRFTISRDNSKNTLYLQMNSLRAEDTAVYYCAKDNFILLNSWFD (SEQ ID NO: 232)

2995-C04
EVQLLESGGGLVQPGGSLRLSCAASGFTFSNYSMHWVRQAPGKGLEWVALISNGGTIIY
YADSVKGRFTISRDNSKNTLYLQMNSLRAEDTAVYYCAKDNFILLNSWFD (SEQ ID NO: 233)

2995-B03
EVQLLESGGGLVQPGGSLRLSCAASGFTFSDYWMHWVRQAPGKGLEWVATISYNGAY
KYYADSVKGRFTISRDNSKNTLYLQMNSLRAEDTAVYYCAKDNFILLNSWFD (SEQ ID NO: 234)

2995-C11
EVQLLESGGGLVQPGGSLRLSCAASGFTFSNYWMHWVRQAPGKGLEWVAVISDGGGY
TYYADSVKGRFTISRDNSKNTLYLQMNSLRAEDTAVYYCAKDNFILLNSWFD (SEQ ID NO: 235)

2995-F03
EVQLLESGGGLVQPGGSLRLSCAASGFTFSDYWMHWVRQAPGKGLEWVSAISYNGAYI
YYADSVKGRFTISRDNSKNTLYLQMNSLRAEDTAVYYCAKDNFILLNSWFD (SEQ ID NO: 236)

FIG. 34E continued

2995-E01
EVQLLESGGGLVQPGGSLRLSCAASGFTFSSYAMSWVRQAPGKGLEWVALISSGGGYT
YYADSVKGRFTISRDNSKNTLYLQMNSLRAEDTAVYYCAKDNFILLNSWFD (SEQ ID NO: 237)

2995-D05
EVQLLESGGGLVQPGGSLRLSCAASGFTFSSYAMNWVRQAPGKGLEWVALISNGSAYT
YYADSVKGRFTISRDNSKNTLYLQMNSLRAEDTAVYYCAKDNFILLNSWFD (SEQ ID NO: 238)

2995-F06
EVQLLESGGGLVQPGGSLRLSCAASGFTFSSYWMNWVRQAPGKGLEWVSNISAGGAIK
YYADSVKGRFTISRDNSKNTLYLQMNSLRAEDTAVYYCAKDNFILLNSWFD (SEQ ID NO: 239)

2995-G07
EVQLLESGGGLVQPGGSLRLSCAASGFTFSDYWMSWVRQAPGKGLEWVAVISNGGGY
TYYADSVKGRFTISRDNSKNTLYLQMNSLRAEDTAVYYCAKDNFILLNSWFD (SEQ ID NO: 240)

2995-F04
EVQLLESGGGLVQPGGSLRLSCAASGFTFSDYWMNWVRQAPGKGLEWVAVISYNGAYI
YYADSVKGRFTISRDNSKNTLYLQMNSLRAEDTAVYYCAKDNFILLNSWFD (SEQ ID NO: 241)

FIG. 34E continued

3000-B09
EVQLLESGGGLVQPGGSLRLSCAASGFTFSDYWMHWVRQAPGKGLEWVALISSGGGY
KYYADSVKGRFTISRDNSKNTLYLQMNSLRAEDTAVYYCAKDNEKNLYTWLD (SEQ
ID NO: 242)

3000-A08
EVQLLESGGGLVQPGGSLRLSCAASGFTFSSYWMNWVRQAPGKGLEWVALISNGGGIK
YYADSVKGRFTISRDNSKNTLYLQMNSLRAEDTAVYYCAKDNEKNLYTWLD (SEQ ID
NO: 243)

3000-A05
EVQLLESGGGLVQPGGSLRLSCAASGFTFSDYWMHWVRQAPGKGLEWVALISAGGTY
KYYADSVKGRFTISRDNSKNTLYLQMNSLRAEDTAVYYCAKDNEKNLYTWLD (SEQ
ID NO: 244)

3000-B06
EVQLLESGGGLVQPGGSLRLSCAASGFTFSSYWMHWVRQAPGKGLEWVALISNNGAYI
YYADSVKGRFTISRDNSKNTLYLQMNSLRAEDTAVYYCAKDNEKNLYTWLD (SEQ ID
NO: 245)

3000-A07
EVQLLESGGGLVQPGGSLRLSCAASGFTFSDYWMHWVRQAPGKGLEWVAVISGGGAY
KYYADSVKGRFTISRDNSKNTLYLQMNSLRAEDTAVYYCAKDNEKNLYTWLD (SEQ
ID NO: 246)

3000-C07
EVQLLESGGGLVQPGGSLRLSCAASGFTFSSYWMSWVRQAPGKGLEWVALISNGGSIK
YYADSVKGRFTISRDNSKNTLYLQMNSLRAEDTAVYYCAKDNEKNLYTWLD (SEQ ID
NO: 247)

3000-E01
EVQLLESGGGLVQPGGSLRLSCAASGFTFSSYWMHWVRQAPGKGLEWVALISNNGAYT
YYADSVKGRFTISRDNSKNTLYLQMNSLRAEDTAVYYCAKDNEKNLYTWLD (SEQ ID
NO: 248)

FIG. 34F

3000-E04
EVQLLESGGGLVQPGGSLRLSCAASGFTFSDYWMHWVRQAPGKGLEWVAVISWGGAY
KYYADSVKGRFTISRDNSKNTLYLQMNSLRAEDTAVYYCAKDNEKNLYTWLD (SEQ
ID NO: 249)

3000-H03
EVQLLESGGGLVQPGGSLRLSCAASGFTFSDYWMHWVRQAPGKGLEWVSLISNGGGYT
YYADSVKGRFTISRDNSKNTLYLQMNSLRAEDTAVYYCAKDNEKNLYTWLD (SEQ ID
NO: 250)

3000-B02
EVQLLESGGGLVQPGGSLRLSCAASGFTFSSYWMHWVRQAPGKGLEWVAVISSGGNYI
YYADSVKGRFTISRDNSKNTLYLQMNSLRAEDTAVYYCAKDNEKNLYTWLD (SEQ ID
NO: 251)

3000-F09
EVQLLESGGGLVQPGGSLRLSCAASGFTFSSYWMHWVRQAPGKGLEWVALISSSGGITY
YADSVKGRFTISRDNSKNTLYLQMNSLRAEDTAVYYCAKDNEKNLYTWLD (SEQ
ID NO: 252)

3000-E07
EVQLLESGGGLVQPGGSLRLSCAASGFTFSNYWMHWVRQAPGKGLEWVALISGGGGNI
YYADSVKGRFTISRDNSKNTLYLQMNSLRAEDTAVYYCAKDNEKNLYTWLD (SEQ ID
NO: 253)

3000-A04
EVQLLESGGGLVQPGGSLRLSCAASGFTFSSYWMHWVRQAPGKGLEWVALISAGGTSK
YYADSVKGRFTISRDNSKNTLYLQMNSLRAEDTAVYYCAKDNEKNLYTWLD (SEQ ID
NO: 254)

3000-A11
EVQLLESGGGLVQPGGSLRLSCAASGFTFSSYWMHWVRQAPGKGLEWVALISWGGGT
KYYADSVKGRFTISRDNSKNTLYLQMNSLRAEDTAVYYCAKDNEKNLYTWLD (SEQ
ID NO: 255)

FIG. 34F continued

3000-D07
EVQLLESGGGLVQPGGSLRLSCAASGFTFSSYWMHWVRQAPGKGLEWVSLISASGSIKY
YADSVKGRFTISRDNSKNTLYLQMNSLRAEDTAVYYCAKDNEKNLYTWLD (SEQ ID
NO: 256)

3000-G09
EVQLLESGGGLVQPGGSLRLSCAASGFTFSSYWMHWVRQAPGKGLEWVALISNGGGY
KYYADSVKGRFTISRDNSKNTLYLQMNSLRAEDTAVYYCAKDNEKNLYTWLD (SEQ
ID NO: 257)

3000-C03
EVQLLESGGGLVQPGGSLRLSCAASGFTFSSYWMHWVRQAPGKGLEWVALISNNGTYK
YYADSVKGRFTISRDNSKNTLYLQMNSLRAEDTAVYYCAKDNEKNLYTWLD (SEQ ID
NO: 258)

3000-B03
EVQLLESGGGLVQPGGSLRLSCAASGFTFSNYWMHWVRQAPGKGLEWVALISNNGTY
TYYADSVKGRFTISRDNSKNTLYLQMNSLRAEDTAVYYCAKDNEKNLYTWLD (SEQ
ID NO: 259)

3000-C08
EVQLLESGGGLVQPGGSLRLSCAASGFTFSSYWMHWVRQAPGKGLEWVAVISNNGRY
KYYADSVKGRFTISRDNSKNTLYLQMNSLRAEDTAVYYCAKDNEKNLYTWLD (SEQ
ID NO: 260)

3000-E10
EVQLLESGGGLVQPGGSLRLSCAASGFTFSNYWMHWVRQAPGKGLEWVAVISWGGSI
KYYADSVKGRFTISRDNSKNTLYLQMNSLRAEDTAVYYCAKDNEKNLYTWLD (SEQ
ID NO: 261)

3000-F05
EVQLLESGGGLVQPGGSLRLSCAASGFTFSDYAMHWVRQAPGKGLEWVALISSGGRYK
YYADSVKGRFTISRDNSKNTLYLQMNSLRAEDTAVYYCAKDNEKNLYTWLD (SEQ ID
NO: 262)

FIG. 34F continued

3000-A01
EVQLLESGGGLVQPGGSLRLSCAASGFTFSSYWMHWVRQAPGKGLEWVSLISGNGRYK
YYADSVKGRFTISRDNSKNTLYLQMNSLRAEDTAVYYCAKDNEKNLYTWLD (SEQ ID
NO: 263)

3000-B01
EVQLLESGGGLVQPGGSLRLSCAASGFTFSSYWMHWVRQAPGKGLEWVALISYSGGNI
YYADSVKGRFTISRDNSKNTLYLQMNSLRAEDTAVYYCAKDNEKNLYTWLD (SEQ ID
NO: 264)

3000-D12
EVQLLESGGGLVQPGGSLRLSCAASGFTFSDYWMHWVRQAPGKGLEWVAVISSNGRY
TYYADSVKGRFTISRDNSKNTLYLQMNSLRAEDTAVYYCAKDNEKNLYTWLD (SEQ
ID NO: 265)

3000-A03
EVQLLESGGGLVQPGGSLRLSCAASGFTFSSYWMHWVRQAPGKGLEWVAVISGGGGYI
YYADSVKGRFTISRDNSKNTLYLQMNSLRAEDTAVYYCAKDNEKNLYTWLD (SEQ ID
NO: 266)

3000-A09
EVQLLESGGGLVQPGGSLRLSCAASGFTFSNYWMHWVRQAPGKGLEWVSVISAGSTIK
YYADSVKGRFTISRDNSKNTLYLQMNSLRAEDTAVYYCAKDNEKNLYTWLD (SEQ ID
NO: 267)

3000-A02
EVQLLESGGGLVQPGGSLRLSCAASGFTFSSYWMHWVRQAPGKGLEWVALISYGGTYK
YYADSVKGRFTISRDNSKNTLYLQMNSLRAEDTAVYYCAKDNEKNLYTWLD (SEQ ID
NO: 268)

3000-B07
EVQLLESGGGLVQPGGSLRLSCAASGFTFSNYWMNWVRQAPGKGLEWVSLISYNGAY
KYYADSVKGRFTISRDNSKNTLYLQMNSLRAEDTAVYYCAKDNEKNLYTWLD (SEQ
ID NO: 269)

FIG. 34F continued

3000-G04
EVQLLESGGGLVQPGGSLRLSCAASGFTFSDYWMNWVRQAPGKGLEWVALISSSGTYK
YYADSVKGRFTISRDNSKNTLYLQMNSLRAEDTAVYYCAKDNEKNLYTWLD (SEQ ID
NO: 270)

3000-A06
EVQLLESGGGLVQPGGSLRLSCAASGFTFSNYWMHWVRQAPGKGLEWVALISGSGSNK
YYADSVKGRFTISRDNSKNTLYLQMNSLRAEDTAVYYCAKDNEKNLYTWLD (SEQ ID
NO: 271)

3000-F12
EVQLLESGGGLVQPGGSLRLSCAASGFTFSDYWMNWVRQAPGKGLEWVANISNGGTYI
YYADSVKGRFTISRDNSKNTLYLQMNSLRAEDTAVYYCAKDNEKNLYTWLD (SEQ ID
NO: 272)

3000-C04
EVQLLESGGGLVQPGGSLRLSCAASGFTFSNYWMHWVRQAPGKGLEWVAAISNSGGY
KYYADSVKGRFTISRDNSKNTLYLQMNSLRAEDTAVYYCAKDNEKNLYTWLD (SEQ
ID NO: 273)

3000-C01
EVQLLESGGGLVQPGGSLRLSCAASGFTFSSYWMHWVRQAPGKGLEWVATISAGGAN
KYYADSVKGRFTISRDNSKNTLYLQMNSLRAEDTAVYYCAKDNEKNLYTWLD (SEQ
ID NO: 274)

3000-C05
EVQLLESGGGLVQPGGSLRLSCAASGFTFSDYWMHWVRQAPGKGLEWVALISSNSSST
YYADSVKGRFTISRDNSKNTLYLQMNSLRAEDTAVYYCAKDNEKNLYTWLD (SEQ ID
NO: 275)

FIG. 34F Continued

611-HER2-CTF
MPIWKFPDEEGACQPCPINCTHSCVDLDDKGCPAEQRASPLTSIISAVVGILLVVVLGVV
FGILIKRRQQKIRKYTMRRLLQETELVEPLTPSGAMPNQAQMRILKETELRKVKVLGSGA
FGTVYKGIWIPDGENVKIPVAIKVLRENTSPKANKEILDEAYVMAGVGSPYVSRLLGICL
TSTVQLVTQLMPYGCLLDHVRENRGRLGSQDLLNWCMQIAKGMSYLEDVRLVHRDLA
ARNVLVKSPNHVKITDFGLARLLDIDETEYHADGGKVPIKWMALESILRRRFTHQSDVW
SYGVTVWELMTFGAKPYDGIPAREIPDLLEKGERLPQPPICTIDVYMIMVKCWMIDSECR
PRFRELVSEFSRMARDPQRFVVIQNEDLGPASPLDSTFYRSLLEDDDMGDLVDAEEYLV
PQQGFFCPDPAPGAGGMVHHRHRSSSTRSGGGDLTLGLEPSEEEAPRSPLAPSEGAGSD
VFDGDLGMGAAKGLQSLPTHDPSPLQRYSEDPTVPLPSETDGYVAPLTCSPQPEYVNQP
DVRPQPPSPREGPLPAARPAGATLERPKTLSPGKNGVVKDVFAFGGAVENPEYLTPQGG
AAPQPHPPPAFSPAFDNLYYWDQDPPERGAPPSTFKGTPTAENPEYLGLDVPV (SEQ ID NO: 66)

A648-HER2-CTF
ASPLTSIISAVVGILLVVVLGVVFGILIKRRQQKIRKYTMRRLLQETELVEPLTPSGAMPN
QAQMRILKETELRKVKVLGSGAFGTVYKGIWIPDGENVKIPVAIKVLRENTSPKANKEIL
DEAYVMAGVGSPYVSRLLGICLTSTVQLVTQLMPYGCLLDHVRENRGRLGSQDLLNWC
MQIAKGMSYLEDVRLVHRDLAARNVLVKSPNHVKITDFGLARLLDIDETEYHADGGKV
PIKWMALESILRRRFTHQSDVWSYGVTVWELMTFGAKPYDGIPAREIPDLLEKGERLPQ
PPICTIDVYMIMVKCWMIDSECRPRFRELVSEFSRMARDPQRFVVIQNEDLGPASPLDST
FYRSLLEDDDMGDLVDAEEYLVPQQGFFCPDPAPGAGGMVHHRHRSSSTRSGGGDLTL
GLEPSEEEAPRSPLAPSEGAGSDVFDGDLGMGAAKGLQSLPTHDPSPLQRYSEDPTVPLP
SETDGYVAPLTCSPQPEYVNQPDVRPQPPSPREGPLPAARPAGATLERPKTLSPGKNGVV
KDVFAFGGAVENPEYLTPQGGAAPQPHPPPAFSPAFDNLYYWDQDPPERGAPPSTFKGT
PTAENPEYLGLDVPV (SEQ ID NO: 67)

K676-HER2-CTF
KRRQQKIRKYTMRRLLQETELVEPLTPSGAMPNQAQMRILKETELRKVKVLGSGAFGT
VYKGIWIPDGENVKIPVAIKVLRENTSPKANKEILDEAYVMAGVGSPYVSRLLGICLTST
VQLVTQLMPYGCLLDHVRENRGRLGSQDLLNWCMQIAKGMSYLEDVRLVHRDLAAR
NVLVKSPNHVKITDFGLARLLDIDETEYHADGGKVPIKWMALESILRRRFTHQSDVWSY
GVTVWELMTFGAKPYDGIPAREIPDLLEKGERLPQPPICTIDVYMIMVKCWMIDSECRPR
FRELVSEFSRMARDPQRFVVIQNEDLGPASPLDSTFYRSLLEDDDMGDLVDAEEYLVPQ
QGFFCPDPAPGAGGMVHHRHRSSSTRSGGGDLTLGLEPSEEEAPRSPLAPSEGAGSDVF
DGDLGMGAAKGLQSLPTHDPSPLQRYSEDPTVPLPSETDGYVAPLTCSPQPEYVNQPDV
RPQPPSPREGPLPAARPAGATLERPKTLSPGKNGVVKDVFAFGGAVENPEYLTPQGGAA
PQPHPPPAFSPAFDNLYYWDQDPPERGAPPSTFKGTPTAENPEYLGLDVPV (SEQ ID NO: 68)

FIG. 36A

687-HER2-CTF
MRRLLQETELVEPLTPSGAMPNQAQMRILKETELRKVKVLGSGAFGTVYKGIWIPDGEN
VKIPVAIKVLRENTSPKANKEILDEAYVMAGVGSPYVSRLLGICLTSTVQLVTQLMPYGC
LLDHVRENRGRLGSQDLLNWCMQIAKGMSYLEDVRLVHRDLAARNVLVKSPNHVKIT
DFGLARLLDIDETEYHADGGKVPIKWMALESILRRRFTHQSDVWSYGVTVWELMTFGA
KPYDGIPAREIPDLLEKGERLPQPPICTIDVYMIMVKCWMIDSECRPRFRELVSEFSRMAR
DPQRFVVIQNEDLGPASPLDSTFYRSLLEDDDMGDLVDAEEYLVPQQGFFCPDPAPGAG
GMVHHRHRSSSTRSGGGDLTLGLEPSEEEAPRSPLAPSEGAGSDVFDGDLGMGAAKGL
QSLPTHDPSPLQRYSEDPTVPLPSETDGYVAPLTCSPQPEYVNQPDVRPQPPSPREGPLPA
ARPAGATLERPKTLSPGKNGVVKDVFAFGGAVENPEYLTPQGGAAPQPHPPPAFSPAFD
NLYYWDQDPPERGAPPSTFKGTPTAENPEYLGLDVPV  (SEQ ID NO: 69)

FIG. 36B

SKBR3 Cells

BT474 Cells

3140A10-T57L_Lk10_Fus1 (EGFR-specific Vh) (SL-396)

DNA (SL-396)

Atggaaacgacaccctgctgtgtggtgtcctgctgtgggtgtccaggctctaccggcgcgaagtcatcaggtgttgtggaatcaggcggaggagcttgcgactgtcgtg
tgcggcctccggttcacctctcagactatgggatgaattgggtgcgccaaggtctttgagtggtggccgtcattaaggactcggaaactacatctacgcggattccgtc
aaaggacggtttacaattccagagagacaacttcgaagaaacacgtctacctccagatgaatagcttaggcgcggaggacacggcggtctattactgcacggaggatcagaggtgattat
ctctccttggcgctggattactggggacagggaaccctgactgtgaccgtgagcagcgcccagcaccaagggcccagcgtttccccaaccgtctgcaccctctccagctccgccagtctctgcct
gggcaccaccatccggctgacctgcctgcccctcaggtctcctgttctccggcatcttccggaacgtggcccctgtactgtgttcctctggtacctcccagtcc
gacaagtcccaggcgcccaggccgttcgcccacgtgttcctgttctgcaccaggaccctgacctccagcccagcagccagcgtccctcctcctgaccctgaccgtttcctcctctcgaggaactgcaggcaacaa
ggccacccgtgtgcctgatgaacgacttctacctgaccctgaccctgacctgaatctgaccgtgaaggcgacgagccaccccctcaccaggggtgagatgacacaccctccaagcagtcaacaac
aagtacgccgcctcctcactgtccctgaccccgagcagtggcaggcctcccggcgctccactcttgccagtcatcacgaggtctcaccgtggaaaagaccgtggcccctgccgaatgttctt
gatga (SEQ ID NO: 182)

protein (SL-396)

GluValGlnLeuLeuGluSerGlyGlyGlyGlyLeuValGlnProGlyGlySerLeuArgLeuSerCysAlaAlaSerGlyPheThrPheSerAspTyrGlyMetAsnTrp
ValArgGlnAlaProGlyLysGlyLeuGluTrpValAlaValIleLysAspSerGlyAsnTyrIleTyrTyrAlaAspSerValLysGlyArgPheThrIleSerArgAsp
AsnSerLysAsnThrLeuTyrLeuGlnMetAsnSerLeuArgAlaGluAspThrAlaValTyrTyrCysAlaArgGluAspIleArgGlyIleAspTyrLeuSerLeu
AlaLeuAspTyrTrpGlyGlnGlyThrLeuValThrValSerSerAlaSerThrLysGlyProSerValPheProLeuAlaProSerSerLysSerThrSerGlyGlyThrAlaAlaLeuGlyCysLeuValLysAspTyrPheProGluProValThrValSerTrpAsnSerGlyAlaLeuThrSerGlyValHisThrPheProAlaValLeuGlnSerSerGlyLeuTyrSerLeuSerSerValValThrValProSerSerSerLeuGlyThrGlnThrTyrIleCysAsnValAsnHisLysProSerAsnThrLysValAspLysArgValGluProLysSerCysAspLysThrHisThrCysProProCysProAlaProGluLeuLeuGlyGlyProSerValPheLeuPheProProLysProLysAspThrLeuMetIleSerArgThrProGluValThrCysValValValAspValSerHisGluAspProGluValLysPheAsnTrpTyrValAspGlyValGluValHisAsnAlaLysThrLysProArgGluGluGlnTyrAsnSerThrTyrArgValValSerValLeuThrValLeuHisGlnAspTrpLeuAsnGlyLysGluTyrLysCysLysValSerAsnLysAlaLeuProAlaProIleGluLysThrIleSerLysAlaLysGlyGlnProArgGluProGlnValTyrThrLeuProProSerArgAspGluLeuThrLysAsnGlnValSerLeuThrCysLeuValLysGlyPheTyrProSerAspIleAlaValGluTrpGluSerAsnGlyGlnProGluAsnAsnTyrLysThrThrProProValLeuAspSerAspGlySerPhePheLeuTyrSerLysLeuThrValAspLysSerArgTrpGlnGlnGlyAsnValPheSerCysSerValMetHisGluAlaLeuHisAsnHisTyrThrGlnLysSerLeuSerLeuSerProGlyLysAlaAlaProThrLysValAlaProThrLysValAlaProThrLysValAlaProThrLysAlaAlaProSerValThrLeuPheProProSerSerGluGluLeuGlnAlaAsnLysAlaThrLeuValCysLeuMetAsnAspPheTyrProGlyIleLeuThrValThrTrp
LysAlaAspGlyThrProIleThrGlnGlyValGluMetThrThrProSerLysGlnSerAsnAsnLysTyrAlaAlaSerSerTyrLeuSerLeuThrProGluGlnTrp
ArgSerArgArgSerTyrSerCysGlnValMetHisGluGlySerThrValGluLysThrValAlaProAlaGluCysSer (SEQ ID NO: 183)

(Heavy chain CDRs 1, 2, and 3 highlighted and underlined)

FIG. 41A

VpreB1_Lk10_2716F05-G1bdK (ErbB3-specific Vh) (2716-F05)

DNA (2716-F05)

atggaaaccgacaccctgctgtgggtgctcctgctgtgggtgccaggctctaccggccagcctgtgctgcaccagctccgccatgtctctgcctgctggcaccaccatccggctgacctgta
ccctgcgggaacgaccacgacatccgcgtgtactccgtgtactggtatcagcagcggcctggccaccctcctggtttctgctgtgggtactcccagtccgacctccgccagaggtgcc
cctccgttctccaaggacgtggccccgaacctgatgtcagatctccgagctgcagctgcaggggccaagcctgagcgtgtccaggctgcagcctgagcaccccagccctcgagcagccgggagatcctgcgccgtgaccac
gtgtttcggcctctggtaccagcttgacctgagcgctgagcctgagatactgatgcagcgtgcaccaccccagcccaaggccagctgactgctgagggtctgtacagcccggaggagcttgcgactgtc
gtgtgcggcctccgggttacacaatttccagagaacaactcgaagacccctgactgtatcgtctgactgtatcgtctgctgaactgtgtcgtgtactgtcagcccttccgccagagtcttctctgagctgctgctgagcccacctgcccc
cgtcaaaggacgtttacacaatttccagagaacaactccgtgactgtatcgtctgactgtcgaactgtgtccagtctcagacagcggtcttattactgcgaaagataacgagaagaatctgta
cactggtcgatggcttcagcctgactgcctcgcgctgagtgtcatccgtgctgaactcgtgctgactgtcagacactacctgggcacgcgtctgtgggc
tgcctggtcaaggactacttccctgagcctgtggcgaccctgacacctgcacccagcacctgtgtccagcaccaccaccaacgtgacctccctggaactgttcctcccctaaggacaccctgatgatctccgcgaccctgaaagtgtgagctaagtctgcgacaagaccacacctgtccc
acagtgcctagctcctgagcctgctgggcggacgcgtgagggcacaacgccaagcagccaagacaccctgatgatctcccgaccctgaagtgacgtgtgacgtgtccacgaggatcc
ttgaagtgaagttttaattggtacgtggacggcgtggaggtgcacaacgccaagacaccaagacagcccatccaagccagacagtacaactccaccctaccggtgtggtgtccgttgacagtgctgaccaggac
tggctgaacggcaaagaatacaagtgcaaggtgtccaacaaggccctgccggctgaaaaagaccatcgaaaagaccatcgaaaagaccatcgagaactacaagaccaccctc
cctgccccatcgagaaaaccatctccaaggctaaagggcagccccgtgagtaccctgcccccatctcgagatgagctgaccaagaaccaggtcagcctgacctgcctgtcaagggcttctatcctttcgatatcgccgtggagtgggagtgtaacggccagcctgagaacaactacaagaccacccct
ctgctggactccgacggctccttcttcctctactccaagctcaccgtggacaagagcaggtggcagcaggcaacgtgttctcctgctccgtgatgcatgaggctctgcacaaccactacaccca
gaagtccctgtccctgtctccgctgatga (SEQ ID NO: 184)

FIG. 41B

Protein (2716-F05)

GlnProValLeuHisGlnProProAlaMetSerSerAlaLeuGlyThrThrIleArgLeuThrCysThrLeuArgAsnAspHisAspIleGlyValTyrSerValTyrTrp
TyrGlnGlnArgProGlyHisProProArgPheLeuLeuArgTyrPheSerGlnSerAspLysSerGlnGlyProGlnValProProArgPheSerGlySerLysAspVa
lAlaArgAsnArgGlyThrLeuSerIleSerGlnLeuGlnProGluAspGluAlaMetTyrTyrCysAlaMetGlyAlaArgSerValThrHisValPheGlySerGl
yThrGlnLeuThrValLeuSerGlnProLysAlaThrProSerValThrGluValThrGlyGlyLeuValGlnLeuGluSerGlyGlyGlyLeuValGlnProGlyGlySerLeuArgLeuS
erCysAlaAlaSerGlyPheThrPheSerAsnTyrTrpMetHis<u>TrpValAlaLeuIleSerGlyGlyGlyAsn</u>
<u>ThrTyr</u>TyrAlaAspSerValLysGlyArgPheThrIleSerArgAspAsnSerLysAsnThrLeuTyrLeuGlnMetAsnSerLeuArgAlaGluAspThrAlaValT
yrTyrCys<u>AlaLysAspAsnGluLysAsnLeuTyrThrTrpLeuAsp</u>TyrTrpGlyGlnGlyThrLeuValThrValSerSerAlaSerThrLysGlyProSerValPhe
ProLeuAlaProSerSerLysSerThrSerGlyGlyThrAlaAlaLeuGlyCysLeuValLysAspTyrPheProGluProValThrValSerTrpAsnSerGlyAlaLeu
ThrSerGlyValHisThrPheProAlaValLeuGlnSerSerGlyLeuTyrSerLeuSerSerValValThrValProSerSerSerLeuGlyThrGlnThrTyrIleCysAs
nValAsnHisLysProSerAsnThrLysValAspLysLysValGluProLysSerCysAspLysThrHisThrCysProProCysProAlaProGluLeuLeuGlyGly
ProSerValPheLeuPheProProLysProLysAspThrLeuMetIleSerArgThrProGluValThrCysValValValAspValSerHisGluAspProGluValLys
PheAsnTrpTyrValAspGlyValGluValHisAsnAlaLysThrLysProArgGluGluGlnTyrAsnSerThrTyrArgValValSerValLeuThrValLeuHisG
lnAspTrpLeuAsnGlyLysGluTyrLysCysLysValSerAsnLysAlaLeuProAlaProIleGluLysThrIleSerLysAlaLysGlyGlnProArgGluProGlnV
alTyrThrLeuProProSerArgAspGluLeuThrLysAsnGlnValSerLeuThrCysLeuValLysGlyPheTyrProSerAspIleAlaValGluTrpGluSerAsn
GlyGlnProGluAsnAsnTyrLysThrThrProProValLeuAspSerAspGlySerPhePheLeuTyrSerLysLeuThrValAspLysSerArgTrpGlnGlnGly
AsnValPheSerCysSerValMetHisGluAlaLeuHisAsnHisTyrThrGlnLysSerLeuSerLeuSerProGly (SEQ ID NO: 185)

(Heavy chain CDRs 1, 2, and 3 highlighted and underlined)

FIG. 41C

I.  Full length heavy chain (2817-CO1)

Mature protein sequence (NO leader seq)
EVQLLESGGGLVQPGGSLRLSCAASGFTFSTYAMNWVRQAPGKGLEWVALISSGGSYK
YYADSVKGRFTISRDNSKNTLYLQMNSLRAEDTAVYYCAKDNFILLNSWFDYWGQGTL
VTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPG (SEQ ID NO: 186)

Corresponding DNA sequence
gaagtccagttgttggaatcaggcggaggtctggtacagcccggagggagcttgcgactgtcgtgtgcggcctccgggttcaccttctcga
cgtacgcgatgaattgggtgcgccaagccccaggaagggtcttgagtgggtggccctcatttcctcgggagggtcatacaagtattacgc
ggattccgtcaaaggacggtttacaatttccagagacaactcgaagaacacgctctacctccagatgaatagccttagggcggaggacacg
gcggtctattactgcgcaaaagacaacttcatcttgctgaacagctggtttgattactggggacagggaaccctcgtgactgtatcgtcagcct
ccaccaagggcccttccgtgttccctctggcccccttccagcaagtctacctctggcggcaccgctgctctgggctgcctggtcaaggactac
ttccctgagcctgtgacagtgtcctggaactctggcgccctgacctccggcgtgcacaccttccctgccgtgctgcagtcttctggcctgtact
ccctgtccagcgtggtcacagtgcctagctcttccctgggcacccagacctacatctgcaacgtgaaccacaagccttccaacaccaaggt
ggacaagaaggtggagcctaagtcctgcgacaagacccacacctgtccccctgtcctgctcctgagctgctgggcggaccctccgtgttc
ctgttccctcctaagcctaaggacaccctgatgatctcccggacccctgaagtgacctgtgtggtggtggacgtgtcccacgaggatcctga
agtgaagttcaattggtacgtggacggcgtggaggtgcacaacgccaagaccaagccacgggaggaacagtacaactccacctaccgg
gtggtgtccgtgctgacagtgctgcaccaggactggctgaacggcaaagaatacaagtgcaaggtgtccaacaaggccctgcctgcccct
atcgaaaagaccatctccaaggccaagggccagcctcgggaacctcaggtgtacaccctgcctccatctcgggacgaactgaccaagaa
ccaggtgtccctgacctgtctcgtcaagggcttctatccttccgatatcgccgtggagtgggagtctaacggccagcctgagaacaactaca
agaccacccctcctgtgctggactccgacggctccttcttcctgtactccaagctgaccgtggacaagtcccggtggcagcagggcaacgt
gttctcctgctccgtgatgcacgaggccctgcacaaccactacacccagaagtccctgtccctgtctcctggc (SEQ ID NO: 187)

FIG. 43A

II. Full length heavy chain (2716-F05)

Mature protein sequence (NO leader seq)
EVQLLESGGGLVQPGGSLRLSCAASGFTFSNYWMHWVRQAPGKGLEWVALISGGGGN
TYYADSVKGRFTISRDNSKNTLYLQMNSLRAEDTAVYYCAKDNEKNLYTWLDYWGQG
TLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPG (SEQ ID NO: 188)

Corresponding DNA sequence
gaagtccagttgttggaatcaggcggaggtctggtacagcccggagggagcttgcgactgtcgtgtgcggcctccgggttcaccttctcga
attactggatgcactgggtgcgccaagccccagggaagggtcttgagtgggtggccttgatctcaggggggaggaggtaacacatactacg
cggattccgtcaaaggacggtttacaatttccagagacaactcgaagaacacgctctacctccagatgaatagccttagggcggaggacac
ggcggtctattactgcgcgaaagataacgagaagaatctgtacacgtggctcgactactggggacagggaaccctcgtgactgtatcgtca
gcctccaccaagggcccttccgtgttccctctggccccttccagcaagtctacctctggcggcaccgctgctctgggctgcctggtcaagga
ctacttccctgagcctgtgacagtgtcctggaactctggcgccctgacctccggcgtgcacaccttccctgccgtgctgcagtcttctggcct
gtactccctgtccagcgtggtcacagtgcctagctcttccctgggcacccagacctacatctgcaacgtgaaccacaagcttccaacacca
aggtggacaagaaggtggagcctaagtcctgcgacaagacccacacctgtccccttgtcctgctcctgagctgctgggcggaccctccg
tgttcctgttccctcctaagcctaaggacaccctgatgatctcccggacccctgaagtgacctgtgtggtggtggacgtgtcccacgaggatc
ctgaagtgaagttcaattggtacgtggacggcgtggaggtgcacaacgccaagaccaagccacgggaggaacagtacaactccacctac
cgggtggtgtccgtgctgacagtgctgcaccaggactggctgaacggcaaagaatacaagtgcaaggtgtccaacaaggccctgcctgc
ccctatcgaaaagaccatctccaaggccaagggccagcctcgggaacctcaggtgtacaccctgcctccatctcgggacgaactgaccaa
gaaccaggtgtccctgacctgtctcgtcaagggcttctatccttccgatatcgccgtggagtgggagtctaacggccagcctgagaacaact
acaagaccaccccctcctgtgctggactccgacggctccttcttcctgtactccaagctgaccgtggacaagtcccggtggcagcagggcaa
cgtgttctcctgctccgtgatgcacgaggccctgcacaaccactacacccagaagtccctgtccctgtctcctggctgatga (SEQ ID NO: 189)

FIG. 43B

SEQUENCE LISTING

```
<160> NUMBER OF SEQ ID NOS: 311

<210> SEQ ID NO 1
<211> LENGTH: 145
<212> TYPE: PRT
<213> ORGANISM: Homo sapiens

<400> SEQUENCE: 1

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60
```

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
            85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Glu Arg Glu
            115                 120                 125

Arg Glu Trp Glu Glu Glu Met Glu Pro Thr Ala Ala Arg Thr Arg Val
130                 135                 140

Pro
145

<210> SEQ ID NO 2
<211> LENGTH: 142
<212> TYPE: PRT
<213> ORGANISM: Mus musculus

<400> SEQUENCE: 2

Met Ala Trp Thr Ser Val Leu Leu Met Leu Leu Ala His Leu Thr Gly
1               5                   10                  15

Cys Gly Pro Gln Pro Met Val His Gln Pro Ser Ala Ser Ser Ser
            20                  25                  30

Leu Gly Ala Thr Ile Arg Leu Ser Cys Thr Leu Ser Asn Asp His Asn
            35                  40                  45

Ile Gly Ile Tyr Ser Ile Tyr Trp Tyr Gln Gln Arg Pro Gly His Pro
50                  55                  60

Pro Arg Phe Leu Leu Arg Tyr Phe Ser His Ser Asp Lys His Gln Gly
65                  70                  75                  80

Pro Asp Ile Pro Pro Arg Phe Ser Gly Ser Lys Asp Thr Ala Arg Asn
            85                  90                  95

Leu Gly Tyr Leu Ser Ile Ser Glu Leu Gln Pro Glu Asp Glu Ala Val
            100                 105                 110

Tyr Tyr Cys Ala Val Gly Leu Arg Ser His Glu Lys Lys Arg Met Glu
            115                 120                 125

Arg Glu Trp Glu Gly Glu Lys Ser Tyr Thr Asp Leu Gly Ser
130                 135                 140

<210> SEQ ID NO 3
<211> LENGTH: 171
<212> TYPE: PRT
<213> ORGANISM: Mus musculus

<400> SEQUENCE: 3

Met Ala Trp Thr Ser Val Leu Leu Met Leu Leu Ala His Leu Thr Gly
1               5                   10                  15

Lys Gly Thr Leu Gly Val Gln Gly Phe Leu Ala Pro Val Ala Leu
            20                  25                  30

Leu Cys Pro Ser Asp Gly His Ala Ser Ile Phe Ser Gly Cys Gly Pro
            35                  40                  45

Gln Pro Met Val His Gln Pro Ser Ala Ser Ser Leu Gly Ala
50                  55                  60

Thr Ile Arg Leu Ser Cys Thr Leu Ser Asn Asp His Asn Ile Gly Ile
65                  70                  75                  80

Tyr Ser Ile Tyr Trp Tyr Gln Gln Arg Pro Gly His Pro Pro Arg Phe
            85                  90                  95

```
Leu Leu Arg Tyr Phe Ser His Ser Asp Lys His Gln Gly Pro Asp Ile
            100                 105                 110

Pro Pro Arg Phe Ser Gly Ser Lys Asp Thr Ala Arg Asn Leu Gly Tyr
            115                 120                 125

Leu Ser Ile Ser Glu Leu Gln Pro Glu Asp Glu Ala Val Tyr Tyr Cys
        130                 135                 140

Ala Val Gly Leu Arg Ser His Glu Lys Lys Arg Met Glu Arg Glu Trp
145                 150                 155                 160

Glu Gly Glu Lys Ser Tyr Thr Asp Leu Gly Ser
                165                 170

<210> SEQ ID NO 4
<211> LENGTH: 123
<212> TYPE: PRT
<213> ORGANISM: Homo sapiens

<400> SEQUENCE: 4

Met Ala Cys Arg Cys Leu Ser Phe Leu Leu Met Gly Thr Phe Leu Ser
  1               5                  10                  15

Val Ser Gln Thr Val Leu Ala Gln Leu Asp Ala Leu Leu Val Phe Pro
             20                  25                  30

Gly Gln Val Ala Gln Leu Ser Cys Thr Leu Ser Pro Gln His Val Thr
         35                  40                  45

Ile Arg Asp Tyr Gly Val Ser Trp Tyr Gln Gln Arg Ala Gly Ser Ala
     50                  55                  60

Pro Arg Tyr Leu Leu Tyr Tyr Arg Ser Glu Glu Asp His His Arg Pro
 65                  70                  75                  80

Ala Asp Ile Pro Asp Arg Phe Ser Ala Ala Lys Asp Glu Ala His Asn
                 85                  90                  95

Ala Cys Val Leu Thr Ile Ser Pro Val Gln Pro Glu Asp Asp Ala Asp
            100                 105                 110

Tyr Tyr Cys Ser Val Gly Tyr Gly Phe Ser Pro
        115                 120

<210> SEQ ID NO 5
<211> LENGTH: 209
<212> TYPE: PRT
<213> ORGANISM: Mus musculus

<400> SEQUENCE: 5

Met Lys Leu Arg Val Gly Gln Thr Leu Gly Thr Ile Pro Arg Gln Cys
  1               5                  10                  15

Glu Val Leu Leu Leu Leu Leu Leu Leu Gly Leu Val Asp Gly Val His
             20                  25                  30

His Ile Leu Ser Pro Ser Ser Ala Glu Arg Ser Arg Ala Val Gly Pro
         35                  40                  45

Gly Ala Ser Val Gly Ser Asn Arg Pro Ser Leu Trp Ala Leu Pro Gly
     50                  55                  60

Arg Leu Leu Phe Gln Ile Ile Pro Arg Gly Ala Gly Pro Arg Cys Ser
 65                  70                  75                  80

Pro His Arg Leu Pro Ser Lys Pro Gln Phe Trp Tyr Val Phe Gly Gly
                 85                  90                  95

Gly Thr Gln Leu Thr Ile Leu Gly Gln Pro Lys Ser Asp Pro Leu Val
            100                 105                 110

Thr Leu Phe Leu Pro Ser Leu Lys Asn Leu Gln Pro Thr Arg Pro His
            115                 120                 125
```

Val Val Cys Leu Val Ser Glu Phe Tyr Pro Gly Thr Leu Val Val Asp
            130                 135                 140

Trp Lys Val Asp Gly Val Pro Val Thr Gln Gly Val Glu Thr Thr Gln
145                 150                 155                 160

Pro Ser Lys Gln Thr Asn Asn Lys Tyr Met Val Ser Ser Tyr Leu Thr
                165                 170                 175

Leu Ile Ser Asp Gln Trp Met Pro His Ser Arg Tyr Ser Cys Arg Val
            180                 185                 190

Thr His Glu Gly Asn Thr Val Glu Lys Ser Val Ser Pro Ala Glu Cys
            195                 200                 205

Ser

<210> SEQ ID NO 6
<211> LENGTH: 213
<212> TYPE: PRT
<213> ORGANISM: Homo sapiens

<400> SEQUENCE: 6

Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Gly Leu Ala
                20                  25                  30

Val Val Thr His Gly Leu Leu Arg Pro Thr Ala Ala Ser Gln Ser Arg
            35                  40                  45

Ala Leu Gly Pro Gly Ala Pro Gly Gly Ser Ser Arg Ser Ser Leu Arg
        50                  55                  60

Ser Arg Trp Gly Arg Phe Leu Leu Gln Arg Gly Ser Trp Thr Gly Pro
65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
        115                 120                 125

Asn Lys Ala Thr Leu Val Cys Leu Met Asn Asp Phe Tyr Pro Gly Ile
    130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Arg Ser Tyr
            180                 185                 190

Ser Cys Gln Val Met His Glu Gly Ser Thr Val Glu Lys Thr Val Ala
        195                 200                 205

Pro Ala Glu Cys Ser
    210

<210> SEQ ID NO 7
<211> LENGTH: 158
<212> TYPE: PRT
<213> ORGANISM: Artificial Sequence
<220> FEATURE:
<223> OTHER INFORMATION: Synthetic Construct

<400> SEQUENCE: 7

Met Arg Pro Gly Thr Gly Gln Gly Gly Leu Glu Ala Pro Gly Glu Pro

```
                1               5                  10                 15
            Gly Pro Asn Leu Arg Gln Arg Trp Pro Leu Leu Leu Gly Leu Ala
                        20                  25                  30

Val Val Thr His Gly Ser Val Thr His Val Phe Gly Ser Gly Thr Gln
                        35                  40                  45

Leu Thr Val Leu Ser Gln Pro Lys Ala Thr Pro Ser Val Thr Leu Phe
                        50                  55                  60

Pro Pro Ser Ser Glu Glu Leu Gln Ala Asn Lys Ala Thr Leu Val Cys
            65                  70                  75                  80

Leu Met Asn Asp Phe Tyr Pro Gly Ile Leu Thr Val Thr Trp Lys Ala
                                85                  90                  95

Asp Gly Thr Pro Ile Thr Gln Gly Val Glu Met Thr Thr Pro Ser Lys
                        100                 105                 110

Gln Ser Asn Asn Lys Tyr Ala Ala Ser Ser Tyr Leu Ser Leu Thr Pro
                        115                 120                 125

Glu Gln Trp Arg Ser Arg Arg Ser Tyr Ser Cys Gln Val Met His Glu
                        130                 135                 140

Gly Ser Thr Val Glu Lys Thr Val Ala Pro Ala Glu Cys Ser
            145                 150                 155
```

<210> SEQ ID NO 8

<400> SEQUENCE: 8

000

<210> SEQ ID NO 9

<400> SEQUENCE: 9

000

<210> SEQ ID NO 10
<211> LENGTH: 242
<212> TYPE: PRT
<213> ORGANISM: Artificial Sequence
<220> FEATURE:
<223> OTHER INFORMATION: Synthetic Construct

<400> SEQUENCE: 10

```
            Met Ser Trp Ala Pro Val Leu Leu Met Leu Phe Val Tyr Cys Thr Gly
            1               5                   10                  15

Cys Gly Pro Gln Pro Val Leu His Gln Pro Pro Ala Met Ser Ser Ala
                        20                  25                  30

Leu Gly Thr Thr Ile Arg Leu Thr Cys Thr Leu Arg Asn Asp His Asp
                        35                  40                  45

Ile Gly Val Tyr Ser Val Tyr Trp Tyr Gln Gln Arg Pro Gly His Pro
                        50                  55                  60

Pro Arg Phe Leu Leu Arg Tyr Phe Ser Gln Ser Asp Lys Ser Gln Gly
            65                  70                  75                  80

Pro Gln Val Pro Pro Arg Phe Ser Gly Ser Lys Asp Val Ala Arg Asn
                        85                  90                  95

Arg Gly Tyr Leu Ser Ile Ser Glu Leu Gln Pro Glu Asp Glu Ala Met
                        100                 105                 110

Tyr Tyr Cys Ala Met Gly Ala Arg Ser Ser Val Thr His Val Phe Gly
                        115                 120                 125

Ser Gly Thr Gln Leu Thr Val Leu Ser Gln Pro Lys Ala Thr Pro Ser
                        130                 135                 140
```

```
Val Thr Leu Phe Pro Pro Ser Glu Glu Leu Gln Ala Asn Lys Ala
145                 150                 155                 160

Thr Leu Val Cys Leu Met Asn Asp Phe Tyr Pro Gly Ile Leu Thr Val
            165                 170                 175

Thr Trp Lys Ala Asp Gly Thr Pro Ile Thr Gln Gly Val Glu Met Thr
            180                 185                 190

Thr Pro Ser Lys Gln Ser Asn Asn Lys Tyr Ala Ala Ser Ser Tyr Leu
            195                 200                 205

Ser Leu Thr Pro Glu Gln Trp Arg Ser Arg Arg Ser Tyr Ser Cys Gln
        210                 215                 220

Val Met His Glu Gly Ser Thr Val Glu Lys Thr Val Ala Pro Ala Glu
225                 230                 235                 240

Cys Ser

<210> SEQ ID NO 11
<211> LENGTH: 243
<212> TYPE: PRT
<213> ORGANISM: Artificial Sequence
<220> FEATURE:
<223> OTHER INFORMATION: Synthetic Construct

<400> SEQUENCE: 11

Met Glu Thr Asp Thr Leu Leu Leu Trp Val Leu Leu Leu Trp Val Pro
1               5                   10                  15

Gly Ser Thr Gly Gln Pro Val Leu His Gln Pro Pro Ala Met Ser Ser
            20                  25                  30

Ala Leu Gly Thr Thr Ile Arg Leu Thr Cys Thr Leu Arg Asn Asp His
        35                  40                  45

Asp Ile Gly Val Tyr Ser Val Tyr Trp Tyr Gln Gln Arg Pro Gly His
    50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Val Thr His Val Phe
        115                 120                 125

Gly Gly Gly Thr Lys Leu Thr Val Leu Ser Gln Pro Lys Ala Ala Pro
130                 135                 140

Ser Val Thr Leu Phe Pro Pro Ser Ser Glu Glu Leu Gln Ala Asn Thr
145                 150                 155                 160

Ala Thr Leu Val Cys Leu Ile Ser Asp Phe Tyr Pro Gly Ala Val Thr
            165                 170                 175

Val Ala Trp Lys Ala Asp Ser Ser Pro Val Lys Ala Gly Val Glu Thr
            180                 185                 190

Thr Thr Pro Ser Lys Gln Ser Asn Asn Lys Tyr Ala Ala Ser Ser Tyr
            195                 200                 205

Leu Ser Leu Thr Pro Glu Gln Trp Lys Ser His Arg Ser Tyr Ser Cys
        210                 215                 220

Gln Val Thr His Glu Gly Ser Thr Val Glu Lys Thr Val Ala Pro Thr
225                 230                 235                 240

Glu Cys Ser
```

<210> SEQ ID NO 12
<211> LENGTH: 256
<212> TYPE: PRT
<213> ORGANISM: Artificial Sequence
<220> FEATURE:
<223> OTHER INFORMATION: Synthetic Construct

<400> SEQUENCE: 12

```
Val Lys Lys Leu Leu Leu Phe Ala Ile Pro Leu Val Val Pro Phe Tyr
 1               5                  10                  15

Ser His Ser Ala Gln Pro Val Leu His Gln Pro Pro Ala Met Ser Ser
            20                  25                  30

Ala Leu Gly Thr Thr Ile Arg Leu Thr Cys Thr Leu Arg Asn Asp His
        35                  40                  45

Asp Ile Gly Val Tyr Ser Val Tyr Trp Tyr Gln Gln Arg Pro Gly His
    50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Val Thr His Val Phe
        115                 120                 125

Gly Ser Gly Thr Gln Leu Thr Val Leu Ser Gln Pro Lys Ala Thr Pro
    130                 135                 140

Ser Val Thr Leu Phe Pro Pro Ser Ser Glu Glu Leu Gln Ala Asn Lys
145                 150                 155                 160

Ala Thr Leu Val Cys Leu Met Asn Asp Phe Tyr Pro Gly Ile Leu Thr
                165                 170                 175

Val Thr Trp Lys Ala Asp Gly Thr Pro Ile Thr Gln Gly Val Glu Met
            180                 185                 190

Thr Thr Pro Ser Lys Gln Ser Asn Asn Lys Tyr Ala Ala Ser Ser Tyr
        195                 200                 205

Leu Ser Leu Thr Pro Glu Gln Trp Arg Ser Arg Arg Ser Tyr Ser Cys
    210                 215                 220

Gln Val Met His Glu Gly Ser Thr Val Glu Lys Thr Val Ala Pro Ala
225                 230                 235                 240

Glu Cys Ser Gly Ala Pro Val Pro Tyr Pro Asp Pro Leu Glu Pro Arg
                245                 250                 255
```

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<400> SEQUENCE: 21
000

<210> SEQ ID NO 22
<400> SEQUENCE: 22
000

<210> SEQ ID NO 23
<400> SEQUENCE: 23
000

<210> SEQ ID NO 24
<400> SEQUENCE: 24
000

<210> SEQ ID NO 25
<400> SEQUENCE: 25
000

<210> SEQ ID NO 26
<400> SEQUENCE: 26
000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36
<211> LENGTH: 1342
<212> TYPE: PRT
<213> ORGANISM: Homo sapiens

<400> SEQUENCE: 36

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60
```

-continued

```
Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                 85                  90                  95

Leu Pro Leu Pro Asn Leu Arg Val Arg Gly Thr Gln Val Tyr Asp
             100                 105                 110

Gly Lys Phe Ala Ile Phe Val Met Leu Asn Tyr Asn Thr Asn Ser Ser
             115                 120                 125

His Ala Leu Arg Gln Leu Arg Leu Thr Gln Leu Thr Glu Ile Leu Ser
         130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                 165                 170                 175

Lys Asp Asn Gly Arg Ser Cys Pro Pro Cys His Glu Val Cys Lys Gly
             180                 185                 190

Arg Cys Trp Gly Pro Gly Ser Glu Asp Cys Gln Thr Leu Thr Lys Thr
         195                 200                 205

Ile Cys Ala Pro Gln Cys Asn Gly His Cys Phe Gly Pro Asn Pro Asn
         210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                 245                 250                 255

Pro Arg Cys Pro Gln Pro Leu Val Tyr Asn Lys Leu Thr Phe Gln Leu
             260                 265                 270

Glu Pro Asn Pro His Thr Lys Tyr Gln Tyr Gly Gly Val Cys Val Ala
         275                 280                 285

Ser Cys Pro His Asn Phe Val Val Asp Gln Thr Ser Cys Val Arg Ala
         290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                 325                 330                 335

Gly Ser Arg Phe Gln Thr Val Asp Ser Ser Asn Ile Asp Gly Phe Val
             340                 345                 350

Asn Cys Thr Lys Ile Leu Gly Asn Leu Asp Phe Leu Ile Thr Gly Leu
         355                 360                 365

Asn Gly Asp Pro Trp His Lys Ile Pro Ala Leu Asp Pro Glu Lys Leu
         370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                 405                 410                 415

Thr Ile Gly Gly Arg Ser Leu Tyr Asn Arg Gly Phe Ser Leu Leu Ile
             420                 425                 430

Met Lys Asn Leu Asn Val Thr Ser Leu Gly Phe Arg Ser Leu Lys Glu
         435                 440                 445

Ile Ser Ala Gly Arg Ile Tyr Ile Ser Ala Asn Arg Gln Leu Cys Tyr
         450                 455                 460

His His Ser Leu Asn Trp Thr Lys Val Leu Arg Gly Pro Thr Glu Glu
465                 470                 475                 480
```

```
Arg Leu Asp Ile Lys His Asn Arg Pro Arg Arg Asp Cys Val Ala Glu
            485                 490                 495

Gly Lys Val Cys Asp Pro Leu Cys Ser Ser Gly Gly Cys Trp Gly Pro
        500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
        530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
        610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
        690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
        770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
        850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
```

```
                900             905              910
Ala Gly Leu Arg Leu Ala Glu Val Pro Asp Leu Leu Glu Lys Gly Glu
            915                  920             925

Arg Leu Ala Gln Pro Gln Ile Cys Thr Ile Asp Val Tyr Met Val Met
            930                  935             940

Val Lys Cys Trp Met Ile Asp Glu Asn Ile Arg Pro Thr Phe Lys Glu
945                 950                  955                 960

Leu Ala Asn Glu Phe Thr Arg Met Ala Arg Asp Pro Pro Arg Tyr Leu
            965                  970             975

Val Ile Lys Arg Glu Ser Gly Pro Gly Ile Ala Pro Gly Pro Glu Pro
            980                  985             990

His Gly Leu Thr Asn Lys Lys Leu Glu Glu Val Glu Leu Glu Pro Glu
            995                  1000            1005

Leu Asp Leu Asp Leu Asp Leu Glu Ala Glu Glu Asp Asn Leu Ala Thr
            1010                 1015            1020

Thr Thr Leu Gly Ser Ala Leu Ser Leu Pro Val Gly Thr Leu Asn Arg
1025                1030                 1035                1040

Pro Arg Gly Ser Gln Ser Leu Leu Ser Pro Ser Ser Gly Tyr Met Pro
            1045                 1050            1055

Met Asn Gln Gly Asn Leu Gly Glu Ser Cys Gln Glu Ser Ala Val Ser
            1060                 1065            1070

Gly Ser Ser Glu Arg Cys Pro Arg Pro Val Ser Leu His Pro Met Pro
            1075                 1080            1085

Arg Gly Cys Leu Ala Ser Glu Ser Ser Glu Gly His Val Thr Gly Ser
            1090                 1095            1100

Glu Ala Glu Leu Gln Glu Lys Val Ser Met Cys Arg Ser Arg Ser Arg
1105                1110                 1115                1120

Ser Arg Ser Pro Arg Pro Arg Gly Asp Ser Ala Tyr His Ser Gln Arg
            1125                 1130            1135

His Ser Leu Leu Thr Pro Val Thr Pro Leu Ser Pro Pro Gly Leu Glu
            1140                 1145            1150

Glu Glu Asp Val Asn Gly Tyr Val Met Pro Asp Thr His Leu Lys Gly
            1155                 1160            1165

Thr Pro Ser Ser Arg Glu Gly Thr Leu Ser Ser Val Gly Leu Ser Ser
    1170                 1175            1180

Val Leu Gly Thr Glu Glu Glu Asp Glu Asp Glu Glu Tyr Glu Tyr Met
1185                1190                 1195                1200

Asn Arg Arg Arg Arg His Ser Pro Pro His Pro Pro Arg Pro Ser Ser
            1205                 1210            1215

Leu Glu Glu Leu Gly Tyr Glu Tyr Met Asp Val Gly Ser Asp Leu Ser
            1220                 1225            1230

Ala Ser Leu Gly Ser Thr Gln Ser Cys Pro Leu His Pro Val Pro Ile
            1235                 1240            1245

Met Pro Thr Ala Gly Thr Thr Pro Asp Glu Asp Tyr Glu Tyr Met Asn
            1250                 1255            1260

Arg Gln Arg Asp Gly Gly Gly Pro Gly Gly Asp Tyr Ala Ala Met Gly
1265                1270                 1275                1280

Ala Cys Pro Ala Ser Glu Gln Gly Tyr Glu Glu Met Arg Ala Phe Gln
            1285                 1290            1295

Gly Pro Gly His Gln Ala Pro His Val His Tyr Ala Arg Leu Lys Thr
            1300                 1305            1310

Leu Arg Ser Leu Glu Ala Thr Asp Ser Ala Phe Asp Asn Pro Asp Tyr
            1315                 1320            1325
```

Trp His Ser Arg Leu Phe Pro Lys Ala Asn Ala Gln Arg Thr
      1330                1335                1340

<210> SEQ ID NO 37
<211> LENGTH: 1339
<212> TYPE: PRT
<213> ORGANISM: Homo sapiens

<400> SEQUENCE: 37

Met Ser Ala Ile Gly Thr Leu Gln Val Leu Gly Phe Leu Leu Ser Leu
 1               5                  10                  15

Ala Arg Gly Ser Glu Met Gly Asn Ser Gln Ala Val Cys Pro Gly Thr
            20                  25                  30

Leu Asn Gly Leu Ser Val Thr Gly Asp Ala Asp Asn Gln Tyr Gln Thr
        35                  40                  45

Leu Tyr Lys Leu Tyr Glu Lys Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Val
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Phe Thr Gln Leu Thr Glu Ile Leu Leu
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Val Pro Asp Ala Glu Ile Val Val
                165                 170                 175

Lys Asn Asn Gly Gly Asn Cys Pro Pro Cys His Glu Val Cys Lys Gly
            180                 185                 190

Arg Cys Trp Gly Pro Gly Pro Glu Asp Cys Gln Ile Leu Thr Lys Thr
        195                 200                 205

Ile Cys Ala Pro Gln Cys Asn Gly Arg Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Ala Pro Leu Val Tyr Asn Lys Leu Thr Phe Gln Leu
            260                 265                 270

Glu Pro Asn Pro His Ile Lys Tyr Gln Tyr Gly Gly Val Cys Val Ala
        275                 280                 285

Ser Cys Pro His Asn Phe Val Val Asp Gln Thr Phe Cys Val Arg Ala
    290                 295                 300

Cys Pro Ala Asp Lys Met Glu Val Asp Lys Asn Gly Leu Lys Met Cys
305                 310                 315                 320

Glu Pro Cys Arg Gly Leu Cys Pro Lys Ala Cys Glu Gly Thr Gly Ser
                325                 330                 335

Gly Ser Arg Tyr Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu

```
            355                 360                 365
Asn Gly Asp Pro Trp His Lys Ile Pro Ala Leu Asp Pro Glu Lys Leu
370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
            420                 425                 430
Met Lys Asn Leu Asn Val Thr Ser Leu Gly Phe Arg Ser Leu Lys Glu
            435                 440                 445
Ile Ser Ala Gly Arg Val Tyr Ile Ser Ala Asn Gln Gln Leu Cys Tyr
            450                 455                 460
His His Ser Leu Asn Trp Thr Arg Leu Leu Arg Gly Pro Ala Glu Glu
465                 470                 475                 480
Arg Leu Asp Ile Lys Tyr Asn Arg Pro Leu Gly Glu Cys Val Ala Glu
                485                 490                 495
Gly Lys Val Cys Asp Pro Leu Cys Ser Ser Gly Gly Cys Trp Gly Pro
                500                 505                 510
Gly Pro Gly Gln Cys Leu Ser Cys Arg Asn Tyr Ser Arg Glu Gly Val
            515                 520                 525
Cys Val Thr His Cys Asn Val Leu Gln Gly Glu Pro Arg Glu Phe Val
            530                 535                 540
His Glu Ala His Cys Phe Ser Cys His Pro Glu Cys Gln Pro Met Glu
545                 550                 555                 560
Gly Thr Ser Thr Cys Asn Gly Ser Gly Ser Asp Ala Cys Ala Arg Cys
                565                 570                 575
Ala His Phe Arg Asp Gly Pro His Cys Val Asn Ser Cys Pro His Gly
                580                 585                 590
Ile Leu Gly Ala Lys Gly Pro Ile Tyr Lys Tyr Pro Asp Ala Gln Asn
            595                 600                 605
Glu Cys Arg Pro Cys His Glu Asn Cys Thr Gln Gly Cys Lys Gly Pro
            610                 615                 620
Glu Leu Gln Asp Cys Leu Gly Gln Ala Glu Val Leu Met Ser Lys Pro
625                 630                 635                 640
His Leu Val Ile Ala Val Thr Val Gly Leu Thr Val Ile Phe Leu Ile
                645                 650                 655
Leu Gly Gly Ser Phe Leu Tyr Trp Arg Gly Arg Arg Ile Gln Asn Lys
                660                 665                 670
Arg Ala Met Arg Arg Tyr Leu Glu Arg Gly Glu Ser Ile Glu Pro Leu
            675                 680                 685
Asp Pro Ser Glu Lys Ala Asn Lys Val Leu Ala Arg Ile Phe Lys Glu
            690                 695                 700
Thr Glu Leu Arg Lys Leu Lys Val Leu Gly Ser Gly Val Phe Gly Thr
705                 710                 715                 720
Val His Lys Gly Ile Trp Ile Pro Glu Gly Glu Ser Ile Lys Ile Pro
                725                 730                 735
Val Cys Ile Lys Val Ile Glu Asp Lys Ser Gly Arg Gln Ser Phe Gln
            740                 745                 750
Ala Val Thr Asp His Met Leu Ala Val Gly Ser Leu Asp His Ala His
            755                 760                 765
Ile Val Arg Leu Leu Gly Leu Cys Pro Gly Ser Ser Leu Gln Leu Val
            770                 775                 780
```

-continued

```
Thr Gln Tyr Leu Pro Leu Gly Ser Leu Leu Asp His Val Arg Gln His
785                 790                 795                 800

Arg Glu Thr Leu Gly Pro Gln Leu Leu Leu Asn Trp Gly Val Gln Ile
            805                 810                 815

Ala Lys Gly Met Tyr Tyr Leu Glu Glu His Ser Met Val His Arg Asp
            820                 825                 830

Leu Ala Leu Arg Asn Val Met Leu Lys Ser Pro Ser Gln Val Gln Val
            835                 840                 845

Ala Asp Phe Gly Val Ala Asp Leu Leu Pro Pro Asp Asp Lys Gln Leu
            850                 855                 860

Leu His Ser Glu Ala Lys Thr Pro Ile Lys Trp Met Ala Leu Glu Ser
865                 870                 875                 880

Ile His Phe Gly Lys Tyr Thr His Gln Ser Asp Val Trp Ser Tyr Gly
                885                 890                 895

Val Thr Val Trp Glu Leu Met Thr Phe Gly Ala Glu Pro Tyr Ala Gly
            900                 905                 910

Leu Arg Leu Ala Glu Ile Pro Asp Leu Leu Glu Lys Gly Glu Arg Leu
            915                 920                 925

Ala Gln Pro Gln Ile Cys Thr Ile Asp Val Tyr Met Val Met Val Lys
            930                 935                 940

Cys Trp Met Ile Asp Glu Asn Ile Arg Pro Thr Phe Lys Glu Leu Ala
945                 950                 955                 960

Asn Glu Phe Thr Arg Met Ala Arg Asp Pro Pro Arg Tyr Leu Val Ile
                965                 970                 975

Lys Arg Ala Ser Gly Pro Gly Ile Pro Pro Ala Ala Glu Pro Ser Ala
            980                 985                 990

Leu Ser Thr Lys Glu Leu Gln Asp Ala Glu Leu Glu Pro Asp Leu Asp
            995                 1000                1005

Leu Asp Leu Asp Val Glu Val Glu Glu Glu Gly Leu Ala Thr Thr Leu
            1010                1015                1020

Gly Ser Ala Leu Ser Leu Pro Thr Gly Thr Leu Thr Arg Pro Arg Gly
1025                1030                1035                1040

Ser Gln Ser Leu Leu Ser Pro Ser Ser Gly Tyr Met Pro Met Asn Gln
                1045                1050                1055

Ser Asn Leu Gly Glu Ala Cys Leu Asp Ser Ala Val Leu Gly Gly Arg
                1060                1065                1070

Glu Gln Phe Ser Arg Pro Ile Ser Leu His Pro Ile Pro Arg Gly Arg
                1075                1080                1085

Gln Thr Ser Glu Ser Ser Glu Gly His Val Thr Gly Ser Glu Ala Glu
                1090                1095                1100

Leu Gln Glu Arg Val Ser Met Cys Arg Ser Arg Ser Arg Ser Arg Ser
1105                1110                1115                1120

Pro Arg Pro Arg Gly Asp Ser Ala Tyr His Ser Gln Arg His Ser Leu
                1125                1130                1135

Leu Thr Pro Val Thr Pro Leu Ser Pro Pro Gly Leu Glu Glu Glu Asp
                1140                1145                1150

Gly Asn Gly Tyr Val Met Pro Asp Thr His Leu Arg Gly Thr Ser Ser
                1155                1160                1165

Ser Arg Glu Gly Thr Leu Ser Ser Val Gly Leu Ser Ser Val Leu Gly
            1170                1175                1180

Thr Glu Glu Glu Asp Glu Asp Glu Glu Tyr Glu Tyr Met Asn Arg Lys
1185                1190                1195                1200
```

Arg Arg Gly Ser Pro Ala Arg Pro Pro Arg Pro Gly Ser Leu Glu Glu
                1205                1210                1215

Leu Gly Tyr Glu Tyr Met Asp Val Gly Ser Asp Leu Ala Ser Leu
        1220                1225                1230

Gly Ser Thr Gln Ser Cys Pro Leu His Pro Met Ala Ile Val Pro Ser
            1235                1240                1245

Ala Gly Thr Thr Pro Asp Glu Asp Tyr Glu Tyr Met Asn Arg Arg Arg
    1250                1255                1260

Gly Ala Gly Gly Ser Gly Gly Asp Tyr Ala Ala Met Gly Ala Cys Pro
1265                1270                1275                1280

Ala Ala Glu Gln Gly Tyr Glu Glu Met Arg Ala Phe Gln Gly Pro Gly
                1285                1290                1295

His Gln Ala Pro His Val Arg Tyr Ala Arg Leu Lys Thr Leu Arg Ser
                1300                1305                1310

Leu Glu Ala Thr Asp Ser Ala Phe Asp Asn Pro Asp Tyr Trp His Ser
        1315                1320                1325

Arg Leu Phe Pro Lys Ala Asn Ala Gln Arg Ile
        1330                1335

<210> SEQ ID NO 38
<211> LENGTH: 121
<212> TYPE: PRT
<213> ORGANISM: Homo sapiens

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Leu Ile Ser Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp Tyr Trp Gly
            100                 105                 110

Gln Gly Thr Leu Val Thr Val Ser Ser
        115                 120

<210> SEQ ID NO 39
<211> LENGTH: 6
<212> TYPE: PRT
<213> ORGANISM: Homo sapiens

<400> SEQUENCE: 39

Ser Asn Tyr Trp Met His
1               5

<210> SEQ ID NO 40
<211> LENGTH: 13
<212> TYPE: PRT
<213> ORGANISM: Homo sapiens

<400> SEQUENCE: 40

Trp Val Ala Leu Ile Ser Gly Gly Gly Gly Asn Thr Tyr

<210> SEQ ID NO 41
<211> LENGTH: 13
<212> TYPE: PRT
<213> ORGANISM: Homo sapiens

<400> SEQUENCE: 41

Ala Lys Asp Asn Glu Lys Asn Leu Tyr Thr Trp Leu Asp
1               5                   10

<210> SEQ ID NO 42
<211> LENGTH: 121
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Leu Ile Ser Ser Gly Gly Ser Tyr Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp Tyr Trp Gly
            100                 105                 110

Gln Gly Thr Leu Val Thr Val Ser Ser
        115                 120

<210> SEQ ID NO 43
<211> LENGTH: 6
<212> TYPE: PRT
<213> ORGANISM: Homo sapiens

<400> SEQUENCE: 43

Ser Thr Tyr Ala Met Asn
1               5

<210> SEQ ID NO 44
<211> LENGTH: 13
<212> TYPE: PRT
<213> ORGANISM: Homo sapiens

<400> SEQUENCE: 44

Trp Val Ala Leu Ile Ser Ser Gly Gly Ser Tyr Lys Tyr
1               5                   10

<210> SEQ ID NO 45
<211> LENGTH: 13
<212> TYPE: PRT
<213> ORGANISM: Homo sapiens

<400> SEQUENCE: 45

Ala Lys Asp Asn Phe Ile Leu Leu Asn Ser Trp Phe Asp
1               5                   10

```
<210> SEQ ID NO 46
<211> LENGTH: 121
<212> TYPE: PRT
<213> ORGANISM: Homo sapiens

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Val Tyr Thr Gly Thr Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Asn Ala Ile Thr Val Asn Arg Ser Leu Asp Tyr Trp Gly
            100                 105                 110

Gln Gly Thr Leu Val Thr Val Ser Ser
        115                 120

<210> SEQ ID NO 47
<211> LENGTH: 6
<212> TYPE: PRT
<213> ORGANISM: Homo sapiens

<400> SEQUENCE: 47

Ser Ser Tyr Ala Ile Ser
1               5

<210> SEQ ID NO 48
<211> LENGTH: 13
<212> TYPE: PRT
<213> ORGANISM: Homo sapiens

<400> SEQUENCE: 48

Trp Met Gly Gly Ile Thr Val Tyr Thr Gly Thr Thr Asn
1               5                   10

<210> SEQ ID NO 49
<211> LENGTH: 13
<212> TYPE: PRT
<213> ORGANISM: Homo sapiens

<400> SEQUENCE: 49

Ala Arg Ala Asn Ala Ile Thr Val Asn Arg Ser Leu Asp
1               5                   10

<210> SEQ ID NO 50
<211> LENGTH: 119
<212> TYPE: PRT
<213> ORGANISM: Homo sapiens

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Asn Tyr
            20                  25                  30

Ser Met Ser Trp Val Arg Gln Ala Pro Gly Lys Gly Leu Glu Trp Val
```

```
                35                  40                  45
Ala Ala Ile Ser Tyr Gly Gly Ala Tyr Lys Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Val Gly Leu Asp Tyr Ala Met Asp Tyr Trp Gly Gln Gly
             100                 105                 110

Thr Leu Val Thr Val Ser Ser
            115
```

<210> SEQ ID NO 51
<211> LENGTH: 6
<212> TYPE: PRT
<213> ORGANISM: Homo sapiens

<400> SEQUENCE: 51

```
Arg Asn Tyr Ser Met Ser
 1               5
```

<210> SEQ ID NO 52
<211> LENGTH: 13
<212> TYPE: PRT
<213> ORGANISM: Homo sapiens

<400> SEQUENCE: 52

```
Trp Val Ala Ala Ile Ser Tyr Gly Gly Ala Tyr Lys Tyr
 1               5                  10
```

<210> SEQ ID NO 53
<211> LENGTH: 11
<212> TYPE: PRT
<213> ORGANISM: Homo sapiens

<400> SEQUENCE: 53

```
Ala Arg Glu Val Gly Leu Asp Tyr Ala Met Asp
 1               5                  10
```

<210> SEQ ID NO 54
<211> LENGTH: 121
<212> TYPE: PRT
<213> ORGANISM: Homo sapiens

<400> SEQUENCE: 54

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
             20                  25                  30

Ser Met Ser Trp Val Arg Gln Ala Pro Gly Lys Gly Leu Glu Trp Val
         35                  40                  45

Ala Asn Ile Ser Ala Gly Gly Ala Tyr Lys Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Phe Lys Tyr Leu Trp Ser Trp Phe Tyr Trp Gly
             100                 105                 110
```

-continued

```
Gln Gly Thr Leu Val Thr Val Ser Ser
        115                 120

<210> SEQ ID NO 55
<211> LENGTH: 6
<212> TYPE: PRT
<213> ORGANISM: Homo sapiens

<400> SEQUENCE: 55

Ser Asn Tyr Ser Met Ser
1               5

<210> SEQ ID NO 56
<211> LENGTH: 13
<212> TYPE: PRT
<213> ORGANISM: Homo sapiens

<400> SEQUENCE: 56

Trp Val Ala Asn Ile Ser Ala Gly Gly Ala Tyr Lys Tyr
1               5                   10

<210> SEQ ID NO 57
<211> LENGTH: 13
<212> TYPE: PRT
<213> ORGANISM: Homo sapiens

<400> SEQUENCE: 57

Ala Arg Asp Arg Phe Lys Tyr Leu Trp Ser Trp Phe Asp
1               5                   10

<210> SEQ ID NO 58
<211> LENGTH: 121
<212> TYPE: PRT
<213> ORGANISM: Homo sapiens

<400> SEQUENCE: 58

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Val Ile Ser Asn Gly Gly Ala Tyr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Ala Ile Trp Leu Trp Ala Trp Phe Asp Tyr Trp Gly
            100                 105                 110

Gln Gly Thr Leu Val Thr Val Ser Ser
        115                 120

<210> SEQ ID NO 59
<211> LENGTH: 6
<212> TYPE: PRT
<213> ORGANISM: Homo sapiens

<400> SEQUENCE: 59

Ser Ser Tyr Trp Met His
1               5
```

<210> SEQ ID NO 60
<211> LENGTH: 13
<212> TYPE: PRT
<213> ORGANISM: Homo sapiens

<400> SEQUENCE: 60

Trp Val Ala Val Ile Ser Asn Gly Gly Ala Tyr Lys Tyr
1               5                   10

<210> SEQ ID NO 61
<211> LENGTH: 13
<212> TYPE: PRT
<213> ORGANISM: Homo sapiens

<400> SEQUENCE: 61

Ala Arg Asp Asn Ala Ile Trp Leu Trp Ala Trp Phe Asp
1               5                   10

<210> SEQ ID NO 62
<211> LENGTH: 121
<212> TYPE: PRT
<213> ORGANISM: Homo sapiens

<400> SEQUENCE: 62

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Glu Met Ser Trp Val Arg Gln Ala Pro Gly Lys Gly Leu Glu Trp Val
        35                  40                  45

Ala Thr Ile Ser Tyr Asp Gly Gly Tyr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Ser Tyr Leu Leu Tyr Tyr Trp Phe Asp Tyr Trp Gly
            100                 105                 110

Gln Gly Thr Leu Val Thr Val Ser Ser
        115                 120

<210> SEQ ID NO 63
<211> LENGTH: 6
<212> TYPE: PRT
<213> ORGANISM: Homo sapiens

<400> SEQUENCE: 63

Ser Asn Tyr Glu Met Ser
1               5

<210> SEQ ID NO 64
<211> LENGTH: 13
<212> TYPE: PRT
<213> ORGANISM: Homo sapiens

<400> SEQUENCE: 64

Trp Val Ala Thr Ile Ser Tyr Asp Gly Gly Tyr Lys Tyr
1               5                   10

<210> SEQ ID NO 65
<211> LENGTH: 13

<212> TYPE: PRT
<213> ORGANISM: Homo sapiens

<400> SEQUENCE: 65

```
Ala Arg Asp Asn Ser Tyr Leu Leu Tyr Tyr Trp Phe Asp
1               5                   10
```

<210> SEQ ID NO 66
<211> LENGTH: 645
<212> TYPE: PRT
<213> ORGANISM: Homo sapiens

<400> SEQUENCE: 66

```
Met Pro Ile Trp Lys Phe Pro Asp Glu Glu Gly Ala Cys Gln Pro Cys
1               5                   10                  15

Pro Ile Asn Cys Thr His Ser Cys Val Asp Leu Asp Asp Lys Gly Cys
            20                  25                  30

Pro Ala Glu Gln Arg Ala Ser Pro Leu Thr Ser Ile Ile Ser Ala Val
        35                  40                  45

Val Gly Ile Leu Leu Val Val Val Leu Gly Val Val Phe Gly Ile Leu
    50                  55                  60

Ile Lys Arg Arg Gln Gln Lys Ile Arg Lys Tyr Thr Met Arg Arg Leu
65                  70                  75                  80

Leu Gln Glu Thr Glu Leu Val Glu Pro Leu Thr Pro Ser Gly Ala Met
                85                  90                  95

Pro Asn Gln Ala Gln Met Arg Ile Leu Lys Glu Thr Glu Leu Arg Lys
            100                 105                 110

Val Lys Val Leu Gly Ser Gly Ala Phe Gly Thr Val Tyr Lys Gly Ile
        115                 120                 125

Trp Ile Pro Asp Gly Glu Asn Val Lys Ile Pro Val Ala Ile Lys Val
    130                 135                 140

Leu Arg Glu Asn Thr Ser Pro Lys Ala Asn Lys Glu Ile Leu Asp Glu
145                 150                 155                 160

Ala Tyr Val Met Ala Gly Val Gly Ser Pro Tyr Val Ser Arg Leu Leu
                165                 170                 175

Gly Ile Cys Leu Thr Ser Thr Val Gln Leu Val Thr Gln Leu Met Pro
            180                 185                 190

Tyr Gly Cys Leu Leu Asp His Val Arg Glu Asn Arg Gly Arg Leu Gly
        195                 200                 205

Ser Gln Asp Leu Leu Asn Trp Cys Met Gln Ile Ala Lys Gly Met Ser
    210                 215                 220

Tyr Leu Glu Asp Val Arg Leu Val His Arg Asp Leu Ala Ala Arg Asn
225                 230                 235                 240

Val Leu Val Lys Ser Pro Asn His Val Lys Ile Thr Asp Phe Gly Leu
                245                 250                 255

Ala Arg Leu Leu Asp Ile Asp Glu Thr Glu Tyr His Ala Asp Gly Gly
            260                 265                 270

Lys Val Pro Ile Lys Trp Met Ala Leu Glu Ser Ile Leu Arg Arg Arg
        275                 280                 285

Phe Thr His Gln Ser Asp Val Trp Ser Tyr Gly Val Thr Val Trp Glu
    290                 295                 300

Leu Met Thr Phe Gly Ala Lys Pro Tyr Asp Gly Ile Pro Ala Arg Glu
305                 310                 315                 320

Ile Pro Asp Leu Leu Glu Lys Gly Glu Arg Leu Pro Gln Pro Pro Ile
                325                 330                 335
```

```
Cys Thr Ile Asp Val Tyr Met Ile Met Val Lys Cys Trp Met Ile Asp
                340                 345                 350

Ser Glu Cys Arg Pro Arg Phe Arg Glu Leu Val Ser Glu Phe Ser Arg
            355                 360                 365

Met Ala Arg Asp Pro Gln Arg Phe Val Val Ile Gln Asn Glu Asp Leu
        370                 375                 380

Gly Pro Ala Ser Pro Leu Asp Ser Thr Phe Tyr Arg Ser Leu Leu Glu
385                 390                 395                 400

Asp Asp Asp Met Gly Asp Leu Val Asp Ala Glu Glu Tyr Leu Val Pro
                405                 410                 415

Gln Gln Gly Phe Phe Cys Pro Asp Pro Ala Pro Gly Ala Gly Gly Met
            420                 425                 430

Val His His Arg His Arg Ser Ser Thr Arg Ser Gly Gly Gly Asp
        435                 440                 445

Leu Thr Leu Gly Leu Glu Pro Ser Glu Glu Glu Ala Pro Arg Ser Pro
        450                 455                 460

Leu Ala Pro Ser Glu Gly Ala Gly Ser Asp Val Phe Asp Gly Asp Leu
465                 470                 475                 480

Gly Met Gly Ala Ala Lys Gly Leu Gln Ser Leu Pro Thr His Asp Pro
                485                 490                 495

Ser Pro Leu Gln Arg Tyr Ser Glu Asp Pro Thr Val Pro Leu Pro Ser
            500                 505                 510

Glu Thr Asp Gly Tyr Val Ala Pro Leu Thr Cys Ser Pro Gln Pro Glu
            515                 520                 525

Tyr Val Asn Gln Pro Asp Val Arg Pro Gln Pro Pro Ser Pro Arg Glu
            530                 535                 540

Gly Pro Leu Pro Ala Ala Arg Pro Ala Gly Ala Thr Leu Glu Arg Pro
545                 550                 555                 560

Lys Thr Leu Ser Pro Gly Lys Asn Gly Val Val Lys Asp Val Phe Ala
                565                 570                 575

Phe Gly Gly Ala Val Glu Asn Pro Glu Tyr Leu Thr Pro Gln Gly Gly
            580                 585                 590

Ala Ala Pro Gln Pro His Pro Pro Ala Phe Ser Pro Ala Phe Asp
            595                 600                 605

Asn Leu Tyr Tyr Trp Asp Gln Asp Pro Pro Glu Arg Gly Ala Pro Pro
        610                 615                 620

Ser Thr Phe Lys Gly Thr Pro Thr Ala Glu Asn Pro Glu Tyr Leu Gly
625                 630                 635                 640

Leu Asp Val Pro Val
                645

<210> SEQ ID NO 67
<211> LENGTH: 608
<212> TYPE: PRT
<213> ORGANISM: Homo sapiens

<400> SEQUENCE: 67

Ala Ser Pro Leu Thr Ser Ile Ile Ser Ala Val Val Gly Ile Leu Leu
1               5                   10                  15

Val Val Val Leu Gly Val Val Phe Gly Ile Leu Ile Lys Arg Arg Gln
                20                  25                  30

Gln Lys Ile Arg Lys Tyr Thr Met Arg Arg Leu Leu Gln Glu Thr Glu
            35                  40                  45

Leu Val Glu Pro Leu Thr Pro Ser Gly Ala Met Pro Asn Gln Ala Gln
        50                  55                  60
```

```
Met Arg Ile Leu Lys Glu Thr Glu Leu Arg Lys Val Lys Val Leu Gly
 65                  70                  75                  80

Ser Gly Ala Phe Gly Thr Val Tyr Lys Gly Ile Trp Ile Pro Asp Gly
                 85                  90                  95

Glu Asn Val Lys Ile Pro Val Ala Ile Lys Val Leu Arg Glu Asn Thr
            100                 105                 110

Ser Pro Lys Ala Asn Lys Glu Ile Leu Asp Glu Ala Tyr Val Met Ala
        115                 120                 125

Gly Val Gly Ser Pro Tyr Val Ser Arg Leu Leu Gly Ile Cys Leu Thr
    130                 135                 140

Ser Thr Val Gln Leu Val Thr Gln Leu Met Pro Tyr Gly Cys Leu Leu
145                 150                 155                 160

Asp His Val Arg Glu Asn Arg Gly Arg Leu Gly Ser Gln Asp Leu Leu
                165                 170                 175

Asn Trp Cys Met Gln Ile Ala Lys Gly Met Ser Tyr Leu Glu Asp Val
            180                 185                 190

Arg Leu Val His Arg Asp Leu Ala Ala Arg Asn Val Leu Val Lys Ser
        195                 200                 205

Pro Asn His Val Lys Ile Thr Asp Phe Gly Leu Ala Arg Leu Leu Asp
    210                 215                 220

Ile Asp Glu Thr Glu Tyr His Ala Asp Gly Gly Lys Val Pro Ile Lys
225                 230                 235                 240

Trp Met Ala Leu Glu Ser Ile Leu Arg Arg Arg Phe Thr His Gln Ser
                245                 250                 255

Asp Val Trp Ser Tyr Gly Val Thr Val Trp Glu Leu Met Thr Phe Gly
            260                 265                 270

Ala Lys Pro Tyr Asp Gly Ile Pro Ala Arg Glu Ile Pro Asp Leu Leu
        275                 280                 285

Glu Lys Gly Glu Arg Leu Pro Gln Pro Pro Ile Cys Thr Ile Asp Val
    290                 295                 300

Tyr Met Ile Met Val Lys Cys Trp Met Ile Asp Ser Glu Cys Arg Pro
305                 310                 315                 320

Arg Phe Arg Glu Leu Val Ser Glu Phe Ser Arg Met Ala Arg Asp Pro
                325                 330                 335

Gln Arg Phe Val Val Ile Gln Asn Glu Asp Leu Gly Pro Ala Ser Pro
            340                 345                 350

Leu Asp Ser Thr Phe Tyr Arg Ser Leu Leu Glu Asp Asp Asp Met Gly
        355                 360                 365

Asp Leu Val Asp Ala Glu Glu Tyr Leu Val Pro Gln Gln Gly Phe Phe
    370                 375                 380

Cys Pro Asp Pro Ala Pro Gly Ala Gly Gly Met Val His His Arg His
385                 390                 395                 400

Arg Ser Ser Ser Thr Arg Ser Gly Gly Gly Asp Leu Thr Leu Gly Leu
                405                 410                 415

Glu Pro Ser Glu Glu Glu Ala Pro Arg Ser Pro Leu Ala Pro Ser Glu
            420                 425                 430

Gly Ala Gly Ser Asp Val Phe Asp Gly Asp Leu Gly Met Gly Ala Ala
        435                 440                 445

Lys Gly Leu Gln Ser Leu Pro Thr His Asp Pro Ser Pro Leu Gln Arg
    450                 455                 460

Tyr Ser Glu Asp Pro Thr Val Pro Leu Pro Ser Glu Thr Asp Gly Tyr
465                 470                 475                 480
```

Val Ala Pro Leu Thr Cys Ser Pro Gln Pro Glu Tyr Val Asn Gln Pro
            485                 490                 495

Asp Val Arg Pro Gln Pro Ser Pro Arg Glu Gly Pro Leu Pro Ala
        500                 505                 510

Ala Arg Pro Ala Gly Ala Thr Leu Glu Arg Pro Lys Thr Leu Ser Pro
        515                 520                 525

Gly Lys Asn Gly Val Val Lys Asp Val Phe Ala Phe Gly Gly Ala Val
        530                 535                 540

Glu Asn Pro Glu Tyr Leu Thr Pro Gln Gly Gly Ala Ala Pro Gln Pro
545                 550                 555                 560

His Pro Pro Ala Phe Ser Pro Ala Phe Asp Asn Leu Tyr Tyr Trp
            565                 570                 575

Asp Gln Asp Pro Pro Glu Arg Gly Ala Pro Pro Ser Thr Phe Lys Gly
        580                 585                 590

Thr Pro Thr Ala Glu Asn Pro Glu Tyr Leu Gly Leu Asp Val Pro Val
        595                 600                 605

<210> SEQ ID NO 68
<211> LENGTH: 580
<212> TYPE: PRT
<213> ORGANISM: Homo sapiens

<400> SEQUENCE: 68

Lys Arg Arg Gln Gln Lys Ile Arg Lys Tyr Thr Met Arg Arg Leu Leu
1               5                   10                  15

Gln Glu Thr Glu Leu Val Glu Pro Leu Thr Pro Ser Gly Ala Met Pro
            20                  25                  30

Asn Gln Ala Gln Met Arg Ile Leu Lys Glu Thr Glu Leu Arg Lys Val
        35                  40                  45

Lys Val Leu Gly Ser Gly Ala Phe Gly Thr Val Tyr Lys Gly Ile Trp
    50                  55                  60

Ile Pro Asp Gly Glu Asn Val Lys Ile Pro Val Ala Ile Lys Val Leu
65                  70                  75                  80

Arg Glu Asn Thr Ser Pro Lys Ala Asn Lys Glu Ile Leu Asp Glu Ala
                85                  90                  95

Tyr Val Met Ala Gly Val Gly Ser Pro Tyr Val Ser Arg Leu Leu Gly
            100                 105                 110

Ile Cys Leu Thr Ser Thr Val Gln Leu Val Thr Gln Leu Met Pro Tyr
        115                 120                 125

Gly Cys Leu Leu Asp His Val Arg Glu Asn Arg Gly Arg Leu Gly Ser
    130                 135                 140

Gln Asp Leu Leu Asn Trp Cys Met Gln Ile Ala Lys Gly Met Ser Tyr
145                 150                 155                 160

Leu Glu Asp Val Arg Leu Val His Arg Asp Leu Ala Ala Arg Asn Val
                165                 170                 175

Leu Val Lys Ser Pro Asn His Val Lys Ile Thr Asp Phe Gly Leu Ala
            180                 185                 190

Arg Leu Leu Asp Ile Asp Glu Thr Glu Tyr His Ala Asp Gly Gly Lys
        195                 200                 205

Val Pro Ile Lys Trp Met Ala Leu Glu Ser Ile Leu Arg Arg Arg Phe
    210                 215                 220

Thr His Gln Ser Asp Val Trp Ser Tyr Gly Val Thr Val Trp Glu Leu
225                 230                 235                 240

Met Thr Phe Gly Ala Lys Pro Tyr Asp Gly Ile Pro Ala Arg Glu Ile
                245                 250                 255

```
Pro Asp Leu Leu Glu Lys Gly Glu Arg Leu Pro Gln Pro Ile Cys
            260                 265                 270

Thr Ile Asp Val Tyr Met Ile Met Val Lys Cys Trp Met Ile Asp Ser
        275                 280                 285

Glu Cys Arg Pro Arg Phe Arg Glu Leu Val Ser Glu Phe Ser Arg Met
    290                 295                 300

Ala Arg Asp Pro Gln Arg Phe Val Val Ile Gln Asn Glu Asp Leu Gly
305                 310                 315                 320

Pro Ala Ser Pro Leu Asp Ser Thr Phe Tyr Arg Ser Leu Leu Glu Asp
                325                 330                 335

Asp Asp Met Gly Asp Leu Val Asp Ala Glu Glu Tyr Leu Val Pro Gln
            340                 345                 350

Gln Gly Phe Phe Cys Pro Asp Pro Ala Pro Gly Ala Gly Gly Met Val
        355                 360                 365

His His Arg His Arg Ser Ser Ser Thr Arg Ser Gly Gly Gly Asp Leu
    370                 375                 380

Thr Leu Gly Leu Glu Pro Ser Glu Glu Glu Ala Pro Arg Ser Pro Leu
385                 390                 395                 400

Ala Pro Ser Glu Gly Ala Gly Ser Asp Val Phe Asp Gly Asp Leu Gly
                405                 410                 415

Met Gly Ala Ala Lys Gly Leu Gln Ser Leu Pro Thr His Asp Pro Ser
            420                 425                 430

Pro Leu Gln Arg Tyr Ser Glu Asp Pro Thr Val Pro Leu Pro Ser Glu
        435                 440                 445

Thr Asp Gly Tyr Val Ala Pro Leu Thr Cys Ser Pro Gln Pro Glu Tyr
    450                 455                 460

Val Asn Gln Pro Asp Val Arg Pro Gln Pro Pro Ser Pro Arg Glu Gly
465                 470                 475                 480

Pro Leu Pro Ala Ala Arg Pro Ala Gly Ala Thr Leu Glu Arg Pro Lys
                485                 490                 495

Thr Leu Ser Pro Gly Lys Asn Gly Val Val Lys Asp Val Phe Ala Phe
            500                 505                 510

Gly Gly Ala Val Glu Asn Pro Glu Tyr Leu Thr Pro Gln Gly Gly Ala
        515                 520                 525

Ala Pro Gln Pro His Pro Pro Ala Phe Ser Pro Ala Phe Asp Asn
    530                 535                 540

Leu Tyr Tyr Trp Asp Gln Asp Pro Pro Glu Arg Gly Ala Pro Pro Ser
545                 550                 555                 560

Thr Phe Lys Gly Thr Pro Thr Ala Glu Asn Pro Glu Tyr Leu Gly Leu
                565                 570                 575

Asp Val Pro Val
            580

<210> SEQ ID NO 69
<211> LENGTH: 569
<212> TYPE: PRT
<213> ORGANISM: Homo sapiens

<400> SEQUENCE: 69

Met Arg Arg Leu Leu Gln Glu Thr Glu Leu Val Glu Pro Leu Thr Pro
  1               5                  10                  15

Ser Gly Ala Met Pro Asn Gln Ala Gln Met Arg Ile Leu Lys Glu Thr
             20                  25                  30

Glu Leu Arg Lys Val Lys Val Leu Gly Ser Gly Ala Phe Gly Thr Val
```

```
            35                  40                  45
Tyr Lys Gly Ile Trp Ile Pro Asp Gly Glu Asn Val Lys Ile Pro Val
 50                  55                  60

Ala Ile Lys Val Leu Arg Glu Asn Thr Ser Pro Lys Ala Asn Lys Glu
 65                  70                  75                  80

Ile Leu Asp Glu Ala Tyr Val Met Ala Gly Val Gly Ser Pro Tyr Val
                 85                  90                  95

Ser Arg Leu Leu Gly Ile Cys Leu Thr Ser Thr Val Gln Leu Val Thr
            100                 105                 110

Gln Leu Met Pro Tyr Gly Cys Leu Leu Asp His Val Arg Glu Asn Arg
        115                 120                 125

Gly Arg Leu Gly Ser Gln Asp Leu Leu Asn Trp Cys Met Gln Ile Ala
    130                 135                 140

Lys Gly Met Ser Tyr Leu Glu Asp Val Arg Leu Val His Arg Asp Leu
145                 150                 155                 160

Ala Ala Arg Asn Val Leu Val Lys Ser Pro Asn His Val Lys Ile Thr
                165                 170                 175

Asp Phe Gly Leu Ala Arg Leu Leu Asp Ile Asp Glu Thr Glu Tyr His
            180                 185                 190

Ala Asp Gly Gly Lys Val Pro Ile Lys Trp Met Ala Leu Glu Ser Ile
        195                 200                 205

Leu Arg Arg Arg Phe Thr His Gln Ser Asp Val Trp Ser Tyr Gly Val
    210                 215                 220

Thr Val Trp Glu Leu Met Thr Phe Gly Ala Lys Pro Tyr Asp Gly Ile
225                 230                 235                 240

Pro Ala Arg Glu Ile Pro Asp Leu Leu Glu Lys Gly Glu Arg Leu Pro
                245                 250                 255

Gln Pro Pro Ile Cys Thr Ile Asp Val Tyr Met Ile Met Val Lys Cys
            260                 265                 270

Trp Met Ile Asp Ser Glu Cys Arg Pro Arg Phe Arg Glu Leu Val Ser
        275                 280                 285

Glu Phe Ser Arg Met Ala Arg Asp Pro Gln Arg Phe Val Val Ile Gln
    290                 295                 300

Asn Glu Asp Leu Gly Pro Ala Ser Pro Leu Asp Ser Thr Phe Tyr Arg
305                 310                 315                 320

Ser Leu Leu Glu Asp Asp Met Gly Asp Leu Val Asp Ala Glu Glu
                325                 330                 335

Tyr Leu Val Pro Gln Gln Gly Phe Phe Cys Pro Asp Pro Ala Pro Gly
            340                 345                 350

Ala Gly Gly Met Val His His Arg His Arg Ser Ser Ser Thr Arg Ser
        355                 360                 365

Gly Gly Gly Asp Leu Thr Leu Gly Leu Glu Pro Ser Glu Glu Glu Ala
    370                 375                 380

Pro Arg Ser Pro Leu Ala Pro Ser Glu Gly Ala Gly Ser Asp Val Phe
385                 390                 395                 400

Asp Gly Asp Leu Gly Met Gly Ala Ala Lys Gly Leu Gln Ser Leu Pro
                405                 410                 415

Thr His Asp Pro Ser Pro Leu Gln Arg Tyr Ser Glu Asp Pro Thr Val
            420                 425                 430

Pro Leu Pro Ser Glu Thr Asp Gly Tyr Val Ala Pro Leu Thr Cys Ser
        435                 440                 445

Pro Gln Pro Glu Tyr Val Asn Gln Pro Asp Val Arg Pro Gln Pro Pro
    450                 455                 460
```

-continued

Ser Pro Arg Glu Gly Pro Leu Pro Ala Ala Arg Pro Ala Gly Ala Thr
465                 470                 475                 480

Leu Glu Arg Pro Lys Thr Leu Ser Pro Gly Lys Asn Gly Val Val Lys
            485                 490                 495

Asp Val Phe Ala Phe Gly Gly Ala Val Glu Asn Pro Gly Tyr Leu Thr
        500                 505                 510

Pro Gln Gly Gly Ala Ala Pro Gln Pro His Pro Pro Ala Phe Ser
        515                 520                 525

Pro Ala Phe Asp Asn Leu Tyr Tyr Trp Asp Gln Asp Pro Pro Glu Arg
530                 535                 540

Gly Ala Pro Pro Ser Thr Phe Lys Gly Thr Pro Thr Ala Glu Asn Pro
545                 550                 555                 560

Glu Tyr Leu Gly Leu Asp Val Pro Val
                565

<210> SEQ ID NO 70
<211> LENGTH: 119
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Leu Ile Ser Ser Gly Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp Tyr Trp Gly
            100                 105                 110

Gln Gly Thr Leu Val Thr Val
        115

<210> SEQ ID NO 71
<211> LENGTH: 119
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Leu Ile Ser Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Asp Asn Glu Lys Asn Leu Tyr Thr Trp Leu Asp Tyr Trp Gly
            100                 105                 110

Gln Gly Thr Leu Val Thr Val
            115
```

<210> SEQ ID NO 72
<211> LENGTH: 121
<212> TYPE: PRT
<213> ORGANISM: Homo sapiens

<400> SEQUENCE: 72

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Thr Val Tyr Thr Gly Thr Thr Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Asn Ala Ile Thr Val Asn Arg Ser Leu Asp Tyr Trp Gly
            100                 105                 110

Gln Gly Thr Leu Val Thr Val Ser Ser
            115                 120
```

<210> SEQ ID NO 73
<211> LENGTH: 121
<212> TYPE: PRT
<213> ORGANISM: Homo sapiens

<400> SEQUENCE: 73

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Thr Val Tyr Thr Gly Thr Thr Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Ser Gly Ala Val Thr Ser Asn Tyr Thr Leu Asp Tyr Trp Gly
            100                 105                 110

Gln Gly Thr Leu Val Thr Val Ser Ser
            115                 120
```

<210> SEQ ID NO 74
<211> LENGTH: 121
<212> TYPE: PRT
<213> ORGANISM: Homo sapiens

<400> SEQUENCE: 74

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Ala Tyr Thr Gly Gly Ala Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asn Ala Val Thr Arg Asn Tyr Tyr Leu Asp Tyr Trp Gly
            100                 105                 110

Gln Gly Thr Leu Val Thr Val Ser Ser
            115                 120
```

<210> SEQ ID NO 75
<211> LENGTH: 121
<212> TYPE: PRT
<213> ORGANISM: Homo sapiens

<400> SEQUENCE: 75

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ile Tyr
            20                  25                  30

Thr Met Asn Trp Val Arg Gln Ala Pro Gly Gln Gly Leu Glu Trp Met
        35                  40                  45

Gly Gly Ile Asn Val Tyr Ser Gly Gly Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Arg Ala Ile Ser Arg Asn Ala Ser Leu Asp Tyr Trp Gly
            100                 105                 110

Gln Gly Thr Leu Val Thr Val Ser Ser
            115                 120
```

<210> SEQ ID NO 76
<211> LENGTH: 121
<212> TYPE: PRT
<213> ORGANISM: Homo sapiens

<400> SEQUENCE: 76

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ile Tyr
            20                  25                  30

Thr Met Asn Trp Val Arg Gln Ala Pro Gly Gln Gly Leu Glu Trp Met
        35                  40                  45

Gly Gly Ile Ile Val Tyr Asn Gly Gly Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80
```

-continued

```
Met Glu Leu Ser Ser Leu Arg Ser Glu Asp Thr Ala Val Tyr Tyr Cys
             85                  90                  95

Ala Arg Ala His Ala Ile Ser Arg Asn Ala Ser Leu Asp Tyr Trp Gly
            100                 105                 110

Gln Gly Thr Leu Val Thr Val Ser Ser
        115                 120

<210> SEQ ID NO 77
<211> LENGTH: 121
<212> TYPE: PRT
<213> ORGANISM: Homo sapiens

<400> SEQUENCE: 77

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Thr Tyr
            20                  25                  30

Ala Met Asn Trp Val Arg Gln Ala Pro Gly Gln Gly Leu Glu Trp Met
        35                  40                  45

Gly Ser Ile Ile Val Tyr Ser Gly Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
             85                  90                  95

Ala Arg Ala Thr Ala Val Ser Arg Asn Val Ser Leu Asp Tyr Trp Gly
            100                 105                 110

Gln Gly Thr Leu Val Thr Val Ser Ser
        115                 120

<210> SEQ ID NO 78
<211> LENGTH: 121
<212> TYPE: PRT
<213> ORGANISM: Homo sapiens

<400> SEQUENCE: 78

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
            20                  25                  30

Thr Met Asn Trp Val Arg Gln Ala Pro Gly Gln Gly Leu Glu Trp Met
        35                  40                  45

Gly Gly Ile Ile Val Tyr Asn Gly Gly Thr Ser Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
             85                  90                  95

Ala Arg Gly Asn Ala Ile Ser Arg Asn Gly Gly Leu Asp Tyr Trp Gly
            100                 105                 110

Gln Gly Thr Leu Val Thr Val Ser Ser
        115                 120

<210> SEQ ID NO 79
<211> LENGTH: 121
<212> TYPE: PRT
<213> ORGANISM: Homo sapiens
```

-continued

<400> SEQUENCE: 79

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ile Tyr
            20                  25                  30

Thr Ile Asn Trp Val Arg Gln Ala Pro Gly Gln Gly Leu Glu Trp Met
        35                  40                  45

Gly Gly Ile Thr Pro Gly Thr Gly Gly Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Ala Ile Ser Arg Trp Ala Gly Leu Asp Tyr Trp Gly
            100                 105                 110

Gln Gly Thr Leu Val Thr Val Ser Ser
        115                 120

<210> SEQ ID NO 80
<211> LENGTH: 121
<212> TYPE: PRT
<213> ORGANISM: Homo sapiens

<400> SEQUENCE: 80

Gln Val Lys Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Thr Met Asn Trp Val Arg Gln Ala Pro Gly Gln Gly Leu Glu Trp Met
        35                  40                  45

Gly Gly Ile Thr Pro Gly Thr Gly Asn Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ala Ile Thr Arg Asn Pro Ala Leu Asp Tyr Trp Gly
            100                 105                 110

Gln Gly Thr Leu Val Thr Val Ser Ser
        115                 120

<210> SEQ ID NO 81
<211> LENGTH: 862
<212> TYPE: PRT
<213> ORGANISM: Artificial Sequence
<220> FEATURE:
<223> OTHER INFORMATION: Fusion

<400> SEQUENCE: 81

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

```
Ala His Asn Gln Val Arg Gln Val Pro Leu Gln Arg Leu Arg Ile Val
 65                  70                  75                  80

Arg Gly Thr Gln Leu Phe Glu Asp Asn Tyr Ala Leu Ala Val Leu Asp
                 85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ser Cys Pro Pro Cys His Glu Val
                165                 170                 175

Cys Lys Gly Arg Cys Trp Gly Pro Gly Ser Glu Asp Cys Gln Thr Leu
            180                 185                 190

Thr Lys Thr Ile Cys Ala Pro Gln Cys Asn Gly His Cys Phe Gly Pro
        195                 200                 205

Asn Pro Asn Gln Cys Cys His Asp Glu Cys Ala Gly Gly Cys Ser Gly
    210                 215                 220

Pro Gln Asp Thr Asp Cys Phe Ala Cys Arg His Phe Asn Asp Ser Gly
225                 230                 235                 240

Ala Cys Val Pro Arg Cys Pro Gln Pro Leu Val Tyr Asn Lys Leu Thr
                245                 250                 255

Phe Gln Leu Glu Pro Asn Pro His Thr Lys Tyr Gln Tyr Gly Gly Val
            260                 265                 270

Cys Val Ala Ser Cys Pro His Asn Phe Val Val Asp Gln Thr Ser Cys
        275                 280                 285

Val Arg Ala Cys Pro Pro Asp Lys Met Glu Val Asp Lys Asn Gly Leu
    290                 295                 300

Lys Met Cys Glu Pro Cys Gly Gly Leu Cys Pro Lys Ala Cys Glu Gly
305                 310                 315                 320

Thr Gly Ser Gly Ser Arg Phe Gln Thr Val Asp Ser Ser Asn Ile Asp
                325                 330                 335

Gly Phe Val Asn Cys Thr Lys Ile Leu Gly Asn Leu Asp Phe Leu Ile
            340                 345                 350

Thr Gly Leu Asn Gly Asp Pro Trp His Lys Ile Pro Ala Leu Asp Pro
        355                 360                 365

Glu Lys Leu Asn Val Phe Arg Thr Val Arg Glu Ile Thr Gly Tyr Leu
    370                 375                 380

Asn Ile Gln Ser Trp Pro Pro His Met His Asn Phe Ser Val Phe Ser
385                 390                 395                 400

Asn Leu Thr Thr Ile Gly Gly Arg Ser Leu Tyr Asn Arg Gly Phe Ser
                405                 410                 415

Leu Leu Ile Met Lys Asn Leu Asn Val Thr Ser Leu Gly Phe Arg Ser
            420                 425                 430

Leu Lys Glu Ile Ser Ala Gly Arg Ile Tyr Ile Ser Ala Asn Arg Gln
        435                 440                 445

Leu Cys Tyr His His Ser Leu Asn Trp Thr Lys Val Leu Arg Gly Pro
    450                 455                 460

Thr Glu Glu Arg Leu Asp Ile Lys His Asn Arg Pro Arg Arg Asp Cys
465                 470                 475                 480
```

Val Ala Glu Gly Lys Val Cys Asp Pro Leu Cys Ser Ser Gly Gly Cys
            485                 490                 495

Trp Gly Pro Gly Pro Gly Gln Cys Leu Ser Cys Arg Asn Tyr Ser Arg
        500                 505                 510

Gly Gly Val Cys Val Thr His Cys Asn Phe Leu Asn Gly Glu Pro Arg
        515                 520                 525

Glu Phe Ala His Glu Ala Glu Cys Phe Ser Cys His Pro Glu Cys Gln
    530                 535                 540

Pro Met Glu Gly Thr Ala Thr Cys Asn Gly Ser Gly Ser Asp Thr Cys
545                 550                 555                 560

Ala Gln Cys Ala His Phe Arg Asp Gly Pro His Cys Val Ser Ser Cys
                565                 570                 575

Pro His Gly Val Leu Gly Ala Lys Gly Pro Ile Tyr Lys Tyr Pro Asp
            580                 585                 590

Val Gln Asn Glu Cys Arg Pro Cys His Glu Asn Cys Thr Gln Gly Cys
        595                 600                 605

Lys Gly Pro Glu Leu Gln Asp Cys Leu Gly Gln Thr Leu Val Leu Ile
        610                 615                 620

Gly Lys Thr His Leu Thr Ile Glu Gly Arg Met Asp Asp Lys Thr His
625                 630                 635                 640

Thr Cys Pro Pro Cys Pro Ala Pro Glu Leu Leu Gly Gly Pro Ser Val
                645                 650                 655

Phe Leu Phe Pro Pro Lys Pro Lys Asp Thr Leu Met Ile Ser Arg Thr
            660                 665                 670

Pro Glu Val Thr Cys Val Val Val Asp Val Ser His Glu Asp Pro Glu
        675                 680                 685

Val Lys Phe Asn Trp Tyr Val Asp Gly Val Glu Val His Asn Ala Lys
        690                 695                 700

Thr Lys Pro Arg Glu Glu Gln Tyr Asn Ser Thr Tyr Arg Val Val Ser
705                 710                 715                 720

Val Leu Thr Val Leu His Gln Asp Trp Leu Asn Gly Lys Glu Tyr Lys
                725                 730                 735

Cys Lys Val Ser Asn Lys Ala Leu Pro Ala Pro Ile Glu Lys Thr Ile
            740                 745                 750

Ser Lys Ala Lys Gly Gln Pro Arg Glu Pro Gln Val Tyr Thr Leu Pro
        755                 760                 765

Pro Ser Arg Asp Glu Leu Thr Lys Asn Gln Val Ser Leu Thr Cys Leu
        770                 775                 780

Val Lys Gly Phe Tyr Pro Ser Asp Ile Ala Val Glu Trp Glu Ser Asn
785                 790                 795                 800

Gly Gln Pro Glu Asn Asn Tyr Lys Thr Thr Pro Pro Val Leu Asp Ser
                805                 810                 815

Asp Gly Ser Phe Phe Leu Tyr Ser Lys Leu Thr Val Asp Lys Ser Arg
            820                 825                 830

Trp Gln Gln Gly Asn Val Phe Ser Cys Ser Val Met His Glu Ala Leu
        835                 840                 845

His Asn His Tyr Thr Gln Lys Ser Leu Ser Leu Ser Pro Gly
    850                 855                 860

<210> SEQ ID NO 82
<211> LENGTH: 853
<212> TYPE: PRT
<213> ORGANISM: Artificial Sequence
<220> FEATURE:
<223> OTHER INFORMATION: Fusion

<400> SEQUENCE: 82

```
Gly Asn Ser Gln Ala Val Cys Pro Gly Thr Leu Asn Gly Leu Ser Val
1               5                   10                  15

Thr Gly Asp Ala Glu Asn Gln Tyr Gln Thr Leu Tyr Lys Leu Tyr Glu
            20                  25                  30

Arg Cys Glu Val Val Met Gly Asn Leu Glu Ile Val Leu Thr Gly His
        35                  40                  45

Asn Ala Asp Leu Ser Phe Leu Gln Trp Ile Arg Glu Val Thr Gly Tyr
    50                  55                  60

Val Leu Val Ala Met Asn Glu Phe Ser Thr Leu Pro Leu Pro Asn Leu
65                  70                  75                  80

Arg Val Val Arg Gly Thr Gln Val Tyr Asp Gly Lys Phe Ala Ile Phe
                85                  90                  95

Val Met Leu Asn Tyr Asn Thr Asn Ser Ser His Ala Leu Arg Gln Leu
            100                 105                 110

Arg Leu Thr Gln Leu Thr Glu Ile Leu Ser Gly Gly Val Tyr Ile Glu
        115                 120                 125

Lys Asn Asp Lys Leu Cys His Met Asp Thr Ile Asp Trp Arg Asp Ile
    130                 135                 140

Val Arg Asp Arg Asp Ala Glu Ile Val Val Lys Asp Asn Gly Arg Ser
145                 150                 155                 160

Cys Pro Pro Cys His Glu Val Cys Lys Gly Arg Cys Trp Gly Pro Gly
                165                 170                 175

Ser Glu Asp Cys Gln Thr Leu Thr Lys Thr Ile Cys Ala Pro Gln Cys
            180                 185                 190

Asn Gly His Cys Phe Gly Pro Asn Pro Asn Gln Cys Cys His Asp Glu
        195                 200                 205

Cys Ala Gly Gly Cys Ser Gly Pro Gln Asp Thr Asp Cys Phe Ala Cys
    210                 215                 220

Arg His Phe Asn Asp Ser Gly Ala Cys Val Pro Arg Cys Pro Gln Pro
225                 230                 235                 240

Leu Val Tyr Asn Lys Leu Thr Phe Gln Leu Glu Pro Asn Pro His Thr
                245                 250                 255

Lys Tyr Gln Tyr Gly Gly Val Cys Val Ala Ser Cys Pro His Asn Phe
            260                 265                 270

Val Val Asp Gln Thr Ser Cys Val Arg Ala Cys Pro Pro Asp Lys Met
        275                 280                 285

Glu Val Asp Lys Asn Gly Leu Lys Met Cys Glu Pro Cys Gly Gly Leu
    290                 295                 300

Cys Pro Lys Ala Cys Tyr Gly Leu Gly Met Glu His Leu Arg Glu Val
305                 310                 315                 320

Arg Ala Val Thr Ser Ala Asn Ile Gln Glu Phe Ala Gly Cys Lys Lys
                325                 330                 335

Ile Phe Gly Ser Leu Ala Phe Leu Pro Glu Ser Phe Asp Gly Asp Pro
            340                 345                 350

Ala Ser Asn Thr Ala Pro Leu Gln Pro Glu Gln Leu Gln Val Phe Glu
        355                 360                 365

Thr Leu Glu Glu Ile Thr Gly Tyr Leu Tyr Ile Ser Ala Trp Pro Asp
    370                 375                 380

Ser Leu Pro Asp Leu Ser Val Phe Gln Asn Leu Gln Val Ile Arg Gly
385                 390                 395                 400

Arg Ile Leu His Asn Gly Ala Tyr Ser Leu Thr Leu Gln Gly Leu Gly
```

```
                    405                 410                 415
Ile Ser Trp Leu Gly Leu Arg Ser Leu Arg Glu Leu Gly Ser Gly Leu
            420                 425                 430

Ala Leu Ile His His Asn Thr His Leu Cys Phe Val His Thr Val Pro
            435                 440                 445

Trp Asp Gln Leu Phe Arg Asn Pro His Gln Ala Leu Leu His Thr Ala
    450                 455                 460

Asn Arg Pro Glu Asp Glu Cys Val Gly Glu Gly Lys Val Cys Asp Pro
465                 470                 475                 480

Leu Cys Ser Ser Gly Gly Cys Trp Gly Pro Gly Pro Gly Gln Cys Leu
                485                 490                 495

Ser Cys Arg Asn Tyr Ser Arg Gly Gly Val Cys Val Thr His Cys Asn
            500                 505                 510

Phe Leu Asn Gly Glu Pro Arg Glu Phe Ala His Glu Ala Glu Cys Phe
            515                 520                 525

Ser Cys His Pro Glu Cys Gln Pro Met Glu Gly Thr Ala Thr Cys Asn
        530                 535                 540

Gly Ser Gly Ser Asp Thr Cys Ala Gln Cys Ala His Phe Arg Asp Gly
545                 550                 555                 560

Pro His Cys Val Ser Ser Cys Pro His Gly Val Leu Gly Ala Lys Gly
                565                 570                 575

Pro Ile Tyr Lys Tyr Pro Asp Val Gln Asn Glu Cys Arg Pro Cys His
            580                 585                 590

Glu Asn Cys Thr Gln Gly Cys Lys Gly Pro Glu Leu Gln Asp Cys Leu
        595                 600                 605

Gly Gln Thr Leu Val Leu Ile Gly Lys Thr His Leu Thr Ile Glu Gly
        610                 615                 620

Arg Met Asp Asp Lys Thr His Thr Cys Pro Pro Cys Pro Ala Pro Glu
625                 630                 635                 640

Leu Leu Gly Gly Pro Ser Val Phe Leu Phe Pro Pro Lys Pro Lys Asp
                645                 650                 655

Thr Leu Met Ile Ser Arg Thr Pro Glu Val Thr Cys Val Val Val Asp
            660                 665                 670

Val Ser His Glu Asp Pro Glu Val Lys Phe Asn Trp Tyr Val Asp Gly
            675                 680                 685

Val Glu Val His Asn Ala Lys Thr Lys Pro Arg Glu Glu Gln Tyr Asn
        690                 695                 700

Ser Thr Tyr Arg Val Val Ser Val Leu Thr Val Leu His Gln Asp Trp
705                 710                 715                 720

Leu Asn Gly Lys Glu Tyr Lys Cys Lys Val Ser Asn Lys Ala Leu Pro
                725                 730                 735

Ala Pro Ile Glu Lys Thr Ile Ser Ala Lys Gly Gln Pro Arg Glu
            740                 745                 750

Pro Gln Val Tyr Thr Leu Pro Pro Ser Arg Asp Glu Leu Thr Lys Asn
            755                 760                 765

Gln Val Ser Leu Thr Cys Leu Val Lys Gly Phe Tyr Pro Ser Asp Ile
        770                 775                 780

Ala Val Glu Trp Glu Ser Asn Gly Gln Pro Glu Asn Asn Tyr Lys Thr
785                 790                 795                 800

Thr Pro Pro Val Leu Asp Ser Asp Gly Ser Phe Phe Leu Tyr Ser Lys
                805                 810                 815

Leu Thr Val Asp Lys Ser Arg Trp Gln Gln Gly Asn Val Phe Ser Cys
            820                 825                 830
```

```
Ser Val Met His Glu Ala Leu His Asn His Tyr Thr Gln Lys Ser Leu
        835                 840                 845

Ser Leu Ser Pro Gly
    850
```

<210> SEQ ID NO 83
<211> LENGTH: 851
<212> TYPE: PRT
<213> ORGANISM: Artificial Sequence
<220> FEATURE:
<223> OTHER INFORMATION: Fusion

<400> SEQUENCE: 83

```
Gly Asn Ser Gln Ala Val Cys Pro Gly Thr Leu Asn Gly Leu Ser Val
  1               5                  10                  15

Thr Gly Asp Ala Glu Asn Gln Tyr Gln Thr Leu Tyr Lys Leu Tyr Glu
             20                  25                  30

Arg Cys Glu Val Val Met Gly Asn Leu Glu Ile Val Leu Thr Gly His
         35                  40                  45

Asn Ala Asp Leu Ser Phe Leu Gln Trp Ile Arg Glu Val Thr Gly Tyr
     50                  55                  60

Val Leu Val Ala Met Asn Glu Phe Ser Thr Leu Pro Leu Pro Asn Leu
 65                  70                  75                  80

Arg Val Val Arg Gly Thr Gln Val Tyr Asp Gly Lys Phe Ala Ile Phe
                 85                  90                  95

Val Met Leu Asn Tyr Asn Thr Asn Ser Ser His Ala Leu Arg Gln Leu
            100                 105                 110

Arg Leu Thr Gln Leu Thr Glu Ile Leu Ser Gly Gly Val Tyr Ile Glu
        115                 120                 125

Lys Asn Asp Lys Leu Cys His Met Asp Thr Ile Asp Trp Arg Asp Ile
    130                 135                 140

Val Arg Asp Arg Asp Ala Glu Ile Val Val Lys Asp Asn Gly Arg Ser
145                 150                 155                 160

Cys Pro Pro Cys His Glu Val Cys Lys Gly Arg Cys Trp Gly Pro Gly
                165                 170                 175

Ser Glu Asp Cys Gln Thr Leu Thr Lys Thr Ile Cys Ala Pro Gln Cys
            180                 185                 190

Asn Gly His Cys Phe Gly Pro Asn Pro Asn Gln Cys Cys His Asp Glu
        195                 200                 205

Cys Ala Gly Gly Cys Ser Gly Pro Gln Asp Thr Asp Cys Phe Ala Cys
    210                 215                 220

Arg His Phe Asn Asp Ser Gly Ala Cys Val Pro Arg Cys Pro Gln Pro
225                 230                 235                 240

Leu Val Tyr Asn Lys Leu Thr Phe Gln Leu Glu Pro Asn Pro His Thr
                245                 250                 255

Lys Tyr Gln Tyr Gly Gly Val Cys Val Ala Ser Cys Pro His Asn Phe
            260                 265                 270

Val Val Asp Gln Thr Ser Cys Val Arg Ala Cys Pro Pro Asp Lys Met
        275                 280                 285

Glu Val Asp Lys Asn Gly Leu Lys Met Cys Glu Pro Cys Gly Gly Leu
    290                 295                 300

Cys Pro Lys Ala Cys Glu Gly Thr Gly Ser Gly Ser Arg Phe Gln Thr
305                 310                 315                 320

Val Asp Ser Ser Asn Ile Asp Gly Phe Val Asn Cys Thr Lys Ile Leu
                325                 330                 335
```

```
Gly Asn Leu Asp Phe Leu Ile Thr Gly Leu Asn Gly Asp Pro Trp His
            340                 345                 350

Lys Ile Pro Ala Leu Asp Pro Glu Lys Leu Asn Val Phe Arg Thr Val
            355                 360                 365

Arg Glu Ile Thr Gly Tyr Leu Asn Ile Gln Ser Trp Pro Pro His Met
370                 375                 380

His Asn Phe Ser Val Phe Ser Asn Leu Thr Thr Ile Gly Gly Arg Ser
385                 390                 395                 400

Leu Tyr Asn Arg Gly Phe Ser Leu Leu Ile Met Lys Asn Leu Asn Val
                405                 410                 415

Thr Ser Leu Gly Phe Arg Ser Leu Lys Glu Ile Ser Ala Gly Arg Ile
            420                 425                 430

Tyr Ile Ser Ala Asn Arg Gln Leu Cys Tyr His His Ser Leu Asn Trp
            435                 440                 445

Thr Lys Val Leu Arg Gly Pro Thr Glu Glu Arg Leu Asp Ile Lys His
            450                 455                 460

Asn Arg Pro Arg Arg Asp Cys Val Ala Glu Gly Leu Ala Cys His Gln
465                 470                 475                 480

Leu Cys Ala Arg Gly His Cys Trp Gly Pro Gly Pro Thr Gln Cys Val
                485                 490                 495

Asn Cys Ser Gln Phe Leu Arg Gly Gln Glu Cys Val Glu Glu Cys Arg
            500                 505                 510

Val Leu Gln Gly Leu Pro Arg Glu Tyr Val Asn Ala Arg His Cys Leu
            515                 520                 525

Pro Cys His Pro Glu Cys Gln Pro Gln Asn Gly Ser Val Thr Cys Phe
            530                 535                 540

Gly Pro Glu Ala Asp Gln Cys Val Ala Cys Ala His Tyr Lys Asp Pro
545                 550                 555                 560

Pro Phe Cys Val Ala Arg Cys Pro Ser Gly Val Lys Pro Asp Leu Ser
                565                 570                 575

Tyr Met Pro Ile Trp Lys Phe Pro Asp Glu Glu Gly Ala Cys Gln Pro
            580                 585                 590

Cys Pro Ile Asn Cys Thr His Ser Cys Val Asp Leu Asp Asp Lys Gly
            595                 600                 605

Cys Pro Ala Glu Gln Arg Ala Ser Pro Leu Thr Ile Glu Gly Arg Met
610                 615                 620

Asp Asp Lys Thr His Thr Cys Pro Pro Cys Pro Ala Pro Glu Leu Leu
625                 630                 635                 640

Gly Gly Pro Ser Val Phe Leu Phe Pro Pro Lys Pro Lys Asp Thr Leu
                645                 650                 655

Met Ile Ser Arg Thr Pro Glu Val Thr Cys Val Val Val Asp Val Ser
            660                 665                 670

His Glu Asp Pro Glu Val Lys Phe Asn Trp Tyr Val Asp Gly Val Glu
            675                 680                 685

Val His Asn Ala Lys Thr Lys Pro Arg Glu Glu Gln Tyr Asn Ser Thr
            690                 695                 700

Tyr Arg Val Val Ser Val Leu Thr Val Leu His Gln Asp Trp Leu Asn
705                 710                 715                 720

Gly Lys Glu Tyr Lys Cys Lys Val Ser Asn Lys Ala Leu Pro Ala Pro
                725                 730                 735

Ile Glu Lys Thr Ile Ser Lys Ala Lys Gly Gln Pro Arg Glu Pro Gln
            740                 745                 750
```

```
Val Tyr Thr Leu Pro Pro Ser Arg Asp Glu Leu Thr Lys Asn Gln Val
            755                 760                 765
Ser Leu Thr Cys Leu Val Lys Gly Phe Tyr Pro Ser Asp Ile Ala Val
    770                 775                 780
Glu Trp Glu Ser Asn Gly Gln Pro Glu Asn Asn Tyr Lys Thr Thr Pro
785                 790                 795                 800
Pro Val Leu Asp Ser Asp Gly Ser Phe Phe Leu Tyr Ser Lys Leu Thr
                805                 810                 815
Val Asp Lys Ser Arg Trp Gln Gln Gly Asn Val Phe Ser Cys Ser Val
            820                 825                 830
Met His Glu Ala Leu His Asn His Tyr Thr Gln Lys Ser Leu Ser Leu
835                 840                 845

Ser Pro Gly
    850

<210> SEQ ID NO 84
<211> LENGTH: 406
<212> TYPE: DNA
<213> ORGANISM: Homo sapiens

<400> SEQUENCE: 84
gaagtccagt tgttggaatc aggcggaggt ctggtacagc ccggagggag cttgcgactg      60
tcgtgtgcgg cctccgggtt caccttctcg aattactgga tgcactgggt gcgccaagcc    120
ccagggaagg gtcttgagtg ggtggccttg atctcagggg gaggaggtaa cacatactac    180
gcggattccg tcaaaggacg gtttacaatt ccagagaca actcgaagaa cacgctctac     240
ctccagatga atagccttag gcggaggac acggcggtct attactgcgc gaaagataac    300
gagaagaatc tgtacacgtg gctcgactac tggggacagg gaaccctcgt gactgtatcg    360
tcagtttgat tactggggac agggtacact cgtgacggtg agcagc                   406

<210> SEQ ID NO 85
<211> LENGTH: 363
<212> TYPE: DNA
<213> ORGANISM: Homo sapiens

<400> SEQUENCE: 85
gaagtccagt tgttggaatc aggcggaggt ctggtacagc ccggagggag cttgcgactg      60
tcgtgtgcgg cctccgggtt caccttctcg acgtacgcga tgaattgggt gcgccaagcc    120
ccagggaagg gtcttgagtg ggtggccctc atttcctcgg gagggtcata caagtattac    180
gcggattccg tcaaaggacg gtttacaatt ccagagaca actcgaagaa cacgctctac     240
ctccagatga atagccttag gcggaggac acggcggtct attactgcgc aaaagacaac    300
ttcatcttgc tgaacagctg gtttgattac tggggacagg gaaccctcgt gactgtatcg    360
tca                                                                  363

<210> SEQ ID NO 86
<211> LENGTH: 363
<212> TYPE: DNA
<213> ORGANISM: Homo sapiens

<400> SEQUENCE: 86
caggtccagc ttgtacaatc aggagcagag gtcaagaaac ccggatcgtc agtcaaagta     60
agctgcaagg cgtccggcgg tacctttagc agctacgcga tctcgtgggt gaggcaggcg   120
ccaggacagg gtttggaatg gatgggaggg atcacggtgt acacggggac tacaaactat   180
```

```
gcacagaagt tccaagggcg ggtcactatc acagctgaca atccacgtc aacagcgtat    240 atggagctgt cgtccttgag atcggaagat accgccgtgt actattgtgc ccgagcgaac    300
gcaattacgg tgaatcgctc gctcgattac tggggacagg ggacgctcgt gacggtgagc    360
tcg                                                                  363

<210> SEQ ID NO 87
<211> LENGTH: 357
<212> TYPE: DNA
<213> ORGANISM: Homo sapiens

<400> SEQUENCE: 87
gaggtccagc tcgtggaaag cggtgggggt ttggtaaagc cgggaggctc gctgcggctt     60
tcatgtgcgg cctccggatt cacctttcgg aactactcca tgtcgtgggt cagacaggct    120
cccggtaaag ggttggaatg ggtcgcggca atctcatacg ggggtgccta taagtactac    180
gcggactcag taaagggaag gtttacaatt tcgcgagata atgccaaaaa ctccttgtat    240
ctccaaatga actcactgag agcagaggat actgccgtgt actattgcgc gagggaggtg    300
ggactcgatt atgctatgga ctactgggga caggggtacac tcgtgacggt gagcagc       357

<210> SEQ ID NO 88
<211> LENGTH: 363
<212> TYPE: DNA
<213> ORGANISM: Homo sapiens

<400> SEQUENCE: 88
gaggtccagc tcgtggaaag cggtgggggt ttggtaaagc cgggaggctc gctgcggctt     60
tcatgtgcgg cctccggatt cacctttttcg aactattcaa tgtcgtgggt cagacaggct   120
cccggtaaag ggttggaatg ggtggcaaac atcagcgcgg gtggagccta caaatactac    180
gcggactcag taaagggaag gtttacaatt tcgcgagata atgccaaaaa ctccttgtat    240
ctccaaatga actcactgag agcagaggat actgccgtgt actattgcgc tcgggacagg    300
ttcaagtatc tctggtcctg gtttgattac tggggacagg gtacactcgt gacggtgagc    360
agc                                                                  363

<210> SEQ ID NO 89
<211> LENGTH: 363
<212> TYPE: DNA
<213> ORGANISM: Homo sapiens

<400> SEQUENCE: 89
gaggtccagc tcgtggaaag cggtgggggt ttggtaaagc cgggaggctc gctgcggctt     60
tcatgtgcgg cctccggatt caccttttcc aattacgaga tgtcgtgggt cagacaggct    120
cccggtaaag ggttggaatg ggtggccacg atctcatatg atgggggata caagtactac    180
gcggactcag taaagggaag gtttacaatt tcgcgagata atgccaaaaa ctccttgtat    240
ctccaaatga actcactgag agcagaggat actgccgtgt actattgcgc gagagacaac    300
agctatctct tgtattactg gttcgactac tggggacagg gtacactcgt gacggtgagc    360
agc                                                                  363

<210> SEQ ID NO 90
<211> LENGTH: 135
<212> TYPE: PRT
<213> ORGANISM: Artificial Sequence
<220> FEATURE:
<223> OTHER INFORMATION: Synthetic Construct
```

<400> SEQUENCE: 90

Ala Gln Pro Val Leu His Gln Pro Pro Ala Met Ser Ser Ala Leu Gly
1               5                   10                  15

Thr Thr Ile Arg Leu Thr Cys Thr Leu Arg Asn Asp His Asp Ile Gly
            20                  25                  30

Val Tyr Ser Val Tyr Trp Tyr Gln Gln Arg Pro Gly His Pro Pro Arg
        35                  40                  45

Phe Leu Leu Arg Tyr Phe Ser Gln Ser Asp Lys Ser Gln Gly Pro Gln
    50                  55                  60

Val Pro Pro Arg Phe Ser Gly Ser Lys Asp Val Ala Arg Asn Arg Gly
65                  70                  75                  80

Tyr Leu Ser Ile Ser Glu Leu Gln Pro Glu Asp Glu Ala Met Tyr Tyr
                85                  90                  95

Cys Ala Met Gly Ala Arg Ser Ser Glu Lys Glu Arg Leu Pro Ser Lys
                100                 105                 110

Pro Gln Phe Trp Tyr Val Phe Gly Gly Gly Thr Gln Leu Thr Ile Leu
            115                 120                 125

Gly Gln Pro Lys Ser Asp Pro
    130                 135

<210> SEQ ID NO 91
<211> LENGTH: 104
<212> TYPE: PRT
<213> ORGANISM: Homo sapiens

<400> SEQUENCE: 91

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100

<210> SEQ ID NO 92
<211> LENGTH: 105
<212> TYPE: PRT
<213> ORGANISM: Homo sapiens

<400> SEQUENCE: 92

Gln Pro Val Leu Thr Gln Pro Ser Ser His Ser Ala Ser Ser Gly Ala
1               5                   10                  15

Ser Val Arg Leu Thr Cys Met Leu Ser Ser Gly Phe Ser Val Gly Asp
            20                  25                  30

Phe Trp Ile Arg Trp Tyr Gln Gln Lys Pro Gly Asn Pro Pro Arg Tyr
        35                  40                  45

Leu Leu Tyr Tyr His Ser Asp Ser Asn Lys Gly Gln Gly Ser Gly Val
    50                  55                  60

```
Pro Ser Arg Phe Ser Gly Asn Asp Ala Ser Ala Asn Ala Gly Ile
 65                  70                  75                  80

Leu Arg Ile Ser Gly Leu Gln Pro Glu Asp Glu Ala Asp Tyr Tyr Cys
                 85                  90                  95

Gly Thr Trp His Ser Asn Ser Lys Thr
            100                 105
```

<210> SEQ ID NO 93
<211> LENGTH: 104
<212> TYPE: PRT
<213> ORGANISM: Homo sapiens

<400> SEQUENCE: 93

```
Gln Pro Val Leu Thr Gln Pro Ser Ser Ala Ser Pro Gly Glu
 1               5                  10                  15

Ser Ala Arg Leu Thr Cys Thr Leu Pro Ser Asp Ile Asn Val Gly Ser
                 20                  25                  30

Tyr Asn Ile Tyr Trp Tyr Gln Gln Lys Pro Gly Ser Pro Pro Arg Tyr
             35                  40                  45

Leu Leu Tyr Tyr Tyr Ser Asp Ser Asp Lys Gly Gln Gly Ser Gly Val
 50                  55                  60

Pro Ser Arg Phe Ser Gly Ser Lys Asp Ala Ser Ala Asn Thr Gly Ile
 65                  70                  75                  80

Leu Leu Ile Ser Gly Leu Gln Ser Glu Asp Glu Ala Asp Tyr Tyr Cys
                 85                  90                  95

Met Ile Trp Pro Ser Asn Ala Ser
            100
```

<210> SEQ ID NO 94
<211> LENGTH: 113
<212> TYPE: PRT
<213> ORGANISM: Homo sapiens

<400> SEQUENCE: 94

```
Gly Thr Lys Leu Thr Val Leu Arg Gln Pro Lys Ala Ala Pro Ser Val
 1               5                  10                  15

Thr Leu Phe Pro Pro Ser Ser Glu Glu Leu Gln Ala Asn Lys Ala Thr
                 20                  25                  30

Leu Val Cys Leu Ile Ser Asp Phe Tyr Pro Gly Ala Val Thr Val Ala
             35                  40                  45

Trp Lys Ala Asp Gly Ser Pro Val Lys Ala Gly Val Glu Thr Thr Thr
 50                  55                  60

Pro Ser Lys Gln Ser Asn Asn Lys Tyr Ala Ala Ser Ser Tyr Leu Ser
 65                  70                  75                  80

Leu Thr Pro Glu Gln Trp Lys Ser His Lys Ser Tyr Ser Cys Gln Val
                 85                  90                  95

Thr His Glu Gly Ser Thr Val Glu Lys Thr Val Ala Pro Thr Glu Cys
            100                 105                 110

Ser
```

<210> SEQ ID NO 95
<211> LENGTH: 213
<212> TYPE: PRT
<213> ORGANISM: Homo sapiens

<400> SEQUENCE: 95

```
Met Arg Pro Gly Thr Gly Gln Gly Gly Leu Glu Ala Pro Gly Glu Pro
 1               5                  10                  15
```

Gly Pro Asn Leu Arg Gln Arg Trp Pro Leu Leu Leu Gly Leu Ala
            20                  25                  30

Val Val Thr His Gly Leu Leu Arg Pro Thr Ala Ala Ser Gln Ser Arg
            35                  40                  45

Ala Leu Gly Pro Gly Ala Pro Gly Gly Ser Ser Arg Ser Ser Leu Arg
 50                  55                  60

Ser Arg Trp Gly Arg Phe Leu Leu Gln Arg Gly Ser Trp Thr Gly Pro
 65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
            115                 120                 125

Asn Lys Ala Thr Leu Val Cys Leu Met Asn Asp Phe Tyr Pro Gly Ile
            130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Ser Tyr
            180                 185                 190

Ser Cys Gln Val Met His Glu Gly Ser Thr Val Glu Lys Thr Val Ala
            195                 200                 205

Pro Ala Glu Cys Ser
        210

<210> SEQ ID NO 96
<211> LENGTH: 213
<212> TYPE: PRT
<213> ORGANISM: Homo sapiens

<400> SEQUENCE: 96

Met Arg Pro Gly Thr Gly Gln Gly Gly Leu Glu Ala Pro Gly Glu Pro
 1               5                  10                  15

Gly Pro Asn Leu Arg Gln Arg Trp Pro Leu Leu Leu Gly Leu Ala
            20                  25                  30

Val Val Thr His Gly Leu Leu Arg Pro Thr Ala Ala Ser Gln Ser Arg
            35                  40                  45

Ala Leu Gly Pro Gly Ala Pro Gly Gly Ser Ser Arg Ser Ser Leu Arg
 50                  55                  60

Ser Arg Trp Gly Arg Phe Leu Leu Gln Arg Gly Ser Trp Thr Gly Pro
 65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
            100                 105                 110

Thr Pro Ser Val Thr Leu Phe Pro Pro Ser Ser Glu Glu Leu Gln Ala
            115                 120                 125

Asn Lys Ala Thr Leu Val Cys Leu Met Asn Asp Phe Tyr Pro Gly Ile
            130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser

```
            165                 170                 175
Ser Tyr Leu Ser Leu Thr Pro Glu Gln Trp Arg Ser Arg Arg Ser Tyr
        180                 185                 190

Ser Cys Gln Val Met His Glu Gly Ser Thr Val Glu Lys Thr Val Ala
        195                 200                 205

Pro Ala Glu Cys Ser
    210
```

<210> SEQ ID NO 97
<211> LENGTH: 107
<212> TYPE: PRT
<213> ORGANISM: Homo sapiens

<400> SEQUENCE: 97

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 98
<211> LENGTH: 145
<212> TYPE: PRT
<213> ORGANISM: Homo sapiens

<400> SEQUENCE: 98

```
Met Ser Trp Ala Pro Val Leu Leu Met Leu Phe Val Tyr Cys Thr Gly
 1               5                  10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Glu Arg Glu
        115                 120                 125

Arg Glu Trp Glu Glu Met Glu Pro Thr Ala Ala Arg Thr Arg Val
    130                 135                 140

Pro
145
```

<210> SEQ ID NO 99
<211> LENGTH: 121
<212> TYPE: PRT
<213> ORGANISM: Artificial Sequence
<220> FEATURE:
<223> OTHER INFORMATION: Synthetic Construct

<400> SEQUENCE: 99

Gly Ser Gln Ser Val Leu Thr Gln Pro Pro Ser Val Ser Ala Ala Pro
1               5                   10                  15
Gly Gln Lys Val Thr Ile Ser Cys Ser Gly Ser Ser Ser Asn Ile Gly
            20                  25                  30
Asn Asn Tyr Val Ser Trp Tyr Gln Gln Leu Pro Gly Thr Ala Pro Lys
        35                  40                  45
Leu Leu Ile Tyr Asp Asn Asn Lys Arg Pro Ser Gly Ile Pro Asp Arg
    50                  55                  60
Phe Ser Gly Ser Lys Ser Gly Thr Ser Ala Thr Leu Gly Ile Thr Gly
65                  70                  75                  80
Leu Gln Thr Gly Asp Glu Ala Asp Tyr Tyr Cys Gly Thr Trp Asp Ser
                85                  90                  95
Ser Leu Ser Ala Val Val Phe Gly Gly Gly Thr Lys Leu Thr Val Leu
            100                 105                 110
Arg Thr Ala Ser Gly Ala Ala Ala
        115                 120

<210> SEQ ID NO 100
<211> LENGTH: 213
<212> TYPE: PRT
<213> ORGANISM: Homo sapiens

<400> SEQUENCE: 100

Met Arg Pro Gly Thr Gly Gln Gly Gly Leu Glu Ala Pro Gly Glu Pro
1               5                   10                  15
Gly Pro Asn Leu Arg Gln Arg Trp Pro Leu Leu Leu Leu Gly Leu Ala
            20                  25                  30
Val Val Thr His Gly Leu Leu Arg Pro Thr Ala Ala Ser Gln Ser Arg
        35                  40                  45
Ala Leu Gly Pro Gly Ala Pro Gly Gly Ser Ser Arg Ser Ser Leu Arg
    50                  55                  60
Ser Arg Trp Gly Arg Phe Leu Leu Gln Arg Gly Ser Trp Thr Gly Pro
65                  70                  75                  80
Arg Cys Trp Pro Arg Gly Phe Gln Ser Lys His Asn Ser Val Thr His
                85                  90                  95
Val Phe Gly Ser Gly Thr Gln Leu Thr Val Leu Ser Gln Pro Lys Ala
            100                 105                 110
Thr Pro Ser Val Thr Leu Phe Pro Pro Ser Ser Glu Leu Gln Ala
        115                 120                 125
Asn Lys Ala Thr Leu Val Cys Leu Met Asn Asp Phe Tyr Pro Gly Ile
    130                 135                 140
Leu Thr Val Thr Trp Lys Ala Asp Gly Thr Pro Ile Thr Gln Gly Val
145                 150                 155                 160
Glu Met Thr Thr Pro Ser Lys Gln Ser Asn Asn Lys Tyr Ala Ala Ser
                165                 170                 175
Ser Tyr Leu Ser Leu Thr Pro Glu Gln Trp Arg Ser Arg Ser Tyr
            180                 185                 190
Ser Cys Gln Val Met His Glu Gly Ser Thr Val Glu Lys Thr Val Ala
        195                 200                 205

Pro Ala Glu Cys Ser
        210

<210> SEQ ID NO 101
<211> LENGTH: 111
<212> TYPE: PRT
<213> ORGANISM: Homo sapiens

<400> SEQUENCE: 101

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
            20                  25                  30

Asn Val Val Ser Trp Tyr Gln Gln His Pro Gly Lys Ala Pro Lys Leu
        35                  40                  45

Ile Ile Tyr Glu Val Ser Gln Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Cys Ser Tyr Ala Gly Ser
                85                  90                  95

Ser Ile Phe Val Ile Phe Gly Gly Thr Lys Val Thr Val Leu
            100                 105                 110

<210> SEQ ID NO 102
<211> LENGTH: 119
<212> TYPE: PRT
<213> ORGANISM: Homo sapiens

<400> SEQUENCE: 102

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Ser Gly Gly Trp Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser
        115

<210> SEQ ID NO 103
<211> LENGTH: 113
<212> TYPE: PRT
<213> ORGANISM: Homo sapiens

<400> SEQUENCE: 103

Asp Ile Glu Met Thr Gln Ser Pro Asp Ser Leu Ala Val Ser Leu Gly
 1               5                  10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Asn Gly Thr Lys Val Glu Ile
            100                 105                 110

Lys

<210> SEQ ID NO 104
<211> LENGTH: 117
<212> TYPE: PRT
<213> ORGANISM: Homo sapiens

<400> SEQUENCE: 104

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser
        115

<210> SEQ ID NO 105
<211> LENGTH: 6
<212> TYPE: PRT
<213> ORGANISM: Homo sapiens

<400> SEQUENCE: 105

Ser Thr Tyr Ala Met Asn
1               5

<210> SEQ ID NO 106
<211> LENGTH: 6
<212> TYPE: PRT
<213> ORGANISM: Homo sapiens

<400> SEQUENCE: 106

Ser Asn Tyr Gly Met His
1               5

<210> SEQ ID NO 107
<211> LENGTH: 6
<212> TYPE: PRT
<213> ORGANISM: Homo sapiens

<400> SEQUENCE: 107

Ser Asp Tyr Trp Met Asn
1               5

<210> SEQ ID NO 108
<211> LENGTH: 6
<212> TYPE: PRT
<213> ORGANISM: Homo sapiens

<400> SEQUENCE: 108

Ser Ser Tyr Ala Met His
1               5

<210> SEQ ID NO 109
<211> LENGTH: 6
<212> TYPE: PRT
<213> ORGANISM: Homo sapiens

<400> SEQUENCE: 109

Ser Asp Tyr Trp Met His
1               5

<210> SEQ ID NO 110
<211> LENGTH: 6
<212> TYPE: PRT
<213> ORGANISM: Homo sapiens

<400> SEQUENCE: 110

Ser Asp Tyr Trp Met His
1               5

<210> SEQ ID NO 111
<211> LENGTH: 6
<212> TYPE: PRT
<213> ORGANISM: Homo sapiens

<400> SEQUENCE: 111

Ser Ser Tyr Trp Met Asn
1               5

<210> SEQ ID NO 112
<211> LENGTH: 6
<212> TYPE: PRT
<213> ORGANISM: Homo sapiens

<400> SEQUENCE: 112

Ser Ser Tyr Trp Met His
1               5

<210> SEQ ID NO 113
<211> LENGTH: 6
<212> TYPE: PRT
<213> ORGANISM: Homo sapiens

<400> SEQUENCE: 113

Ser Asn Tyr Trp Met His
1               5

<210> SEQ ID NO 114
<211> LENGTH: 6
<212> TYPE: PRT
<213> ORGANISM: Homo sapiens

<400> SEQUENCE: 114

Ser Asn Tyr Trp Met Asn
1               5

<210> SEQ ID NO 115
<211> LENGTH: 6
<212> TYPE: PRT
<213> ORGANISM: Homo sapiens

<400> SEQUENCE: 115

Ser Ser Tyr Trp Met Ser
1               5

<210> SEQ ID NO 116
<211> LENGTH: 6
<212> TYPE: PRT
<213> ORGANISM: Homo sapiens

<400> SEQUENCE: 116

Ser Asp Tyr Ala Met His
1               5

<210> SEQ ID NO 117
<211> LENGTH: 13
<212> TYPE: PRT
<213> ORGANISM: Homo sapiens

<400> SEQUENCE: 117

Trp Val Ala Leu Ile Ser Ser Gly Gly Ser Tyr Lys Tyr
1               5                   10

<210> SEQ ID NO 118
<211> LENGTH: 13
<212> TYPE: PRT
<213> ORGANISM: Homo sapiens

<400> SEQUENCE: 118

Trp Val Ala Leu Ile Ser Ser Gly Gly Ala Tyr Thr Tyr
1               5                   10

<210> SEQ ID NO 119
<211> LENGTH: 13
<212> TYPE: PRT
<213> ORGANISM: Homo sapiens

<400> SEQUENCE: 119

Trp Val Ala Asn Ile Ser Gly Gly Gly Gly Tyr Ile Tyr
1               5                   10

<210> SEQ ID NO 120
<211> LENGTH: 13
<212> TYPE: PRT
<213> ORGANISM: Homo sapiens

<400> SEQUENCE: 120

Trp Val Ala Leu Ile Ser Asn Gly Ser Gly Tyr Lys Tyr
1               5                   10

<210> SEQ ID NO 121
<211> LENGTH: 13
<212> TYPE: PRT
<213> ORGANISM: Homo sapiens

<400> SEQUENCE: 121

Trp Val Ala Ala Ile Ser Ser Gly Ser Ser Tyr Thr Tyr
1               5                   10

```
<210> SEQ ID NO 122
<211> LENGTH: 13
<212> TYPE: PRT
<213> ORGANISM: Homo sapiens

<400> SEQUENCE: 122

Trp Val Ala Val Ile Ser Ser Asn Gly Arg Tyr Thr Tyr
1               5                   10

<210> SEQ ID NO 123
<211> LENGTH: 13
<212> TYPE: PRT
<213> ORGANISM: Homo sapiens

<400> SEQUENCE: 123

Trp Val Ala Leu Ile Ser Asn Gly Gly Gly Ile Lys Tyr
1               5                   10

<210> SEQ ID NO 124
<211> LENGTH: 13
<212> TYPE: PRT
<213> ORGANISM: Homo sapiens

<400> SEQUENCE: 124

Trp Val Ala Gly Ile Ser Gly Gly Gly Ala Tyr Thr Tyr
1               5                   10

<210> SEQ ID NO 125
<211> LENGTH: 13
<212> TYPE: PRT
<213> ORGANISM: Homo sapiens

<400> SEQUENCE: 125

Trp Val Ala Gly Ile Ser Asn Gly Gly Ser Ile Ile Tyr
1               5                   10

<210> SEQ ID NO 126
<211> LENGTH: 13
<212> TYPE: PRT
<213> ORGANISM: Homo sapiens

<400> SEQUENCE: 126

Trp Val Ala Ser Ile Ser Asn Gly Gly Arg Tyr Ile Tyr
1               5                   10

<210> SEQ ID NO 127
<211> LENGTH: 13
<212> TYPE: PRT
<213> ORGANISM: Homo sapiens

<400> SEQUENCE: 127

Trp Val Ala Leu Ile Ser Asn Asn Gly Thr Tyr Thr Tyr
1               5                   10

<210> SEQ ID NO 128
<211> LENGTH: 13
<212> TYPE: PRT
<213> ORGANISM: Homo sapiens

<400> SEQUENCE: 128

Trp Val Ala Asn Ile Ser Asn Gly Gly Thr Tyr Ile Tyr
1               5                   10

<210> SEQ ID NO 129
<211> LENGTH: 13
```

```
<212> TYPE: PRT
<213> ORGANISM: Homo sapiens

<400> SEQUENCE: 129

Trp Val Ala Ala Ile Ser Asn Gly Ser Ser Tyr Thr Tyr
1               5                   10

<210> SEQ ID NO 130
<211> LENGTH: 13
<212> TYPE: PRT
<213> ORGANISM: Homo sapiens

<400> SEQUENCE: 130

Trp Val Ala Gly Ile Ser Ser Gly Gly Ala Tyr Thr Tyr
1               5                   10

<210> SEQ ID NO 131
<211> LENGTH: 13
<212> TYPE: PRT
<213> ORGANISM: Homo sapiens

<400> SEQUENCE: 131

Trp Val Ala Leu Ile Ser Asn Asn Gly Ser Tyr Thr Tyr
1               5                   10

<210> SEQ ID NO 132
<211> LENGTH: 13
<212> TYPE: PRT
<213> ORGANISM: Homo sapiens

<400> SEQUENCE: 132

Trp Val Ala Val Ile Ser Gly Gly Gly Ala Tyr Lys Tyr
1               5                   10

<210> SEQ ID NO 133
<211> LENGTH: 13
<212> TYPE: PRT
<213> ORGANISM: Homo sapiens

<400> SEQUENCE: 133

Trp Val Ala Val Ile Ser Asn Asn Gly Arg Tyr Lys Tyr
1               5                   10

<210> SEQ ID NO 134
<211> LENGTH: 13
<212> TYPE: PRT
<213> ORGANISM: Homo sapiens

<400> SEQUENCE: 134

Trp Val Ala Gly Ile Ser Gly Gly Gly Arg Tyr Thr Tyr
1               5                   10

<210> SEQ ID NO 135
<211> LENGTH: 13
<212> TYPE: PRT
<213> ORGANISM: Homo sapiens

<400> SEQUENCE: 135

Trp Val Ala Asn Ile Ser Ser Gly Gly Ser Tyr Thr Tyr
1               5                   10

<210> SEQ ID NO 136
<211> LENGTH: 13
<212> TYPE: PRT
<213> ORGANISM: Homo sapiens
```

<400> SEQUENCE: 136

Trp Val Ser Ala Ile Ser Ser Gly Gly Gly Tyr Ile Tyr
1               5                   10

<210> SEQ ID NO 137
<211> LENGTH: 13
<212> TYPE: PRT
<213> ORGANISM: Mus musculus

<400> SEQUENCE: 137

Trp Val Ala Gly Ile Ser Asp Gly Gly Ala Tyr Thr Tyr
1               5                   10

<210> SEQ ID NO 138
<211> LENGTH: 13
<212> TYPE: PRT
<213> ORGANISM: Homo sapiens

<400> SEQUENCE: 138

Trp Val Ala Ala Ile Ser Ala Gly Ser Gly Tyr Ile Tyr
1               5                   10

<210> SEQ ID NO 139
<211> LENGTH: 13
<212> TYPE: PRT
<213> ORGANISM: Homo sapiens

<400> SEQUENCE: 139

Trp Val Ala Ala Ile Ser Asn Gly Gly Gly Tyr Lys Tyr
1               5                   10

<210> SEQ ID NO 140
<211> LENGTH: 13
<212> TYPE: PRT
<213> ORGANISM: Homo sapiens

<400> SEQUENCE: 140

Trp Val Ala Leu Ile Ser Asn Gly Gly Ser Ile Lys Tyr
1               5                   10

<210> SEQ ID NO 141
<211> LENGTH: 13
<212> TYPE: PRT
<213> ORGANISM: Homo sapiens

<400> SEQUENCE: 141

Trp Val Ala Gly Ile Ser Ser Gly Gly Ser Tyr Lys Tyr
1               5                   10

<210> SEQ ID NO 142
<211> LENGTH: 13
<212> TYPE: PRT
<213> ORGANISM: Homo sapiens

<400> SEQUENCE: 142

Trp Val Ala Leu Ile Ser Ser Gly Ser Thr Tyr Ile Ser
1               5                   10

<210> SEQ ID NO 143
<211> LENGTH: 13
<212> TYPE: PRT
<213> ORGANISM: Homo sapiens

<400> SEQUENCE: 143

-continued

Trp Val Ala Gly Ile Ser Tyr Gly Gly Thr Tyr Thr Tyr
1               5                   10

<210> SEQ ID NO 144
<211> LENGTH: 13
<212> TYPE: PRT
<213> ORGANISM: Homo sapiens

<400> SEQUENCE: 144

Trp Val Ala Leu Ile Ser Ser Gly Gly Arg Tyr Lys Tyr
1               5                   10

<210> SEQ ID NO 145
<211> LENGTH: 13
<212> TYPE: PRT
<213> ORGANISM: Homo sapiens

<400> SEQUENCE: 145

Trp Val Ala Ala Ile Ser Trp Gly Gly Ser Tyr Thr Tyr
1               5                   10

<210> SEQ ID NO 146
<211> LENGTH: 13
<212> TYPE: PRT
<213> ORGANISM: Homo sapiens

<400> SEQUENCE: 146

Trp Val Ala Leu Ile Ser Ser Gly Ser Thr Tyr Ile Ser
1               5                   10

<210> SEQ ID NO 147
<211> LENGTH: 13
<212> TYPE: PRT
<213> ORGANISM: Homo sapiens

<400> SEQUENCE: 147

Trp Val Ser Gly Ile Ser Asn Asn Gly Arg Tyr Lys Tyr
1               5                   10

<210> SEQ ID NO 148
<211> LENGTH: 13
<212> TYPE: PRT
<213> ORGANISM: Homo sapiens

<400> SEQUENCE: 148

Trp Val Ser Ala Ile Ser Ser Ser Gly Gly Tyr Lys Tyr
1               5                   10

<210> SEQ ID NO 149
<211> LENGTH: 13
<212> TYPE: PRT
<213> ORGANISM: Homo sapiens

<400> SEQUENCE: 149

Trp Val Ala Ala Ile Ser Ser Ser Gly Thr Tyr Thr Tyr
1               5                   10

<210> SEQ ID NO 150
<211> LENGTH: 13
<212> TYPE: PRT
<213> ORGANISM: Homo sapiens

<400> SEQUENCE: 150

Ala Lys Asp Asn Phe Ile Leu Leu Asn Ser Trp Phe Asp

```
<210> SEQ ID NO 151
<211> LENGTH: 6
<212> TYPE: PRT
<213> ORGANISM: Homo sapiens

<400> SEQUENCE: 151

Ser Asn Tyr Trp Met His
1               5

<210> SEQ ID NO 152
<211> LENGTH: 6
<212> TYPE: PRT
<213> ORGANISM: Homo sapiens

<400> SEQUENCE: 152

Ser Asp Tyr Trp Met His
1               5

<210> SEQ ID NO 153
<211> LENGTH: 6
<212> TYPE: PRT
<213> ORGANISM: Homo sapiens

<400> SEQUENCE: 153

Ser Ser Tyr Trp Met Asn
1               5

<210> SEQ ID NO 154
<211> LENGTH: 6
<212> TYPE: PRT
<213> ORGANISM: Homo sapiens

<400> SEQUENCE: 154

Ser Ser Tyr Trp Met His
1               5

<210> SEQ ID NO 155
<211> LENGTH: 6
<212> TYPE: PRT
<213> ORGANISM: Homo sapiens

<400> SEQUENCE: 155

Ser Ser Tyr Trp Met Ser
1               5

<210> SEQ ID NO 156
<211> LENGTH: 6
<212> TYPE: PRT
<213> ORGANISM: Homo sapiens

<400> SEQUENCE: 156

Ser Asn Tyr Trp Met His
1               5

<210> SEQ ID NO 157
<211> LENGTH: 13
<212> TYPE: PRT
<213> ORGANISM: Homo sapiens

<400> SEQUENCE: 157

Trp Val Ala Leu Ile Ser Gly Gly Gly Gly Asn Thr Tyr
1               5                   10
```

<210> SEQ ID NO 158
<211> LENGTH: 13
<212> TYPE: PRT
<213> ORGANISM: Homo sapiens

<400> SEQUENCE: 158

Trp Val Ala Leu Ile Ser Ser Gly Gly Gly Tyr Lys Tyr
1               5                   10

<210> SEQ ID NO 159
<211> LENGTH: 13
<212> TYPE: PRT
<213> ORGANISM: Homo sapiens

<400> SEQUENCE: 159

Trp Val Ala Leu Ile Ser Asn Gly Gly Gly Ile Lys Tyr
1               5                   10

<210> SEQ ID NO 160
<211> LENGTH: 13
<212> TYPE: PRT
<213> ORGANISM: Homo sapiens

<400> SEQUENCE: 160

Trp Val Ala Leu Ile Ser Ala Gly Gly Thr Tyr Lys Tyr
1               5                   10

<210> SEQ ID NO 161
<211> LENGTH: 13
<212> TYPE: PRT
<213> ORGANISM: Homo sapiens

<400> SEQUENCE: 161

Trp Val Ala Leu Ile Ser Asn Asn Gly Ala Tyr Ile Tyr
1               5                   10

<210> SEQ ID NO 162
<211> LENGTH: 13
<212> TYPE: PRT
<213> ORGANISM: Homo sapiens

<400> SEQUENCE: 162

Trp Val Ala Val Ile Ser Gly Gly Gly Ala Tyr Lys Tyr
1               5                   10

<210> SEQ ID NO 163
<211> LENGTH: 13
<212> TYPE: PRT
<213> ORGANISM: Homo sapiens

<400> SEQUENCE: 163

Trp Val Ala Leu Ile Ser Asn Gly Gly Ser Ile Lys Tyr
1               5                   10

<210> SEQ ID NO 164
<211> LENGTH: 13
<212> TYPE: PRT
<213> ORGANISM: Homo sapiens

<400> SEQUENCE: 164

Trp Val Ala Leu Ile Ser Asn Asn Gly Ala Tyr Thr Tyr
1               5                   10

<210> SEQ ID NO 165

<211> LENGTH: 13
<212> TYPE: PRT
<213> ORGANISM: Homo sapiens

<400> SEQUENCE: 165

Trp Val Ala Val Ile Ser Trp Gly Gly Ala Tyr Lys Tyr
1               5                   10

<210> SEQ ID NO 166
<211> LENGTH: 13
<212> TYPE: PRT
<213> ORGANISM: Homo sapiens

<400> SEQUENCE: 166

Trp Val Ser Leu Ile Ser Asn Gly Gly Gly Tyr Thr Tyr
1               5                   10

<210> SEQ ID NO 167
<211> LENGTH: 13
<212> TYPE: PRT
<213> ORGANISM: Homo sapiens

<400> SEQUENCE: 167

Trp Val Ala Val Ile Ser Ser Gly Gly Asn Tyr Ile Tyr
1               5                   10

<210> SEQ ID NO 168
<211> LENGTH: 13
<212> TYPE: PRT
<213> ORGANISM: Homo sapiens

<400> SEQUENCE: 168

Trp Val Ala Leu Ile Ser Ser Ser Gly Gly Ile Thr Tyr
1               5                   10

<210> SEQ ID NO 169
<211> LENGTH: 13
<212> TYPE: PRT
<213> ORGANISM: Homo sapiens

<400> SEQUENCE: 169

Trp Val Ala Leu Ile Ser Gly Gly Gly Gly Asn Ile Tyr
1               5                   10

<210> SEQ ID NO 170
<211> LENGTH: 13
<212> TYPE: PRT
<213> ORGANISM: Homo sapiens

<400> SEQUENCE: 170

Trp Val Ala Leu Ile Ser Ala Gly Gly Thr Ser Lys Tyr
1               5                   10

<210> SEQ ID NO 171
<211> LENGTH: 13
<212> TYPE: PRT
<213> ORGANISM: Homo sapiens

<400> SEQUENCE: 171

Trp Val Ala Leu Ile Ser Trp Gly Gly Gly Thr Lys Tyr
1               5                   10

<210> SEQ ID NO 172
<211> LENGTH: 13
<212> TYPE: PRT

<213> ORGANISM: Homo sapiens

<400> SEQUENCE: 172

Trp Val Ser Leu Ile Ser Ala Ser Gly Ser Ile Lys Tyr
1               5                   10

<210> SEQ ID NO 173
<211> LENGTH: 13
<212> TYPE: PRT
<213> ORGANISM: Homo sapiens

<400> SEQUENCE: 173

Trp Val Ala Leu Ile Ser Asn Gly Gly Gly Tyr Lys Tyr
1               5                   10

<210> SEQ ID NO 174
<211> LENGTH: 13
<212> TYPE: PRT
<213> ORGANISM: Homo sapiens

<400> SEQUENCE: 174

Trp Val Ala Leu Ile Ser Asn Asn Gly Thr Tyr Lys Tyr
1               5                   10

<210> SEQ ID NO 175
<211> LENGTH: 13
<212> TYPE: PRT
<213> ORGANISM: Homo sapiens

<400> SEQUENCE: 175

Trp Val Ala Leu Ile Ser Asn Asn Gly Thr Tyr Thr Tyr
1               5                   10

<210> SEQ ID NO 176
<211> LENGTH: 13
<212> TYPE: PRT
<213> ORGANISM: Homo sapiens

<400> SEQUENCE: 176

Trp Val Ala Val Ile Ser Asn Asn Gly Arg Tyr Lys Tyr
1               5                   10

<210> SEQ ID NO 177
<211> LENGTH: 13
<212> TYPE: PRT
<213> ORGANISM: Homo sapiens

<400> SEQUENCE: 177

Ala Lys Asp Asn Glu Lys Asn Leu Tyr Thr Trp Leu Asp
1               5                   10

<210> SEQ ID NO 178
<211> LENGTH: 6
<212> TYPE: PRT
<213> ORGANISM: Homo sapiens
<220> FEATURE:
<221> NAME/KEY: VARIANT
<222> LOCATION: (2)...(2)
<223> OTHER INFORMATION: Xaa = T, N, D or S
<220> FEATURE:
<221> NAME/KEY: VARIANT
<222> LOCATION: (4)...(4)
<223> OTHER INFORMATION: Xaa = A, G or W
<220> FEATURE:
<221> NAME/KEY: VARIANT
<222> LOCATION: (6)...(6)
<223> OTHER INFORMATION: Xaa = N, H, or S

<400> SEQUENCE: 178

Ser Xaa Tyr Xaa Met Xaa
 1               5

<210> SEQ ID NO 179
<211> LENGTH: 13
<212> TYPE: PRT
<213> ORGANISM: Homo sapiens
<220> FEATURE:
<221> NAME/KEY: VARIANT
<222> LOCATION: (3)...(3)
<223> OTHER INFORMATION: Xaa = A or S
<220> FEATURE:
<221> NAME/KEY: VARIANT
<222> LOCATION: (4)...(4)
<223> OTHER INFORMATION: Xaa = L, N, A, V, G or S
<220> FEATURE:
<221> NAME/KEY: VARIANT
<222> LOCATION: (7)...(7)
<223> OTHER INFORMATION: Xaa = S, G, N, D, A, Y or W
<220> FEATURE:
<221> NAME/KEY: VARIANT
<222> LOCATION: (8)...(8)
<223> OTHER INFORMATION: Xaa = G, N or S
<220> FEATURE:
<221> NAME/KEY: VARIANT
<222> LOCATION: (9)...(9)
<223> OTHER INFORMATION: Xaa = G or S
<220> FEATURE:
<221> NAME/KEY: VARIANT
<222> LOCATION: (10)...(10)
<223> OTHER INFORMATION: Xaa = S, A, G, R, A or T
<220> FEATURE:
<221> NAME/KEY: VARIANT
<222> LOCATION: (11)...(11)
<223> OTHER INFORMATION: Xaa = Y or I
<220> FEATURE:
<221> NAME/KEY: VARIANT
<222> LOCATION: (12)...(12)
<223> OTHER INFORMATION: Xaa = K, T or I
<220> FEATURE:
<221> NAME/KEY: VARIANT
<222> LOCATION: (13)...(13)
<223> OTHER INFORMATION: Xaa = Y or S

<400> SEQUENCE: 179

Trp Val Xaa Xaa Ile Ser Xaa Xaa Xaa Xaa Xaa Xaa
 1               5                  10

<210> SEQ ID NO 180
<211> LENGTH: 6
<212> TYPE: PRT
<213> ORGANISM: Homo sapiens
<220> FEATURE:
<221> NAME/KEY: VARIANT
<222> LOCATION: (2)...(2)
<223> OTHER INFORMATION: Xaa = N, D or S
<220> FEATURE:
<221> NAME/KEY: VARIANT
<222> LOCATION: (6)...(6)
<223> OTHER INFORMATION: Xaa = H, N or S

<400> SEQUENCE: 180

Ser Xaa Tyr Trp Met Xaa
 1               5

<210> SEQ ID NO 181
<211> LENGTH: 13
<212> TYPE: PRT
<213> ORGANISM: Homo sapiens
<220> FEATURE:
<221> NAME/KEY: VARIANT
<222> LOCATION: (3)...(3)
<223> OTHER INFORMATION: Xaa = A or S
<220> FEATURE:
<221> NAME/KEY: VARIANT
<222> LOCATION: (4)...(4)
<223> OTHER INFORMATION: Xaa = L or V
<220> FEATURE:
<221> NAME/KEY: VARIANT
<222> LOCATION: (7)...(7)
<223> OTHER INFORMATION: Xaa = G, S, N, A or W
<220> FEATURE:
<221> NAME/KEY: VARIANT
<222> LOCATION: (8)...(8)
<223> OTHER INFORMATION: Xaa = G, N or S
<220> FEATURE:
<221> NAME/KEY: VARIANT
<222> LOCATION: (10)...(10)
<223> OTHER INFORMATION: Xaa = G, T, A, S, N or R
<220> FEATURE:
<221> NAME/KEY: VARIANT
<222> LOCATION: (11)...(11)
<223> OTHER INFORMATION: Xaa = N, Y, I, S or T
<220> FEATURE:
<221> NAME/KEY: VARIANT
<222> LOCATION: (12)...(12)
<223> OTHER INFORMATION: Xaa = T, I or K

<400> SEQUENCE: 181

Trp Val Xaa Xaa Ile Ser Xaa Xaa Gly Xaa Xaa Xaa Tyr
1 5 10

<210> SEQ ID NO 182
<211> LENGTH: 1137
<212> TYPE: DNA
<213> ORGANISM: Homo sapiens

<400> SEQUENCE: 182
atggaaaccg acaccctgct gctgtgggtg ctcctgctgt gggtcccagg ctctaccggc 60
gaagtccagt tgttggaatc aggcggaggt ctggtacagc ccggagggag cttgcgactg 120
tcgtgtgcgg cctccgggtt caccttctca gactatggga tgaattgggt gcgccaagcc 180
ccagggaagg gtcttgagtg ggtggccgtc attaaggact cgggaaacta catctactac 240
gcggattccg tcaaaggacg gtttacaatt tccagagaca actcgaagaa cacgctctac 300
ctccagatga atagccttag ggcggaggac acggcggtct attactgcgc acgggaggac 360
aggatcagag gtgattatct ctccttggcg ctggattact ggggacaggg taccctggtg 420
accgtgagca gcgccagcac caagggcccc agcgtgttcc cccaaccggt gctgcaccag 480
cctcccgcca tgtcctctgc cctgggcacc accatccggc tgacctgtac cctgcggaac 540
gaccacgaca tcggcgtgta ctccgtgtac tggtatcagc agcggcctgg ccaccctcct 600
cggtttctgc tgcggtactt ctcccagtcc gacaagtccc agggccctca ggtgccccct 660
cggttctccg gctccaagga cgtggcccgg aaccggggct acctgtccat ctccgagctg 720
cagcctgagg acgaggccat gtactactgc gccatgggcg ccagatcctc cgtgacccac 780
gtgttcggct ctggcaccca gctgaccgtg ctgtcccagc ctaaggccac cccttccgtg 840
accctgttcc ctccttcctc cgaggaactg caggccaaca aggccaccct ggtctgcctg 900
atgaacgact tctaccctgg catcctgacc gtgacctgga aggccgacgg cacccctatc 960
acccagggcg tggagatgac caccccctcc aagcagtcca acaacaagta cgccgcctcc 1020
tcctacctgt ccctgacccc tgagcagtgg cggtcccggc ggtcctactc ttgccaggtc 1080
atgcacgagg gctccaccgt ggaaaagacc gtggcccctg ccgaatgttc ttgatga 1137

<210> SEQ ID NO 183
<211> LENGTH: 357
<212> TYPE: PRT
<213> ORGANISM: Homo sapiens

<400> SEQUENCE: 183

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Asn Trp Val Arg Gln Ala Pro Gly Lys Gly Leu Glu Trp Val
        35                  40                  45

Ala Val Ile Lys Asp Ser Gly Asn Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Arg Ile Arg Gly Asp Tyr Leu Ser Leu Ala Leu Asp
            100                 105                 110

Tyr Trp Gly Gln Gly Thr Leu Val Thr Val Ser Ser Ala Ser Thr Lys
        115                 120                 125

Gly Pro Ser Val Phe Pro Gln Pro Val Leu His Gln Pro Pro Ala Met
    130                 135                 140

Ser Ser Ala Leu Gly Thr Thr Ile Arg Leu Thr Cys Thr Leu Arg Asn
145                 150                 155                 160

Asp His Asp Ile Gly Val Tyr Ser Val Tyr Trp Tyr Gln Gln Arg Pro
                165                 170                 175

Gly His Pro Pro Arg Phe Leu Leu Arg Tyr Phe Ser Gln Ser Asp Lys
            180                 185                 190

Ser Gln Gly Pro Gln Val Pro Pro Arg Phe Ser Gly Ser Lys Asp Val
        195                 200                 205

Ala Arg Asn Arg Gly Tyr Leu Ser Ile Ser Glu Leu Gln Pro Glu Asp
    210                 215                 220

Glu Ala Met Tyr Tyr Cys Ala Met Gly Ala Arg Ser Ser Val Thr His
225                 230                 235                 240

Val Phe Gly Ser Gly Thr Gln Leu Thr Val Leu Ser Gln Pro Lys Ala
                245                 250                 255

Thr Pro Ser Val Thr Leu Phe Pro Pro Ser Ser Glu Glu Leu Gln Ala
            260                 265                 270

Asn Lys Ala Thr Leu Val Cys Leu Met Asn Asp Phe Tyr Pro Gly Ile
        275                 280                 285

Leu Thr Val Thr Trp Lys Ala Asp Gly Thr Pro Ile Thr Gln Gly Val
    290                 295                 300

Glu Met Thr Thr Pro Ser Lys Gln Ser Asn Asn Lys Tyr Ala Ala Ser
305                 310                 315                 320

Ser Tyr Leu Ser Leu Thr Pro Glu Gln Trp Arg Ser Arg Arg Ser Tyr
                325                 330                 335

Ser Cys Gln Val Met His Glu Gly Ser Thr Val Glu Lys Thr Val Ala
            340                 345                 350

Pro Ala Glu Cys Ser
        355

<210> SEQ ID NO 184
<211> LENGTH: 1797

<212> TYPE: DNA
<213> ORGANISM: Homo sapiens

<400> SEQUENCE: 184

```
atggaaaccg acaccctgct gctgtgggtg ctcctgctgt gggtcccagg ctctaccggc    60
cagcctgtgc tgcaccagcc tcccgccatg tcctctgccc tgggcaccac catccggctg   120
acctgtaccc tgcggaacga ccacgacatc ggcgtgtact ccgtgtactg gtatcagcag   180
cggcctggcc accctcctcg gtttctgctg cggtacttct cccagtccga caagtcccag   240
ggccctcagg tgccccctcg gttctccggc tccaaggacg tggcccggaa ccggggctac   300
ctgtccatct ccgagctgca gcctgaggac gaggccatgt actactgcgc catgggcgcc   360
agatcctccg tgacccacgt gttcggctct ggtacccagc tgaccgtgct gagccagccc   420
aaggccaccc ccagcgtgac cgaagtccaa ttgttggaat caggcggagg tctggtacag   480
cccggaggga gcttgcgact gtcgtgtgcg gcctccgggt tcaccttctc gaattactgg   540
atgcactggg tgcgccaagc cccagggaag ggtcttgagt gggtggcctt gatctcaggg   600
ggaggaggta acacatacta cgcggattcc gtcaaggacg gtttacaatt tccagagac   660
aactcgaaga cacgctcta cctccagatg aatagcctta gggcggagga cacggcggtc   720
tattactgcg cgaaagataa cgagaagaat ctgtacacgt ggctcgacta ctggggacag   780
ggaaccctcg tgactgtatc gtcagcctcc accaagggcc cttccgtgtt ccctctggcc   840
ccttccagca agtctacctc tggcggcacc gctgctctgg gctgcctggt caaggactac   900
ttccctgagc ctgtgacagt gtcctggaac tctggcgccc tgacctccgg cgtgcacacc   960
ttccctgccg tgctgcagtc ttctggcctg tactccctgt ccagcgtggt cacagtgcct  1020
agctcttccc tgggcaccca gacctacatc tgcaacgtga accacaagcc ttccaacacc  1080
aaggtggaca agaaggtgga gcctaagtcc tgcgacaaga cccacacctg tccccttgt  1140
cctgctcctg agctgctggg cggaccctcc gtgttcctgt ccctcctaa gcctaaggac  1200
accctgatga tctcccggac ccctgaagtg acctgtgtgg tggtggacgt gtcccacgag  1260
gatcctgaag tgaagtttaa ttggtacgtg gacggcgtgg aggtgcacaa cgccaagacc  1320
aagccacggg aggaacagta caactccacc taccgggtgg tgtccgtgct gacagtgctg  1380
caccaggact ggctgaacgg caaagaatac aagtgcaagg tgtccaacaa ggcccctgcct  1440
gcccctatcg aaaagaccat ctccaaggcc aagggccagc ctcgggaacc tcaggtgtac  1500
accctgcctc catctcggga cgaactgacc aagaaccagg tgtccctgac ctgtctcgtc  1560
aagggcttct atccttccga tatcgccgtg gagtgggagt ctaacggcca gcctgagaac  1620
aactacaaga ccacccctcc tgtgctggac tccgacggct ccttcttcct gtactccaag  1680
ctgaccgtgg acaagtcccg gtggcagcag ggcaacgtgt tctcctgctc cgtgatgcac  1740
gaggccctgc acaaccacta cacccagaag tccctgtccc tgtctcctgg ctgatga     1797
```

<210> SEQ ID NO 185
<211> LENGTH: 577
<212> TYPE: PRT
<213> ORGANISM: Homo sapiens

<400> SEQUENCE: 185

```
Gln Pro Val Leu His Gln Pro Pro Ala Met Ser Ser Ala Leu Gly Thr
 1               5                   10                  15

Thr Ile Arg Leu Thr Cys Thr Leu Arg Asn Asp His Asp Ile Gly Val
            20                  25                  30
```

```
Tyr Ser Val Tyr Trp Tyr Gln Gln Arg Pro Gly His Pro Pro Arg Phe
         35                  40                  45
Leu Leu Arg Tyr Phe Ser Gln Ser Asp Lys Ser Gln Gly Pro Gln Val
 50                  55                  60
Pro Pro Arg Phe Ser Gly Ser Lys Asp Val Ala Arg Asn Arg Gly Tyr
 65                  70                  75                  80
Leu Ser Ile Ser Glu Leu Gln Pro Glu Asp Glu Ala Met Tyr Tyr Cys
                 85                  90                  95
Ala Met Gly Ala Arg Ser Ser Val Thr His Val Phe Gly Ser Gly Thr
            100                 105                 110
Gln Leu Thr Val Leu Ser Gln Pro Lys Ala Thr Pro Ser Val Thr Glu
            115                 120                 125
Val Gln Leu Leu Glu Ser Gly Gly Leu Val Gln Pro Gly Gly Ser
130                 135                 140
Leu Arg Leu Ser Cys Ala Ala Ser Gly Phe Thr Phe Ser Asn Tyr Trp
145                 150                 155                 160
Met His Trp Val Arg Gln Ala Pro Gly Lys Gly Leu Glu Trp Val Ala
                165                 170                 175
Leu Ile Ser Gly Gly Gly Gly Asn Thr Tyr Tyr Ala Asp Ser Val Lys
            180                 185                 190
Gly Arg Phe Thr Ile Ser Arg Asp Asn Ser Lys Asn Thr Leu Tyr Leu
            195                 200                 205
Gln Met Asn Ser Leu Arg Ala Glu Asp Thr Ala Val Tyr Tyr Cys Ala
            210                 215                 220
Lys Asp Asn Glu Lys Asn Leu Tyr Thr Trp Leu Asp Tyr Trp Gly Gln
225                 230                 235                 240
Gly Thr Leu Val Thr Val Ser Ser Ala Ser Thr Lys Gly Pro Ser Val
                245                 250                 255
Phe Pro Leu Ala Pro Ser Ser Lys Ser Thr Ser Gly Gly Thr Ala Ala
                260                 265                 270
Leu Gly Cys Leu Val Lys Asp Tyr Phe Pro Glu Pro Val Thr Val Ser
            275                 280                 285
Trp Asn Ser Gly Ala Leu Thr Ser Gly Val His Thr Phe Pro Ala Val
290                 295                 300
Leu Gln Ser Ser Gly Leu Tyr Ser Leu Ser Ser Val Val Thr Val Pro
305                 310                 315                 320
Ser Ser Ser Leu Gly Thr Gln Thr Tyr Ile Cys Asn Val Asn His Lys
            325                 330                 335
Pro Ser Asn Thr Lys Val Asp Lys Lys Val Glu Pro Lys Ser Cys Asp
            340                 345                 350
Lys Thr His Thr Cys Pro Pro Cys Pro Ala Pro Glu Leu Leu Gly Gly
            355                 360                 365
Pro Ser Val Phe Leu Phe Pro Pro Lys Pro Lys Asp Thr Leu Met Ile
370                 375                 380
Ser Arg Thr Pro Glu Val Thr Cys Val Val Val Asp Val Ser His Glu
385                 390                 395                 400
Asp Pro Glu Val Lys Phe Asn Trp Tyr Val Asp Gly Val Glu Val His
                405                 410                 415
Asn Ala Lys Thr Lys Pro Arg Glu Glu Gln Tyr Asn Ser Thr Tyr Arg
            420                 425                 430
Val Val Ser Val Leu Thr Val Leu His Gln Asp Trp Leu Asn Gly Lys
            435                 440                 445
Glu Tyr Lys Cys Lys Val Ser Asn Lys Ala Leu Pro Ala Pro Ile Glu
```

450                 455                 460
Lys Thr Ile Ser Lys Ala Lys Gly Gln Pro Arg Glu Pro Gln Val Tyr
465                 470                 475                 480

Thr Leu Pro Pro Ser Arg Asp Glu Leu Thr Lys Asn Gln Val Ser Leu
                485                 490                 495

Thr Cys Leu Val Lys Gly Phe Tyr Pro Ser Asp Ile Ala Val Glu Trp
                500                 505                 510

Glu Ser Asn Gly Gln Pro Glu Asn Asn Tyr Lys Thr Thr Pro Pro Val
                515                 520                 525

Leu Asp Ser Asp Gly Ser Phe Phe Leu Tyr Ser Lys Leu Thr Val Asp
                530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly

<210> SEQ ID NO 186
<211> LENGTH: 450
<212> TYPE: PRT
<213> ORGANISM: Homo sapiens

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Ala Leu Ile Ser Ser Gly Gly Ser Tyr Lys Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
                210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met

```
                    245                 250                 255
Ile Ser Arg Thr Pro Glu Val Thr Cys Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 187
<211> LENGTH: 1350
<212> TYPE: DNA
<213> ORGANISM: Homo sapiens

<400> SEQUENCE: 187
gaagtccagt tgttggaatc aggcggaggt ctggtacagc cggagggag cttgcgactg      60 tcgtgtgcgg cctccgggtt caccttctcg acgtacgcga tgaattgggt gcgccaagcc    120
ccagggaagg tcttgagtg gtggccctc atttcctcgg gagggtcata caagtattac      180
gcggattccg tcaaaggacg gtttacaatt ccagagaca actcgaagaa cacgctctac     240
ctccagatga atagccttag gcggaggac acggcggtct attactgcgc aaaagacaac    300
ttcatcttgc tgaacagctg gtttgattac tggggacagg gaaccctcgt gactgtatcg   360
tcagcctcca ccaagggccc ttccgtgttc cctctggccc cttccagcaa gtctacctct    420
ggcggcaccg ctgctctggg ctgcctggtc aaggactact ccctgagcc tgtgacagtg    480 tcctggaact ctggcgccct gacctccggc gtgcacacct ccctgccgt gctgcagtct     540 tctggcctgt actccctgtc cagcgtggtc acagtgccta gctcttccct gggcacccag    600
acctacatct gcaacgtgaa ccacaagcct tccaacacca ggtggacaa gaaggtggag    660 cctaagtcct gcgacaagac ccacacctgt ccccccttgtc ctgctcctga gctgctgggc   720
ggaccctccg tgttcctgtt ccctcctaag cctaaggaca cctgatgat ctcccggacc    780 cctgaagtga cctgtgtggt ggtggacgtg tcccacgagg atcctgaagt gaagttcaat    840
tggtacgtgg acggcgtgga ggtgcacaac gccaagacca gccacgggga ggaacagtac    900
```

```
aactccacct accgggtggt gtccgtgctg acagtgctgc accaggactg gctgaacggc    960
aaagaataca agtgcaaggt gtccaacaag gccctgcctg ccctatcga aagaccatc    1020 tccaaggcca agggccagcc tcgggaacct caggtgtaca ccctgcctcc atctcgggac    1080
gaactgacca agaaccaggt gtccctgacc tgtctcgtca agggcttcta tccttccgat    1140
atcgccgtgg agtgggagtc taacggccag cctgagaaca actacaagac caccctcct    1200 gtgctggact ccgacggctc cttcttcctg tactccaagc tgaccgtgga caagtcccgg    1260
tggcagcagg gcaacgtgtt ctcctgctcc gtgatgcacg aggccctgca caaccactac    1320
acccagaagt ccctgtccct gtctcctggc                                     1350
```

<210> SEQ ID NO 188
<211> LENGTH: 450
<212> TYPE: PRT
<213> ORGANISM: Homo sapiens

<400> SEQUENCE: 188

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Trp Met His Val Arg Gln Ala Pro Gly Lys Gly Leu Glu Trp Val
         35                  40                  45

Ala Leu Ile Ser Gly Gly Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Glu Lys Asn Leu Tyr Thr Trp Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
               290                 295                 300

Arg Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly
    450

<210> SEQ ID NO 189
<211> LENGTH: 1356
<212> TYPE: DNA
<213> ORGANISM: Homo sapiens

<400> SEQUENCE: 189
gaagtccagt tgttggaatc aggcggaggt ctggtacagc ccggagggag cttgcgactg      60
tcgtgtgcgg cctccgggtt caccttctcg aattactgga tgcactgggt gcgccaagcc    120
ccagggaagg gtcttgagtg ggtggccttg atctcagggg aggaggtaa cacatactac      180 gcggattccg tcaaaggacg gtttacaatt tccagagaca actcgaagaa cacgctctac    240
ctccagatga atagccttag gcggaggac acggcgtgtct attactgcgc gaaagataac      300
gagaagaatc tgtacacgtg gctcgactac tggggacagg gaaccctcgt gactgtatcg    360
tcagcctcca ccaagggccc ttccgtgttc cctctggccc cttccagcaa gtctacctct    420
ggcggcaccg ctgctctggg ctgcctggtc aaggactact ccctgagcc tgtgacagtg      480 tcctggaact ctggcgccct gacctccggc gtgcacacct ccctgccgt gctgcagtct    540 tctggcctgt actccctgtc cagcgtggtc acagtgccta gctcttccct gggcacccag    600
acctacatct gcaacgtgaa ccacaagcct tccaacacca aggtggacaa gaaggtggag    660
cctaagtcct gcgacaagac ccacacctgt cccccttgtc ctgctcctga gctgctgggc    720 ggacccctccg tgttcctgtt ccctcctaag cctaaggaca ccctgatgat ctcccggacc    780
cctgaagtga cctgtgtggt ggtggacgtg tcccacgagg atcctgaagt gaagttcaat    840
tggtacgtgg acggcgtgga ggtgcacaac gccaagacaa gccacgggga ggaacagtac    900
aactccacct accgggtggt gtccgtgctg acagtgctgc accaggactg gctgaacggc    960
aaagaataca agtgcaaggt gtccaacaag gccctgcctg ccctatcga aagaccatc    1020 tccaaggcca agggcagcc tcgggaacct caggtgtaca ccctgcctcc atctcgggac    1080
gaactgacca gaaccaggt gtccctgacc tgtctcgtca agggcttcta tccttccgat    1140
atcgccgtgg agtgggagtc taacggccag cctgagaaca actacaagac cacccctcct    1200
```

```
gtgctggact ccgacggctc cttcttcctg tactccaagc tgaccgtgga caagtcccgg    1260
tggcagcagg gcaacgtgtt ctcctgctcc gtgatgcacg aggccctgca caaccactac    1320
acccagaagt ccctgtccct gtctcctggc tgatga                              1356
```

```
<210> SEQ ID NO 190
<211> LENGTH: 10
<212> TYPE: PRT
<213> ORGANISM: Homo sapiens
<220> FEATURE:
<221> NAME/KEY: VARIANT
<222> LOCATION: (1)...(1)
<223> OTHER INFORMATION: Xaa = D or E
<220> FEATURE:
<221> NAME/KEY: VARIANT
<222> LOCATION: (2)...(2)
<223> OTHER INFORMATION: Xaa = I, V or L
<220> FEATURE:
<221> NAME/KEY: VARIANT
<222> LOCATION: (3)...(3)
<223> OTHER INFORMATION: Xaa = G or A
<220> FEATURE:
<221> NAME/KEY: VARIANT
<222> LOCATION: (4)...(4)
<223> OTHER INFORMATION: Xaa = V, I or L
<220> FEATURE:
<221> NAME/KEY: VARIANT
<222> LOCATION: (5)...(5)
<223> OTHER INFORMATION: Xaa = Y or F
<220> FEATURE:
<221> NAME/KEY: VARIANT
<222> LOCATION: (6)...(6)
<223> OTHER INFORMATION: Xaa = S or T
<220> FEATURE:
<221> NAME/KEY: VARIANT
<222> LOCATION: (7)...(7)
<223> OTHER INFORMATION: Xaa = V, I or L
<220> FEATURE:
<221> NAME/KEY: VARIANT
<222> LOCATION: (8)...(8)
<223> OTHER INFORMATION: Xaa = Y or F
<220> FEATURE:
<221> NAME/KEY: VARIANT
<222> LOCATION: (10)...(10)
<223> OTHER INFORMATION: Xaa = Y or F

<400> SEQUENCE: 190

Xaa Xaa Xaa Xaa Xaa Xaa Xaa Xaa Trp Xaa
 1               5                  10

<210> SEQ ID NO 191
<211> LENGTH: 13
<212> TYPE: PRT
<213> ORGANISM: Homo sapiens
<220> FEATURE:
<221> NAME/KEY: VARIANT
<222> LOCATION: (1)...(2)
<223> OTHER INFORMATION: Xaa = L, I or V
<220> FEATURE:
<221> NAME/KEY: VARIANT
<222> LOCATION: (3)...(3)
<223> OTHER INFORMATION: Xaa = R or K
<220> FEATURE:
<221> NAME/KEY: VARIANT
<222> LOCATION: (4)...(4)
<223> OTHER INFORMATION: Xaa = Y or F
<220> FEATURE:
<221> NAME/KEY: VARIANT
<222> LOCATION: (5)...(5)
<223> OTHER INFORMATION: Xaa = F or Y
<220> FEATURE:
<221> NAME/KEY: VARIANT
<222> LOCATION: (6)...(6)
<223> OTHER INFORMATION: Xaa = S or T
```

```
<220> FEATURE:
<221> NAME/KEY: VARIANT
<222> LOCATION: (7)...(7)
<223> OTHER INFORMATION: Xaa = Q or N
<220> FEATURE:
<221> NAME/KEY: VARIANT
<222> LOCATION: (8)...(8)
<223> OTHER INFORMATION: Xaa = S or T
<220> FEATURE:
<221> NAME/KEY: VARIANT
<222> LOCATION: (9)...(9)
<223> OTHER INFORMATION: Xaa = D or E
<220> FEATURE:
<221> NAME/KEY: VARIANT
<222> LOCATION: (10)...(10)
<223> OTHER INFORMATION: Xaa = K or R
<220> FEATURE:
<221> NAME/KEY: VARIANT
<222> LOCATION: (11)...(11)
<223> OTHER INFORMATION: Xaa = S or T
<220> FEATURE:
<221> NAME/KEY: VARIANT
<222> LOCATION: (12)...(12)
<223> OTHER INFORMATION: Xaa = Q or N
<220> FEATURE:
<221> NAME/KEY: VARIANT
<222> LOCATION: (13)...(13)
<223> OTHER INFORMATION: Xaa = G or A

<400> SEQUENCE: 191

Xaa Xaa Xaa Xaa Xaa Xaa Xaa Xaa Xaa Xaa Xaa Xaa Xaa
1               5                   10

<210> SEQ ID NO 192
<211> LENGTH: 10
<212> TYPE: PRT
<213> ORGANISM: Homo sapiens
<220> FEATURE:
<221> NAME/KEY: VARIANT
<222> LOCATION: (1)...(1)
<223> OTHER INFORMATION: Xaa = A or G
<220> FEATURE:
<221> NAME/KEY: VARIANT
<222> LOCATION: (2)...(2)
<223> OTHER INFORMATION: Xaa = M or L
<220> FEATURE:
<221> NAME/KEY: VARIANT
<222> LOCATION: (3)...(3)
<223> OTHER INFORMATION: Xaa = G or A
<220> FEATURE:
<221> NAME/KEY: VARIANT
<222> LOCATION: (4)...(4)
<223> OTHER INFORMATION: Xaa = A or G
<220> FEATURE:
<221> NAME/KEY: VARIANT
<222> LOCATION: (5)...(5)
<223> OTHER INFORMATION: Xaa = R or K
<220> FEATURE:
<221> NAME/KEY: VARIANT
<222> LOCATION: 6, 7
<223> OTHER INFORMATION: Xaa = S or T
<220> FEATURE:
<221> NAME/KEY: VARIANT
<222> LOCATION: (8)...(8)
<223> OTHER INFORMATION: Xaa = V, I or L
<220> FEATURE:
<221> NAME/KEY: VARIANT
<222> LOCATION: (9)...(9)
<223> OTHER INFORMATION: Xaa = T or S

<400> SEQUENCE: 192

Xaa Xaa Xaa Xaa Xaa Xaa Xaa Xaa Xaa His
1               5                   10

<210> SEQ ID NO 193
```

<211> LENGTH: 109
<212> TYPE: PRT
<213> ORGANISM: Homo sapiens

<400> SEQUENCE: 193

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Leu Ile Ser Ser Gly Gly Ala Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 194
<211> LENGTH: 109
<212> TYPE: PRT
<213> ORGANISM: Homo sapiens

<400> SEQUENCE: 194

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Asn Ile Ser Gly Gly Gly Tyr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 195
<211> LENGTH: 109
<212> TYPE: PRT
<213> ORGANISM: Homo sapiens

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Leu Ile Ser Asn Gly Ser Gly Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
            100                 105

<210> SEQ ID NO 196
<211> LENGTH: 109
<212> TYPE: PRT
<213> ORGANISM: Homo sapiens

<400> SEQUENCE: 196

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Ala Ile Ser Ser Gly Ser Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 197
<211> LENGTH: 109
<212> TYPE: PRT
<213> ORGANISM: Homo sapiens

<400> SEQUENCE: 197

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Val Ile Ser Ser Asn Gly Arg Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 198
<211> LENGTH: 109
<212> TYPE: PRT
<213> ORGANISM: Homo sapiens

<400> SEQUENCE: 198

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
```

```
            35                  40                  45
Ala Leu Ile Ser Asn Gly Gly Ile Lys Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Asn Phe Ile Leu Leu Asn Ser Trp Phe Asp
            100                 105
```

<210> SEQ ID NO 199
<211> LENGTH: 109
<212> TYPE: PRT
<213> ORGANISM: Homo sapiens

<400> SEQUENCE: 199

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Trp Met His Trp Val Arg Gln Ala Pro Gly Lys Gly Leu Glu Trp Val
         35                  40                  45
Ala Gly Ile Ser Gly Gly Gly Ala Tyr Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Asn Phe Ile Leu Leu Asn Ser Trp Phe Asp
            100                 105
```

<210> SEQ ID NO 200
<211> LENGTH: 109
<212> TYPE: PRT
<213> ORGANISM: Homo sapiens

<400> SEQUENCE: 200

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Trp Met His Trp Val Arg Gln Ala Pro Gly Lys Gly Leu Glu Trp Val
         35                  40                  45
Ala Gly Ile Ser Asn Gly Gly Ser Ile Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Asn Phe Ile Leu Leu Asn Ser Trp Phe Asp
            100                 105
```

<210> SEQ ID NO 201
<211> LENGTH: 109
<212> TYPE: PRT
<213> ORGANISM: Homo sapiens

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Ser Ile Ser Asn Gly Gly Arg Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 202
<211> LENGTH: 109
<212> TYPE: PRT
<213> ORGANISM: Homo sapiens

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Leu Ile Ser Asn Asn Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 203
<211> LENGTH: 109
<212> TYPE: PRT
<213> ORGANISM: Homo sapiens

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Asn Ile Ser Asn Gly Gly Thr Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 204
<211> LENGTH: 109
<212> TYPE: PRT
<213> ORGANISM: Homo sapiens

<400> SEQUENCE: 204

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Ala Ile Ser Asn Gly Ser Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 205
<211> LENGTH: 109
<212> TYPE: PRT
<213> ORGANISM: Homo sapiens

<400> SEQUENCE: 205

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Gly Ile Ser Ser Gly Gly Ala Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 206
<211> LENGTH: 109
<212> TYPE: PRT
<213> ORGANISM: Homo sapiens

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Leu Ile Ser Asn Asn Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Asn Phe Ile Leu Leu Asn Ser Trp Phe Asp
            100                 105

<210> SEQ ID NO 207
<211> LENGTH: 109
<212> TYPE: PRT
<213> ORGANISM: Homo sapiens

<400> SEQUENCE: 207

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Val Ile Ser Gly Gly Ala Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Asn Phe Ile Leu Leu Asn Ser Trp Phe Asp
            100                 105

<210> SEQ ID NO 208
<211> LENGTH: 109
<212> TYPE: PRT
<213> ORGANISM: Homo sapiens

<400> SEQUENCE: 208

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Val Ile Ser Asn Asn Gly Arg Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Asn Phe Ile Leu Leu Asn Ser Trp Phe Asp
            100                 105

<210> SEQ ID NO 209
<211> LENGTH: 109
<212> TYPE: PRT
<213> ORGANISM: Homo sapiens

<400> SEQUENCE: 209

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
            20                  25                  30
Trp Met His Trp Val Arg Gln Ala Pro Gly Lys Gly Leu Glu Trp Val
         35                  40                  45

Ala Gly Ile Ser Gly Gly Gly Arg Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
                100                 105
```

<210> SEQ ID NO 210
<211> LENGTH: 109
<212> TYPE: PRT
<213> ORGANISM: Homo sapiens

<400> SEQUENCE: 210

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Trp Met Asn Trp Val Arg Gln Ala Pro Gly Lys Gly Leu Glu Trp Val
         35                  40                  45

Ala Asn Ile Ser Ser Gly Gly Ser Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
                100                 105
```

<210> SEQ ID NO 211
<211> LENGTH: 109
<212> TYPE: PRT
<213> ORGANISM: Homo sapiens

<400> SEQUENCE: 211

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met His Trp Val Arg Gln Ala Pro Gly Lys Gly Leu Glu Trp Val
         35                  40                  45

Ser Ala Ile Ser Ser Gly Gly Gly Tyr Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
                100                 105
```

<210> SEQ ID NO 212
<211> LENGTH: 109
<212> TYPE: PRT

<213> ORGANISM: Homo sapiens

<400> SEQUENCE: 212

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Gly Ile Ser Asp Gly Gly Ala Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 213
<211> LENGTH: 109
<212> TYPE: PRT
<213> ORGANISM: Homo sapiens

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Ala Ile Ser Ala Gly Ser Gly Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 214
<211> LENGTH: 109
<212> TYPE: PRT
<213> ORGANISM: Homo sapiens

<400> SEQUENCE: 214

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Ala Ile Ser Asn Gly Gly Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Asp Asn Phe Ile Leu Leu Asn Ser Trp Phe Asp
            100                 105
```

<210> SEQ ID NO 215
<211> LENGTH: 109
<212> TYPE: PRT
<213> ORGANISM: Homo sapiens

<400> SEQUENCE: 215

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Leu Ile Ser Asn Gly Gly Ser Ile Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
            100                 105
```

<210> SEQ ID NO 216
<211> LENGTH: 109
<212> TYPE: PRT
<213> ORGANISM: Homo sapiens

<400> SEQUENCE: 216

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met His Trp Val Arg Gln Ala Pro Gly Lys Gly Leu Glu Trp Val
         35                  40                  45

Ala Gly Ile Ser Ser Gly Gly Ser Tyr Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
            100                 105
```

<210> SEQ ID NO 217
<211> LENGTH: 109
<212> TYPE: PRT
<213> ORGANISM: Homo sapiens

<400> SEQUENCE: 217

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Trp Met His Trp Val Arg Gln Ala Pro Gly Lys Gly Leu Glu Trp Val
         35                  40                  45
```

```
Ala Leu Ile Ser Ser Gly Ser Thr Tyr Ile Ser Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
            100                 105
```

<210> SEQ ID NO 218
<211> LENGTH: 109
<212> TYPE: PRT
<213> ORGANISM: Homo sapiens

<400> SEQUENCE: 218

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met His Trp Val Arg Gln Ala Pro Gly Lys Gly Leu Glu Trp Val
             35                  40                  45

Ala Gly Ile Ser Tyr Gly Gly Thr Tyr Thr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
            100                 105
```

<210> SEQ ID NO 219
<211> LENGTH: 109
<212> TYPE: PRT
<213> ORGANISM: Homo sapiens

<400> SEQUENCE: 219

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Ala Met His Trp Val Arg Gln Ala Pro Gly Lys Gly Leu Glu Trp Val
             35                  40                  45

Ala Leu Ile Ser Ser Gly Gly Arg Tyr Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
            100                 105
```

<210> SEQ ID NO 220
<211> LENGTH: 109
<212> TYPE: PRT
<213> ORGANISM: Homo sapiens

<400> SEQUENCE: 220

```
Glu Val Gln Leu Leu Glu Ser Gly Gly Gly Leu Val Gln Pro Gly Gly
```

```
                1               5                   10                  15
            Ser Leu Arg Leu Ser Cys Ala Ala Ser Gly Phe Thr Phe Ser Ser Tyr
                        20                  25                  30

Trp Met His Trp Val Arg Gln Ala Pro Gly Lys Gly Leu Glu Trp Val
                        35                  40                  45

Ala Gly Ile Ser Ser Gly Gly Ser Tyr Lys Tyr Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Lys Asp Asn Phe Ile Leu Leu Asn Ser Trp Phe Asp
                        100                 105

<210> SEQ ID NO 221
<211> LENGTH: 109
<212> TYPE: PRT
<213> ORGANISM: Homo sapiens

<400> SEQUENCE: 221

Glu Val Gln Leu Leu Glu Ser Gly Gly Gly Leu Val Gln Pro Gly Gly
             1               5                   10                  15

Ser Leu Arg Leu Ser Cys Ala Ala Ser Gly Phe Thr Phe Ser Asp Tyr
                        20                  25                  30

Trp Met His Trp Val Arg Gln Ala Pro Gly Lys Gly Leu Glu Trp Val
                        35                  40                  45

Ala Ala Ile Ser Trp Gly Gly Ser Tyr Thr Tyr Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Lys Asp Asn Phe Ile Leu Leu Asn Ser Trp Phe Asp
                        100                 105

<210> SEQ ID NO 222
<211> LENGTH: 109
<212> TYPE: PRT
<213> ORGANISM: Homo sapiens

<400> SEQUENCE: 222

Glu Val Gln Leu Leu Glu Ser Gly Gly Gly Leu Val Gln Pro Gly Gly
             1               5                   10                  15

Ser Leu Arg Leu Ser Cys Ala Ala Ser Gly Phe Thr Phe Ser Asn Tyr
                        20                  25                  30

Trp Met His Trp Val Arg Gln Ala Pro Gly Lys Gly Leu Glu Trp Val
                        35                  40                  45

Ala Leu Ile Ser Ser Gly Ser Thr Tyr Ile Ser Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Lys Asp Asn Phe Ile Leu Leu Asn Ser Trp Leu Asp
                        100                 105
```

<210> SEQ ID NO 223
<211> LENGTH: 109
<212> TYPE: PRT
<213> ORGANISM: Homo sapiens

<400> SEQUENCE: 223

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Gly Ile Ser Asn Asn Gly Arg Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 224
<211> LENGTH: 109
<212> TYPE: PRT
<213> ORGANISM: Homo sapiens

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ser Ala Ile Ser Ser Ser Gly Gly Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 225
<211> LENGTH: 109
<212> TYPE: PRT
<213> ORGANISM: Homo sapiens

<400> SEQUENCE: 225

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Ala Ile Ser Ser Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 226
<211> LENGTH: 109
<212> TYPE: PRT
<213> ORGANISM: Homo sapiens

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Ala Ile Ser Asn Asn Ser Arg Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 227
<211> LENGTH: 109
<212> TYPE: PRT
<213> ORGANISM: Homo sapiens

<400> SEQUENCE: 227

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Ser Ile Ser Gly Gly Gly Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 228
<211> LENGTH: 109
<212> TYPE: PRT
<213> ORGANISM: Homo sapiens

<400> SEQUENCE: 228

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

Glu Met His Trp Val Arg Gln Ala Pro Gly Lys Gly Leu Glu Trp Val
            35                  40                  45

Ala Leu Ile Ser Asn Gly Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
            100                 105

<210> SEQ ID NO 229
<211> LENGTH: 109
<212> TYPE: PRT
<213> ORGANISM: Homo sapiens

<400> SEQUENCE: 229

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met His Trp Val Arg Gln Ala Pro Gly Lys Gly Leu Glu Trp Val
         35                  40                  45

Ala Leu Ile Ser Ala Gly Ser Ala Thr Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
            100                 105

<210> SEQ ID NO 230
<211> LENGTH: 109
<212> TYPE: PRT
<213> ORGANISM: Homo sapiens

<400> SEQUENCE: 230

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met His Trp Val Arg Gln Ala Pro Gly Lys Gly Leu Glu Trp Val
         35                  40                  45

Ala Val Ile Ser Ser Asn Ser Ser Tyr Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Phe Ile Leu Leu Asn Ser Trp Phe Asp
            100                 105

<210> SEQ ID NO 231
<211> LENGTH: 109
<212> TYPE: PRT
<213> ORGANISM: Homo sapiens

```
<400> SEQUENCE: 231

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Ala Ile Ser Asn Ser Gly Ala Tyr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 232
<211> LENGTH: 109
<212> TYPE: PRT
<213> ORGANISM: Homo sapiens

<400> SEQUENCE: 232

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met His Trp Val Arg Gln Ala Pro Gly Lys Gly Leu Glu Trp Val
        35                  40                  45

Ala Leu Ile Ser Tyr Gly Gly Ala Asn Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 233
<211> LENGTH: 109
<212> TYPE: PRT
<213> ORGANISM: Homo sapiens

<400> SEQUENCE: 233

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met His Trp Val Arg Gln Ala Pro Gly Lys Gly Leu Glu Trp Val
        35                  40                  45

Ala Leu Ile Ser Asn Gly Gly Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
```

<210> SEQ ID NO 234
<211> LENGTH: 109
<212> TYPE: PRT
<213> ORGANISM: Homo sapiens

<400> SEQUENCE: 234

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Thr Ile Ser Tyr Asn Gly Ala Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 235
<211> LENGTH: 109
<212> TYPE: PRT
<213> ORGANISM: Homo sapiens

<400> SEQUENCE: 235

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Val Ile Ser Asp Gly Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 236
<211> LENGTH: 109
<212> TYPE: PRT
<213> ORGANISM: Homo sapiens

<400> SEQUENCE: 236

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ser Ala Ile Ser Tyr Asn Gly Ala Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 237
<211> LENGTH: 109
<212> TYPE: PRT
<213> ORGANISM: Homo sapiens

<400> SEQUENCE: 237

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Leu Ile Ser Ser Gly Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 238
<211> LENGTH: 109
<212> TYPE: PRT
<213> ORGANISM: Homo sapiens

<400> SEQUENCE: 238

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Leu Ile Ser Asn Gly Ser Ala Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 239
<211> LENGTH: 109
<212> TYPE: PRT
<213> ORGANISM: Homo sapiens

<400> SEQUENCE: 239

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Asn Ile Ser Ala Gly Gly Ala Ile Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 240
<211> LENGTH: 109
<212> TYPE: PRT
<213> ORGANISM: Homo sapiens

<400> SEQUENCE: 240

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Ala Val Ile Ser Asn Gly Gly Gly Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 241
<211> LENGTH: 109
<212> TYPE: PRT
<213> ORGANISM: Homo sapiens

<400> SEQUENCE: 241

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Val Ile Ser Tyr Asn Gly Ala Tyr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Asn Phe Ile Leu Leu Asn Ser Trp Phe Asp
            100                 105

<210> SEQ ID NO 242
<211> LENGTH: 109

```
<212> TYPE: PRT
<213> ORGANISM: Homo sapiens

<400> SEQUENCE: 242

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Leu Ile Ser Ser Gly Gly Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 243
<211> LENGTH: 109
<212> TYPE: PRT
<213> ORGANISM: Homo sapiens

<400> SEQUENCE: 243

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Leu Ile Ser Asn Gly Gly Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 244
<211> LENGTH: 109
<212> TYPE: PRT
<213> ORGANISM: Homo sapiens

<400> SEQUENCE: 244

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Leu Ile Ser Ala Gly Gly Thr Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                        85                  90                  95

Ala Lys Asp Asn Glu Lys Asn Leu Tyr Thr Trp Leu Asp
            100                 105

<210> SEQ ID NO 245
<211> LENGTH: 109
<212> TYPE: PRT
<213> ORGANISM: Homo sapiens

<400> SEQUENCE: 245

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Leu Ile Ser Asn Asn Gly Ala Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 246
<211> LENGTH: 109
<212> TYPE: PRT
<213> ORGANISM: Homo sapiens

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Val Ile Ser Gly Gly Gly Ala Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 247
<211> LENGTH: 109
<212> TYPE: PRT
<213> ORGANISM: Homo sapiens

<400> SEQUENCE: 247

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45
```

Ala Leu Ile Ser Asn Gly Gly Ser Ile Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Glu Lys Asn Leu Tyr Thr Trp Leu Asp
            100                 105

<210> SEQ ID NO 248
<211> LENGTH: 109
<212> TYPE: PRT
<213> ORGANISM: Homo sapiens

<400> SEQUENCE: 248

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Met His Trp Val Arg Gln Ala Pro Gly Lys Gly Leu Glu Trp Val
            35                  40                  45

Ala Leu Ile Ser Asn Asn Gly Ala Tyr Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Glu Lys Asn Leu Tyr Thr Trp Leu Asp
            100                 105

<210> SEQ ID NO 249
<211> LENGTH: 109
<212> TYPE: PRT
<213> ORGANISM: Homo sapiens

<400> SEQUENCE: 249

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Trp Met His Trp Val Arg Gln Ala Pro Gly Lys Gly Leu Glu Trp Val
            35                  40                  45

Ala Val Ile Ser Trp Gly Gly Ala Tyr Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Glu Lys Asn Leu Tyr Thr Trp Leu Asp
            100                 105

<210> SEQ ID NO 250
<211> LENGTH: 109
<212> TYPE: PRT
<213> ORGANISM: Homo sapiens

<400> SEQUENCE: 250

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ser Leu Ile Ser Asn Gly Gly Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Asn Glu Lys Asn Leu Tyr Thr Trp Leu Asp
            100                 105

<210> SEQ ID NO 251
<211> LENGTH: 109
<212> TYPE: PRT
<213> ORGANISM: Homo sapiens

<400> SEQUENCE: 251

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Val Ile Ser Ser Gly Gly Asn Tyr Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Asn Glu Lys Asn Leu Tyr Thr Trp Leu Asp
            100                 105

<210> SEQ ID NO 252
<211> LENGTH: 109
<212> TYPE: PRT
<213> ORGANISM: Homo sapiens

<400> SEQUENCE: 252

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Leu Ile Ser Ser Ser Gly Gly Ile Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Asn Glu Lys Asn Leu Tyr Thr Trp Leu Asp
            100                 105

<210> SEQ ID NO 253
<211> LENGTH: 109
<212> TYPE: PRT
<213> ORGANISM: Homo sapiens

<400> SEQUENCE: 253

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Leu Ile Ser Gly Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 254
<211> LENGTH: 109
<212> TYPE: PRT
<213> ORGANISM: Homo sapiens

<400> SEQUENCE: 254

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Leu Ile Ser Ala Gly Gly Thr Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 255
<211> LENGTH: 109
<212> TYPE: PRT
<213> ORGANISM: Homo sapiens

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Leu Ile Ser Trp Gly Gly Gly Thr Lys Tyr Tyr Ala Asp Ser Val
    50                  55                  60

Lys Gly Arg Phe Thr Ile Ser Arg Asp Asn Ser Lys Asn Thr Leu Tyr

```
65                  70                  75                  80
Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105
```

<210> SEQ ID NO 256
<211> LENGTH: 109
<212> TYPE: PRT
<213> ORGANISM: Homo sapiens

<400> SEQUENCE: 256

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Leu Ile Ser Ala Ser Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105
```

<210> SEQ ID NO 257
<211> LENGTH: 109
<212> TYPE: PRT
<213> ORGANISM: Homo sapiens

<400> SEQUENCE: 257

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Leu Ile Ser Asn Gly Gly Gly Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105
```

<210> SEQ ID NO 258
<211> LENGTH: 109
<212> TYPE: PRT
<213> ORGANISM: Homo sapiens

<400> SEQUENCE: 258

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Trp Met His Trp Val Arg Gln Ala Pro Gly Lys Gly Leu Glu Trp Val
            35                  40                  45

Ala Leu Ile Ser Asn Asn Gly Thr Tyr Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 259
<211> LENGTH: 109
<212> TYPE: PRT
<213> ORGANISM: Homo sapiens

<400> SEQUENCE: 259

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
            35                  40                  45

Ala Leu Ile Ser Asn Asn Gly Thr Tyr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 260
<211> LENGTH: 109
<212> TYPE: PRT
<213> ORGANISM: Homo sapiens

<400> SEQUENCE: 260

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
            35                  40                  45

Ala Val Ile Ser Asn Asn Gly Arg Tyr Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 261
<211> LENGTH: 109
<212> TYPE: PRT
<213> ORGANISM: Homo sapiens

<400> SEQUENCE: 261

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Val Ile Ser Trp Gly Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 262
<211> LENGTH: 109
<212> TYPE: PRT
<213> ORGANISM: Homo sapiens

<400> SEQUENCE: 262

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
        35                  40                  45

Ala Leu Ile Ser Ser Gly Gly Arg Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 263
<211> LENGTH: 109
<212> TYPE: PRT
<213> ORGANISM: Homo sapiens

<400> SEQUENCE: 263

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Leu Ile Ser Gly Asn Gly Arg Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 264
<211> LENGTH: 109
<212> TYPE: PRT
<213> ORGANISM: Homo sapiens

<400> SEQUENCE: 264

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Leu Ile Ser Tyr Ser Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 265
<211> LENGTH: 109
<212> TYPE: PRT
<213> ORGANISM: Homo sapiens

<400> SEQUENCE: 265

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Val Ile Ser Ser Asn Gly Arg Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 266
<211> LENGTH: 109
<212> TYPE: PRT
<213> ORGANISM: Homo sapiens

<400> SEQUENCE: 266

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Val Ile Ser Gly Gly Gly Gly Tyr Ile Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Asp Asn Glu Lys Asn Leu Tyr Thr Trp Leu Asp
                100                 105
```

<210> SEQ ID NO 267
<211> LENGTH: 109
<212> TYPE: PRT
<213> ORGANISM: Homo sapiens

<400> SEQUENCE: 267

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Trp Met His Trp Val Arg Gln Ala Pro Gly Lys Gly Leu Glu Trp Val
             35                  40                  45

Ser Val Ile Ser Ala Gly Ser Thr Ile Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Glu Lys Asn Leu Tyr Thr Trp Leu Asp
                100                 105
```

<210> SEQ ID NO 268
<211> LENGTH: 109
<212> TYPE: PRT
<213> ORGANISM: Homo sapiens

<400> SEQUENCE: 268

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Met His Trp Val Arg Gln Ala Pro Gly Lys Gly Leu Glu Trp Val
             35                  40                  45

Ala Leu Ile Ser Tyr Gly Gly Thr Tyr Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Asn Glu Lys Asn Leu Tyr Thr Trp Leu Asp
                100                 105
```

<210> SEQ ID NO 269
<211> LENGTH: 109
<212> TYPE: PRT
<213> ORGANISM: Homo sapiens

<400> SEQUENCE: 269

```
Glu Val Gln Leu Leu Glu Ser Gly Gly Gly Leu Val Gln Pro Gly Gly
  1               5                  10                  15
```

```
Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ser Leu Ile Ser Tyr Asn Gly Ala Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105
```

<210> SEQ ID NO 270
<211> LENGTH: 109
<212> TYPE: PRT
<213> ORGANISM: Homo sapiens

<400> SEQUENCE: 270

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Leu Ile Ser Ser Ser Gly Thr Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105
```

<210> SEQ ID NO 271
<211> LENGTH: 109
<212> TYPE: PRT
<213> ORGANISM: Homo sapiens

<400> SEQUENCE: 271

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Leu Ile Ser Gly Ser Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105
```

<210> SEQ ID NO 272

```
<211> LENGTH: 109
<212> TYPE: PRT
<213> ORGANISM: Homo sapiens

<400> SEQUENCE: 272

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Asn Ile Ser Asn Gly Gly Thr Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 273
<211> LENGTH: 109
<212> TYPE: PRT
<213> ORGANISM: Homo sapiens

<400> SEQUENCE: 273

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ala Ala Ile Ser Asn Ser Gly Gly Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 274
<211> LENGTH: 109
<212> TYPE: PRT
<213> ORGANISM: Homo sapiens

<400> SEQUENCE: 274

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ala Thr Ile Ser Ala Gly Gly Ala Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 275
<211> LENGTH: 109
<212> TYPE: PRT
<213> ORGANISM: Homo sapiens

<400> SEQUENCE: 275

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Ala Leu Ile Ser Ser Asn Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Glu Lys Asn Leu Tyr Thr Trp Leu Asp
            100                 105

<210> SEQ ID NO 276
<211> LENGTH: 223
<212> TYPE: PRT
<213> ORGANISM: Artificial Sequence
<220> FEATURE:
<223> OTHER INFORMATION: Synthetic Construct

<400> SEQUENCE: 276

Gln Pro Val Leu His Gln Pro Ala Met Ser Ser Ala Leu Gly Thr
1               5                   10                  15

Thr Ile Arg Leu Thr Cys Thr Leu Arg Asn Asp His Asp Ile Gly Val
            20                  25                  30

Tyr Ser Val Tyr Trp Tyr Gln Gln Arg Pro Gly His Pro Pro Arg Phe
        35                  40                  45

Leu Leu Arg Tyr Phe Ser Gln Ser Asp Lys Ser Gln Gly Pro Gln Val
    50                  55                  60

Pro Pro Arg Phe Ser Gly Ser Lys Asp Val Ala Arg Asn Arg Gly Tyr
65                  70                  75                  80

Leu Ser Ile Ser Glu Leu Gln Pro Glu Asp Glu Ala Met Tyr Tyr Cys
                85                  90                  95

Ala Met Gly Ala Arg Ser Ser Val Thr His Val Phe Gly Ser Gly Thr
            100                 105                 110

Gln Leu Thr Val Leu Ser Gln Pro Lys Ala Thr Pro Ser Val Thr Leu
        115                 120                 125

Phe Pro Pro Ser Ser Glu Glu Leu Gln Ala Asn Lys Ala Thr Leu Val
    130                 135                 140

Cys Leu Met Asn Asp Phe Tyr Pro Gly Ile Leu Thr Val Thr Trp Lys
145                 150                 155                 160

Ala Asp Gly Thr Pro Ile Thr Gln Gly Val Glu Met Thr Thr Pro Ser
                165                 170                 175

Lys Gln Ser Asn Asn Lys Tyr Ala Ala Ser Ser Tyr Leu Ser Leu Thr

```
                180             185                 190
Pro Glu Gln Trp Arg Ser Arg Arg Ser Tyr Ser Cys Gln Val Met His
            195                 200                 205

Glu Gly Ser Thr Val Glu Lys Thr Val Ala Pro Ala Glu Cys Ser
        210                 215                 220

<210> SEQ ID NO 277
<211> LENGTH: 6
<212> TYPE: PRT
<213> ORGANISM: Homo sapiens
<220> FEATURE:
<221> NAME/KEY: VARIANT
<222> LOCATION: (2)...(2)
<223> OTHER INFORMATION: Xaa = N, D or S
<220> FEATURE:
<221> NAME/KEY: VARIANT
<222> LOCATION: (4)...(4)
<223> OTHER INFORMATION: Xaa = G, W, A, E or S
<220> FEATURE:
<221> NAME/KEY: VARIANT
<222> LOCATION: (6)...(6)
<223> OTHER INFORMATION: Xaa = H, N or S

<400> SEQUENCE: 277

Ser Xaa Tyr Xaa Met Xaa
 1               5

<210> SEQ ID NO 278
<211> LENGTH: 13
<212> TYPE: PRT
<213> ORGANISM: Homo sapiens
<220> FEATURE:
<221> NAME/KEY: VARIANT
<222> LOCATION: (3)...(3)
<223> OTHER INFORMATION: Xaa = A or S
<220> FEATURE:
<221> NAME/KEY: VARIANT
<222> LOCATION: (4)...(4)
<223> OTHER INFORMATION: Xaa = L, N, A, V, G, S or T
<220> FEATURE:
<221> NAME/KEY: VARIANT
<222> LOCATION: (7)...(7)
<223> OTHER INFORMATION: Xaa = S, G, N, D, A, Y or W
<220> FEATURE:
<221> NAME/KEY: VARIANT
<222> LOCATION: (8)...(8)
<223> OTHER INFORMATION: Xaa = G, N or S
<220> FEATURE:
<221> NAME/KEY: VARIANT
<222> LOCATION: (9)...(9)
<223> OTHER INFORMATION: Xaa = G or S
<220> FEATURE:
<221> NAME/KEY: VARIANT
<222> LOCATION: (10)...(10)
<223> OTHER INFORMATION: Xaa = A, G, S, R or T
<220> FEATURE:
<221> NAME/KEY: VARIANT
<222> LOCATION: (11)...(11)
<223> OTHER INFORMATION: Xaa = Y, I, T or N
<220> FEATURE:
<221> NAME/KEY: VARIANT
<222> LOCATION: (12)...(12)
<223> OTHER INFORMATION: Xaa = T, I or K
<220> FEATURE:
<221> NAME/KEY: VARIANT
<222> LOCATION: (13)...(13)
<223> OTHER INFORMATION: Xaa = Y or S

<400> SEQUENCE: 278

Trp Val Xaa Xaa Ile Ser Xaa Xaa Xaa Xaa Xaa Xaa Xaa
 1               5                  10
```

```
<210> SEQ ID NO 279
<211> LENGTH: 6
<212> TYPE: PRT
<213> ORGANISM: Homo sapiens
<220> FEATURE:
<221> NAME/KEY: VARIANT
<222> LOCATION: (2)...(2)
<223> OTHER INFORMATION: Xaa = D, S or N
<220> FEATURE:
<221> NAME/KEY: VARIANT
<222> LOCATION: (4)...(4)
<223> OTHER INFORMATION: Xaa = W or A
<220> FEATURE:
<221> NAME/KEY: VARIANT
<222> LOCATION: (6)...(6)
<223> OTHER INFORMATION: Xaa = H, N or S

<400> SEQUENCE: 279

Ser Xaa Tyr Xaa Met Xaa
 1               5

<210> SEQ ID NO 280
<211> LENGTH: 13
<212> TYPE: PRT
<213> ORGANISM: Homo sapiens
<220> FEATURE:
<221> NAME/KEY: VARIANT
<222> LOCATION: (3)...(3)
<223> OTHER INFORMATION: Xaa = A or S
<220> FEATURE:
<221> NAME/KEY: VARIANT
<222> LOCATION: (4)...(4)
<223> OTHER INFORMATION: Xaa = L, V, N, A or T
<220> FEATURE:
<221> NAME/KEY: VARIANT
<222> LOCATION: (7)...(7)
<223> OTHER INFORMATION: Xaa = S, N, A, G, W or Y
<220> FEATURE:
<221> NAME/KEY: VARIANT
<222> LOCATION: (8)...(8)
<223> OTHER INFORMATION: Xaa = G, N or S
<220> FEATURE:
<221> NAME/KEY: VARIANT
<222> LOCATION: (9)...(9)
<223> OTHER INFORMATION: Xaa = G or S
<220> FEATURE:
<221> NAME/KEY: VARIANT
<222> LOCATION: (10)...(10)
<223> OTHER INFORMATION: Xaa = G, T, S, A, N or R
<220> FEATURE:
<221> NAME/KEY: VARIANT
<222> LOCATION: (11)...(11)
<223> OTHER INFORMATION: Xaa = Y, I, N or S
<220> FEATURE:
<221> NAME/KEY: VARIANT
<222> LOCATION: (12)...(12)
<223> OTHER INFORMATION: Xaa = K, I or T

<400> SEQUENCE: 280

Trp Val Xaa Xaa Ile Ser Xaa Xaa Xaa Xaa Xaa Tyr
 1               5                  10

<210> SEQ ID NO 281
<211> LENGTH: 15
<212> TYPE: PRT
<213> ORGANISM: Artificial Sequence
<220> FEATURE:
<223> OTHER INFORMATION: Synthetic Linker Construct

<400> SEQUENCE: 281

Gly Gly Gly Gly Ser Gly Gly Gly Ser Gly Gly Gly Gly Ser
 1               5                  10                  15
```

```
<210> SEQ ID NO 282
<211> LENGTH: 10
<212> TYPE: PRT
<213> ORGANISM: Homo sapiens

<400> SEQUENCE: 282

Asp Ile Gly Val Tyr Ser Val Tyr Trp Tyr
1               5                   10

<210> SEQ ID NO 283
<211> LENGTH: 10
<212> TYPE: PRT
<213> ORGANISM: Homo sapiens

<400> SEQUENCE: 283

Glu Val Ala Ile Phe Thr Ile Phe Trp Phe
1               5                   10

<210> SEQ ID NO 284
<211> LENGTH: 10
<212> TYPE: PRT
<213> ORGANISM: Homo sapiens

<400> SEQUENCE: 284

Asp Leu Gly Leu Tyr Ser Leu Tyr Trp Tyr
1               5                   10

<210> SEQ ID NO 285
<211> LENGTH: 13
<212> TYPE: PRT
<213> ORGANISM: Homo sapiens

<400> SEQUENCE: 285

Leu Leu Arg Tyr Phe Ser Gln Ser Asp Lys Ser Gln Gly
1               5                   10

<210> SEQ ID NO 286
<211> LENGTH: 13
<212> TYPE: PRT
<213> ORGANISM: Homo sapiens

<400> SEQUENCE: 286

Ile Ile Lys Phe Tyr Thr Asn Thr Glu Arg Thr Asn Ala
1               5                   10

<210> SEQ ID NO 287
<211> LENGTH: 13
<212> TYPE: PRT
<213> ORGANISM: Homo sapiens

<400> SEQUENCE: 287

Val Val Arg Tyr Phe Ser Gln Ser Asp Lys Ser Gln Gly
1               5                   10

<210> SEQ ID NO 288
<211> LENGTH: 10
<212> TYPE: PRT
<213> ORGANISM: Homo sapiens

<400> SEQUENCE: 288

Ala Met Gly Ala Arg Ser Ser Val Thr His
1               5                   10

<210> SEQ ID NO 289
<211> LENGTH: 10
```

```
<212> TYPE: PRT
<213> ORGANISM: Homo sapiens

<400> SEQUENCE: 289

Gly Leu Ala Gly Lys Thr Thr Ile Ser His
1               5                   10

<210> SEQ ID NO 290
<211> LENGTH: 10
<212> TYPE: PRT
<213> ORGANISM: Homo sapiens

<400> SEQUENCE: 290

Ala Met Gly Ala Arg Ser Ser Leu Thr His
1               5                   10

<210> SEQ ID NO 291
<211> LENGTH: 6
<212> TYPE: PRT
<213> ORGANISM: Homo sapiens

<400> SEQUENCE: 291

Ser Asn Tyr Gly Met His
1               5

<210> SEQ ID NO 292
<211> LENGTH: 6
<212> TYPE: PRT
<213> ORGANISM: Homo sapiens

<400> SEQUENCE: 292

Ser Asp Tyr Trp Met Asn
1               5

<210> SEQ ID NO 293
<211> LENGTH: 6
<212> TYPE: PRT
<213> ORGANISM: Homo sapiens

<400> SEQUENCE: 293

Ser Ser Tyr Ala Met Ser
1               5

<210> SEQ ID NO 294
<211> LENGTH: 6
<212> TYPE: PRT
<213> ORGANISM: Homo sapiens

<400> SEQUENCE: 294

Ser Asn Tyr Glu Met His
1               5

<210> SEQ ID NO 295
<211> LENGTH: 6
<212> TYPE: PRT
<213> ORGANISM: Homo sapiens

<400> SEQUENCE: 295

Ser Asn Tyr Ser Met His
1               5

<210> SEQ ID NO 296
<211> LENGTH: 13
<212> TYPE: PRT
<213> ORGANISM: Homo sapiens
```

<400> SEQUENCE: 296

Trp Val Ala Leu Ile Ser Ser Gly Gly Ala Tyr Thr Tyr
1               5                   10

<210> SEQ ID NO 297
<211> LENGTH: 13
<212> TYPE: PRT
<213> ORGANISM: Homo sapiens

<400> SEQUENCE: 297

Trp Val Ser Asn Ile Ser Gly Asn Ser Gly Ile Ile Ser
1               5                   10

<210> SEQ ID NO 298
<211> LENGTH: 13
<212> TYPE: PRT
<213> ORGANISM: Homo sapiens

<400> SEQUENCE: 298

Trp Val Ala Ala Ile Ser Asn Ser Gly Ser Thr Lys Tyr
1               5                   10

<210> SEQ ID NO 299
<211> LENGTH: 13
<212> TYPE: PRT
<213> ORGANISM: Homo sapiens

<400> SEQUENCE: 299

Trp Val Ala Val Ile Ser Asp Gly Gly Arg Asn Thr Tyr
1               5                   10

<210> SEQ ID NO 300
<211> LENGTH: 13
<212> TYPE: PRT
<213> ORGANISM: Homo sapiens

<400> SEQUENCE: 300

Trp Val Ala Gly Ile Ser Ala Gly Gly Thr Tyr Thr Tyr
1               5                   10

<210> SEQ ID NO 301
<211> LENGTH: 13
<212> TYPE: PRT
<213> ORGANISM: Homo sapiens

<400> SEQUENCE: 301

Trp Val Ala Ser Ile Ser Tyr Gly Gly Ala Tyr Thr Tyr
1               5                   10

<210> SEQ ID NO 302
<211> LENGTH: 13
<212> TYPE: PRT
<213> ORGANISM: Homo sapiens

<400> SEQUENCE: 302

Trp Val Ala Thr Ile Ser Trp Gly Gly Ala Tyr Thr Tyr
1               5                   10

<210> SEQ ID NO 303
<211> LENGTH: 6
<212> TYPE: PRT
<213> ORGANISM: Homo sapiens

<400> SEQUENCE: 303

-continued

Ser Asp Tyr Trp Met His
1               5

<210> SEQ ID NO 304
<211> LENGTH: 6
<212> TYPE: PRT
<213> ORGANISM: Homo sapiens

<400> SEQUENCE: 304

Ser Ser Tyr Ala Met Asn
1               5

<210> SEQ ID NO 305
<211> LENGTH: 6
<212> TYPE: PRT
<213> ORGANISM: Homo sapiens

<400> SEQUENCE: 305

Ser Asn Tyr Trp Met Ser
1               5

<210> SEQ ID NO 306
<211> LENGTH: 13
<212> TYPE: PRT
<213> ORGANISM: Homo sapiens

<400> SEQUENCE: 306

Trp Val Ala Leu Ile Ser Ser Gly Gly Gly Tyr Lys Tyr
1               5                   10

<210> SEQ ID NO 307
<211> LENGTH: 13
<212> TYPE: PRT
<213> ORGANISM: Homo sapiens

<400> SEQUENCE: 307

Trp Val Ser Val Ile Ser Asn Asn Ser Thr Ile Ile Tyr
1               5                   10

<210> SEQ ID NO 308
<211> LENGTH: 13
<212> TYPE: PRT
<213> ORGANISM: Homo sapiens

<400> SEQUENCE: 308

Trp Val Ala Asn Ile Ser Ala Ser Gly Ser Asn Thr Tyr
1               5                   10

<210> SEQ ID NO 309
<211> LENGTH: 13
<212> TYPE: PRT
<213> ORGANISM: Homo sapiens

<400> SEQUENCE: 309

Trp Val Ala Ala Ile Ser Gly Gly Gly Ala Ser Lys Tyr
1               5                   10

<210> SEQ ID NO 310
<211> LENGTH: 13
<212> TYPE: PRT
<213> ORGANISM: Homo sapiens

<400> SEQUENCE: 310

Trp Val Ala Thr Ile Ser Trp Gly Gly Asn Tyr Lys Tyr

```
<210> SEQ ID NO 311
<211> LENGTH: 13
<212> TYPE: PRT
<213> ORGANISM: Homo sapiens

<400> SEQUENCE: 311

Trp Val Ala Leu Ile Ser Tyr Gly Gly Arg Tyr Lys Tyr
1               5                   10
```

SUR-BINDING PROTEINS AGAINST ERBB3

CROSS-REFERENCE TO RELATED APPLICATION

The present application claims priority under 35 U.S.C. § 119(e) to U.S. provisional patent application Nos. 61/512,774, filed Jul. 28, 2011; 61/589,111, filed Jan. 20, 2012; 61/640,575, filed Apr. 30, 2012; and 61/640,635, filed Apr. 30, 2012. The aforementioned priority applications are incorporated herein by reference in their entireties.

SEQUENCE LISTING

The present application is amended to include a Sequence Listing in electronic format. The Sequence Listing is provided as a file entitled SEQUENCE_SLBIO001NP.TXT, created Jan. 17, 2014 and last modified Jan. 27, 2014, which is 247,064 bytes in size. The information in the electronic format of the Sequence Listing is incorporated herein by reference in its entirety.

FIELD

The present invention generally relates to surrogate light chain constructs and other binding proteins.

BACKGROUND

The ErbB/HER subfamily of polypeptide growth factor receptors include the epidermal growth factor (EGF) receptor (EGFR/ErbB1/HER1), the neu oncogene product (ErbB2/HER2), and the more recently identified ErbB3/HER3 and ErbB4/HER4 receptor proteins (see, e.g., Hynes et. al. (1994) Biochim. Biophys. Acta Rev. Cancer 1198, 165-184). Each of these receptors is predicted to include of an ectodomain (extracellular ligand-binding domain), a membrane-spanning domain, a cytosolic, protein tyrosine kinase (PTK) domain and a C-terminal phosphorylation domain (see, e.g., Kim et al., (1998) Biochem. J. 334, 189-195). The ectodomains of the ErbB receptors are further characterized as being divided into four domains (I-IV). Domains I and III of the ErbB ectodomain are involved in ligand binding (see, e.g., Hynes et. al. (2005) Nature Rev. Cancer 5, 341-354). Ligands for these receptors include heregulin (HRG) and betacellulin (BTC).

Experiments in vitro have indicated that the protein tyrosine kinase activity of the ErbB3 receptor (ErbB3) protein is attenuated significantly relative to that of other ErbB/HER family members and this attenuation has been attributed, in part, to the occurrence of non-conservative amino acid substitutions in the predicted intracellular catalytic domain of ErbB3 (see, e.g., Guy et al. (1994) Proc. Natl. Acad. Sci. USA. 91, 8132-8136; Sierke et al. (1997) Biochem. J. 322, 757-763). However, the ErbB3 protein has been shown to be phosphorylated in a variety of cellular contexts. For example, ErbB3 is constitutively phosphorylated on tyrosine residues in a subset of human breast cancer cell lines overexpressing this protein (see, e.g., Kraus et al. (1993) Proc. Natl. Acad. Sci. USA. 90, 2900-2904; and Kim et al. Supra; see, also, Schaefer et al. (2006) Neoplasia 8(7):613-22 and Schaefer et al. Cancer Res (2004) 64(10): 3395-405).

Markedly elevated levels of ErbB3 have been associated with certain human mammary tumor cell lines indicating that ErbB3, like ErbB1 and ErbB2, plays a role in human malignancies. Specifically, ErbB3 has been found to be overexpressed in breast (Lemoine et al., Br. J. Cancer 66:1116-1121, 1992), gastrointestinal (Poller et al., J. Pathol. 168:275-280, 1992; Rajkumer et al., J. Pathol. 170:271-278, 1993; and Sanidas et al., Int. J. Cancer 54:935-940, 1993), and pancreatic cancers (Lemoine et al., J. Pathol. 168:269-273, 1992, and Friess et al., Clinical Cancer Research 1:1413-1420, 1995).

Although, the role of ErbB3 in cancer has been explored (see, e.g., Horst et al. (2005) 115, 519-527; Xue et al. (2006) Cancer Res. 66, 1418-1426), ErbB3 has only recently become appreciated as a target for clinical intervention. Some immunotherapies primarily focus on inhibiting the action of ErbB2 and including inhibiting heterodimerization of ErbB2/ErbB3 complexes (see, e.g., Sliwkowski et al. (1994) J. Biol. Chem. 269(20):14661-14665 (1994).

Signal transduction mediated by the ErbB family of protein receptors occurs, in many instances, upon ligand-induced receptor heterodimerization. "Receptor cross-talking" following heterodimerization results in activation of the ErbB receptor kinase domain and cross-phosphorylation of the ErbB receptors, which is known to occur between, e.g., EGFR and ErbB2, ErbB2 and ErbB3, and ErbB2 and ErbB4, and EGFR and ErbB3 (see, e.g., Wada et al., Cell 61:1339-1347 (1990); Plowman et al., Nature 336:473-475 (1993); Carraway and Cantley, Cell 78:5-8 (1994); Riese et al., Oncogene 12:345-353 (1996); Kokai et al., Cell 58:287-292 (1989); Stern et al., EMBO J. 7:995-1001 (1988); and King et al., Oncogene 4:13-18 (1989)).

SUMMARY

In some embodiments, a sur-binding protein ("SBP") is provided. The SBP can comprise a VpreB sequence, a λ5 sequence, or a VpreB sequence and a λ5 sequence; and a heavy chain variable region amino acid sequence that is paired with the VpreB sequence, the λ5 sequence, or the VpreB sequence and the λ5 sequence to form a sur-binding protein. The sur-binding protein binds to an ErbB3 protein.

In some embodiments, a bispecific sur-binding protein is provided. The bispecific sur-binding protein can comprise a first VpreB sequence, a first λ5 sequence, or a first VpreB sequence and a first λ5 sequence and a first heavy chain variable region amino acid sequence that is paired with the first VpreB sequence, the first λ5 sequence, or the first VpreB sequence and the first λ5 sequence to form a first sur-binding protein binding site. The sur-binding protein binding site binds to and/or inhibits an ErbB3 protein. The bispecific SBP can further comprise a second VpreB sequence, a second λ5 sequence, or a second VpreB sequence and a second λ5 sequence; and a second heavy chain variable region amino acid sequence that is paired with the second VpreB sequence, the second λ5 sequence, or the second VpreB sequence and the second λ5 sequence to form a second sur-binding protein site. The second sur-binding protein site binds to and/or inhibits a second target involved in cancer pathogenesis.

In some embodiments, a bispecific sur-binding protein is provided. The SBP can comprise a VpreB sequence, a λ5 sequence, or a VpreB sequence and a λ5 sequence, a first heavy chain variable region amino acid sequence that is paired with the VpreB sequence, the λ5 sequence, or the VpreB sequence and first λ5 sequence to form a first binding site. The sur-binding protein binding site binds to and/or inhibits an ErbB3 protein. The SBP can further comprise a light chain variable region. The SBP can further comprise a second heavy chain variable region amino acid sequence that is paired with the light chain variable region to form a second binding site, wherein said second binding site binds to and/or inhibits a second target involved in cancer pathogenesis.

In some embodiments, a sur-binding protein is provided that can reduce cancer cell proliferation, cancer cell growth, or cancer cell proliferation and growth, wherein the cancer cell is driven by overexpression of ErbB2.

In some embodiments, provided herein are antibodies that binds ErbB3 and that can reduce cancer cell proliferation, cancer cell growth, or cancer cell proliferation and growth, wherein the cancer cell is driven by overexpression of ErbB2.

In some embodiments, provided herein are antibodies and/or SBPs that bind to a same or an overlapping epitope of any of the sur-binding proteins provided herein.

In some embodiments, an antibody that displaces any one of the sur-binding proteins provided herein is provided, when the antibody binds to an epitope on ErbB3.

In some embodiments, a method for suppressing tumor growth is provided. The method can comprise providing an ErbB3 sur-binding protein to a tumor that comprises a cell that expresses ErbB3, thereby suppressing tumor growth.

In some embodiments, a method for suppressing a cancerous cell is provided. The method comprises identifying a subject having a cancerous cell, wherein said cancerous cell expresses ErbB3, and administering to the subject an ErbB3 sur-binding protein in an amount sufficient to bind to ErbB3 on the cancerous cell and thereby block the PI3K, AKT, or PI3K and AKT pathway.

In some embodiments, a method of treating cancer is provided. The method comprises identifying a subject to receive a treatment for cancer, wherein said cancer involves expression of ErbB2, ErbB3, or ErbB2 and ErbB3; and administering to the subject a sur-binding protein or antigen binding portions thereof.

In some embodiments, a method of treating cancer is provided. The method comprises administering a chemotherapeutic or a biologic to a subject and administering an Erb-3 inhibitor to a subject.

In some embodiments, a method for suppressing a cancerous cell is provided. The method comprises identifying a subject having a cancerous cell, wherein said cancerous cell expresses ErbB3 and administering to the subject an ErbB3 sur-binding protein in an amount sufficient to bind to ErbB3 on the cancerous cell and thereby block the Ras/Raf/MEK pathway.

In some embodiments, a method of treating cancer is provided. The method comprises identifying a subject to receive a treatment for cancer, wherein said cancer involves expression of a variant ErbB2 protein and administering to the subject a sur-binding protein or antigen binding portions thereof, as provided herein.

BRIEF DESCRIPTION OF THE DRAWINGS

FIG. 1A and FIG. 1B depict sequences of ErbB3.

FIG. 2A and FIG. 2B depict sequences of SBP heavy chain variable region sequences and then identify (by separate sequences) the heavy chain CDR1, CDR2, and CDR3. The framework regions are the sequences in the heavy chain variable regions between the CDR sequences.

FIG. 2C depicts a variable heavy chain sequence alignment between 2817-C01 and 2716-F05 to show conserved regions between SBPs that can reduce ErbB3 activity.

FIG. 2D depicts a sequence alignment between several Sab variable heavy chains to show structurally conserved regions. These SBPs also reduce ErbB3 activity.

FIGS. 3A-3D are graphs depicting the activity of various Sabs and SgGs in a functional assay measuring ErbB2/ErbB3 dimerization.

FIGS. 4A and 4B are graphs demonstrating SgGs that can bind to ErbB3 that is expressed on the surface of cells.

FIGS. 7A-7C depict the amino acid sequences for various chimeras of ErbB3 and ErbB2.

FIGS. 11A and 11B are graphs depicting results establishing that SgGs inhibit proliferation of breast cancer cell lines that overexpress ErB2 when cells are not stimulated with NRG.

FIG. 11C is a graph depicting results establishing that SgGs inhibit proliferation of gastric cancer cell line (NCI-N87) that overexpresses ErB2 when cells are not stimulated with NRG.

FIG. 11D is a graph depicting that while several of the cell lines tested secreted measurable amounts of stimulatory factor(s) (presumably NRG), neither BT474 nor SKBR3 cells secreted measurable quantities (<0.13 ng/ml).

FIG. 12A is a graph depicting the percent inhibition of proliferation from various SgGs with and without an anti-EGFR antibody.

FIGS. 12B and 12C are graphs depicting the percent inhibition of proliferation from trastuzumab with and without various SgGs and with and without NRG

FIG. 13C was in the absence of NRG, while FIG. 13D was in the presence of NRG.

FIG. 13E was in the absence of NRG, while FIG. 13F was in the presence of NRG.

FIG. 18 depicts the nucleic acid sequence of some embodiments of the SBPs.

FIG. 22 is the alignment of VpreB1 sequences with antibody λ5 light chain variable region sequences. Regions with the highest degree of sequence similarity are boxed. As shown in the figure, VpreB1 shows only 56%-62% (amino acids 2 to 97) sequence identity to the λ5 light chain variable region germline sequences.

FIG. 23 is the alignment of VpreB1 sequences with antibody λ5 light chain constant region sequences. As shown in the figure, the aligned VpreB1 sequences show only 62% (amino acids 97 to 209) sequence identity to the corresponding antibody λ5 light chain constant region sequences.

FIG. 24 is the alignment of VpreB1 sequences with antibody κ light chain constant region sequences. As shown in the figure, the aligned VpreB1 sequences show only 35% (amino acids 105 to 209) sequence identity to the corresponding antibody κ light chain constant region sequences.

FIG. 25 shows the human VpreB1 sequence of SEQ ID NO: 1. the mouse VpreB2 sequences of SEQ ID NOS: 2 and 3; the human VpreB3 sequence of SEQ ID NO: 4, the human λ5 sequence of SEQ D NO: 6 and the mouse λ5 protein sequence of SEQ ID NO: 5, and sequences of various constructs used in the Examples. The figure also includes various sequences for the surrogate light chain fusion options, such as fusion I (SEQ ID NOs: 10 and 276).

FIG. 27 shows the alignment of human VpreB1 (SEQ ID NO: 98) and human λ5 with antibody λ chain variable and constant regions. VpreB1 shares some sequence similarity to antibody λ chain variable regions, while λ5 shares some similarly to antibody λ chain constant regions and framework region 4. The boxed regions identify VpreB1 and λ5 loop regions 1 (LR1), 2 (LR2), and 3 (LR3).

FIG. 31A displays the results for the items noted individually. FIG. 31B displays the results of the noted items with 100 nM trastuzumab. FIG. 31C displays the results of the noted items with 100 nM pertuzumab.

FIG. 31D displays the results for the items noted individually. FIG. 31E displays the results of the noted items with 100 nM trastuzumab. FIG. 31F displays the results of the noted items with 100 nM pertuzumab.

FIG. 34A is a CDR sequence alignment of 2817-C01 sur-binding proteins. The sequence alignment indicates positions and structures that allow for variation while maintaining EC50s in a useful range. No variation was examined in the CDR3 region.

FIG. 34B is a CDR sequence alignment of 2716-F05 sur-binding proteins. The sequence alignment indicates positions and structures that allow for variation while maintaining EC50s in a useful range. No variation was examined in the CDR3 region.

FIG. 34C is a consensus sequence of the sequences outlined in FIG. 34A.

FIG. 34D is a consensus sequence of the sequences outlined in FIG. 34B.

FIG. 34E includes the sequences of additional variants of the heavy chain variable region of 2817-C01.

FIG. 34F includes the sequences of additional variants of the heavy chain variable region of 2716-F05.

FIG. 36A and FIG. 36B depict the sequences of various forms of some embodiments of variants of ErbB2.

FIG. 41A depicts the nucleic acid sequence (with leader sequence) and amino acid sequence (without leader sequence) of the SBP SL-396.

FIG. 41B depicts the nucleic acid sequence of 2716-F05 (SVD).

FIG. 41C depicts the amino acid sequence of 2716-F05 (SVD).

FIGS. 43A and 43B depict examples of the full length amino acid and nucleic acid sequences of some embodiments of the heavy chain sequences for 2817-CO 1 and 2716-F05.

DETAILED DESCRIPTION OF VARIOUS EMBODIMENTS

Figure 5:
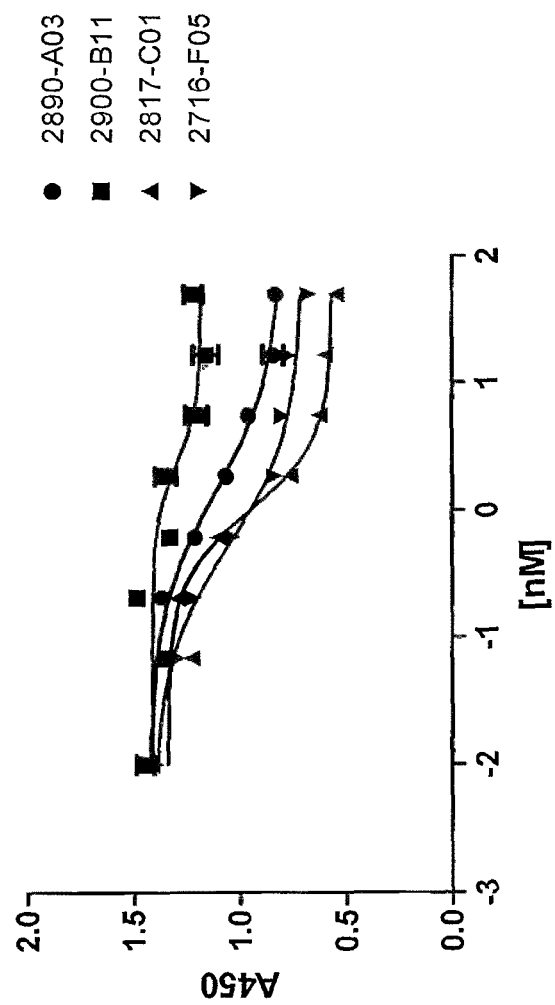
FIG. 5 is a graph depicting the ability of Sabs to inhibit the binding of NRG to ErbB3.

ErbB3 serves as a receptor for NRG1. Signaling through ErbB3 can occur through the formation of ErbB3 heterodimers (such as ErbB3-ErbB1, ErbB3-ErbB2, or ErbB3-ErbB4). As such, molecules that interact with, modulate, and/or reduce these interactions, can reduce ErbB3 dependent signaling events, which include ErbB3 related disorders such as cancer. In light of this, some of the embodiments provided herein are directed to sur-binding proteins ("SBPs") which can block and/or reduce such ErbB3 dependent signaling events by binding to ErbB3 alone, or ErbB3 and other ErbB members. In some embodiments, the SBPs bind to ErbB3 and prevent and/or reduce ErbB3 dimerization. In some embodiments, the SBPs bind to ErbB3 and prevent and/or reduce NRG (such as NRG-1, NRG-2, etc) binding to ErbB3. In some embodiments, the SBPs bind to ErbB3 and prevent and/or reduce ErbB3 NRG dependent activation. In some embodiments, the SBPs bind to an ErbB3 that is already bound to NRG and can displace the NRG to reduce ErbB3 dependent signaling, even in the presence of NRG. In some embodiments, the SBPs bind to ErbB3 that is already bound to NRG and reduce and/or block the dimerization of ErbB3 with other ErbB members. In some embodiments, the SBPs bind to an ErbB3 that is already bound to NRG and reduce and/or block the signaling of ErbB3. In some embodiments, any of the above can be antibodies or antibody-like molecules instead of SBPs. Such antibodies or antibody-like molecules can include the SBP heavy chain variable regions or one or more of the heavy chain CDRs described herein.

The present specification first provides a list of definitions and/or embodiments. The specification then goes on to discuss various embodiments of the SBPs and/or antibodies. That section is then followed by a description of various aspects regarding SBPs generically (setting forth additional embodiments for the specific SBPs, exemplary VpreB and λ5 sequences, etc.). That section is then followed by a set of examples for ErbB3 embodiments, which is then followed by a set of examples regarding SBPs generally (which, of course, are contemplated in combination with the specific SBP embodiments disclosed herein). The headings and sections provided herein are provided for convenience only and are not to be read as limiting in any way on the embodiments or combinations provided by this disclosure to those of skill in the art.

A. DEFINITIONS

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

One skilled in the art will recognize many methods and materials similar or equivalent to those described herein, which can be used in the practice of the present invention. Indeed, the present invention is in no way limited to the methods and materials described. For purposes of the present invention, the following terms are defined below.

The term "surrogate light chain," as used herein, refers to either a VpreB, λ5, or a VpreB and a λ5 protein.

The term "VpreB" is used herein in the broadest sense and refers to any native sequence, fragment, or variant VpreB polypeptide, specifically including, without limitation, human VpreB1 of SEQ ID NO: 1, mouse VpreB2 of SEQ ID NOS: 2 and 3, human VpreB3 of SEQ ID NO: 4 and isoforms, including splice variants and variants formed by posttranslational modifications, other mammalian homologues thereof, as well as variants of such native sequence polypeptides.

The term "λ5" is used herein in the broadest sense and refers to any native sequence, fragment, or variant λ5 polypeptide, specifically including, without limitation, human λ5 of SEQ ID NO: 6, mouse λ5 protein of SEQ ID NO: 5, and their isoforms, including splice variants and variants formed by posttranslational modifications, other mammalian homologous thereof, as well a variants of such native sequence polypeptides.

The terms "variant VpreB polypeptide" and "a variant of a VpreB polypeptide" are used interchangeably, and are defined herein as a polypeptide differing from a native sequence VpreB polypeptide at one or more amino acid positions as a result of an amino acid modification. The "variant VpreB polypeptide," as defined herein, will be different from a native antibody λ or κ light chain sequence, or a fragment thereof. The "variant VpreB polypeptide" will preferably retain at least about 65%, or at least about 70%, or at least about 75%, or at least about 80%, or at least about 85%, or at least about 90%, or at least about 95%, or at least about 98% sequence identity with a native sequence VpreB polypeptide. In another embodiment the "variant VpreB polypeptide" can contain up to 80%, or up to 90%, or up to 100% antibody light chain variable framework regions. In another preferred embodiment, the "variant VpreB polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant VpreB polypeptides specifically include, without limitation, VpreB polypeptides in which the non-Ig-like unique tail at the C-terminus of the VpreB sequence is partially or completely removed.

The terms "variant λ5 polypeptide" and "a variant of a λ5 polypeptide" are used interchangeably, and are defined herein as a polypeptide differing from a native sequence λ5 polypeptide at one or more amino acid positions as a result of an amino acid modification. The "variant λ5 polypeptide," as defined herein, will be different from a native antibody λ or κ light chain sequence, or a fragment thereof. The "variant λ5 polypeptide" will preferably retain at least about 65%, or at least about 70%, or at least about 75%, or at least about 80%, or at least about 85%, or at least about 90%, or at least about 95%, or at least about 98% sequence identity with a native sequence λ5 polypeptide. In another embodiment the "variant λ5 polypeptide" can contain upto 80%, or up to 90%, or up to 100% antibody light chain variable J regions. In another embodiment the "variant λ5 polypeptide" can contain upto 80%, or up to 90%, or up to 100% antibody light chain constant regions. In another preferred embodiment, the "variant λ5 polypeptide" will be less than 95%, or less than 90%, or less than 85%, or less than 80%, or less than 75%, or less than 70%, or less than 65%, or less than 60% identical in its amino acid sequence to a native antibody λ or κ light chain sequence. Variant λ5 polypeptides specifically include, without limitation, λ5 polypeptides in which the unique tail at the N-terminus of the λ5 sequence is partially or completely removed.

Percent amino acid sequence identity can be determined using the sequence comparison program NCBI-BLAST2 (Altschul et al., Nucleic Acids Res. 25:3389-3402 (1997)). The NCBI-BLAST2 sequence comparison program can be downloaded from the world wide web (www) at the following address ncbi.nlm.nih.gov or otherwise obtained from the National Institute of Health,Bethesda,MD. NCBI-BLAST2 uses several search parameters,wherein all of those search parameters are set to default values including,for example, unmask=yes,strand=all, expected occurrences=10 minimum low complexity length=15/5,multi-pass e-value=0.01, constant for muti-pass=25, dropoff for final gapped alignment=25 and scoring matrix=BLOSUM62.

The term "VpreB sequence" is used herein to refer to the sequence of "VpreB," as hereinabove defined, or a fragment thereof.

The term "λ5 sequence" is used herein to refers to the sequence of "λ5," as hereinabove defined, or a fragment thereof.

The term "surrogate light chain sequence," as defined herein, means any polypeptide sequence that comprises a "VpreB sequence" and/or a "λ5 sequence," as hereinabove defined. The "surrogate light chain sequence," as defined herein, specifically includes, without limitation, the human VpreB1 sequence of SEQ ID NO 1, the mouse VpreB2 sequences of SEQ ID NOS: 2 and 3, and the human VpreB3 sequence of SEQ ID NO: 4, and their various isoforms, including splice variants and variants formed by posttranslational modifications, homologues thereof in other mammalian species, as well as fragments and variants thereof. The term "surrogate light chain sequence" additionally includes, without limitation, the human λ5 sequence of SEQ ID NO: 6, the mouse λ5 sequence of SEQ ID NO: 5, and their isoforms, including splice variants and variants formed by posttranslational modifications, homologues thereof in other mammalian species, as well as fragments and variants thereof. The term "surrogate light chain sequence" additionally includes a sequence comprising both VpreB and λ5 sequences as hereinabove defined. In some embodiments, the surrogate light chain can include any of the surrogate light chain options noted in the figures, for example, in FIG. 22, 23, 24, 25, or 27.

For the three-dimensional structure of the pre-B-cell receptor (pre-BCR), including the structure of the surrogate light chain (SCL) and its components see, e.g. Lanig et al., *Mol. Immunol.* 40(17):1263-72 (2004).

The surrogate light chain sequence can be optionally conjugated to a heterogeneous amino acid sequence, or any other heterogeneous component, to form a "surrogate light chain construct" herein. Thus, the term, "surrogate light chain construct" is used in the broadest sense and includes any and all additional heterogeneous components, including a heterogeneous amino acid sequence, nucleic acid, and other molecules conjugated to a surrogate light chain sequence, wherein "conjugation" is defined below.

In the context of the polypeptides of the present invention, the term "heterogeneous amino acid sequence," relative to a first amino acid sequence, is used to refer to an amino acid sequence not naturally associated with the first amino acid sequence, at least not in the form it is present in the SBPs herein. Thus, a "heterogenous amino acid sequence" relative to a VpreB is any amino acid sequence not associated with native VpreB in its native environment, including, without limitation, λ5 sequences that are different from those λ5 sequences that, together with VpreB, form the surrogate light chain on developing B cells, such as amino acid sequence variants, e.g. truncated and/or derivatized λ5 sequences. A "heterogeneous amino acid sequence" relative to a VpreB also includes λ5 sequences covalently associated with, e.g. fused to, VpreB, including native sequence λ5, since in their native environment, the VpreB and λ5 sequences are not covalently associated, e.g. fused, to each other. Heterogeneous amino acid sequences also include, without limitation, antibody sequences, including antibody and heavy chain sequences and fragments thereof, such as, for example, antibody light and heavy chain variable region sequences, and antibody light and heavy chain constant region sequences.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example through Van der Waals forces, or by using a leucine zipper.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

As used herein, the term "target" is a substance that interacts with a polypeptide herein. In some embodiments, targets, as defined herein, specifically include antigens with which the lambda-5-containing constructs, VpreB-containing constructs, or both the lambda-5-containing constructs and the VpreB-containing constructs interact. In some embodiments, as defined herein, "targets" specifically include antigens with which the heavy chain interacts, e.g., CDRH1, CDRH2, CDRH3, and any combination thereof. Preferably, interaction takes place by direct binding.

As used herein, the terms "peptide," "polypeptide" and "protein" all refer to a primary sequence of amino acids that are joined by covalent "peptide linkages." In general, a peptide consists of a few amino acids, typically from about 2 to about 50 amino acids, and is shorter than a protein. The term "polypeptide," as defined herein, encompasses peptides and proteins.

The term "amino acid" or "amino acid residue" typically refers to an amino acid having its art recognized definition such as an amino acid selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val) although modified, synthetic, or rare amino acids can be used as desired. Thus, modified and unusual amino acids listed in 37 CFR 1.822 (b)(4) are specifically included within this definition and expressly incorporated herein by reference. Amino acids can be subdivided into various sub-groups. Thus, amino acids can be grouped as having a nonpolar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr). Amino acids can also be grouped as small amino acids (Gly, Ala), nucleophilic amino acids (Ser, His, Thr, Cys), hydrophobic amino acids (Val, Leu, Ile, Met, Pro), aromatic amino acids (Phe, Tyr, Trp, Asp, Glu), amides (Asp, Glu), and basic amino acids (Lys, Arg).

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides can be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

An "amino acid modification" refers to a change in the amino acid sequence of a predetermined amino acid sequence. Exemplary modifications include an amino acid substitution, insertion and/or deletion.

An "amino acid modification at" a specified position, refers to the substitution or deletion of the specified residue, or the insertion of at least one amino acid residue adjacent the specified residue. By insertion "adjacent" a specified residue is meant insertion within one to two residues thereof. The insertion can be N-terminal or C-terminal to the specified residue.

An "amino acid substitution" refers to the replacement of at least one existing amino acid residue in a predetermined amino acid sequence with another different "replacement" amino acid residue. The replacement residue or residues can be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein.

A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. *Meth. Enzym.* 202:301 336 (1991). To generate such non-naturally occurring amino acid residues, the procedures of Noren et al. *Science* 244:182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) can be naturally occurring or non-naturally occurring as disclosed above.

An "amino acid deletion" refers to the removal of at least one amino acid residue from a predetermined amino acid sequence.

The term "mutagenesis" refers to, unless otherwise specified, any art recognized technique for altering a polynucleotide or polypeptide sequence. Preferred types of mutagenesis include error prone PCR mutagenesis, saturation mutagenesis, or other site directed mutagenesis.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

The term "and/or" designates both the option of "and" as well as the option of "or" in that particular circumstance. However, unless otherwise specified in the specification, the use of the term "or" or "and" encompasses a description of both option as well. Thus, the use of the term "or" should not be taken as excluding the option of "and", unless additional context indicates that it should (this definition does not apply to the language in the claims). The use of the singular or plural forms of a term encompasses both options (singlular or plural) as well as both options combined (singular and plural), unless indicated otherwise.

In the context of the present invention, the term "antibody" (Ab) is used in its broadest sense. This includes, for example, a native antibody composed of both a recombined heavy chain, a product typically derived from V(D)J gene recombination and a recombined light chain also a product typically derived from VJ gene recombination, or a fragment thereof.

A "native antibody" is heterotetrameric glycoprotein of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains, Chothia et al., J. Mol. Biol. 186:651 (1985); Novotny and Haber, Proc. Natl. Acad. Sci. U.S.A. 82:4592 (1985).

The term "monoclonal antibody" as used herein refers to an antibody obtained from or prepared as a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is typically directed against a single determinant on the antigen. Monoclonal antibodies can be prepared using any art recognized technique and those described herein such as, for example, a hybridoma method, as described by Kohler et al. (1975) Nature, 256:495, a transgenic animal, as described by, for example, (see e.g., Lonberg, et al. (1994) Nature 368(6474): 856-859), recombinant DNA methods (see, e.g., U.S. Pat. No. 4,816,567), or using phage antibody libraries using the techniques described in, for example, Clackson et al., Nature, 352:624-628 (1991) and Marks et al., J. Mol. Biol., 222:581-597 (1991). Monoclonal antibodies include chimeric antibodies, human antibodies and humanized antibodies and can occur naturally or be recombinantly produced.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies can have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric immunoglobulin" or "chimeric antibody" refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody," as used herein, is intended to include antibodies having variable regions in which both the framework and CDR regions are derived from human germline immunoglobulin sequences as described, for example, by Kabat et al. (See Kabat, et al. (1991) Sequences of proteins of Immunological Interest, Fifth Edition, U.S. Department of Health and Human Services, NIH Publication No. 91-3242). Furthermore, if the antibody contains a constant region, the constant region also is derived from human germline immunoglobulin sequences. The human antibodies can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one ore more amino acids replaced with an amino acid residue, e.g., an activity enhancing amino acid residue which is not encoded by the human germline immunoglobulin sequence. Typically, the human antibody can have up to twenty positions replaced with amino acid residues which are not part of the human germline immunoglobulin sequence. In a particular embodiment, these replacements are within the CDR regions as described in detail below.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially similar to a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

A "bispecific" or "bifunctional" Surrobody™ protein and/or antibody is an artificial hybrid SBP and/or antibody having two different heavy/light chain pairs and two or more different binding sites. Bispecific SBPs and/or antibodies can be produced by a variety of methods including fusion of hybridomas or linking of Fab' fragments. See, e.g., Songsivilai & Lachmann, (1990) Clin. Exp. Immunol. 79, 315-321; Kostelny et al. (1992) J. Immunol. 148, 1547-1553. In a particular embodiment, a bispecific SBP and/or antibody includes binding sites for both ErbB3 and IGF1-R (i.e., insulin-like growth factor 1-receptor). In some embodiments, a bispecific SBP and/or antibody includes binding sites for both ErbB3 and C-MET. In some embodiments, a bispecific SBP includes a binding site for ErbB3 and a binding site for ErbB2, ErbB3, ErbB4, EGFR, Lewis Y, MUC-1, EpCAM, CA125, prostate specific membrane antigen, PDGFR-.alpha, PDGFR-beta., C-KIT, or any of the FGF receptors. In some embodiments, the bispecific antibody and/or SBP binds to and/or inhibits ErbB3 and EGFR. In some embodiments, the bispecific antibody and/or SBP binds to and/or inhibits ErbB3 and ErbB2. In some embodiments, the SBP is angiogenic. In some embodiments, the bispecific antibody and/or SBP is anti-angiogenic.

As used herein, a "heterologous antibody" is defined in relation to the transgenic non-human organism or plant producing such an antibody.

An "isolated antibody," as used herein, is intended to refer to an antibody which is substantially free of other antibodies having different antigenic specificities (e.g., an isolated antibody that specifically binds to ErbB3 is substantially free of antibodies that specifically bind antigens other than ErbB3). In addition, an isolated antibody is typically substantially free of other cellular material and/or proteins. In some embodiments, a combination of "isolated" antibodies having different ErbB3 binding specificities are combined in a well defined composition.

As used herein, "isotype" refers to the antibody class (e.g., IgM or IgG1) or SBP that is encoded by heavy chain constant region genes. In some embodiments, an antibody or antigen binding portion thereof is of an isotype selected from an IgG1, an IgG2, an IgG3, an IgG4, an IgM, an IgA1, an IgA2, an IgAsec, an IgD, or an IgE antibody isotype. In some embodiments, an antibody is of the IgG1 isotype. In some embodiments, an antibody is of the IgG2 isotype.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the non-switched isotype is typically the first CH gene immediately downstream from the functionally rearranged VDJ gene. Isotype switching has been classified as classical or non-classical isotype switching. Classical isotype switching occurs by recombination events which involve at least one switch sequence regions in a gene encoding an antibody.

Non-classical isotype switching may occur by, for example, homologous recombination between human sigma$_{mu}$ and human .SIGMA$_{mu}$ (.delta.-associated deletion). Alternative non-classical switching mechanisms, such as intertransgene and/or interchromosomal recombination, among others, may occur and effectuate isotype switching.

The term "variable" with reference to SBP or antibody (for heavy and antibody light chains, but not for the surrogate light chain) chains is used to refer to portions of the SBP and/or antibody chains which differ extensively in sequence among SBP or antibody heavy chains and participate in the binding and specificity of each particular SBP and/or antibody for its particular antigen. Such variability is concentrated in three segments called hypervariable regions in the heavy chain variable domains for the SBPs (but in both the light chain and the heavy chain variable domains for antibodies). The more highly conserved portions of variable domains are called the framework region (FR). The variable domains of native heavy and antibody light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991), pages 647-669). The constant domains are not involved directly in binding an SBP and/or antibody to an antigen, but exhibit various effector functions, such as participation of the antibody and/or the SBP in antibody-dependent or SBP-dependent cellular toxicity, respectively.

The term "hypervariable region" when used herein refers to the amino acid residues of an SBP and/or antibody that are primarily responsible for antigen-binding. The hypervariable region comprises amino acid residues from a "complementarity determining region" or "CDR" that has a great propensity for target contact (i.e., residues 30-35 (H1), 47-58 (H2) and 93-101 (H3) in the heavy chain variable domain; MacCallum et al, *J Mol Biol.* 262(5):732-45 (1996). Alternatively they are defined by others to similar regions see Chothia and/or Kabat.

The term "loop region" ("LR"), "LR1 region" and "LR2" denotes a region in the VpreB that forms a looped structure adjacent, or proximal, to heavy chain CDRs. "Loop region" or "LR3 region" can also denote the small predicted loop structure (approximately 10 amino acids long) created through recombinant fusion of 1) VpreB and λ5, or 2) VpreB and constant light chain that may contain a J-region, or 3) Variable light region, with or without a J-region and λ5.

The term "framework region" refers to the art recognized portions of an antibody and/or SBP variable region that exist between the more divergent regions. Such framework regions are typically referred to as frameworks 1 through 4 (FR1, FR2, FR3, and FR4) and provide a scaffold for holding, in three-dimensional space, the three CDRs found in a heavy or light chain antibody and/or SBP variable region, such that the CDRs can form an antigen-binding surface. As will be appreciated by those of skill in the art, minor variations are possible and contemplated for various embodiments involving framework regions. The term "FR analogous region", "FR1 analogous region", "FR2 analogous region", "FR3 analogous region," or "FR4 analogous region" denotes a region in the VpreB or λ5 that would otherwise correspond to a FR region (or FR1, FR2, FR3, or FR4 region respectively) in an antibody's light chain, or otherwise lies adjacent to the "loop regions".

Depending on the amino acid sequence of the constant domain of their heavy chains, antibodies can be assigned to different classes. There are five major classes of antibodies IgA, IgD, IgE, IgG, and IgM, and several of these can be further divided into subclasses (isotypes), e.g., IgG1, IgG2, IgG3, IgG4, IgA, and IgA2.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains. Any reference to an antibody light chain herein includes both κ and λ light chains.

"Antibody fragments" comprise a portion of a full length antibody, generally the antigen binding or a variable domain thereof. Examples of antibody fragments include, but are not limited to, Fab, Fab', F(ab')$_2$, Dab, scFv, and (scFv)$_2$ fragments. "SBP fragments" or "SBP fragments" comprise a corresponding portion of a full length SBP, generally the antigen binding or a variable domain thereof. Examples of SBP fragments include, but are not limited to, Sab, Sab', S(ab')$_2$, scSv, and (scSv)$_2$ fragments. The term "Sur-binding protein" or "SBP" encompasses both full length surroglobulins (SgGs) and binding fragments thereof, including, but not limited to Sab, SgG, (2-piece or 3 piece), single chain SBP (scSv), and/or SLC domain.

As used herein the term "antibody binding region" refers to one or more portions of an immunoglobulin or antibody variable region capable of binding a target. Typically, the antibody binding region is, for example, an antibody light chain (VL) (or variable region thereof), an antibody heavy chain (VH) (or variable region thereof), a heavy chain Fd region, a combined antibody light and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody. Examples of antibody binding regions encompassed within the term include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$, and $V_H$ domains of a single arm of an antibody, (v) a dAb including VH and VL domains; (vi) a dAb fragment (Ward et al. (1989) Nature 341, 544-546), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, $V_L$, and $V_H$, are coded for by separate genes, they can be joined, using recombinant methods, by a synthetic linker that enables them to be made as a single protein chain in which the $V_L$, and $V_H$ regions pair to form monovalent molecules (known as single chain Fv (scFv); see e.g., Bird et al. (1988) Science 242, 423-426; and Huston et al. (1988) Proc. Natl. Acad. Sci. USA 85, 5879-5883). Such single chain antibodies are also intended to be encompassed within the term "antibody binding region" of an antibody. These antibody fragments are obtained using conventional techniques known to those with skill in the art, and the fragments are screened for utility in the same manner as are intact antibodies. Antibody binding regions can be produced by recombinant DNA techniques, or by enzymatic or chemical cleavage of intact immunoglobulins.

As used herein the term "Sur-binding protein" or "SBP" robody" refers to one or more portions of a Surroglobulin or SBP variable region capable of binding an antigen(s). In some embodiments, the SBP binding region is or includes, for example, an antibody heavy chain (VH) (or variable region thereof), a heavy chain Fd region, a VpreB and/or lambda 5 and an antibody heavy chain (or variable region thereof) such as a Sab, a S(ab')$_2$ (a F(ab')$_2$ type structure) or single chain SBP (scSv), or a full length surroglobulin (SgG). Examples of SBP binding regions encompassed within the term include (i) a Surroglobulin which refers to a bivalent binding protein including the VpreB1 and/or lambda 5 or CL or, VL and lambda 5, $V_H$, CH1 domain, and an Fc (CH2 and CH3 domains); (ii) a Sab fragment, a monovalent fragment including the VpreB1 and/or lambda 5 or CL, $V_H$ and CH1 domains; (iii) a S(ab')$_2$ fragment, a bivalent fragment comprising two Sab fragments linked by a disulfide bridge at the hinge region; (iv) a Fd fragment consisting of the $V_H$ and CH1 domains; (v) a Sv fragment including the VpreB and/or lambda 5 and $V_H$ domains of a single arm of an antibody, (vi) a dAb including VH and VpreB and/or lambda 5 domains; (vii) a dAb fragment (Ward et al. (1989) Nature 341, 544-546), which includes of a $V_H$ domain; (viii) a dAb which includes a VH or a VpreB and/or lambda 5 domain; and (ix) an isolated complementarity determining region (CDR) or (x) a combination of two or more isolated CDRs which may optionally be joined by a synthetic linker. Furthermore, although the two domains of the Sv fragment, VpreB and/or lambda 5 and $V_H$, are coded for by separate genes, they can be joined, using recombinant methods, by a synthetic linker that enables them to be made as a single protein chain in which the VpreB and/or lambda 5 and V_H regions pair to form monovalent molecules (referred here as as single chain Sv (scSv); for corresponding antibody correlates see e.g., Bird et al. (1988) Science 242, 423-426; and Huston et al. (1988) Proc. Natl. Acad. Sci. USA 85, 5879-5883). Such single chain SBPs are also intended to be encompassed within the term "SBP binding region" of an SBP. These SBP fragments are obtained using conventional techniques known to those with skill in the art, and the fragments are screened for utility in the same manner as are intact antibodies or SBPs. SBP binding regions can be produced by recombinant DNA techniques, or by enzymatic or chemical cleavage of intact Surroglobulins.

In some embodiments, the heavy chain CDR is CDR1, CDR2, or CDR3. In some embodiments, two heavy chain CDRs are included, and can be selected from CDR1 and CDR2, CDR2 and CDR3, or CDR1 and CDR3. In some embodiments, the SBP comprises a surrogate light chain sequence and a heavy chain CDR1 (HCDR1), a heavy chain CDR2 (HCDR2), and a heavy chain CDR3 (HCDR3). In some embodiments, the SBP comprises a surrogate light chain sequence and a heavy chain variable region. In some embodiments, the SBP comprises a surrogate light chain sequence and a heavy chain sequence. The term SBP also encompasses Sabs, SgGs, and other forms of variations on antibody type structures (including those outlined herein, for example, Fab, Fab', F(ab')$_2$, scFv, and (scFv)$_2$, except, for example, with at least one VpreB and/or lambda 5 sequence instead of the corresponding light chain section).

As used herein the term "binding region" refers to one or more portions of a binding protein, such as a SBP, capable of binding a target. Typically, the binding region is, for example, an antibody light chain (VL) (or variable region thereof and/or surrogate light chain), an antibody heavy chain (VH) (or variable region thereof), a heavy chain Fd region, a combined antibody light (and/or surrogate light chain) and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody. In some embodiments, the lambda 5 sequence and/or the VpreB sequence is employed in place of an antibody light chain or fragment thereof.

The term "epitope" as used herein, refers to a sequence of at least about 3 to 5, preferably at least about 5 to 10, or at least about 5 to 15 amino acids, and typically not more than about 500, or about 1,000 amino acids, which define a sequence that by itself, or as part of a larger sequence, is bound by a SBP and/or an antibody. An epitope is not limited to a polypeptide having a sequence identical to the portion of the parent protein from which it is derived. Indeed, viral genomes are in a state of constant change and exhibit relatively high degrees of variability between isolates. Thus the term "epitope" encompasses sequences identical to the native sequence, as well as modifications, such as deletions, substitutions and/or insertions to the native sequence. Generally, such modifications are conservative in nature but non-conservative modifications are also contemplated. The term specifically includes "mimotopes," i.e. sequences that do not identify a continuous linear native sequence or do not necessarily occur in a native protein, but functionally mimic an epitope on a native protein. The term "epitope" specifically includes linear and conformational epitopes.

The term "vector" is used to refer to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors. "The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

The term "filamentous phage" refers to a viral particle capable of displaying a heterogenous polypeptide on its surface, and includes, without limitation, fl, fd, Pfl, and M13. The filamentous phage can contain a selectable marker such as tetracycline (e.g., "fd-tet"). Various filamentous phage display systems are well known to those of skill in the art (see, e.g., Zacher et al. *Gene* 9: 127-140 (1980), Smith et al. *Science* 228: 1315-1317 (1985); and Parmley and Smith *Gene* 73: 305-318 (1988)).

The term "panning" is used to refer to the multiple rounds of screening process in identification and isolation of phages carrying compounds, such as antibodies, with high affinity and specificity to a target.

The term "inhibition" as used herein, refers to any statistically significant decrease in biological activity, including full blocking of the activity. For example, "inhibition" can refer to a decrease of about 10%, 20%, 30%, 40%, 50%, 60%, 70%, 80%, 90%, or 100% in biological activity.

The terms "treat" or "prevent" do not require complete treatment or complete prevention under all conditions. A slowing of the onset of a disorder or its symptoms or a decrease in the number of the symptoms can be adequate "prevention" in some embodiments. Similarly, a decrease in the severity of the symptoms of the disorder can also be an effective treatment for a disorder.

The term "consensus sequence", as used herein with respect to complementarity determining regions (CDRs), refers to a composite or generalized sequence for a CDR that has been defined based on information as to which amino acid residues within the CDR are amenable to modification without detriment to antigen binding. Thus, in a "consensus sequence" for a CDR, certain amino acid positions are occupied by one of multiple possible amino acid residues at that position. For example, within a CDR, if antigen binding has been found to be unaffected by the presence of either a tyrosine or a phenylalanine at a particular position, then that particular position within the consensus sequence can be either tyrosine or phenylalanine (T/F). Consensus sequences for CDRs can be defined, for example, by scanning mutagenesis (e.g., alanine scanning mutagenesis) of amino acid residues within the antibody and/or SBP CDRs, followed by evaluation of the binding of the mutants to the antigen to determine whether the mutated amino acid position affects antigen binding.

As used herein, the terms "specific binding," "specifically binds," "selective binding," and "selectively binds," mean that a SBP, antigen-binding portion thereof, or antibody exhibits appreciable affinity for a particular antigen or epitope and, generally, does not exhibit significant non-specific binding with other antigens and epitopes. "Appreciable" or preferred binding includes binding with an affinity of at least $10^6$, $10^7$, $10^8$, $10^9$ $M^{-1}$, or $10^{10}$ $M^{-1}$. Affinities greater than $10^7 M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{19}$ $M^{-1}$, preferably $10^7$ to $10^{10}$ $M^{-1}$, more preferably $10^8$ to $10^{12}$ $M^{-1}$. An antibody and/or SBP that "does not exhibit significant non-specific binding" is one that will not appreciably bind to an undesirable entity (e.g., an undesirable proteinaceous entity). For example, in some embodiments, a SBP and/or antibody or antigen-binding portion thereof that specifically binds to ErbB3 will appreciably bind that ErbB3 molecule but will not significantly react with other ErbB molecules and non-ErbB proteins or peptides. Specific or selective binding can be determined according to any art-recognized means for determining such binding, including, for example, according to Scatchard analysis and/or competitive binding assays.

The term "$K_D$," as used herein, is intended to refer to the dissociation equilibrium constant of a particular SBP and/or antibody-antigen interaction or the affinity of an SBP and/or antibody for an antigen, preferably as measured using a surface plasmon resonance assay (e.g., as determined in a BIACORE 3000 instrument (GE Healthcare) using recombinant ErbB3 as the analyte and the antibody and/or SBP as the ligand) or a cell binding assay. In some embodiments, the SBP, antigen binding portion, and/or antibody binds an antigen (e.g., ErbB3) with an affinity ($K_D$) of 50 nM or better (i.e., or less) (e.g., 40 nM or 30 nM or 20 nM or 10 nM or less). In a particular embodiment, an SBP, antigen binding portion thereof, and/or antibody according to the present invention binds ErbB3 with an affinity ($K_D$) of 8 nM or better (e.g., 7 nM, 6 nM, 5 nM, 4 nM, 2 nM, 1.5 nM, 1.4 nM, 1.3 nM, 1 nM or less. In some embodiments, a SBP, antigen binding portion thereof, and/or antibody binds an antigen (e.g., ErbB3) with an affinity ($K_D$) of approximately less than $10^{-7}$ M, such as approximately less than $10^{-8}$ M, $10^{-9}$ M or $10^{-19}$ M or even lower, and binds to the predetermined antigen with an affinity that is at least two-fold greater than its affinity for binding to a non-specific antigen (e.g., BSA, casein) other than the predetermined antigen or a closely-related antigen. The term "$K_{off}$" as used herein, is intended to refer to the off rate constant for the dissociation of a SBP and/or antibody from their respective antigen bound complexes.

The term "EC50," as used herein, refers to the concentration of a SBP or an antigen-binding portion thereof and/or antibody, which induces a response, either in an in vitro or an in vivo assay, which is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

In some embodiments, SBPs and/or antibodies are provided that bind the same or an overlapping epitope as the SBPs and/or antibodies for which amino acid sequences are disclosed herein, e.g., SBPs and/or antibodies that compete for binding to ErbB3, or bind epitopes which overlap with epitopes bound by the antibodies described herein, e.g., an epitope located on ectodomain of ErbB3, preferably on Domain I of the ectodomain of ErbB3. SBPs and/or antibodies that recognize the same epitope can be identified using routine techniques such as an immunoassay, for example, by showing the ability of one SBP and/or antibody to block the binding of another SBP and/or antibody to a target antigen, i.e., a competitive binding assay. Competitive binding is determined in an assay in which the immunoglobulin under test inhibits specific binding of a reference antibody and/or SBP to a common antigen, such as ErbB3. Numerous types of competitive binding assays are known, for example: solid phase direct or indirect radioimmunoassay (RIA), solid phase direct or indirect enzyme immunoassay (EIA), sandwich competition assay (see Stahli et al., (1983) Methods in Enzymology 9:242); solid phase direct biotin-avidin EIA (see Kirkland et al., (1986) J. Immunol. 137:3614); solid phase direct labeled assay, solid phase direct labeled sandwich assay (see Harlow and Lane, (1988) Antibodies: A Laboratory Manual, Cold Spring Harbor Press); solid phase direct label RIA using 1-125 label (see Morel et al., (1988) Mol. Immunol. 25(1):7); solid phase direct biotin-avidin EIA (Cheung et al., (1990) Virology 176:546); and direct labeled RIA. (Moldenhauer et al., (1990) Scand. J. Immunol. 32:77). Typically, such an assay involves the use of purified antigen (e.g., ErbB3) bound to a solid surface or cells bearing either of these, an unlabeled test surroglobulin and a labeled reference immunoglobulin and/or SBP. Competitive inhibition is measured by determining the amount of label bound to the solid surface or cells in the presence of the test surroglobulin. Usually the test surroglobulin is present in excess. Usually, when a competing SBP and/or antibody is present in excess, it will inhibit specific binding of a reference SBP and/or antibody to a common antigen by at least 50-55%, 55-60%, 60-65%, 65-70% 70-75% or more.

The term "sample" refers to tissue, body fluid, or a cell from a patient or a subject. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues can be obtained and appropriately prepared. Other patient samples, including urine, tear drops, serum, cerebrospinal fluid, feces, sputum, cell extracts etc. can also be useful for particular tumors.

The term "patient" includes human and other mammalian subjects that receive either prophylactic or therapeutic treatment.

As used herein, the term "subject" or "patient" includes any human or non-human animal. For example, the methods and compositions disclosed herein can be used to treat a subject having cancer. In a preferred embodiment, the subject is a human. The term "non-human animal" includes all vertebrates, e.g., mammals and non-mammals, such as non-human primates, sheep, dog, cow, etc.

The terms "anti-cancer agent" and "antineoplastic agent" refer to drugs used to treat malignancies, such as cancerous growths. Drug therapy can be used alone, or in combination with other treatments such as surgery or radiation therapy. Several classes of drugs can be used in cancer treatment, depending on the nature of the organ involved. For example, breast cancers are commonly stimulated by estrogens, and can be treated with drugs which inactive the sex hormones. Similarly, prostate cancer can be treated with drugs that inactivate androgens, the male sex hormone. Anti-cancer agents include, among others, agents recited in Table 0.1

TABLE 0.1

| Anti-Cancer Agent | Comments | Examples |
|---|---|---|
| Antibodies | Antibodies which bind IGF-1R (insulin-like growth factor type 1 receptor), which is expressed on the cell surface of must human cancers | A12 (fully humanized mAb) 19D12 (fully humanized mAb) CP751-871 (fully humanized mAb) H7CIO (humanized mAb) alphaIR3 (mouse) scFV/FC (mouse/human chimera) EM/I64 (mouse) AMG 479 (fully humanized mAb; Amgen) IMCA 12 (fully humanized mAb; Imclone) NSC-742460 (Dyax) MR-0646, F50035 (Pierre Fabre Medicament, Merck) |
| | Antibodies which bind EGFR; Mutations affecting EGFR expression or activity can result in cancer | matuzumab (EMD72000) Erbitux ®/cetuximab (Imclone) Vectibix ®/panitumumab (Amgen) mAb 806 nimotuzumab (TheraCIM) INCB7839 (Incyte) panitumumab (Vectibix ®; Amgen) |
| | Antibodies which bind cMET (mesenchymal epithelial transition factor); a member of the MET family of receptor tyrosine kinases) | AVEO (AV299) (AVEO) AMGI02 (Amgen) 5D5 (OA-5D5) (Genentech) |
| | Anti-ErbB2 antibodies which bind various epitopes Anti-ErbB2 (HER2) antibodies Anti-ErbB3 antibodies | Herceptin ® (trastuzumab; Genentech/Roche) binds ectodomain Domain II of ErbB2; Omnitarg ® (pertuzumab; 2C4, RI273; Genentech/Roche) binds Domain N of ErbB2 1B4C3; 2DID12 (U3 PharmaAG) U3-1287/AMG888 (U3 PharmalAmgen) |
| Small Molecules Targeting IGF1R | IGF-1R (insulin-like growth factor type 1 receptor), which is expressed on the cell surface 0 f must human cancers | NVP-AEW541-A BMS-536,924 (IH-benzoimidazol-2-yl)-IH pyridin-2-one) BMS-554,417 Cycloligan TAE226 PQ401 |
| Small Molecules Targeting EGFR | EGFR; Mutations affecting EGFR expression or activity can result in cancer | Iressa ®/gefitinib (AstraZeneca) CI-1033 (PD 183805) (Pfizer) TYVERB/lapatinib (GlaxoSmithKline) Tykerb ®/lapatinib ditosylate (SmithKline Beecham) Tarceva ®/Erlotinib HCL (OSI Pharma) PKI-166 (Novartis) PD-158780 EKB-569 Tyrphostin AG 1478(4-(3-Chloroanillino)-6,7-dimetboxyquinazoline) |
| Small Molecules Targeting ErbB2 | ErbB2, also known as HER2, a member of the ErbB family of receptors, which is expressed on certain cancer cells | HKI-272 (neratinib; Wyeth) KOS-953 (tanespimycin; Kosan Biosciences) Tykerb ®/lapatinib ditosylate (SmithKline Beecham) |
| Small Molecules Targeting cMET | cMET (Mesenchymal epithelial transition factor); a member of the MET family of receptor tyrosine kinases) | PHA665752 ARQ 197 (ArQule) ARQ-650RP (ArQule) |

TABLE 0.1-continued

| Anti-Cancer Agent | Comments | Examples |
| --- | --- | --- |
| Antimetabolites | An antimetabolite is a chemical with a similar structure to a substance (a metabolite) required for normal biochemical reactions, yet different enough to interfere with the normal functions of cells, including cell division. | flourouracil (5-FU)<br>capecitabine/XELODA ® (HLR Roche)<br>5-trifluoromethyl-2'-deoxyuridine<br>methotrexate sodium (Trexall) (Barr)<br>raltitrexed/Tomudex ® (AstraZaneca)<br>pemetrexed/Alimta ® (Lilly)<br>tegafur<br>cytosine arabinoside (Cytarabine, Ara-C)/<br>tioguanine/Lanvis ® (GlaxoSmithKline)<br>5-azacytidine<br>6-mercaptopurine (Mercaptopurine, 6-MP)<br>azatbioprine/Azasan ® (AAIPHARMA LLC)<br>6-thioguanine (6-TG)/Purinethol ® (TEVA)<br>pentostatin/Nipent ® (Hospira Inc.)<br>fludarabine phosphate/Fludara ® (Bayer Health Care)<br>cladribine/Leustatin ® (2-CdA, 2-chlorodeoxyadenosine) (Ortho Biotech)<br>floxuridine (5-fluoro-2'-deoxyuridine)/<br>FUDR ® (Hospira, Inc,) |
| Alkylating agents | An alkylating antineoplastic agent is an alkylating agent that attaches an alkyl group to DNA. Since cancer cells generally proliferate unrestrictively more than do healthy cells they are more sensitive to DNA damage, and alkylating agents are used clinically to treat a variety of tumors. | Ribonucleotide Reductase Inhibitor (RNR)<br>cyclophosphamide/Cytoxan ® (BMS)/<br>Neosar ® (TEVA)<br>ifosfamide/Mitoxana ® (ASTA Medica)<br>ThioTEPA (Bedford, Abraxis, Teva)<br>BCNU → 1,3-bis(2-chloroethyl)-1-nitosourea<br>CCNU → 1,-(2-chloroethyl)-3-cyclohexyl-l nitrosourea (methyl CCNU)<br>hexamethylmelamine (altretamine, HMM)/<br>Hexalen ® (MGI Pharma Inc.)<br>busulfan/Myleran ® (GlaxoSmithKline)<br>procarbazine HCL/Matulane ® (Sigma Tau)<br>Dacarbazine (DTIC ®)<br>chlorambucil/Leukaran ® (SmithKline Beecham)<br>Melphalan/Alkeran ® (GlaxoSmithKline)<br>cisplatin (Cisplatinum, CDDP)/Platinol (Bristol Myers)<br>carboplatin/Paraplatin (BMS)<br>oxaliplatin/Eloxitan ® (Sanofi-Aventis US)<br>Bendamustine<br>carboquone<br>carmustine<br>chloromethine<br>dacarbazine (DTIC)<br>fotemustine<br>lomustine<br>mannosulfan<br>nedaplatin<br>nimustine<br>prednimustine<br>ranimustine<br>satraplatin<br>semustine<br>streptozocin<br>temozolomide<br>treosulfan<br>triaziquone<br>triethylene melamine<br>triplatin tetranitrate<br>trofosfamide<br>uramustine |
| Topoisomerase inhibitors | Topoisomerase inhibitors are chemotherapy agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. | doxorubicin HCL/Doxil ® (Alza)<br>daunorubicin citrate/Daunoxome ® (Gilead)<br>mitoxantrone HCL/Novantrone (EMD Serono)<br>actinomycin D<br>etoposide/Vepesid ® (BMS)/Etopophos ® (Hospira, Bedford, Teva Parenteral, Etc.)<br>topotecan HCL/Hycamtin ® (GlaxoSmithKline)<br>teniposide (VM-26)Vumon ® (BMS)<br>irinotecan HCL(CPT-II)/<br>camptosar ® (Pharmacia & Upjohn)<br>camptothecin (CPT)<br>belotecan<br>rubitecan |

TABLE 0.1-continued

| Anti-Cancer Agent | Comments | Examples |
|---|---|---|
| Microtubule targeting agents | Microtubules are one of the components of the cytoskeleton. They have diameter of-24 nm and length varying from several micrometers to possibly millimeters in axons of nerve cells. Microtubules serve as structural components within cells and are involved in many cellular processes including mitosis, cytokinesis, and vesicular transport. | vincristine/Oncovin ® (Lilly)<br>vinblastine sulfate/Velban ®(discontinued) (Lilly)<br>vinorelbine tartrate/Navelbine ® (PierreFabre)<br>vindesine sulphate/Eldisine ® (Lilly)<br>paclitaxel/Taxol ® (BMS)<br>docetaxel/Taxotere ® (Sanofi Aventis US)<br>Nanoparticle paclitaxel (ABI-007)!<br>Abraxane ® (Abraxis BioScience, Inc.)<br>ixabepilone/IXEMPRA ™ (BMS)<br>larotaxel<br>ortataxel<br>tesetaxel<br>vinflunine |
| Kinase inhibitors | Tyrosine kinases are enzymes within the cell that function to attach phosphate groups to the amino acid tyrosine. By blocking the ability of protein tyrosine kinases to function, these compounds provide a tool for controling cancerous cell growth. | imatinib mesylate/Gleevec (Novartis)<br>sunitinib malate/Sutent ® (Pfizer)<br>sorafenib tosylate/Nexavar ® (Bayer)<br>nilotinib hydrochloride monohydrate/ Tasigna ® (Novartis)<br>AMG 386 (Amgen)<br>axitinib (AG-013736; Pfizer, Inc.)<br>bosutinib (SKI-606; Wyeth)<br>brivanib alalinate (BMS-582664; BMS)<br>cediranib (AZD2171; Recentin, AstraZeneca)<br>dasatinib (BMS-354825: Sprycel ®; BMS)<br>lestaurtinib (CEP-701; Cephalon)<br>motesanib diphosphage (AMG-706; Amgen/Takeda)<br>pazopanib HCL (GW786034; Armala, GSK)<br>semaxanib (SU5416; Pharmacia)<br>vandetanib (AZD647; Zactima; AstraZeneca)<br>vatalanib (PTK-787; Novartis, Bayer Schering Pharma)<br>XL184 (NSC718781; Exelixis, GSK)<br>Mk-2206 |
| Protein synthesis inhibitors | Induces cell apoptosis | L-asparaginase/Elspar ® (Merck & Co.) |
| Immunotherapeutic agents | Induces cancer patients to exhibit immune responsiveness | Alpha interferon<br>Angiogenesis Inhibitor/Avastin ® (Genentech)<br>IL-2 → Interleukin 2 (Aldesleukin)/ Proleukin ® (Chiron)<br>IL-12 → Interleukin 12 |
| Hormonal therapies | Hormonal therapies associated with menopause and aging seek to increase the amount of certain hormones in the body to compensate for age-or disease-related hormonal declines. Hormonal therapy as a cancer treatment generally either reduces the level of one or more specific hormones, blocks a hormone from interacting with its cellular receptor or otherwise alters the cancer's ability to be stimulated by hormones to grow and spread. Such hormonal therapies thus include hormone antagonists and hormone synthesis inhibitors. In some instances hormone agonists can also be used as anticancer hormonal therapies. | Ttoremifene citrate/Fareston ® (GTX, Inc.)<br>fulvestrant/Faslodex ® (AstraZeneca)<br>raloxifene HCL/Evista ® (Lilly)<br>anastrazole/Arimidex ® (AstraZeneca)<br>letrozole/Femara ® (Novartis)<br>fadrozole (CGS 16949A)<br>exemestane/Aromasin ® (Pharmacia & Upjohn)<br>leuprolide acetate/Eligard ® (QTL USA) Lupron ® (TAP Pharm.)<br>goserelin acetate/Zoladex ® (AstraZeneca)<br>triptorelin pamoate/Trelstar ® (Watson Labs)<br>buserelin/Suprefact ® (Sanofi Aventis)<br>nafarelin<br>cetrorelix/Cetrotide ® (EMD Serono)<br>bicalutamide/Casodex ® (AstraZeneca)<br>nilutamide/Nilandron ® (Aventis Pharm.)<br>megestrol acetate/Megace ® (BMS)<br>somatostatin Analogs (e.g., Octreotide acetate/ Sandostatin ® (Novartis))<br>abarelix (Plenaxis TM; Amgen)<br>abiraterone acetate (CB7630; BTG plc)<br>afunoxifene (TamoGel; Ascend Therapeutics, Inc.)<br>aromatase inhibitor (Atamestane plus toremifene; Intarcia Therapeutics, Inc.)<br>arzoxifene (Eli Lilly & Co)<br>Asentar ™; DN-101 (Novacea; Oregon Health Sciences U)<br>flutamide (Eulexin ®, Schering; Prostacur, Laboratorios Almirall, S.A) |

TABLE 0.1-continued

| Anti-Cancer Agent | Comments | Examples |
|---|---|---|
| | | letrozole (CGS20267) (Femara ®, Chugai; Estrochek ®, (Jagsonpal Pharmaceuticals Ltd;) Delestrogen ®, estradiol valerate (Jagsonpal) magestrol acetate/Megace ® medroxyprogesteone acetate (Veraplex ®; Combiphar) MT206 (Medisyn Technologies, Inc.) nandrolone decanoate (Zestabolin ®; Mankind Pharma Ltd) tamoxifen (Taxifen ®, Yung Shin Pharmaceutical; Tomifen ®, Alkem Laboratories Ltd.) tamoxifen citrate (Nolvadex, AstraZeneca; soltamox, EUSA Pharma Inc; tamoxifen citrate SOPHARMA, Sopharma JSCo.) |
| Glucocorticoids | Anti-inflammatory drugs used to reduce swelling that causes cancer pain. | predinsolone dexamethasone/Decadron ® (Wyeth) prednisone (Deltasone, Orasone, Liquid Pred, Sterapred ®) |
| Aromatase inhibitors mTOR inhibitors | Includes imidazoles The mTOR signaling pathway was originally discovered during studies of the immunosuppressive agent rapamycin. This highly conserved pathway regulates cell proliferation and metabolism in response to environmental factors, linking cell growth factor receptor signaling via phosphoinositide-3-kinase (PI-3K) to cell growth, proliferation, and angiogenesis. | ketoconazole sirolimus (Rapamycin)/Rapamune ® (Wyeth) Temsirolimus (CCI-779)/Torisel ® (Wyeth) Deforolimus (AP23573) (Ariad Pharm.) Everolimus (RAD001)/Certican ® (Novartis) |
| Chemotherapeutic agents | | adriamycin, 5-fluorouracil, cytoxin, bleomycin, mitomycin C, daunomycin, carminomycin, aminopterin, dactinomycin, mitomycins, esperamicins, clofarabine, mercaptopurine, pentostatin, thioguanine, cytarabine, decitabine, floxuridine, gemcitabine (Gemzar), enocitabine, sapacitabine |
| Protein Kinase B (PKB) Inhibitors | | AKT Inhibitor Astex ® (Astex Therapeutics) AKT Inhibitors NERVIANO (Nerviano Medical Sciences) AKT Kinase Inhibitor TELIK (Telik Inc) AKT DECIPHERA (Decipher Pharmaceuticals, LLC) perifosine (KRX0401, D-21266; Keryx Biopharmaceuticals Inc, AEterna Zentaris Inc) perifosine with Docetaxel (Keryx Biopharmaceuticals Inc, AEterna Zentaris Inc) perifosine with Gemcitabine (AEterna Zentaris Inc) perifosine with paclitaxel (AEterna Zentaris Inc) protein kinase-B inhibitor DEVELOGEN (DeveloGen AG) PX316 (Oncothyreon, Inc.) RX0183 (Rexahn Pharmaceuticals Inc) RX0201 (Rexahn Pharmaceuticals Inc) VQD002 (VioQuest Pharmaceuticals Inc) XL418 (Exelixis Inc) ZEN027 (AEterna Zentaris Inc) |
| Phosphatidylinositol 3-Kinase (P13K) Inhibitors | | BEZ235 (Novartis AG) BGT226 (Novartis AG) CAL101 (Calistoga Pharmaceuticals, Inc.) CHR4432 (Chroma Therapeutics Ltd) Erk/P13K Inhibitors ETERNA (AEterna Zentaris Inc) GDC0941 (Genentech Inc/Piramed Limited/Roche Holdings Ltd) |

TABLE 0.1-continued

| Anti-Cancer Agent | Comments | Examples |
|---|---|---|
| | | enzastaurin HCL (LY317615; Enzastaurin; Eli Lilly) |
| | | LY294002/Wortmannin |
| | | PI3K Inhibitors SEMAFORE (Semafore Pharmaceuticals) |
| | | PX866 (Oncothyreon, Inc.) |
| | | SF1126 (Semafore Pharmaceuticals) |
| | | VMD-8000 (VM Discovery, Inc.) |
| | | XL147 (Exelixis Inc) |
| | | XL147 with XL647 (Exelixis Inc) |
| | | XL765 (Exelixis Inc) PI-103 (Roche/Piramed) |
| Cyclin Dependent Kinase Inhibitors | | CYC200, R-roscovitine (Seliciclib; Cyclacel Pharma) NSC-649890, L86-8275, HMR-I275 (alvocidib; NCI) |
| TLr9, CD289 | | IMOxine (Merck KGaA) |
| | | HYB2055 (Idera) IMO-2055 (Isis Pharma) |
| | | 1018 ISS (Dynavax Technologies/UCSF) |
| | | PF-3512676 (Pfizer) |
| Enzyme Inhibitor | | Ionafarnib(SCH66336; Sarasar; SuperGen, U Arizona) |
| Anti-TRAIL | | AMG-655 (Aeterna Zentaris, Keryx Biopharma) |
| | | Apo2L/TRAIL, AMG951 (Genentech, Amgen) |
| | | APOMAB (fully humanized mAb; Genentech) |
| MEK Inhibitors | [Mitogen-Activated Protein Kinase Kinase 1 (MAP2K1); Mitogen Activated Protein Kinase Kinase 2 (MAP2K2)] | ARRY162 (Array BioPharma Inc) |
| | | ARRY704 (Array BioPharma Inc) |
| | | ARRY886 (Array BioPharma Inc) |
| | | AS703026 (Merck Serono S.A) |
| | | AZD6244 (AstraZeneca Plc) |
| | | AZD8330 (AstraZeneca Plc) |
| | | RDEA119 (Ardea Biosciences, Inc.) |
| | | RDEA436 (Ardea Biosciences, Inc.) |
| | | XL518 (Exelixis Inc; Genentech Inc) |
| Miscellaneous Inhibitors | | Imprime PGG (Biothera) |
| | | CHR-2797 (AminopeptidaseM1 inhibitor; Chroma Therapeutics) |
| | | E7820, NSC 719239 (Integrin-alpha2 inhibitor, Eisai) |
| | | INCB007839 (ADAM 17, TACE Inhibitor; Incyte) |
| | | CNF2024, BIIB021 (Hsp90 Inhibitor; Biogen Idec) |
| | | MP470, HPK-56 (Kit/Mel/Ret Inhibitor; Schering-Plough) |
| | | SNDX-275/MS-275 (HDAC Inhibitor; Syndax) |
| | | Zarnestra TM, Tipifarnib, R115777 (Ras Inhibitor; Janssen Pharma) |
| | | volociximab; Eos 200-4, M200 (alpha5β1 integrin inhibitor; Biogen Idec; Eli Lilly/UCSF/PDL BioPharma) |
| | | apricoxib (TP2001; COX-2 Inhibitor, Daiichi Sankyo; Tragara Pharma) |
| | | vemurafenib |

Thus, in some embodiments, any one or more of the compounds in Table 0.1 can be combined with any one or more of the sur-binding proteins provided herein, including 2810-C01 and/or 2716-F05. In addition, one or more of the above items can be applied in a method of treatment of a cancer and/or method of: suppressing tumor growth; suppressing a cancerous cell; treating cancer; blocking the Ras/Raf/MEK pathway; and/or blocking the PI3K, AKT, or PI3K and AKT pathway. The method can include one or more of the molecules from Table 0.1 and one or more of the SBPs provided herein, such as 2817-C01 and/or 2716-F05.

The term "EGF-like ligand," encompasses molecules that bind to and activate ErbB dependent pathways. Such ligands include variations on neuregulin ("NRG") such as NRG-1, NRG-2, NRG-3, and NRG-4, as well as isoforms of these types of neuregulin. The term neuregulin is often used interchangeably with the term heregulin. The heregulin family includes alpha, beta and gamma heregulins (Holmes et al., Science, 256: 1205-1210 (1992); U.S. Pat. No. 5,641,869; and Schaefer et a/. Oncogene 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. Growth Factors 11:235-257 (1994); Lemke, G. Molec. & Cell. Neurosci. 7:247-262 (1996) and Lee etal. Pharm. Rev. 47:51-85 (1995); Falls and D. (2003). "Neuregulins: functions, forms, and signaling strategies." *Experimental Cell Research* 284(1): 14-30. Other EGF-like ligands include EGF, TGF-alpha, epiregulin, betacellulin, heparin-binding EGF-like growth factor, and amphireguling.

The terms "ErbB3," "HER3," "ErbB3 receptor," and "HER3 receptor," as used interchangeably herein, refer to human ErbB3 protein, as described in U.S. Pat. No. 5,480,968 and Plowman et al., Proc. Natl. Acad. Sci. USA, 87:4905-4909 (1990); see, also, Kani et al., Biochemistry 44:15842-857 (2005), Cho and Leahy, Science 297:1330-1333 (2002)). The full-length, human ErbB3 protein sequence (with leader sequence 1-19) is shown in SEQ ID NO: 36. This sequence corresponds to the sequence shown in FIG. 1A. The sequence is also shown in SEQ ID NO: 4 of U.S. Pat. No. 5,480,968, minus the 19 amino acid leader sequence that is cleaved from the mature protein. The full-length, mouse ErbB3 protein sequence (with leader sequence 1-19) is shown in SEQ ID NO: 37 This sequence corresponds to the sequence shown in FIG. 1B.

An "antigen" is an entity (e.g., a proteinaceous entity or peptide) to which a SBP, antigen-binding portion thereof, and/or antibody binds. In various embodiments disclosed herein, the antigen is ErbB3 or a ErbB3-like molecule. In a particular embodiment, the antigen is human ErbB3.

"Cetuximab" and "Panatumumab" are marketed mAbs that target EGFR.

"Pertuzumab" is a mAb that binds domain II of ErbB2 and inhibits its ability to dimerize with ErbB3 (and likely ErbB 1 as well). Domains II are the canonical dimerization domains among the Erbs. For EGFR and ErbB3, domains II are only exposed for dimerization when ligand is bound to the receptor. For ErbB2, there is no known ligand and domain II is constitutively exposed. Consistent with this notion, Pertuzumab primarily inhibits dimerization with ErbB3 when ErbB3 has ligand bound.

"Trastuzumab" is a marketed antibody that targets ErbB2 and binds to the juxtamembrane extracellular domain. It has anti-proliferative activity primarily in cells that overexpress ErbB2.

The term "disease associated with ErbB3 dependent signaling," "ErbB3 related disorder," "disorder associated with ErbB3 dependent signaling," "ErbB3 dependent disorder," or "ErbB3 signaling dependent disorder" as used herein, includes disease states and/or symptoms associated with a disease state, where increased levels of ErbB3 and/or activation of cellular cascades involving ErbB3 are found. It is understood that ErbB3 heterodimerizes with other ErbB proteins such as, EGFR and ErbB2, when increased levels of ErbB3 are found. Accordingly, the term "disease associated with ErbB3 dependent signaling," also includes disease states and/or symptoms associated with disease states where increased levels of EGFR/ErbB3 and/or ErbB2/ErbB3 and/or ErbB3/ErbB4 heterodimers are found. In general, the term "disease associated with ErbB3 dependent signaling," refers to any disorder, the onset, progression or the persistence of the symptoms of which requires, or is influenced by the participation of ErbB3. Exemplary ErbB3-mediated disorders include, but are not limited to, for example, cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In a particular embodiment, a cancer treated or diagnosed using the methods disclosed herein is selected from melanoma, breast cancer, ovarian cancer, renal carcinoma, gastrointestinal cancer and/or colon cancer (including gastric cancer), lung cancer, and prostate cancer, pancreatic cancer, and/or epithelial cancer, including any combination thereof.

The term "effective amount," as used herein, refers to that amount of an antibody, an antigen binding portion thereof, and/or SBP that binds ErbB3, which is sufficient to effect treatment, prognosis or diagnosis of a disease associated with ErbB3 dependent or responsive signaling, as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 microgram to about 3,500 mg, about 5 microgram to about 3,000 mg, about 10 microgram to about 2,600 mg, about 20 microgram to about 2,575 mg, about 30 microgram to about 2,550 mg, about 40 microgram to about 2,500 mg, about 50 microgram to about 2,475 mg, about 100 microgram to about 2,450 mg, about 200 microgram to about 2,425 mg, about 300 microgram to about 2,000, about 400 microgram to about 1,175 mg, about 500 microgram to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody, antigen binding portion thereof, or and/or a SBP. Dosage regimen can be adjusted to provide the optimum therapeutic response. An effective amount is also one in which any toxic or detrimental effects (i.e., side effects) of an antibody, antigen binding portion thereof, and/or SBP are minimized and/or outweighed by the beneficial effects. Additional preferred dosages regimens are described further below in the section pertaining to pharmaceutical compositions.

In some embodiments, SBPs disclosed herein inhibit EGF-like ligand, including NRG mediated phosphorylation of ErbB3 or reduce basal ErbB3 phosphorylation (including ErbB3 phosphorylation driven by overexpression of ErbB2) and, in certain embodiments, exhibit one or more of the following additional properties and/or functions: (i) inhibition of one or more of heregulin, EGF, amphiregulin, hbEGF, epiregulin, epigen, betacellulin, TGF-alpha and biregulin-mediated signaling or ligand-independent signaling through ErbB3; (ii) inhibition of proliferation of cells expressing ErbB3; (iii) the ability to decrease levels of ErbB3 on cell surfaces; (iv) inhibition of VEGF secretion of cells expressing ErbB3; (v) inhibition of the migration of cells expressing ErbB3; (vi) inhibition of spheroid growth of cells expressing ErbB3; (vii) apoptosis of cells expressing ErbB3, and/or (viii) specific binding to an epitope located on Domains III and/or IV of ErbB3. In some embodiments, any of the SBPs disclosed herein can be used to achieve any one or more of the above functions. In some embodiments, a method for achieving any one or more of the above functions can be achieved by application of one or more SBPs disclosed herein.

Accordingly, the phrase "inhibition of ErbB3 phosphorylation," as used herein, refers to the ability of an SBP, antigen binding portion, and/or antibody to statistically significantly decrease the basal level phosphorylation of ErbB3, relative to the phosphorylation in an untreated (control) cell, or that induced by an EGF-like ligand, relative to the phosphorylation in an untreated (control) cell. The cell which expresses ErbB3 can be a naturally occurring, transformed, or immortalized cell or cell line or alternatively it can be recombinantly produced by introducing nucleic acid encoding ErbB3 into a host cell. In some embodiments, the SBP, antigen binding portion thereof, and/or antibody inhibits basal or EGF-like ligand mediated ErbB3 phosphorylation of by at least 10%, or at least 20%, or at least 30%, or at least 40%, or at least 50%, or at least 60%, or at least 70%, or at least 80%, or at least 90%, or about 100%, as determined, for example, by ELISA or Western blotting followed by probing with an anti-phosphotyrosine antibody as described in Kim et al., (1998) Biochem J., 334:189-195 and the Examples infra.

The phrase "inhibition of heregulin, EGF, epiregulin, betacellulin, TGF-alpha, amphiregulin or biregulin-mediated signaling through ErbB3," as used herein, refers to the ability of an SBP, an antigen-binding portion thereof, and/or antibody to statistically significantly decrease signaling mediated by an ligand (e.g., heregulin, epiregullin, epigen betacellulin, TGF-alpha, biregulin, EGF, hbEGF, and amphiregulin) through ErbB3, relative to the signaling in the absence of the SBP and/or antibody (control). ErbB3-ligands are also referred to herein as "heregulin-like ligands" This means that, in the presence of the SBP, antigen binding portion thereof, and/or antibody, a signal mediated in a cell expressing ErbB3 by one or more of heregulin, neuregulin, epiregullin, epigen betacellulin, TGF-alpha, biregulin, EGF, hbEGF, and amphiregulin, relative to a control (no antibody), is statistically significantly decreased. An ErbB3-ligand mediated signal can be measured by assaying for the level or activity of an ErbB3 substrate, and/or a protein which is present in a cellular cascade involving ErbB3. In some embodiments, the SBP, antigen binding portion thereof, and/or antibody decreases the level or activity of an ErbB3 substrate and/or that of a protein in a cellular cascade involving ErbB3, by at least 10%, or at least 20%, or at least 30%, or at least 40%, or at least 50%, or at least 60%, or at least 70%, or at least 80%, or at least 90%, or about 100% relative to the level or activity in the absence of such antibody, antigen binding portion thereof, and/or SBP (control). Such ErbB3-ligand mediated signaling can be measured using art recognized techniques which measure the level or activity of a substrate of ErbB3 (e.g., PI3K) or a protein in a cellular cascade involving ErbB3 (e.g., the AKT pathway—AKT refers to a set of serine/threonine kinases also referred to as protein kinases B or PKB) using kinase assays for such proteins (see, e.g., Horst et al. supra, Sudo et al. (2000) Methods Enzymol, 322:388-92; and Morgan et al. (1990) Eur. J. Biochem., 191:761-767).

In a particular embodiment, the SBP, antigen binding portion thereof, and/or antibody inhibits ErbB3-ligand (e.g., heregulin, or neuregulin) mediated signaling through ErbB3 by inhibiting the binding of the ErbB3-ligand to ErbB3. Some ligands (e.g., biregulin, an artificial chimeric ligand: Barbacci, et al., J Biol Chem 1995 270(16) 9585-9) function both as EGF-like ligands (i.e., bind to EGFR/ErbB1) as well as ErbB3-like ligands (i.e., bind to ErbB3).

The phrase "inhibition of heregulin binding to ErbB3," as used herein, refers to the ability of a SBP, an antigen-binding portion thereof, and/or antibody to statistically significantly decrease the binding of an ErbB3 ligand (e.g., heregulin or neuregulin) to ErbB3, relative to the binding in the absence of the SBP and/or antibody (control). This means that, in the presence of the SBP, antigen binding portion thereof, and/or antibody, the amount of the ErbB3-ligand (e.g., heregulin, neuregulin,) which binds to ErbB3 relative to a control (no SBP and/or antibody), is statistically significantly decreased. The amount of an ErbB3 ligand which binds ErbB3 can be decreased in the presence of an SBP, antigen binding portion thereof, and/or antibody of the present disclosure by at least 10%, or at least 20%, or at least 30%, or at least 40%, or at least 50%, or at least 60%, or at least 70%, or at least 80%, or at least 90%, or 100% relative to the amount in the absence of the SBP, antigen binding portion thereof, and/or antibody (control). A decrease in ErbB3-ligand binding can be measured using art recognized techniques which measure the level of binding of labeled ErbB3-ligand (e.g., radiolabeled heregulin, neuregulin) to cells expressing ErbB3 in the presence or absence (control) of the SBP, antigen binding portion thereof, and/or antibody.

The phrase "inhibition of proliferation of a cell expressing ErbB3," as used herein, refers to the ability of an SBP, antigen binding portion thereof, and/or antibody to statistically significantly decrease proliferation of a cell expressing ErbB3 relative to the proliferation in the absence of the surrobody and/or antibody. In some embodiments, the proliferation of a cell expressing ErbB3 (e.g., a cancer cell) can be decreased by at least 10%, or at least 20%, or at least 30%, or at least 40%, or at least 50%, or at least 60%, or at least 70%, or at least 80%, or at least 90%, or at least 91, 92, 93, 94, 95, 96, 97, 98, 99%, or 100% when the cells are contacted with a SBP, antigen binding portion thereof, and/or antibody of the present disclosure, relative to the proliferation measured in the absence of the SBP, antigen binding portion thereof, and/or antibody (control). Cellular proliferation can be assayed using art recognized techniques which measure cell number and/or rate of cell division, the fraction of cells within a cell population undergoing cell division, and/or rate of cell loss from a cell population due to terminal differentiation or cell death (e.g., using a Cell-Titer-Glo™. assay or thymidine incorporation).

The phrase "the ability to decrease levels of ErbB3 on cell surfaces," as used herein, refers to the ability of an antibody, antigen binding portion thereof, and/or SBP to statistically significantly reduce the amount of ErbB3 found on the surface of a cell which has been exposed to the surrobody and/or antibody relative to an untreated (control) cell. For example, a decrease in levels of ErbB3 on cell surfaces can result from increased internalization of ErbB3 (or increased ErbB3 endocytosis). In some embodiments, the SBP, antigen binding portion thereof, and/or antibody decreases cell surface expression of ErbB3 by at least 10%, or at least 20%, or at least 30%, or at least 40%, or at least 50%, or at least 60%, or at least 70%, or at least 80%, or at least 90%, or 100% and/or increases internalization of the ErbB3 receptor by at least 10%, or at least 20%, or at least 30%, or at least 40%, or at least 50%, or at least 60%, or at least 70%, or at least 80%, or at least 90%, or 100% relative to the cell surface expression or internalization in the absence of the antibody, antigen binding portion thereof, and/or SBP (control). The levels of ErbB3 on surfaces of cells and/or internalization of the ErbB3 receptor in the absence and the presence of an antibody, antigen-binding portion thereof, and/or SBP can be readily measured using art recognized techniques, such as those described in Horst et al., supra and in the examples herein.

The phrase "inhibition of VEGF secretion of cells expressing ErbB3," as used herein, refers to the ability of an antibody, an antigen-binding portion thereof, and/or SBP to statistically significantly decrease VEGF secretion of a cell expressing ErbB3 relative to the VEGF secretion in the absence of the SBP and/or antibody. In some embodiments, the VEGF secretion of a cell expressing ErbB3 (e.g., a cancer cell) can be decreased by at least 10%, or at least 20%, or at least 30%, or at least 40%, or at least 50%, or at least 60%, or at least 70%, or at least 80%, or at least 90%, or 100% when the cells are contacted with an SBP, antigen binding portion thereof, and/or antibody of the present disclosure, relative to the VEGF secretion measured in the absence of the SBP, antigen binding portion thereof, and/or antibody (control). VEGF secretion can be assayed using art recognized techniques, such as those described herein.

The phrase "inhibition of the migration of cells expressing ErbB3," as used herein, refers to the ability of an SBP, antigen binding portion thereof, and/or antibody to statistically significantly decrease the migration of a cell expressing ErbB3 relative to the migration of the cell in the absence of the SBP and/or antibody. In some embodiments, the migration of a cell expressing ErbB3 (e.g., a cancer cell) can be decreased by at least 10%, or at least 20%, or at least 30%, or at least 40%, or at least 50%, or at least 60%, or at least 70%, or at least 80%, or at least 90%, or 100% when the cells are contacted with an antibody, SBP, antigen binding portion thereof, and/or antibody of the present disclosure, relative to cell migration measured in the absence of the SBP, antigen binding portion thereof, and/or antibody (control). Cell migration can be assayed using art recognized techniques, such as those described herein.

The phrase "inhibition of spheroid growth of cells expressing ErbB3," as used herein, refers to the ability of an SBP, antigen binding portion thereof, and/or antibody to statistically significantly decrease the anchorage independent growth of cells expressing ErbB3 relative to the anchorage independent growth of the cells in the absence of the SBP and/or antibody. In some embodiments, the growth of cells expressing ErbB3 (e.g., a cancer cell) can be decreased by at least 10%, or at least 20%, or at least 30%, or at least 40%, or at least 50%, or at least 60%, or at least 70%, or at least 80%, or at least 90%, or 100% when the cells are contacted with an SBP, antigen binding portion thereof, and/or antibody of the present disclosure, relative to cell migration measured in the absence of the SBP, antigen binding portion thereof, and/or antibody (control). Spheroid growth can be assayed using art recognized techniques (e.g. Juergen Friedrich et al. Spheroid-based drug screen: considerations and practical approach. NATURE PROTOCOLS 4: 309. 2009) such as those described herein.

The phrase "apoptosis of cells expressing ErbB3," as used herein, refers to the ability of an SBPs, antigen binding portion thereof, and/or antibody to induce apoptosis of a cell expressing ErbB3 relative to the apoptosis in the absence of the SBP and/or antibody. In some embodiments, the apoptosis of a cell expressing ErbB3 (e.g., a cancer cell) can be increased by at least 10%, or at least 20%, or at least 30%, or at least 40%, or at least 50%, or at least 60%, or at least 70%, or at least 80%, or at least 90%, or at least 91, 92, 93, 94, 95, 96, 97, 98, 99%, or 100% when the cells are contacted with an SBPs, antigen binding portion thereof, and/or antibody of the present disclosure, relative to the apoptosis measured in the absence of the SBPs, antigen binding portion thereof, and/or antibody (control). Cellular apoptosis can be assayed using art recognized techniques which measure cellular viability, metabolic activity, annexin V binding, apoptotic caspase activation, and/or rate of cell loss from a cell population due to terminal differentiation or cell death (e.g., using a CellTiter-Glo™. assay or thymidine incorporation).

The term "human SBP," as used herein, is intended to include SBPs having variable regions in which both the framework and other regions are derived from human heavy chain immunoglobulin sequences as described, for example, by Kabat et al. (See Kabat, et al. (1991) Sequences of proteins of Immunological Interest, Fifth Edition, U.S. Department of Health and Human Services, NIH Publication No. 91-3242). Furthermore, if the SBP contains a constant region, the constant region also is derived from human germline immunoglobulin sequences. The human SBPs can include amino acid residues not only encoded by human germline immunoglobulin sequences (e.g., mutations introduced by random or site-specific mutagenesis in vitro or by somatic mutation in vivo). However, the term "human SBP", as used herein, is not intended to include SBPs in which CDR sequences derived from the germline of another mammalian species, such as a mouse, have been grafted onto human framework sequences.

The term "humanized SBP" refers to a SBP that includes at least one humanized immunoglobulin chain (e.g., a humanized heavy chain). The term "humanized SBP" refers to a SBP chain having a variable region that includes a variable framework region substantially from a human SBP and complementarity determining regions (CDRs) (e.g., at least one CDR, preferably two CDRs, more preferably three CDRs) substantially from a non-human heavy chain.

As used herein, "isotype switching," in reference to a surroglobulin (in the context of a transgenic or ex vivo system) refers to the phenomenon by which the class, or isotype, of a surroglobulin changes, or is changed, from one Ig class to one of the other Ig classes.

B. DETAILED DESCRIPTION

Techniques for performing some of the methods of noted herein are well known in the art and described in standard laboratory textbooks, including, for example, Ausubel et al., *Current Protocols of Molecular Biology*, John Wiley and Sons (1997); *Molecular Cloning: A Laboratory Manual*, Third Edition, J. Sambrook and D. W. Russell, eds., Cold Spring Harbor, N.Y., USA, Cold Spring Harbor Laboratory Press, 2001; *Antibody Phage Display, Methods and Protocols*, Humana Press, 2001; and *Antibodies*, G. Subramanian, ed., Kluwer Academic, 2004. Mutagenesis can, for example, be performed using site-directed mutagenesis (Kunkel et al., *Proc. Natl. Acad. Sci USA* 82:488-492 (1985)). PCR amplification methods are described in U.S. Pat. Nos. 4,683,192, 4,683,202, 4,800,159, and 4,965,188, and in several textbooks including "PCR Technology: Principles and Applications for DNA Amplification", H. Erlich, ed., Stockton Press, New York (1989); and *PCR Protocols: A Guide to Methods and Applications*, Innis et al., eds., Academic Press, San Diego, Calif (1990).

In some embodiments, the present disclosure provides polypeptides comprising VpreB and/or λ5 sequences and having the ability to bind a target. Targets specifically include all types of targets generally referred to as "antigens" in the context of antibody binding. In some embodiments, the target is an ErbB3 protein. In some embodiments, SBPs to ErbB3 are provided herein. In some embodiments, the SBPs bind to ErbB3. In some embodiments, the SBPs bind and prevent and/or reduce one or more signaling aspects related to ErbB3 dependent signaling.

As shown in Example 1 a number of Sabs to ErbB3 were discovered.

Figure 2D:
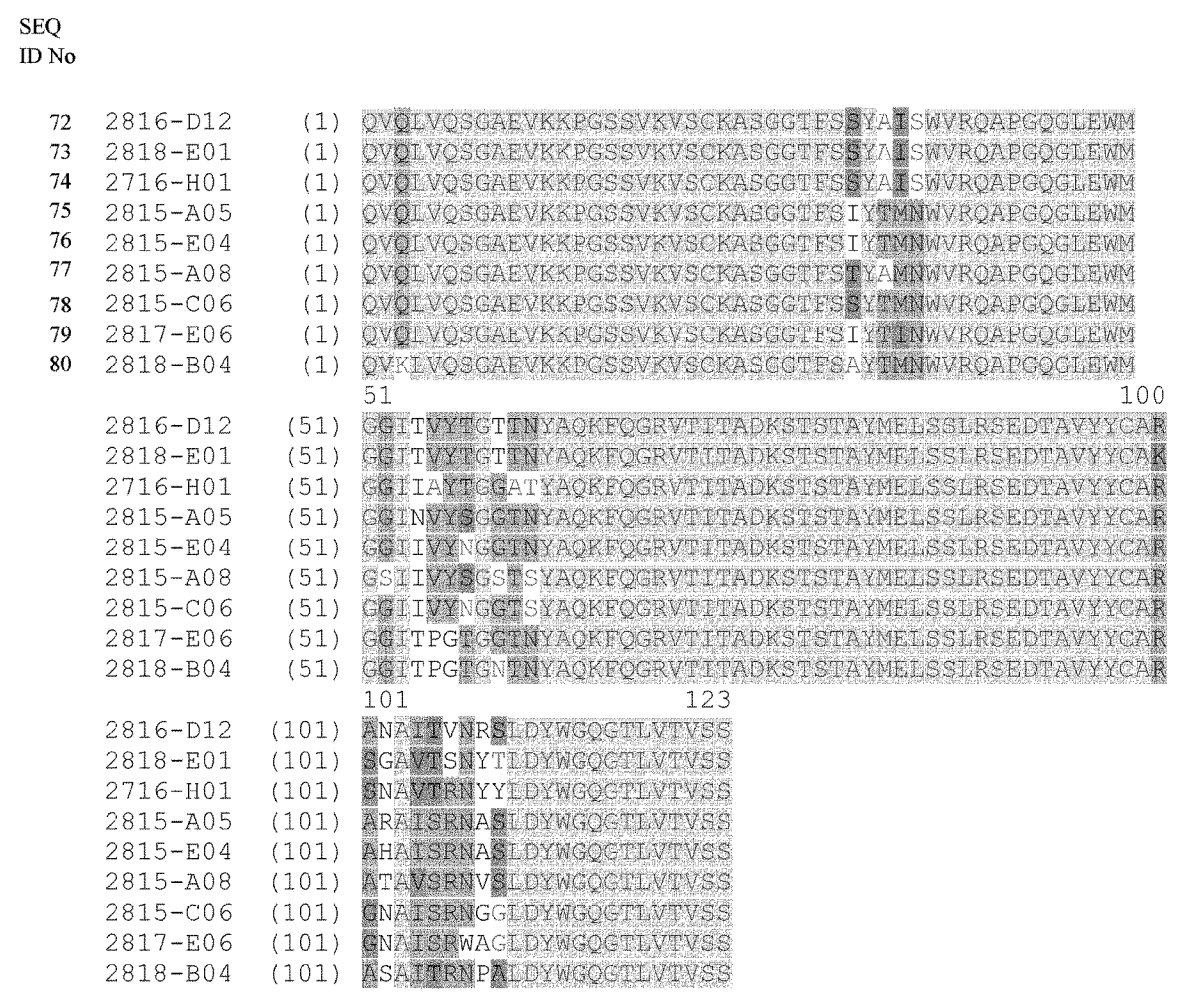

As outlined in Example 2, numerous Sabs demonstrated an ability to inhibit ErbB3 function. The sequences of these Sabs are outlined in FIGS. 2A and 2B, and the results of the corresponding SgGs are outlined in FIGS. 3A-3D.

In some embodiments, the inhibition of ErbB3 signaling is direct. In some embodiments, the inhibition does not need to be direct. In some embodiments, the inhibition can be through a number of possible mechanisms including stimulation of ErbB3 internalization and/or through inhibition of NRG (e.g., NRG-1, NRG-2, NRG-3, and/or NRG-4) binding.

In some embodiments, variants of SBPs are provided. In some embodiments, the SBPs will include a heavy chain variable region that is at least 85% identical to one of the sequences in FIG. 2A or 2B. In some embodiments, the variant heavy chain for the SBPs will be 85, 86, 87, 88, 89, 90, 91, 92, 93, 94, 95, 96, 97, 98, 99, or nearly identical to one of the sequences of 2817-C01. As shown in FIG. 2C, 2817-C01 and 2716-F05 include heavy chain variable regions that are 87.8% identical to one another. In some embodiments, clones that are 86.2% identical to the framework are provided with respect to 2716-F05. In some embodiments, clones that are 83.7% identical to the framework are provided with respect to 2817-C01. Interestingly, not only do these two SBPs share a high percent identity for their heavy chain variable region, but, as shown in the epitope binning example below, they appear to bind to the same, similar, or at least overlapping epitopes on ErbB3. Thus, the noted sequences and alignments, in combination with the high percent identity between the two, may indicate that Sabs or SgGs having this percent identity would have the desired functionality of blocking ErbB3 signaling. In some embodiments, variants of nucleic acids encoding SBPs are provided. In some embodiments, the nucleic acids encoding the SBPs will include have a sequence that encodes a heavy chain variable region that is at least 85% identical to one of the sequences in FIG. 18. In some embodiments, the variant heavy chain for the SBPs will be encoded by a nucleic acid sequence that is at least 85, 86, 87, 88, 89, 90, 91, 92, 93, 94, 95, 96, 97, 98, 99, or nearly identical to one of the sequences in FIG. 18.

In some embodiments, other variants are contemplated for SBPs. FIG. 2D depicts an alignment of another collection of SBPs disclosed herein. As can be seen, these SBPs are all approximately 90% identical to 2816-D12, which is itself 87.8% identical to its framework. Table 0.2 outlines the percent identity of these heavy chain sequences for the Sabs.

TABLE 0.2

| Clone | % identity to 2816-D12 |
|---|---|
| 2818-E01 | 94.3 |
| 2716-H01 | 91.9 |
| 2815-A05 | 91.1 |

TABLE 0.2-continued

| Clone | % identity to 2816-D12 |
|---|---|
| 2815-E04 | 91.1 |
| 2815-A08 | 89.4 |
| 2815-C06 | 90.2 |
| 2817-E06 | 91.1 |
| 2818-B04 | 90.2 |

In some embodiments, the SBPs are binding fragment forms, such as Sabs. In some embodiments, the SBPs are full Surroglobulin forms, such as SgGs. Example 3 outlines a method by which various initial Sabs were converted to SgGs.

In some embodiments, the SBPs bind to both human ErbB3 and mouse ErbB3. In some embodiments, the SBPs bind selectively to human ErbB3 over mouse ErbB3. In some embodiments, the SBPs bind selectively to mouse ErbB3 over human ErbB3. In some embodiments, the EC50 of the SBP for such an interaction with human ErbB3 is less than 0.36 nM, for example 0.3, 0.2, 0.1 0.09, 0.08, 0.07, 0.06, 0.05, 0.04, 0.03 nM or less, including any range lower than any of the preceding values and any range defined between any two of the preceding values. In some embodiments, the EC50 of the SBP for such an interaction with mouse ErbB3 is less than 0.4 nM, for example 0.3, 0.2, 0.1 0.09, 0.08, 0.07, 0.06, 0.05 nM or less, including any range lower than any of the preceding values and any range defined between any two of the preceding values.

In some embodiments, the surroglobulins can bind ErbB3 that is expressed in cells, such as human BxPC-3 cells, as shown in Example 5. In some embodiments, the EC50 of the SBP for such an interaction with human ErbB3 expressed in a cell is less than 0.4 nM, for example 0.3, 0.2, 0.15, 0.1 0.09, 0.08, 0.07, 0.06, 0.05, 0.04, 0.03 nM or less, include any range lower than any of the preceding values and any range defined between any two of the preceding values.

In some embodiments, the surroglobulins can bind ErbB3 and inhibit the binding of NRG to ErbB3, as outlined in Example 6. In some embodiments, the IC50 of the surroglobulin for inhibiting the binding of NRG to ErbB3 is less than 1.39 nM, for example 1.38, 1.37, 1.36, 1.35, 1.3, 1.2, 1.1, 1, 0.9, 0.99, 0.8, 0.7, 0.6, 0.55, 0.52, 0.5, 0.4 nM or less, including any range lower than any of the preceding values and any range defined between any two of the preceding values.

In some embodiments, the surroglobulins can bind to ErbB3 and inhibit binding of NRG. In some embodiments, the surroglobulins can bind to ErbB3 and increase the dissociation of NRG from ErbB3. In some embodiments, the SBPs can bind to ErbB3 and inhibit the dimerization of ErbB3 with other molecules. In some embodiments, the SBPs can bind to ErbB3 and cause internalization or reduction of cell surface ErbB3. In some embodiments, the SBPs can bind to ErbB3 and sequester ErbB3 on the cell surface so it is unavailable for dimerization. In some embodiments, the SBPs can bind to ErbB3 and induce apoptosis or increasing the number of apoptotic cells. In some embodiments, the SBPs can bind to ErbB3 and promote antibody-dependent cell-medicated cytotoxicity.

In some embodiments, the ErbB3 SBP comprises a VpreB sequence, a λ5 sequence, or a VpreB sequence and a λ5 sequence and a heavy chain variable region amino acid sequence that is paired with the VpreB sequence, the λ5 sequence, or the VpreB sequence and the λ5 sequence to form the SBP that can bind to an ErbB3 protein. In some embodiments, a VpreB sequence is fused to a constant light chain sequence.

In some embodiments the ErbB3 protein to which the SBP binds is that depicted in FIG. 1A, FIG. 1B, or both FIG. 1A and FIG. 1B.

In some embodiments, the ErbB3 SBP (or Ab) comprises a heavy chain variable region. In some embodiments, the heavy chain variable region comprises a sequence as shown in FIG. 2A or FIG. 2B. In some embodiments, for example, variants that are 80, 85, 90, 95, 96, 97, 98, 99% identical to the sequences in FIGS. 2A and/or 2B can be employed for the SBP. In some embodiments, the SBP comprises a heavy chain variable region, or variant thereof, from FIG. 2A or 2B in combination with a VpreB sequence and/or a λ5 sequence. In some embodiments, the VpreB sequence and/or λ5 sequence comprises part or all of one or more of the sequences shown in FIG. 18, 22, 23, 24, 25, or 27.

In some embodiments, the ErbB3 surroglobulin, antigen binding portion thereof, and/or antibody comprises one or more heavy chain CDR regions (e.g., 1, 2, or 3). In some embodiments, the heavy chain CDR region comprises a sequence as shown in FIG. 2A or 2B. In some embodiments, for example, variants that are 80, 85, 90, 95, 96, 97, 98, 99% identical to 1, 2, or 3 of the CDR sequences in FIGS. 2A, 2B, 34A, 34B, 34C, 34D, 34E, and/or 34F can be employed for the SBP. In some embodiments, the surroglobulin, antigen binding portion thereof, comprises 1, 2, or 3 CDRs or variants thereof, from FIGS. 2A, 2B, 34A, 34B, 34C, 34D, 34E, and/or 34F in combination with a VpreB sequence and/or a λ5 sequence. In some embodiments, the VpreB sequence and/or λ5 sequence comprises part or all of one or more of the sequences shown in FIG. 27, 22, 23, 24, 25, or 27. In some embodiments, the CDRs are selected from the following group: CDR1, CDR2, CDR3, CDR1 and CDR2, CDR2 and CDR3, CDR1 and CDR3, and CDR1 CDR2 and CDR3. In some embodiments, the CDR is defined as a Kabat sequence. In some embodiments, the CDR is defined as a Chothia sequence.

In some embodiments, the SBP comprises a surroglobulin or antigen binding portion thereof, combination as put forth in Table 0.3A below:

TABLE 0.3A

| Heavy Chain Variable Region and/or CDR (SEQ ID NO:) | VpreB and/or lambda 5 |
|---|---|
| 38 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 42 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 46 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 50 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 54 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 58 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 62 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 39, 40, and/or 41 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 43, 44, and/or 45 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 47, 48, and/or 49 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |

TABLE 0.3A-continued

| Heavy Chain Variable Region and/or CDR (SEQ ID NO:) | VpreB and/or lambda 5 |
|---|---|
| 51, 52, and/or 53 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 55, 56, and/or 57 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 59, 60, and/or 61 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 63, 64, and/or 65 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 39 and 40; 40 and 41; 39 and 41 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 43 and 44; 44 and 45; 43 and 45 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 47 and 48, 49 and 49; 47 and 49 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 51 and 52; 52 and 53; 51 and 53 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 55 and 56; 56 and 57; 55 and 57 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 59 and 60; 60 and 61; 59 and 61 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 63 and 64; 64 and 65; 63 and 65 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| One of a)105, 106, 107, 108, 109, 110, 111, 112, 113, 114, 115, 116, 151, 152, 153, 154, 155, 156, 178, or 180; with one of 117, 118, 119, 120, 121, 122, 123, 124, 124, 126, 127, 128, 129, 130, 131, 132, 133, 134, 135, 136, 137, 138, 139, 140, 141, 142, 143, 144, 145, 146, 147, 148, 149, 157, 158, 159, 160, 161, 162, 163, 164, 165, 166, 167, 168, 169, 170, 171, 172, 173, 174, 175, 176, 179, or 181; with one of 150 or 177 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| A heavy chain variable region of SEQ ID NO: 193-275 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |

TABLE 0.3A-continued

| Heavy Chain Variable Region and/or CDR (SEQ ID NO:) | VpreB and/or lambda 5 |
|---|---|
| All three CDRs within any one of the heavy chain variable regions of SEQ ID NO: 19-275 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| 188, 186, or 185 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| CDRs within SEQ ID NO: 178, 277, 179, and/or 278 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| CDRs within SEQ ID NO: 180, 279, 181, and/or 280 | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |
| CDRs within FIGS. 34A, 34B, 34C, 34D, 34E, 34F | SEQ ID NO: 1, 2, 3, 4, 5, 6, 7, 10, 11, 12, 90, 91, 92, 93, 94, 95, 96, 97, 98, 99, 100, and/or 276 (and varians thereof, such as outlined in SEQ ID NO: 190, 191, and 192) and/or sequences within FIGS.: 22, 23, 24, 25, and/or 27 |

In some embodiments, any of the heavy chain variable regions and/or heavy chains CDR options outlined in Table 0.3A can be combined with an antibody light chain variable region to ErbB3 or one or more light chain CDRs to ErbB3 (e.g., LCDR1, LCDR2, and/or LCDR3). In some embodiments, any light chain, germline or rearranged, can be employed. In some embodiments, lambda is employed. In some embodiments, kappa is employed. In some embodiments, any of the CDRs outlined in FIGS. 2A, 2B, 34A, 34B, 34C, 34D, 34E, and/or 34F can be employed with any of the VpreB and/or lambda 5 sequences of SEQ ID NO: 1, 2, 3, 4, 5, 6, 7, 10, 11, 12, 90, 91, 92, 93, 94, 95, 96, 97, 98, 99, 100, and/or 276. In some embodiments, a sequence that is at least 40% identical to a CDR1 in FIG. 34A can be used as the CDR1 (e.g., at least 50, 60, 70 80, 90, 95, or 99% identical). In some embodiments, a sequence that is at least 69% identical to a CDR2 in FIG. 34A can be used as the CDR2 (e.g., at least 70, 80, 90, 95, or 99% identical). In some embodiments, a sequence that is at least 60% identical to a CDR1 in FIG. 34B can be used as the CDR1 (e.g., at least 70 80, 90, 95, or 99% identical). In some embodiments, a sequence that is at least 54% identical to a CDR2 in FIG. 34B can be used as the CDR2 (e.g., at least 55, 60, 70, 80, 90, 95, or 99% identical). In some embodiments, a sequence that is at least 40% identical to the parent CDR1 in FIG. 34A can be used as the CDR1 (e.g., at least 50, 60, 70 80, 90, 95, or 99% identical). In some embodiments, a sequence that is at least 69% identical to the parent CDR2 in FIG. 34A can be used as the CDR2 (e.g., at least 70, 80, 90, 95, or 99% identical). In some embodiments, a sequence that is at least 60% identical to the parent CDR1 in FIG. 34B can be used as the CDR1 (e.g., at least 70 80, 90, 95, or 99% identical). In some embodiments, a sequence that is at least 54% identical to the parent CDR2 in FIG. 34B can be used as the CDR2 (e.g., at least 55, 60, 70, 80, 90, 95, or 99% identical). In some embodiments, a similar percent identity can be applied to the sequences in CDR3 (e.g., 50% or greater identity to any of the CDR3 in FIGS. 34A and 34B). In some embodiments, HCDR1 of the antibody and/or SBP can be that of SEQ ID NO: 178 and HDR2 can be that of SEQ ID NO: 179 (FIG. 34C). In some embodiments, HCDR1 of the antibody and/or SBP can be that of SEQ ID NO: 180 and HCDR2 can be that of SEQ ID NO: 181 (FIG. 34D). In some embodiments, HCDR1 of the antibody and/or SBP can be that of SEQ ID NO: 178, HCDR2 can be that of SEQ ID NO: 179, and HCDR3 can be SEQ ID NO: 150. In some embodiments, HCDR1 of the antibody and/or SBP can be that of SEQ ID NO: 180, HCDR2 can be that of SEQ ID NO: 181, and HCDR3 can be SEQ ID NO: 177. It is noted that the alignment generated in FIGS. 34A and 34B indicates where variation is permissible, and thus, the consensus sequence, outlined in FIGS. 34C and 34D indicates which positions are expected to be modifiable and how they can be modified. Thus, in some embodiments, the CDRs are permitted to vary by at least this amount and at, at least, these positions. In some embodiments, the above CDR sequences can be used in combination with a traditional antibody light chain, and thus, be employed in an antibody arrangement. In some embodiments, the full length heavy chain variable region of the SBP and/or antibody can be that in FIG. 43A and/or 43B.

In some embodiments, the surrogate light chain can be that of SEQ ID NO: 10, SEQ ID NO: 11, SEQ ID NO: 12, or SEQ ID NO: 276. In some embodiments, the SBPs can have the heavy chain variable sequence of SEQ ID NO: 38 (2716-F05) or SEQ ID NO:42 (2817-F05), with a surrogate light chain of SEQ ID NO: 10 or SEQ ID NO: 276. In some embodiments, the SBPs can have the heavy chain variable sequence of SEQ ID NO: 38 (2716-F05) or SEQ ID NO:42 (2817-F05), with a surrogate light chain of SEQ ID NO: 11. In some embodiments, the SBPs can have the heavy chain variable sequence of SEQ ID NO: 38 (2716-F05) or SEQ ID NO:42 (2817-F05), with a surrogate light chain of SEQ ID NO: 12. In some embodiments, the SBPs can have the heavy chain variable sequence of SEQ ID NO: 38 (2716-F05) or SEQ ID NO:42 (2817-F05), with a surrogate light chain of SEQ ID NO: 276.

In some embodiments, the SBP and/or antibody can have a heavy chain variable region that includes a CDR1 of SEQ ID NO: 39, a CDR2 of SEQ ID NO: 40, and a CDR3 of SEQ ID NO: 41 combined with a surrogate light chain of SEQ ID NO: 10 or SEQ ID NO: 276. In some embodiments, the SBP and/or antibody can have a heavy chain variable region that includes a CDR1 of SEQ ID NO: 39, a CDR2 of SEQ ID NO: 40, and a CDR3 of SEQ ID NO: 41 combined with a surrogate light chain of SEQ ID NO: 11. In some embodiments, the SBP and/or antibody can have a heavy chain variable region that includes a CDR1 of SEQ ID NO: 39, a CDR2 of SEQ ID NO: 40, and a CDR3 of SEQ ID NO: 41 combined with a surrogate light chain of SEQ ID NO: 12. In some embodiments, the SBP and/or antibody can have a heavy chain variable region that includes a CDR1 of SEQ ID NO: 39, a CDR2 of SEQ ID NO: 40, and a CDR3 of SEQ ID NO: 41 combined with a surrogate light chain of SEQ ID NO: 276.

In some embodiments, the SBP and/or antibody can have a heavy chain variable region that includes a CDR1 of SEQ ID NO: 43, a CDR2 of SEQ ID NO: 44, and a CDR3 of SEQ ID NO: 45 combined with a surrogate light chain of SEQ ID NO: 10 or 276. In some embodiments, the SBP and/or antibody can have a heavy chain variable region that includes a CDR1 of SEQ ID NO: 43, a CDR2 of SEQ ID NO: 44, and a CDR3 of SEQ ID NO: 45 combined with a surrogate light chain of SEQ ID NO: 11. In some embodiments, the SBP and/or antibody can have a heavy chain variable region that includes a CDR1 of SEQ ID NO: 43, a CDR2 of SEQ ID NO: 44, and a CDR3 of SEQ ID NO: 45 combined with a surrogate light chain of SEQ ID NO: 12. In some embodiments, the SBP and/or antibody can have a heavy chain variable region that includes a CDR1 of SEQ ID NO: 43, a CDR2 of SEQ ID NO: 44, and a CDR3 of SEQ ID NO: 45 combined with a surrogate light chain of SEQ ID NO: 276.

In some embodiments, variants of SBPs (including those herein and those outlined in Table 0.3A) can be provided that differ at various positions of the surrogate light chain corresponding to loop structures that are adjacent to, or that affect structural features proximal to heavy chain CDR1, CDR2, and/or, CDR3. Such constructs can be expressed and tested singly, in combination, or as a plurality of constructs for improved function.

The selectivity and strength of SBP binding can be attributed to the combination of variable heavy chain frameworks and specific CDR composition. It is predicted that these binding attributes can be altered by judicious substitutions of specific surrogate light chain residues. For example it is predicted that loops in VpreB, lambda 5, or a loop formed by the chimeric fusion of both VpreB and lambda 5, can be substituted with other residues to allow these changes. The nature of these substitutions can be conservative, nonconservative, or a combination of either, or both.

Substitution of any of the residues of the surrogate light chain proximal to, or distant from, the heavy chain CDRs can be made for purposes of affinity optimization. The benefit of these conservative changes can derived from improving access between the target and the heavy chain. By maintaining the side chain chemistry termini and altering the lengths to the peptide backbone, the requisite complementary structure and its' steric accessibility can be improved. Decreasing the side chain or repositioning the side chain termini can provide more free room that can result in better binding. Alternatively, opposing changes that reduce the distance from side chain chemistries to peptide bond could bring interactive chemistries into better and closer position for binding. Tables 0.3B-0.3D provide a list of options for areas of the surrogate light chain that can be changed and examples of how they can be changed.

TABLE 0.3B

| Position | 29 | 30 | 31 | 32 | 33 | 34 | 35 | 36 | 37 | 38 |
|---|---|---|---|---|---|---|---|---|---|---|
| Existing residue SED ID NO: 282 | D | I | G | V | Y | S | V | Y | W | Y |
| Possible residues SEQ ID NO: 283 | E | V | A | I | F | T | I | F |  | F |
| SEQ ID NO: 284 |  | L |  | L |  |  | L |  |  |  |
| SEQ ID NO: 190 | $X_{301}$ | $X_{302}$ | $X_{303}$ | $X_{304}$ | $X_{305}$ | $X_{306}$ | $X_{307}$ | $X_{308}$ | W | $X_{309}$ |

TABLE 0.3C

| Position | 49 | 50 | 51 | 52 | 53 | 54 | 55 | 56 | 57 | 58 | 59 | 60 | 61 |
|---|---|---|---|---|---|---|---|---|---|---|---|---|---|
| Existing residue SEQ ID NO: 285 | L | L | R | Y | F | S | Q | S | D | K | S | Q | G |
| Possible residues SEQ ID NO: 286 | I | I | K | F | Y | T | N | T | E | R | T | N | A |
| SEQ ID NO: 287 | V | V |  |  |  |  |  |  |  |  |  |  |  |
| SEQ ID NO: 191 | $X_{310}$ | $X_{311}$ | $X_{312}$ | $X_{313}$ | $X_{314}$ | $X_{315}$ | $X_{316}$ | $X_{317}$ | $X_{318}$ | $X_{319}$ | $X_{320}$ | $X_{321}$ | $X_{322}$ |

TABLE 0.3D

| Position | 97 | 98 | 99 | 100 | 101 | 102 | 103 | 104 | 105 | 106 |
|---|---|---|---|---|---|---|---|---|---|---|
| Existing residue SEQ ID NO: 288 | A | M | G | A | R | S | S | V | T | H |
| Possible residues SEQ ID NO: 289 | G | L | A | G | K | T | T | I | S |  |
| SEQ ID NO: 290 |  |  |  |  |  |  |  |  | L |  |
| SEQ ID NO: 192 | $X_{323}$ | $X_{324}$ | $X_{325}$ | $X_{326}$ | $X_{327}$ | $X_{328}$ | $X_{329}$ | $X_{330}$ | $X_{331}$ | H |

The numbering of the residues noted above is in regard to SEQ ID NO: 276 (FIG. 25). Thus, any of the residues noted above can be altered within SEQ ID NO: 276 and still be predicted to be acceptable. In some embodiments, other residues within the surrogate light chain can be altered (for example 80%, 85%, 90%, 95%, 98%, and 99% identical sequences to the surrogate light chain sequences provided herein (for example, FIG. 25)).

It is possible to incorporate chemically diverse amino acids that create new opportunistic interactions with either the target or the complementary heavy chain structure in a structurally similarly manner as that described above, except that the improved "fitness" to target is derived from previously nonexisting side chain interactions. Possible substitutions within predicted target adjacent loops (SEQ ID 190-192 as shown by their respective positions within Tables 0.3B, 0.3C, and/or 0.3D). In some embodiments, any of the surrogate light chains provided herein can be paired with any of the heavy chain sequences provided herein.

The above description highlights changes to affinity, but can be extended to other beneficial functions, such as thermal stability, pharmacokinetic properties, immunogenicity, solubility, expression, and aggregation.

In some embodiments, any of the heavy chain variable regions and/or heavy chains CDR options outlined in Table 0.3A can be combined with 1, 2, and/or 3 light chain loop regions from any of the sequences listed in Table 0.3A. In some embodiments, LR1 and LR2 are employed. In some embodiments, LR2 and LR3 are employed. In some embodiments, LR1 and LR3 regions are employed. Exemplary Loop Regions can be found in FIG. 27.

In some embodiments, the surroglobulin, antigen binding portion thereof, and/or antibody binds to an ErbB3 epitope that is in one or more of domains I, II, III, and IV of ErbB3 or combinations thereof. In some embodiments, the epitope is not in domain I. In some embodiments, the epitope is not in domain II. In some embodiments, the epitope is not in domain III. In some embodiments, the epitope is not in domain IV. In some embodiments, the epitope is in domain I. In some embodiments, the epitope is in domain II. In some embodiments, the epitope is in domain III. In some embodiments, the epitope is in domain IV. In some embodiments, the SBP binds to domains III and IV, as shown in Example 7, for example. In some embodiments, the SBP does not require domains I, II, or I and II in order to bind to ErbB3. The domains are outlined below in Table 0.4.

TABLE 0.4

| Domain | Amino acid range in sequence FIG. 1A |
|---|---|
| I | 19-179 |
| II | 180-330 |
| III | 331-491 |
| IV | 498-641 |

In some embodiments, the SBPs bind to an epitope of ErbB3 comprising residues 19-39, 40-59, 60-79, 80-99, 100-119, 120-139, 140-159, 160-179, 180-199, 200-219, 220-239, 240-259, 260-279, 280-299, 300-319, 320-339, 340-359, 360-379, 380-399, 400-419, 420-439, 440-459, 460-479, 480-499, 500-519, 520-539, 540-559, 560-579, 580-599, 600-619, 620-641 of (SEQ ID NO: 36), or tandem combinations, or binary combinations, or tandem binary combinations of these residues.

In some embodiments, the surroglobulin or antigen binding portion thereof, reduces or blocks signal transduction of ErbB3. In some embodiments, this is achieved by the SBP directly blocking binding between ErbB3 and its ligand NRG-1, NRG-2, NRG-3, and/or NRG-4. In some embodiments, this is achieved by the SBPallosterically blocking or reducing binding between ErbB3 and its ligand.

In some embodiments, the surroglobulin or antigen binding portion thereof, is capable of binding to a ligand bound configuration of ErbB3.

In some embodiments, the surroglobulin or antigen binding portion thereof, binds to ErbB3 at an ErbB3/membrane surface interface.

In some embodiments, the surroglobulin or antigen binding portion thereof, binds to a dimerization domain of ErbB3. In some embodiments, the surroglobulin or antigen binding portion thereof, once bound to ErbB3 at the dimerization domain, reduces or blocks ErbB3 dimerization.

In some embodiments, the surroglobulin or antigen binding portion thereof, has a $K_D$ that is less than 20 nM. In some embodiments, the KD is from about 10 nM to about 1 pM.

In some embodiments, the VpreB sequence is selected from the group consisting of a native VpreB1 sequence, a native VpreB2 sequence, a native VpreB3 sequence, fragments of any of the preceding, and variants of any of the preceding. In some embodiments, the native VpreB sequence is selected from the group consisting of human VpreB1 of SEQ ID NO: 1, mouse VpreB2 of SEQ ID NOS: 2 and 3, human VpreB3 of SEQ ID NO: 4, fragments of any of the preceding, and variants of any of the preceding.

In some embodiments, the SBP includes the λ5 sequence. In some embodiments, the λ5 sequence comprises all or part of a human λ5 of SEQ ID NO: 6 or a mouse λ5 polypeptide of SEQ ID NO: 5. In some embodiments, the λ5 sequence is fused to said VpreB sequence. In some embodiments, the SBP comprises a VpreB sequence fused to a λ5 sequence. In some embodiments, the VpreB sequence is selected from the group consisting of human VpreB1 of SEQ ID NO: 1, mouse VpreB2 of SEQ ID NOS: 2 and 3, human VpreB3 of SEQ ID NO: 4, fragments of any of the preceding, variants of any of the preceding, and any combination thereof. In some embodiments, the λ5 sequence is selected from the group consisting of a human λ5 of SEQ ID NO: 6, a mouse λ5 polypeptide of SEQ ID NO:5, fragments of any of the preceding, variants of any of the preceding, and any combination thereof. In some embodiments, the VpreB sequence is fused to the λ5 sequence at or around a LR3 of said VpreB sequence and λ5, respectively. In some embodiments, the λ5 is covalently linked to the VpreB sequences. In some embodiments, the λ5 is covalently linked to the VpreB sequences by a connecting peptide or polypeptide sequence. In some embodiments, the SBPcomprises the VpreB and the λ5 sequence and the VpreB sequence is conjugated to the λ5 sequence by a non-covalent association, and wherein at least one of said VpreB and λ5 sequences is other than a full-length native VpreB and λ5 sequence, respectively. In some embodiments, at least one of said VpreB and λ5 sequences is a fragment or variant of a native VpreB and λ5 sequence, respectively. In some embodiments, the VpreB sequence is fused to the λ5 sequence, and the VpreB sequence fused to the λ5 sequence is paired with the heavy chain variable region amino acid sequence. In some embodiments, the VpreB, λ5, or VpreB and λ5 seqeunce is fused to a variable heavy chain construct as disclosed herein. In some embodiments, the antibody heavy chain variable region amino acid sequence is covalently paired via a peptide linker.

In some embodiments, the SBP comprises a VpreB sequence fused to a λ5 sequence, wherein the antibody heavy chain variable region amino acid sequence is conjugated to the VpreB sequence fused to the λ5 sequence by non-covalent association, to form a dimeric complex. In some embodiments, the SBP comprises a VpreB fused to a constant light sequence. In some embodiments, the SBP comprises a Lambda-5 fused to a variable light sequence.

In some embodiments, the heavy chain variable region amino acid sequence binds to ErbB3 and the VpreB sequence, the λ5 sequence, or the VpreB sequence and the λ5 sequence also bind to ErbB3.

In some embodiments, the antibody heavy chain variable region amino acid sequence binds to a target different from the target to which the VpreB sequence, the λ5 sequence, or the VpreB sequence and the λ5 sequence binds.

In some embodiments, the VpreB sequence, the λ5 sequence, or the VpreB sequence and the λ5 sequence binds to ErbB3 and the antibody heavy chain variable region amino acid sequence binds to a different target and/or epitope.

In some embodiments, the heavy chain variable region amino acid sequence binds to ErbB3 and the VpreB sequence, the λ5 sequence, or the VpreB sequence and the λ5 sequence binds to ErbB 1. In some embodiments, the heavy chain variable region amino acid sequence binds to ErbB3 and the VpreB sequence, the λ5 sequence, or the VpreB sequence and the λ5 sequence binds to ErbB2.

In some embodiments, the heavy chain variable region amino acid sequence binds to ErbB 1 and the VpreB sequence, the λ5 sequence, or the VpreB sequence and the λ5 sequence binds to ErbB3. In some embodiments, the heavy chain variable region amino acid sequence binds to ErbB2 and the VpreB sequence, the λ5 sequence, or the VpreB sequence and the λ5 sequence binds to ErbB3. In some embodiments, the heavy chain variable region amino acid sequence binds to ErbB4 and the VpreB sequence, the λ5 sequence, or the VpreB sequence and the λ5 sequence binds to ErbB3.

In some embodiments, a bispecific surroglobulin or antigen binding portions thereof, comprises a first VpreB sequence, a first λ5 sequence, or a first VpreB sequence and a first λ5 sequence. It can further include a first heavy chain variable region amino acid sequence that is paired with the first VpreB sequence, the first λ5 sequence, or the first VpreB sequence and the first λ5 sequence to form a first SBP site, wherein said surroglobulin or antigen binding portions thereof, binds to and/or inhibits an ErbB3 protein. In some embodiments, it can further include a second VpreB sequence, a second λ5 sequence, or a second VpreB sequence and a second λ5 sequence. In some embodiments, it can further include a second heavy chain variable region amino acid sequence that is paired with the second VpreB sequence, the second λ5 sequence, or the second VpreB sequence and the second λ5 sequence to form a second SBP binding protein site. The second SBP site can bind to and/or inhibit an EGFR protein and/or an ErbB2 protein as part of a bispecific surroglobulin or antigen binding portions thereof, or an independent SBP.

In some embodiments, a bispecific SBP not only works better than either agent alone, or as well as the combination of two SBPs that each bind a different type of GFR, but the bispecific SBPs can work significantly better. Thus, in some embodiments, bispecific SBPs (such as the Surrobody protein in Example 51), are superior to not only other SBPs, but also to other combinations of SBPs. In some embodiments, the bispecific SBP provides at least 10% greater inhibition over the combination of two different SBPs (for example, one to ERbB3 and one to EGFR), for example, at least 10, 50, 100, 200, 300, 400, 500, 600, 700, 800, 900, 1000, 12000, 15000%, or greater superiority (for example concentration required for a particular percent inhibition) than the combination of two, separate, SBPs.

In some embodiments, the bispecific SBP will include at least one of the heavy chain CDRs from SBP 2817-C01 and/or SBP 2716-F05. In some embodiments, the bispecific SBP can include any of the surrogate light chains provided herein. In some embodiments, the bispecific SBP will include at least one heavy chain CDR from SBP 2817-C01 and/or SBP 2716-F05. In some embodiments, the bispecific SBP will include at least two heavy chain CDRs from SBP 2817-C01 and/or SBP 2716-F05. In some embodiments, the bispecific SBP will include at least three heavy chain CDRs from SBP 2817-C01 and/or SBP 2716-F05. In some embodiments, the bispecific SBP will include at least one, two, or three heavy chain CDRs from SL-396 (see, for example, FIG. 41A). In some embodiments, the bispecific SBP will include at least the heavy chain variable region of at least one of SBP 2817-C01 or SBP 2716-F05. In some embodiments, the bispecific SBP will include at least a heavy chain variable region that is at least 85% identical to the sequence of the heavy chain variable region of SBP 2817-C01 or SBP 2716-F05. In some embodiments, the bispecific SBP will include at least a heavy chain variable region that is at least 90% identical to the sequence of the heavy chain variable region of SBP 2817-C01 and/or SBP 2716-F05. In some embodiments, the bispecific SBP will include at least a heavy chain variable region that is at least 95% identical to the sequence of the heavy chain variable region of SBP 2817-C01 or SBP 2716-F05. In some embodiments, the bispecific SBP will include at least a heavy chain variable region that is at least 98% identical to the sequence of the heavy chain variable region of SBP 2817-C01 or SBP 2716-F05. In some embodiments, the bispecific SBP will include at least a heavy chain variable region that is at least 99% identical to the sequence of the heavy chain variable region of SBP 2817-C01 or SBP 2716-F05.

In some embodiments, the bispecific SBP includes one or more of the CDRs (1, 2, or 3) from SBP 2716-F05 (see for example, FIG. 41C).

In some embodiments, the heavy chain variable sequence is the heavy chain variable region within the sequence of SEQ ID NO: 183 (FIG. 41A). In some embodiments, the heavy chain variable sequences are those shown in FIGS. 41A and 41C. In both 41A and 41C the heavy chain variable sequence begins before CDR 1 with "GluValGln" and ends after CDR 3 with "AlaSerThr") In some embodiments, the heavy chain can be from a nucleic acid as shown in SEQ ID NO: 182 and/or 184. In some embodiments, the heavy chains can be the amino acid sequence as in SEQ ID NO: 183 and/or 185. In FIG. 41A, the arrangement of the SBP was Vh-VpreB-lambda5. In FIG. 41C the arrangement of the SBP was VpreB-Vh-CH1-Fc.

In some embodiments, the bispecific SBP includes the heavy chain variable domains for 2716-F05 and SL-396. In some embodiments, the bispecific SBP includes the heavy chain CDRs (1, 2, and 3) for 2716-F05 and SL-396.

In some embodiments, the SBP selectively binds and inhibits ErbB3 signaling and cell growth in vitro and in vivo. In some embodiments, the SBP inhibits ErbB2 overexpressing tumor cell lines in vitro and in vivo. In some embodiments, the SBP is capable of inhibiting ErbB2 overexpressing tumor cell lines in the presence or absence of neuregulin. In some embodiments, the ErbB3 Surrobodies augment the activities of ErbB2 antibody trastuzumab to a greater extent than pertuzumab. In some embodiments, a bispecific Surrobody targeting ErbB3 and another growth factor receptor (e.g., EGFR or any of the others provided in the specification) demonstrate greater anti-proliferative activity than the combination of the two monospecific SBPs.

In some embodiments, the SBP comprises loop regions of a VpreB sequence.

In some embodiments, one or more of the disclosed SBPs bind to a similar, same, or overlapping epitope. In some embodiments, they bind to nonoverlapping epitopes. In some embodiments, 2817-C01 and 2716-F05 bind to overlapping and/or identical epitopes (as shown in Example 8). In some embodiments, surroglobulins or antigen binding portions thereof, that bind to similar, overlapping, or identical epitopes as 2817-C01 and 2716-F05 are contemplated.

In some embodiments, the surroglobulin or antigen binding portions thereof, can bind to any of the epitopes of the SBP s in Table 0.3A can bind to.

In some embodiments, an antibody is provided that binds to a same or an overlapping epitope that any of the SBPs disclosed herein binds to. In some embodiments, the Ab has the same or similar heavy chain CDR, CDRs, or heavy chain variable regions of any of the SBP s herein (including those noted in Table 0.3A). In some embodiments, the antibody displaces the SBP when the antibody binds to an epitope on ErbB3. In some embodiments, the antibody will not displace the SBP if the SBP is already bound to ErbB3.

Surrogate Light Chain Constructs

Precursors of B cells (pre-B cells) have been identified in the bone marrow as lymphocytes at a developmental stage that produce µ A heavy chains but have not yet begun to produce light chains and instead express a set of B lineage-specific genes called VpreB(1-3) and λ5, respectively.

One isoform of human VpreB1 (CAG30495) is a 145 aa-long polypeptide (SEQ ID NO: 1, FIG. 25). It has an Ig V domain-like structure, but lacks the last β-strand ((37) of a typical V domain, and instead has a carboxyl terminal end that shows no sequence homologies to any other proteins. VpreB2 has several isoforms, including a 142-amino acid mouse VpreB2 polypeptide (P13373; SEQ ID NO: 2, FIG. 25), and a 171-amino acid long splice variant of the mouse VpreB2 sequence (CAA019641 SEQ ID NO: 3, FIG. 25). VpreB1 and VpreB2 sequences have been disclosed in EP 0 269 127 and U.S. Pat. No. 5,182,205; Collins et al., Genome Biol. 5(10):R84 (2004); and Hollins et al., Proc. Natl. Acad. Sci. USA 86(14):5552-5556 (1989). One isoform of human VpreB3 (SEQ ID NO: 4, FIG. 25) is a 123 amino acid long protein (CAG30496), disclosed in Collins et al., Genome Biol. 5(10):R84 (2004).

In some situations, VpreB(1-3) can be non-covalently associated with another protein, λ5. The human λ5 is a 213-amino acid polypeptide (NP_064455; SEQ ID NO: 6, FIG. 25) that carries an Ig C domain-like structure with strong homologies to antibody light chains and, towards its amino terminal end, two functionally distinct regions, one of which shows strong homology to the β7 strand of the Vλ domains. A mouse λ5 protein has 209 amino acids (CAA01962; SEQ ID NO: 5, FIG. 25) and shows about 62% sequence identity to the antibody λ light chain constant region.

For further details, see the following review papers: Karasuyama et al., *Adv. Immunol.* 63:1-41 (1996); Melchers et al., *Immunology Today* 14:60-68 (1993); and Melchers, *Proc. Natl. Acad. Sci. USA* 96:2571-2573 (1999).

Traditionally, the VpreB and λ5 polypeptides together form a non-covalently associated, structure, called a surrogate light chain. On the surface of early preB cells, the surrogate light chain is complexed to membrane-bound Ig µ heavy chain in association with a signal transducer CD79a/CD79b heterodimer to form a B cell receptor-like structure, the so-called preB cell receptor (preBCR).

As discussed above, pre-B cells have been identified in the bone marrow as lymphocytes that produce µ heavy chains but instead of the fully developed light chains express a set of B lineage-specific genes called VpreB(1-3) and λ5, respectively. The VpreB and λ5 polypeptides together form a non-covalently associate distructure, called the surrogate light chain. The surrogate light chain, although not an antibody chain, naturally associates with all recombined antibody heavy chains.

In some embodiments, the SBPs include, without limitation, conjugates of VpreB sequences to heterogeneous amino acid sequences, provided that they retain the ability to bind a desired target. The binding of the VpreB sequence to the heterogeneous amino acid sequence can be either covalent or non-covalent, and can occur directly, or through a linker, including peptide linkers.

Specific examples of the polypeptide constructs herein include polypeptides in which a VpreB sequence, such as a VpreB1, VpreB2, or VpreB3 sequence, including fragments and variants of the native sequences, is conjugated to a λ5 sequence, including fragments and variants of the native sequence. Representative fusions of this type are illustrated in FIGS. 19 and 26 and described in the Examples.

In a direct fusion, typically the C-terminus of a VpreB sequence (e.g. a VpreB1, VpreB2 or VpreB3 sequence) is fused to the N-terminus of a λ5 sequence. While it is possible to fuse the entire length of a native VpreB sequence to a full-length λ5 sequence (see, e.g. the first diagram in FIG. 19), typically the fusion takes place at or around a non-immunoglobulin like peptide site in each of the two polypeptides. Such similar sites for VpreB1 and λ5 are illustrated in FIG. 18, and a representative fusion construct is illustrated in FIG. 19. In this embodiment, the fusion can take place within, or at a location within about 10 amino acid residues at either side of this region. In a preferred embodiment, the fusion takes place between about amino acid residues 116-126 of the native human VpreB1 sequence (SEQ ID NO: 1) and between about amino acid residues 87 and 97 of the native human λ5 sequence (SEQ ID NO: 6).

Figure 19:
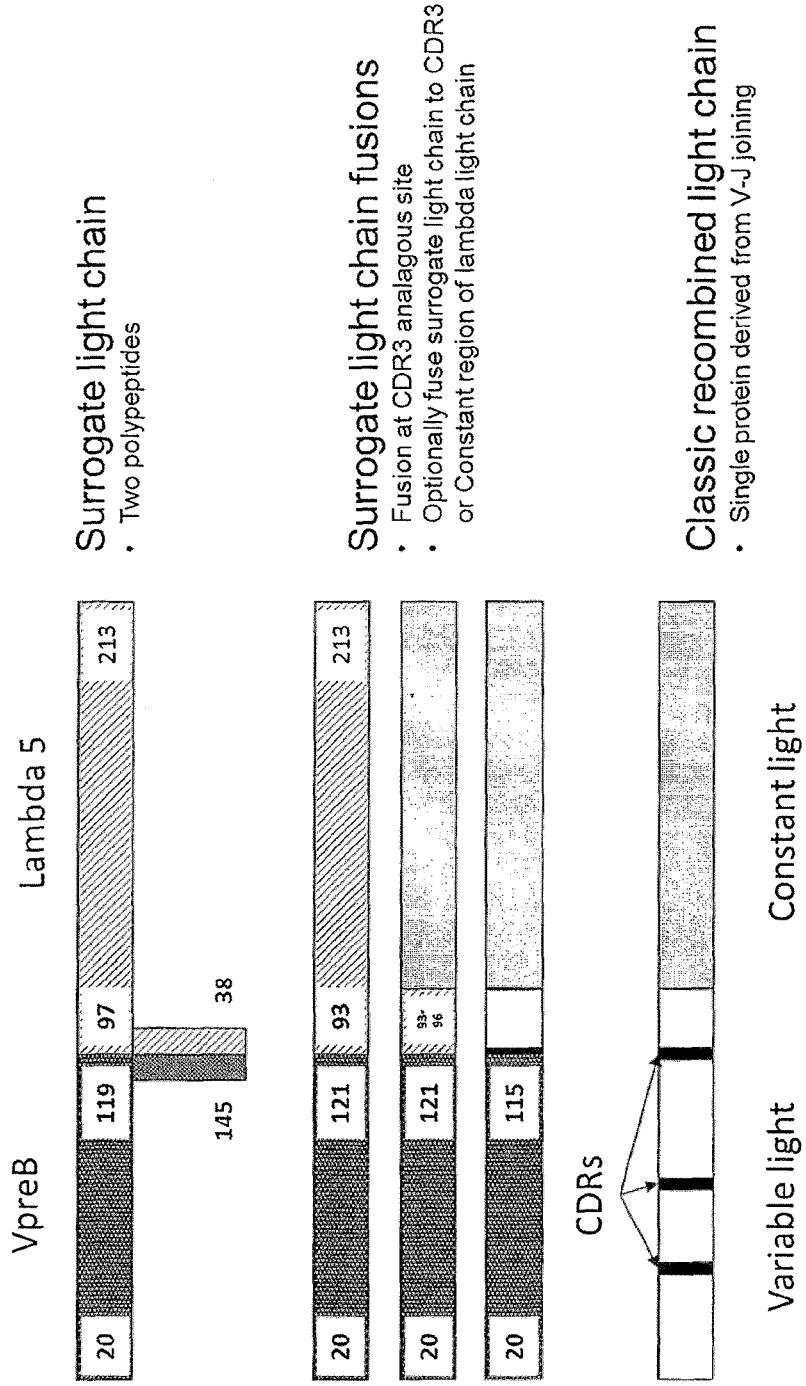
FIG. 19 is a schematic illustration of a surrogate light chain formed by VpreB and λ5 sequences, illustrative fusion polypeptides comprising surrogate light chain sequences, and an antibody light chain structure derived from V-J joining.
Figure 20:
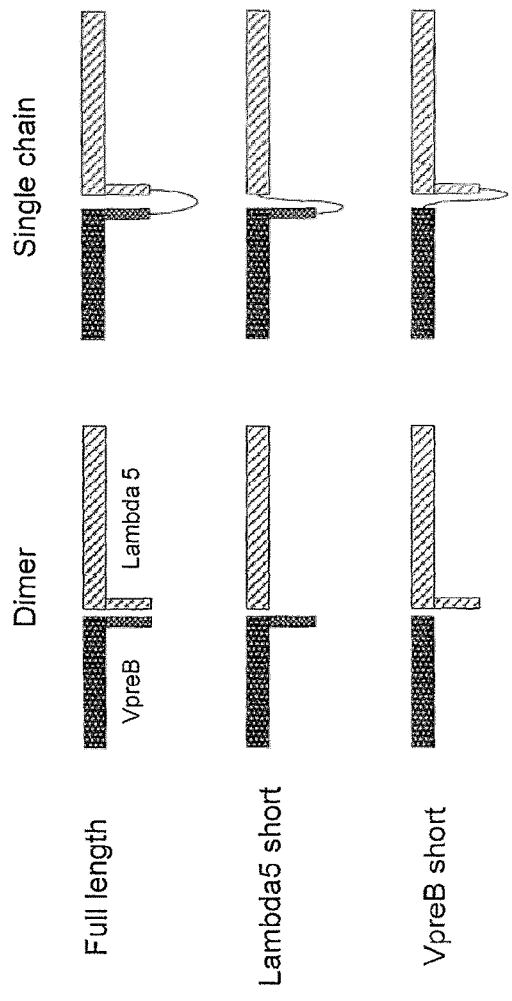
FIG. 20 is a schematic illustration of various surrogate light chain deletion and single chain constructs.

It is also possible to fuse the VpreB sequence to the CDR3 region of an antibody λ light chain, as shown in FIG. 19. It is also possible to fuse the carboxy terminus of a VpreB and λ5 construct to the amino terminus of the constant light region of antibody λ light chain, also as shown in FIG. 19. Further constructs, in which only one of VpreB and λ5 is truncated are shown in FIG. 20. Similar constructs can be prepared using antibody κ light chain sequences.

Figure 26:
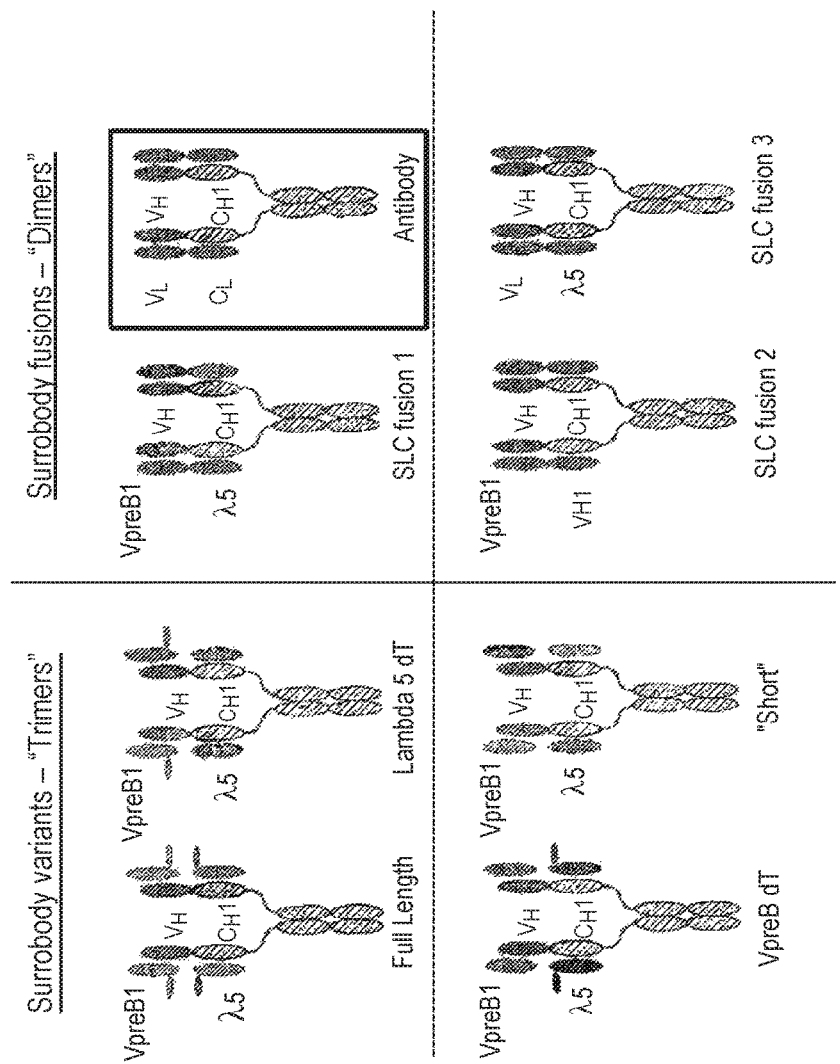
FIG. 26 illustrates various embodiments of trimeric and dimeric SBPs.

Further direct fusion structures are illustrated on the right side of FIG. 26. The structure designated "SLC fusion 1" is a tetramer, composed of two dimers, in which the fusion of a truncated V-preB 1 sequence (lacking the characteristic "tail" at the C-terminus of native VpreB1) to a similarly truncated λ5 sequence is non-covalently associated with an antibody heavy chain. The structure designated "SLC fusion 2" is a tetramer, composed of two dimers, in which the fusion of a truncated VpreB1 sequence (lacking the characteristic "tail" at the C-terminus of native VpreB1) to an antibody light chain constant region is non-covalently associated with an antibody heavy chain. The structure designated "SLC fusion 3" is a tetramer, composed of two dimers, in which the fusion of an antibody light chain variable region to a truncated λ5 sequence (lacking the characteristic "tail" at the N-terminus of native λ5) is non-covalently associated with an antibody heavy chain.

As noted above, in addition to direct fusions, the polypeptide constructs include non-covalent associations of a VpreB sequence (including fragments and variants of a native sequence) with a heterogeneous sequence, such as a λ5 sequence (including fragments and variants of the native sequence), and/or an antibody sequence. Thus, for example, a full-length VpreB sequence can be non-covalently associated with a truncated λ5 sequence. Alternatively, a truncated VpreB sequence can be non-covalently associated with a full-length λ5 sequence.

Surrogate light chain constructs comprising non-covalently associated VpreB1 and λ5 sequences, in non-covalent association with an antibody heavy chain, are shown on the left side of FIG. 26. As the various illustrations show, the structures can include, for example, full-length VpreB1 and λ5 sequences, a full-length VpreB1 sequence associated with a truncated λ5 sequence ("Lambda 5dT"), a truncated VpreB1 sequence associated with a full-length λ5 sequence (VpreB dT") and a truncated VpreB1 sequence associated with a truncated λ5 sequence ("Short").

Although FIG. 26 illustrates certain specific constructs, one of ordinary skill will appreciate that a variety of other constructs can be made and used in a similar fashion. For example, the structures can be asymmetrical, comprising different surrogate light chain sequences in each arm, and/or having trimeric or pentameric structures, as opposed to the structures illustrated in FIG. 26. It is also possible to include different functionalities in various portions of the surrogate light chain constructs, thereby producing multi-specific and/or multivalent constructs.

If desired, the constructs can be engineered, for example, by incorporating or appending known sequences or sequence motifs from the CDR1, CDR2 and/or CDR3 regions of antibodies, including known therapeutic antibodies into similar regions of the surrogate light chain constructs. This allows the creation of molecules that are not antibodies, but will exhibit binding specificities and affinities very similar to those of a known therapeutic antibody.

Figure 21:
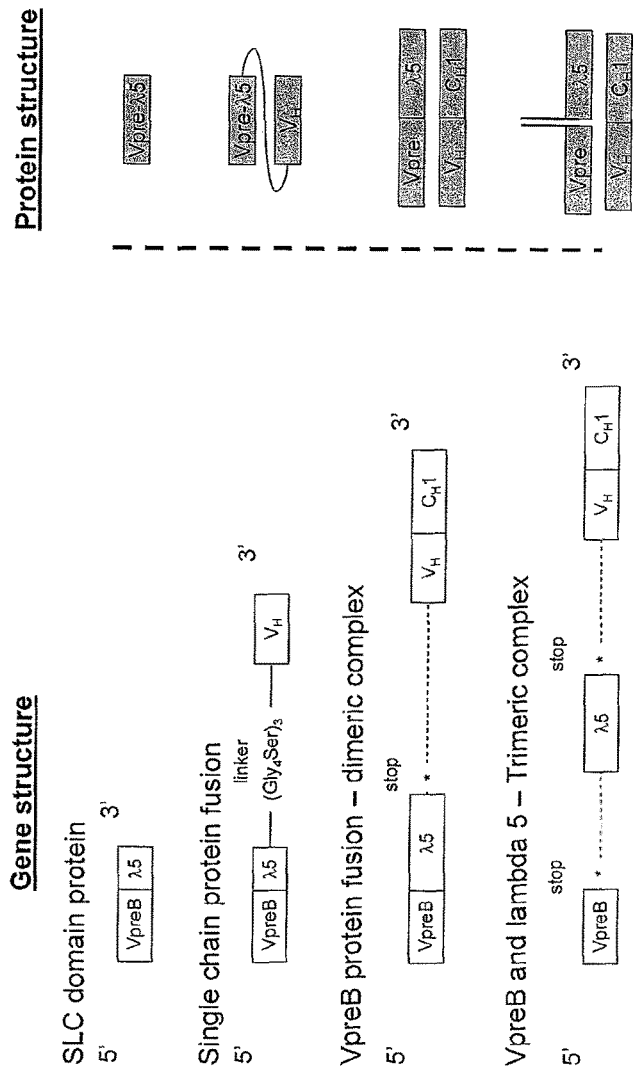
FIG. 21 shows the gene and protein structures of various illustrative sur-binding proteins constructs including an SLC domain protein, a single chain fusion protein (comprising an SLC domain protein fused to a heavy chain variable domain by a (Gly$_4$Ser)$_3$ linker (SEQ ID NO: 281)), a VpreB protein fusion-dimeric complex, and a VpreB and lambda 5-trimeric complex.

All surrogate light chain constructs herein can be associated with antibody heavy chain sequences. For example, as shown in FIG. 21, a VpreB-λ5 fusion can be linked to an antibody heavy chain variable region sequence by a peptide linker. In some embodiments, a VpreB-λ5 fusion is associated with an antibody heavy chain, or a fragment thereof including a variable region sequence to form a dimeric complex. In yet another embodiment, the VpreB and λ5 sequences are associated with each other and an antibody heavy chain, or a fragment thereof including a variable region sequence, thereby forming a trimeric complex. Exemplary constructs comprising an antibody heavy chain are illustrated in FIG. 26.

While the constructs are illustrated by reference to certain embodiments, one of ordinary skill will understand that numerous further embodiments obtained by various permutations of surrogate light chain and antibody sequences are possible, and are within the scope of the present invention. The present invention includes all constructs that comprise surrogate light chain sequences and have the ability to bind a desired target. In certain embodiment, the constructs also have the ability to associate with antibody heavy chain variable region sequences.

The constructs can be used to build libraries of surrogate light chain sequences, which can be used for various purposes, similarly to antibody libraries, including selection of constructs with the desired binding specificities and affinities.

When the VpreB and λ5 surrogate light chain sequences are non-covalently associated with each other, the free ends of one or both components (i.e. the C-terminal end of the VpreB sequence and/or the N-terminal end of the λ5 sequence) are available for incorporating an additional diversity into the library of such sequences. For instance, a random peptide library can be appended or substituted to one of these free ends and panned for specific binding to a particular target. By combining the surrogate light chain identified to have the desired binding specificity with a heavy chain or heavy chain fragment from an antibody to the same target, a molecule can be created that has the ability to bind to the cognate target on two distinct places. This tandem binding, or "chelating" effect, strongly reinforces the binding to a single target, similarly to the avidity effects seen in dimeric immunoglobulins. It is also possible to use components binding to different targets. Thus, for example, the surrogate light chain component with the desired binding specificity can be combined with an antibody heavy chain or heavy fragment binding to a different target. For instance, the surrogate light chain component can bind a tumor antigen while the antibody heavy chain or heavy chain fragment can bind to effector cells. This way, a single entity with targeting and anti-tumor activity can be created. In a particular embodiment, the appendage or the polypeptide that connects the VpreB and λ5 sequences can be an antibody or antibody fragments, such as a Fab or a scFv fragment. The incorporation of an antibody sequence will not only create a "chelating" effect but can also generate bispecificity in a single molecule, without the need of a second independent arm, such as that found in bispecific antibodies. The two specificities can be to different parts of the same target, to disparate targets, or to a target antibody complex. Similarly, multi-specific constructs can be made with any type of molecule, other than antibodies or antibody fragments, including peptides, proteins, enzymes, and the like. For example, the surrogate light chain component with the desired specificity can be combined with any therapeutic peptide or protein.

In some embodiments, the VpreB and λ5 components of the SBP can be modified in numerous ways to improve the structure, performance, and/or stability of resulting SBPs. An approach to improving the qualities of the SBPs can be accomplished by incorporating elements of antibody light chains into the surrogate light chain. One example would be the substitution of one or more framework regions of antibody light chain variable domains into the structurally similar regions of the surrogate light chain. Specifically one could substitute Contact defined variable light chain framework-related Kabat numbered residues 1-29, 37-45, or 56-88, for VpreB residues 21-47, 58-67, or 82-117, respectively. Alternatively, one could substitute Chothia defined variable light chain framework-related Kabat numbered residues 1-23, 35-49, 57-88, for VpreB residues 21-41, 56-71, or 83-117, respectively. These regional substitutions can be done in whole, or as a continuous or discontinuous portion to achieve the desired surrogate light chain. Additionally, substitution of one or more regions of the antibody light chain variable and constant domains into the structurally similar regions of the surrogate light chain can be performed. In this instance one could substitute light chain domain Kabat residues 97-215 for λ5 residues 94-211 respectively. This regional substitution can also be done in whole or as a continuous or discontinuous portion to achieve the desired surrogate light chain. Also combinations of such substitutions for both VpreB and λ5 can be incorporated to achieve the desired light chain. In any event any or all of the modified surrogate light chains and their respective resulting SBPs can be produced in protein expression systems and tested, or used for their potential improved qualities.

In some embodiments, the ability of anti-ErbB3 sur-binding proteins to reduce tumor growth, in vitro, can be influenced by engaging ErbB3 through binding sites located within, and/or proximal to, surface exposed loops in the variable heavy and VpreB domains. While these remain the elements of recognition of ErbB3 in vivo, the overall efficacious potential can be significantly influenced by the composition of the constant heavy regions. For example, in some embodiments, an IgG3-based constant heavy region can be used in the ErbB3 sur-binding proteins to impart maximal effector function for sur-binding protein-dependent cell-mediated cytotoxicity, and even complement mediated cytotoxicity. However, in some situations, an IgG3-based constant heavy region can have a fairly short half-life, compared to an IgG1-origin constant heavy region. Maintaining the use of an IgG3-based constant heavy region for the ErbB3 sur-binding proteins, instead of one based upon IgG1 would be a reasonable and preferable if longer term exposure caused greater drug-related adverse effects and no greater efficacy. However, in the instance where effector function is believed to impart dose limiting undesirable activities to nonpathological tissues, then the choice of an IgG2-based constant heavy region that has minimal effector function capacity can be desirable. Additionally, in some embodiments, various allotypes and designed Fc regions can be used to impart greater levels of desired effector function, as well as variants and Fc chimeras, to specifically tune and optimally empower the ErbB3 sur-binding proteins. In some embodiments, other heavy chain classes, such as IgA, IgM, IgD, IgE can serve as additionally optimized candidates, based upon the overall desired pharmacophore properties.

Preparation of Surrogate Light Chain Constructs

The surrogate light chain constructs can be prepared by methods known in the art, including well known techniques of recombinant DNA technology.

Nucleic acid encoding surrogate light chain, e.g. VpreB and λ5 polypeptides, can be isolated from natural sources, e.g. developing B cells and/or obtained by synthetic or semi-synthetic methods. Once this DNA has been identified and isolated or otherwise produced, it can be ligated into a replicable vector for further cloning or for expression.

Cloning and expression vectors that can be used for expressing the coding sequences of the polypeptides herein are well known in the art and are commercially available. The vector components generally include, but are not limited to, one or more of the following: a signal sequence, an origin of replication, one or more marker genes, an enhancer element, a promoter, and a transcription termination sequence. Suitable host cells for cloning or expressing the DNA encoding the surrogate light chain constructs in the vectors herein are prokaryote, yeast, or higher eukaryote (mammalian) cells, mammalian cells are being preferred.

Examples of suitable mammalian host cell lines include, without limitation, monkey kidney CV1 line transformed bySV40 (COS-7, ATCC CRL 1651); human embryonic kidney line 293 (293 cells) subcloned for growth in suspension culture, Graham et al, *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TM cells (Mather et al., *Annals N.Y. Acad. Sci.* 383:44-68 (1982)); MRC 5 cells; FS4 cells; and a human hepatoma line (Hep G2).

For use in mammalian cells, the control functions on the expression vectors are often provided by viral material. Thus, commonly used promoters can be derived from the genomes of polyoma, Adenovirus2, retroviruses, cytomegalovirus, and Simian Virus 40 (SV40). Other promoters, such as the β-actin protomer, originate from heterologous sources. Examples of suitable promoters include, without limitation, the early and late promoters of SV40 virus (Fiers et al., *Nature,* 273: 113 (1978)), the immediate early promoter of the human cytomegalovirus (Greenaway et al., *Gene,* 18: 355-360 (1982)), and promoter and/or control sequences normally associated with the desired gene sequence, provided such control sequences are compatible with the host cell system.

Transcription of a DNA encoding a desired heterologous polypeptide by higher eukaryotes is increased by inserting an enhancer sequence into the vector. The enhancer is a cis-acting element of DNA, usually about from 10 to 300 bp, that acts on a promoter to enhance its transcription-initiation activity. Enhancers are relatively orientation and position independent, but preferably are located upstream of the promoter sequence present in the expression vector. The enhancer can originate from the same source as the promoter, such as, for example, from a eukaryotic cell virus, e.g. the SV40 enhancer on the late side of the replication origin (bp 100-270), the cytomegalovirus early promoter enhancer, the polyoma enhancer on the late side of the replication origin, and adenovirus enhancers.

Expression vectors used in mammalian host cells also contain polyadenylation sites, such as those derived from viruses such as, e.g., the SV40 (early and late) or HBV.

An origin of replication can be provided either by construction of the vector to include an exogenous origin, such as can be derived from SV40 or other viral (e.g., Polyoma, Adeno, VSV, BPV) source, or can be provided by the host cell.

The expression vectors usually contain a selectable marker that encodes a protein necessary for the survival or growth of a host cell transformed with the vector. Examples of suitable selectable markers for mammalian cells include dihydrofolate reductase (DHFR), thymidine kinase (TK), and neomycin.

Suitable mammalian expression vectors are well known in the art and commercially available. Thus, for example, the surrogate light chain constructs can be produced in mammalian host cells using a pCI expression vector (Promega), carrying the human cytomegalovirus (CMV) immediate-early enhancer/promoter region to promote constitutive expression of a DNA insert. The vector can contain a neomycin phosphotransferase gene as a selectable marker.

The surrogate light chain constructs can also be produced in bacterial host cells. Control elements for use in bacterial systems include promoters, optionally containing operator sequences, and ribosome binding sites. Suitable promoters include, without limitation, galactose (gal), lactose (lac), maltose, tryptophan (trp), β-lactamase promoters, bacteriophage and T7 promoters. In addition, synthetic promoters can be used, such as the tac promoter. Promoters for use in bacterial systems also generally contain a Shine-Dalgarno (SD) sequence operably linked to the DNA encoding the Fab molecule. The origin of replication from the plasmid pBR322 is suitable for most Gram-negative bacteria.

The coding sequences of the individual chains within a multi-chain construct comprising antibody surrogate light chain sequences can be present in the same expression vector, under control of separate regulatory sequences, or in separate expression vectors, used to cotransfect a desired host cells, including eukaryotic and prokaryotic hosts. Thus, multiple genes can be coexpressed using the Duet™ vectors commercially available from Novagen.

The transformed host cells can be cultured in a variety of media. Commercially available media for culturing mammalian host cells include Ham's F10 (Sigma), Minimal Essential Medium ((MEM), (Sigma), RPMI-1640 (Sigma), and Dulbecco's Modified Eagle's Medium ((DMEM), Sigma). In addition, any of the media described in Ham et al., *Meth. Enz.* 58:44 (1979) and Barnes et al., *Anal. Biochem.* 102:255 (1980) can be used as culture media for the host cells. The culture conditions, such as temperature, pH, and the like, are those previously used with the host cell selected for expression, and are included in the manufacturer's instructions or will otherwise be apparent to the ordinarily skilled artisan.

Further suitable media for culturing mammalian, bacterial (e.g. *E. coli*) or other host cells are also described in standard textbooks, such as, for example, Sambrook et al., supra, or Ausubel et al., supra.

Purification can be performed by methods known in the art. In a preferred embodiment, the surrogate antibody molecules are purified in a 6xHis-tagged form, using the Ni-NTA purification system (Invitrogen).

Uses of Surrogate Light Chain Sequences, Constructs and Libraries Containing Same The libraries can be used to identify surrogate light chain sequences and surrogate light chain constructs, such as fusions comprising surrogate light chain sequences, with desired properties. For example, in vitro or in vivo screening of the libraries herein can yield polypeptides comprising surrogate light chain sequences binding to desired targets with high binding specificity and affinity. Thus, the libraries herein can be used to identify molecules for therapeutic and diagnostic purposes, such as polypeptides comprising surrogate light chain sequences that bind to tumor markers or other molecular targets of therapeutic intervention. In addition, by the techniques described above, highly diverse libraries of surrogate light chain polypeptides can be engineered, including libraries comprising a collection of polypeptides binding to the same target, libraries of polypeptides binding to different targets, libraries of polypeptides with multiple specificities, and the like.

As a result of their ability to bind to any desired target, the antibody surrogate light chain constructs can be used in analytical and diagnostic assays, to detect the presence of a desired target molecule, such as a tumor antigen or any polypeptide associated with a disease state or condition. In addition, the surrogate light chain constructs can be used as therapeutic agents, such as, for example, in cancer therapy, to target tumor antigens that have been determined to associate with the development and/or spread of cancer.

Coupling SBPs to Therapeutic Agents or Labels

While, for some embodiments, the binding of the SBPs to ErbB3 can modulate the biological activity of the target cell, the effect of the SBPs on biological activity can be increased by coupling a therapeutic agent to the SBPs. In some embodiments, therefore, the SBPs are derivatized to introduce functional groups permitting the attachment of a therapeutic agent. The SBP can be derivatized to introduce, for example, side chains terminating in hydrazide, hydrazine, primary amine, or secondary amine groups. Therapeutic agents can be conjugated through, for example, a Schiffs base linkage, a hydrazone or acyl hydrazone bond or a hydrazide linker (see, e.g., U.S. Pat. Nos. 5,474,765 and 5,762,918, each of which is specifically incorporated herein by reference). A number of other chemistries suitable for conjugating therapeutic agents to SBP are well known in the art, as exemplified by Hermanson, G., Bioconjugate Techniques, Academic Press, San Diego, Calif (1996).

Therapeutic agents can be selected from, for example, anti-neoplastic agents, anti-metabolic agents, radioactive agents, cytotoxic agents, and chemotherapeutic agents.

Anti-cancer agents include Cytotoxic agents such as the following: auristatins and derivatives, calicheamicins and derivatives, maytansinoids and derivatives, *Pseudomonas* exotoxin, ricin, diphtheria toxin, gemcitabine; methotrexate; 5-FU; FUDR; FdUMP; hydroxyurea; docetaxel; discodermolide; epothilones; vincristine; vinblastine; vinorelbine; meta-pac; irinotecan; SN-38; 10-OH campto; topotecan; etoposide; adriamycin; flavopiridol; cisplatin; carboplatin; bleomycin; mitomycin C; mithraniycin; capecitabine; cytarabine; 2-Cl-2'deoxyadenosine; mitoxantrone; mitozolomide; pentostatin; and raltitrexed.

The SBPs can further be modified or labeled to facilitate diagnostic or therapeutic uses. For example, detectable labels such as a radioactive, fluorescent, heavy metal, or other label, can be conjugated to the SBPs. Single, dual, or multiple labeling of the SBPs can be advantageous. For example, a SBPs can be dual labeled, with both radioactive iodination of one or more residues and the coupling of, for example, $^{90}Y$ via a chelating group to amine-containing side or reactive groups. This combination labeling can be useful for specialized diagnostic needs such as identification of widely dispersed small neoplastic cell masses.

Radioisotopes for radiolabeling the SBPs can include any radioisotope that can be conjugated or coupled to a residue of the SBPs. The radioisotopes can be selected from radioisotopes that emit either beta or gamma radiation, or alternatively, the peptide agents can be modified to contain chelating groups that, for example, can be covalently bonded to lysine residue(s) of the analog. The chelating groups can then be modified to contain any of a variety of radioisotopes, such as gallium, indium, technetium, ytterbium, rhenium, or thallium (e.g., $^{125}I$, $^{67}Ga$, $^{111}In$, $^{99m}Tc$, $^{169}Yb$, $^{186}Re$).

Chelating groups can be used to indirectly couple detectable labels or other molecules to the SBPs. For example, a bifunctional stable chelator can be linked to one or more terminal or internal amino acid reactive groups via an isothiocyanate beta-Ala or an appropriate non alpha-amino acid linker which prevents Edman degradation. Examples of chelators known in the art include, for example, the ininocarboxylic and polyaminopolycarboxylic reactive groups, DTPA (N,N-Bis[2-[bis(carb oxymethypamino]ethyl]glycine), and DOTA (1,4,7,10-tetraazacyclo do decane-1,4,7,10-tetraacetic acid).

In terms of cancer diagnosis and treatment, the SBPs can be used to prepare diagnostic and imaging compositions, and kits utilizing the SBPs in diagnostic and imaging methods (e.g., in vivo and in vitro diagnostic methods). For example, a vascularized tumor can be imaged using a diagnostically effective amount of a SBPs that includes at least a first binding molecule that binds to an accessible component of a tumor cell, tumor vasculature, or tumor stroma, attached to an in vivo diagnostic imaging agent.

In some embodiments in which the disease or disorder is cancer, pre-imaging before cancer treatment can be carried out by: (a) administering to the animal or patient a diagnostically effective amount of a pharmaceutical composition comprising a detectably-labeled SBP that has a first binding molecule that binds with high affinity to a highly expressed receptor characteristic of a tumor cell, or to the tumor vasculature or tumor stroma, and a second binding molecule that binds with at least an order of magnitude lower affinity to a second ubiquitously-expressed receptor; and (b) subsequently detecting the detectably-labeled SBP bound to the tumor cells, tumor blood vessels, or tumor stroma; thereby obtaining an image of the tumor, tumor vasculature, and/or tumor stroma.

Without wishing to be bound by theory, in some embodiments, the SBPs can reduce, prevent, or inhibit cell signaling by competing with a natural ligand for binding to a cell surface receptor. In this situation, the SBPs function by blocking cell signaling induced upon ligand binding. In some embodiments, the SBPs can also act by inducing internalization/downregulation of the cell surface receptors. The reduction in the number of receptors at the cell surface caused by internalization/downregulation results in reduced receptor activation, which reduces or prevents cell signaling along the signal transduction pathway for those receptors. In another embodiment the SBPs can impede ErbB3 signaling that is dependent upon a physically associated receptor such as ErbB2, or on a network associated receptor such as c-met. Finally, in cases where receptor dimerization is required for signal transduction, the SBPs can act by preventing dimerization of the two cell surface receptors.

Therapeutic Uses

In some embodiments, SBPs can be used for/in therapies which involve administering SBPs to an animal, preferably a mammal, and most preferably a human patient, for treating one or more of the described diseases or disorders. Therapeutic compounds include, but are not limited to, SBPs or antigen binding portions thereof. The SBPs or antigen binding portions thereof, can be used to treat, inhibit, or prevent the diseases and disorders disclosed herein that are associated with aberrant expression and/or activity of a cell surface receptor. The treatment and/or prevention of diseases and disorders associated with aberrant expression and/or activity of a cell surface receptor includes, but is not limited to, alleviating symptoms associated with those diseases and disorders. SBPs or antigen binding portions thereof, can be provided in pharmaceutically acceptable compositions as known in the art or as described herein. Armed with the teachings provided herein, one of ordinary skill in the art will know how to use the SBPs or antigen binding portions thereof, for diagnostic, monitoring, or therapeutic purposes without undue experimentation.

In some embodiments, SBPs or antigen binding portions thereof, can be administered alone or in combination with other types of treatments (e.g., radiation therapy, chemotherapy, hormonal therapy, therapeutic antibodies, immunotherapy and anti-tumor agents).

Methods of using SBPs, antigen binding portions thereof, and antibodies that bind ErbB3 in a variety of ex vivo and in vivo diagnostic and therapeutic applications are also provided. For example, SBPs and/or antibodies disclosed herein can be used for treating a disease associated with ErbB3 dependent signaling, including a variety of cancers.

In some embodiments, the present invention provides a method for treating a disease associated with ErbB3 dependent signaling by administering to a subject SBPs, antigen binding portions thereof, and/or antibodies in an amount effective to treat the disease. Suitable diseases include, for example, a variety of cancers including, but not limited to, melanoma, breast cancer, ovarian cancer, renal carcinoma, gastrointestinal cancer, colon cancer, lung cancer (e.g., non-small cell lung cancer), and prostate cancer. In some embodiments, a tumor sample obtained from the patient is tested and treatment is provided in accordance with the methods disclosed in International Application No. PCT/US09/054051, filed Aug. 17, 2009, titled "Methods, Systems And Products For Predicting Response Of Tumor Cells To A Therapeutic Agent And Treating A Patient According To The Predicted Response" which is incorporated herein by reference.

In some embodiments, the cancer comprises a KRAS mutation. SBPs disclosed herein are capable of inhibiting the growth of tumor cells that comprise a KRAS mutation, either when used as a single agent (monotherapy) or in combination with another therapeutic agent. In some embodiments, the cancer comprises a PI3K mutation. SgGs disclosed herein are capable of inhibiting the growth of tumor cells that comprise a PI3K mutation, either when used as a single agent (monotherapy) or in combination with another therapeutic agent. In some embodiments, the cancer overexpressed the Her2 gene product. SgGs disclosed herein are capable of inhibiting the growth of tumor cells that overexpress Her2, either when used as a single agent (monotherapy) or in combination with another therapeutic agent. SgGs disclosed herein are capable of inhibiting the growth of tumor cells that overexpress EGFR, either when used as a single agent (monotherapy) or in combination with another therapeutic agent.

In some embodiments, a SBP, antigen binding portions thereof, and/or antibodies can be administered alone or with another therapeutic agent that acts in conjunction with or synergistically with a SBP, antigen binding portions thereof, and/or antibody to treat the disease associated with ErbB3 mediated signaling. Such therapeutic agents include, for example, the anticancer agents described infra (e.g., cytotoxins, chemotherapeutic agents, small molecules and radiation). In some embodiments, the therapeutic agents for combination therapy include erlotinib (Tarceva™), paclitaxel (Taxol™) and cisplatin (CDDP). In some embodiments, the agents include aromatase inhibitors, estrogen receptor inhibitors, lapatinib, gefitinib, PI3kinase inhibitors, and/or AKT inhibitors.

In certain aspects, SBPs and/or antibodies disclosed herein are administered to patients.

In some embodiments, a method is provided for diagnosing a disease (e.g., a cancer) associated with ErbB3 upregulation in a subject, by contacting SBPs, antigen binding portions thereof, and/or antibodies disclosed herein (e.g., ex vivo or in vivo) with cells from the subject, and measuring the level of binding to ErbB3 on the cells. Abnormally high levels of binding to ErbB3 indicate that the subject has a disease associated with ErbB3 upregulation.

In some embodiments, a method for suppressing tumor growth is provided. The method can include providing an ErbB3 SBP (such as in Table 0.3A) to a tumor that comprises a cell that expresses ErbB3, thereby suppressing tumor growth.

In some embodiments, a method for suppressing a cancerous cell is provided. The method can include identifying a subject having a cancerous cell that expresses ErbB3. In some embodiments, one can then administer to the subject an ErbB3 SBP or antigen binding portion thereof, in an amount sufficient to bind to ErbB3 on the cancerous cell and thereby block the AKT pathway.

In some embodiments, the SBPs or antigen binding portions thereof, disclosed herein can be used to inhibit, block, and/or reduce the proliferation of various cells in vitro (as shown in Example 9), in vivo, or ex vivo. In some embodiments, the SBP can block or reduce the proliferation of various cells (e.g., epithelial, colorectal, and/or pancreatic cancer cell lines) in the absence of NRG.

Figure 8A:
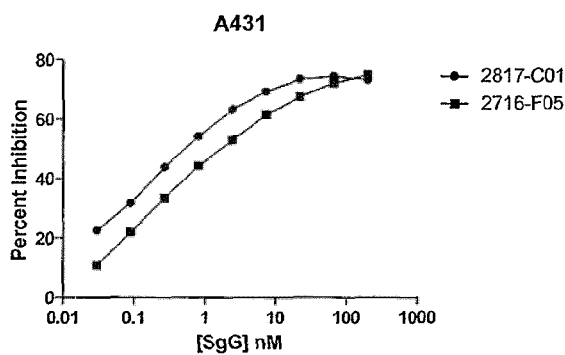
FIGS. 8A-8C are graphs depicting results establishing that SgGs inhibit proliferation of several cell lines, including those for epithelial human cancer, colorectal human cancer and pancreatic human cancer.

In some embodiments, the SBPs or antigen binding portions thereof, inhibit proliferation of cells in the presence and/or absence of an ErbB3 activator, such as NRG. In some embodiments, the SBPs or antigen binding portions thereof, can reduce proliferation of ErbB2 overexpressing cells in the presence and/or absence of NRG-1. In some embodiments, the SBP can achieve 5, 10, 15, 20, 25, 30, 35, 40, 45, 50% or greater inhibition of ErbB3 signaling in the absence of NRG-1 (e.g., as shown in FIG. 8A). In some embodiments, the SBP can achieve 5, 10, 15, 20, 25, 30, 35, 40, 45, 50% or greater inhibition of ErbB3 signaling in the presence of NRG-1. In some embodiments, the SBPs or antigen binding portions thereof, can prevent and/or reduce NRG-1 driven signaling, even when NRG is already bound to ErbB3.

In some embodiments, the SBPs or antigen binding portions thereof, block one or more of the functions or activities of ErbB3 disclosed herein. In some embodiments, the SBPs or antigen binding portions thereof, reduce and/or block NRG binding to ErbB3. In some embodiments, the SBPs or antigen binding portions thereof, block or reduce dimerization of ErbB3 with another ErbB3 molecule and/or ErbB1, and/or ErbB2, and/or ErbB4.

In some embodiments, the SBP or antigen binding portions thereof, can be used to reduce a cancer's resistance, or increase the sensitivity, to another therapy.

Figure 28:
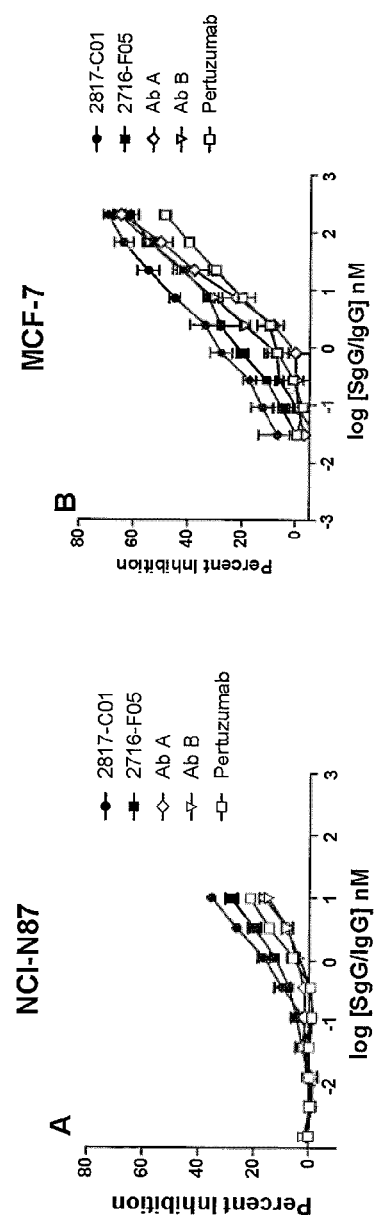
FIG. 28A is a graph depicting data demonstrating that 2817-C01 and 2716-F05 significantly inhibit the proliferation of a gastric (NCI-N87) human cancer cell line.
FIG. 28B is a graph depicting data demonstrating that 2817-C01 and 2716-F05 significantly inhibit the proliferation of a breast (MCF-7) human cancer cell line.
FIG. 28C is a depiction of the sequence of the variable region of an antibody.
FIG. 28D is a depiction of the sequence of the variable region of an antibody.

In some embodiments, one or more of the SBPs or antigen binding portions thereof, noted herein can enhance the antiproliferative activity of Erb targeted antibodies. In some embodiments, the SBPs or antigen binding portions thereof, can be combined with cetuximab or panitimumab to provide a composition with enhanced antiproliferative activity. In some embodiments, the SBPs or antigen binding portions thereof, disclosed herein can be combined with anti-ErbB2 SBPs or anti-ErbB2 antibodies such as trastuzumab and/or pertuzumab. In some embodiments, any one or more of the sur-binding proteins provided herein can be combined with other molecules. In some embodiments, this can provide for enhanced effectiveness. In some embodiments, the SBPs (e.g., 2817-C01 or 2716-F05) or antigen binding portions thereof, can be combined with cetuximab, panitimumab, pertuzumab, trastuzumab, lapatinib, GDC-0941, Ab B (having a VH and VL as shown in FIG. 28C, and/or Ab A (having the VH and VL as shown in FIG. 28D) to provide a composition with enhanced antiproliferative activity and/or inproved inhibition. In some embodiments, this can be effective in the presence of NRG. In some embodiments, this can be effective in the absence of NRG. In some embodiments, this allows for a greater amount of inhibition to be achieved than either molecule acting alone (e.g., at least 10, 50, 100, 200, 300, or 400 percent or more increase in inhibition, or a final inhibition of at least 40, 50, 60, 70, 80, 90, 95, 98, 99, 99.9 or effectively complete inhibition). In some embodiments, 2817-C01 or 2716-F05 can be combined with at least one of cetuximab, panitimumab, pertuzumab, trastuzumab, Ab B, or Ab A to provide for at least one of the following: reduction in cell surface ErbB3, enhancement in antiproliferative activity for EGFR targeted molecules (antibodies or other molecules), enhance the antiproliferative activity of ERB2 targeted molecules (antibodies or other molecules), enhance the activity of PI3K, AKT, mTOR targeted molecules, reduction in ligand-induced ERBB3 phosphorylation, AKT phosphoylation, and/or ERK phosphorylation, and/or improvement in the inhibition of proliferation of cancer cell line (including any provided herein, such as gastric and/or breast cancer cells).

In some embodiments, the amount of trastuzumab used can be enough to demonstrate some improvement or desired effect when used in combination with one or more of the sur-binding proteins provided herein. In some embodiments, the amount of trastuzumab used can be 0.01, 0.1, 1, 10, 50, 100, 150, 200, 500, 1,000, 10,000, 100,000, 1,000,000, 10,000,000, or 100,000,000 nM, including any range defined between any two of these values. In some embodiments, any one of these values and/or ranges can be combined with 0.01, 0.1, 1, 10, 50, 100, 150, 200, 500, 1,000, 10,000, 100,000, 1,000,000, 10,000,000, or 100,000,000 nM (including any range defined with any two of these values) of any of the sur-binding proteins provided herein (for example, 2817-C01 and/or 2716-F05).

In some embodiments, the amount of pertuzumab used can be enough to demonstrate some improvement or desired effect when used in combination with one or more of the sur-binding proteins provided herein. In some embodiments, the amount of pertuzumab used can be 0.01, 0.1, 1, 10, 50, 100, 150, 200, 500, 1,000, 10,000, 100,000, 1,000,000, 10,000,000, or 100,000,000 nM including any range defined between any two of these values. In some embodiments, any one of these values and/or ranges can be combined with 0.01, 0.1, 1, 10, 50, 100, 150, 200, 500, 1,000, 10,000, 100,000, 1,000,000, 10,000,000, or 100,000,000 nM (including any range defined with any two of these values) of any of the sur-binding proteins provided herein (for example, 2817-C01 and/or 2716-F05).

In some embodiments, the amount of lapatinib used can be enough to demonstrate some improvement or desired effect when used in combination with one or more of the sur-binding proteins provided herein. In some embodiments, the amount of Lapatinib used can be 0.01, 0.1, 1, 10, 50, 100, 150, 200, 500, 1,000, 10,000, 100,000, 1,000,000, 10,000,000, or 100,000,000 nM, including any range defined between any two of these values. In some embodiments, any one of these values and/or ranges can be combined with 0.01, 0.1, 1, 10, 50, 100, 150, 200, 500, 1,000, 10,000, 100,000, 1,000,000, 10,000,000, or 100,000,000 nM (including any range defined with any two of these values) of any of the sur-binding proteins provided herein (for example, 2817-C01 and/or 2716-F05).

In some embodiments, the amount of GDC-0941 used can be enough to demonstrate some improvement or desired effect, when used in combination with one or more of the sur-binding proteins provided herein. In some embodiments, the amount of GDC-0941 used can be 0.01, 0.1, 1, 10, 50, 100, 150, 200, 500, 1,000, 10,000, 100,000, 1,000,000, 10,000,000, or 100,000,000 nM, including any range defined between any two of these values. In some embodiments, any one of these values and/or ranges can be combined with 0.01, 0.1, 1, 10, 50, 100, 150, 200, 500, 1,000, 10,000, 100,000, 1,000,000, 10,000,000, or 100,000,000 nM (including any range defined with any two of these values) of any of the sur-binding proteins provided herein (for example, 2817-C01 and/or 2716-F05).

In some embodiments, the amount of cetuximab used can be enough to demonstrate some improvement or desired effect, when used in combination with one or more of the sur-binding proteins provided herein. In some embodiments, the amount of Cetuximab used can be 0.01, 0.1, 1, 10, 50, 100, 150, 200, 500, 1,000, 10,000, 100,000, 1,000,000, 10,000,000, or 100,000,000 nM, including any range defined between any two of these values. In some embodiments, any one of these values and/or ranges can be combined with 0.01, 0.1, 1, 10, 50, 100, 150, 200, 500, 1,000, 10,000, 100,000, 1,000,000, 10,000,000, or 100,000,000 nM (including any range defined with any two of these values) of any of the sur-binding proteins provided herein (for example, 2817-C01 and/or 2716-F05).

In some embodiments, the amount of panitimumab used can be enough to demonstrate some improvement or desired effect when used in combination with one or more of the sur-binding proteins provided herein. In some embodiments, the amount of Panitimumab used can be 0.01, 0.1, 1, 10, 50, 100, 150, 200, 500, 1,000, 10,000, 100,000, 1,000,000, 10,000,000, or 100,000,000 nM including any range defined between any two of these values. In some embodiments, any one of these values and/or ranges can be combined with 0.01, 0.1, 1, 10, 50, 100, 150, 200, 500, 1,000, 10,000, 100,000, 1,000,000, 10,000,000, or 100,000,000 nM (including any range defined with any two of these values) of any of the sur-binding proteins provided herein (for example, 2817-C01 and/or 2716-F05).

In some embodiments, the amount of Ab B and/or Ab A used can be enough to demonstrate some improvement or desired effect, when used in combination with one or more of the sur-binding proteins provided herein. In some embodiments, the amount of Ab B and/or Ab A used can be 0.01, 0.1, 1, 10, 50, 100, 150, 200, 500, 1,000, 10,000, 100,000, 1,000,000, 10,000,000, or 100,000,000 nM, including any range defined between any two of these values. In some embodiments, any one of these values and/or ranges can be combined with 0.01, 0.1, 1, 10, 50, 100, 150, 200, 500, 1,000, 10,000, 100,000, 1,000,000, 10,000, 000, or 100,000,000 nM (including any range defined with any two of these values) of any of the sur-binding proteins provided herein (for example, 2817-C01 and/or 2716-F05).

In some embodiments, the amount of any of the sur-binding proteins provided herein (for example, 2817-C01 and/or 2716-F05) can be used at an amount of at least 0.001 mg/kg of subject weight, e.g., 0.001, 0.01, 0.1, 1, 10, 20, 30, 40, 50, 60, 70, 80, 90, or 100 mg/kg of subject weight, including any range defined between any two of the preceding values. In some embodiments, the amount of the sur-binding protein used is from 0.1 to 100 mg/kg.

In some embodiments, in the combination of any of the antibodies noted herein and any of the sur-binding proteins, the amount of any of the antibodies provided herein can be used in an amount of at least 0.001 mg/kg of subject weight, e.g., 0.001, 0.01, 0.1, 1, 10, 20, 30, 40, 50, 60, 70, 80, 90, or 100 mg/kg of subject weight, including any range defined between any two of the preceding values. In some embodiments, the amount of the antibody used is from 0.1 to 100 mg/kg. In some embodiments, more sur-binding protein is used than antibody. In some embodiments, more antibody is used than sur-binding protein. In some embodiments, an approximately equal amount of the antibody and sur-binding protein is used.

In some embodiments, the result of the combination is a superior degree of inhibition. In some embodiments, the degree of inhibition is greater than what would have been achieved with one or the other compound. In some embodiments, the effectiveness of the compound is greater at lower concentrations of the individual compounds (that is, the potency of the combination is superior). In some embodiments, the effectiveness of a compound that was previously ineffective in the presence of NRG (such as trastuzumab) can still provide a boost in effectiveness in the presence of NRG, when combined with one of the sur-binding proteins. In some embodiments, the effectiveness of a compound that was previously ineffective in the absence of NRG can still provide a boost in effectiveness in the absence of NRG, when combined with one of the sur-binding proteins. In some embodiments, a sur-binding protein combination with trastuzumab is more potent (e.g., 1, 5, 10, 20, 30, 40, 50, 60, 70, 80, 90, or 100%) and/or more effective (e.g., 1, 5, 10, 20, 30, 40, 50, 60, 70, 80, 90, or 100%), than a pertuzumab/trastuzumab combination of a same amount. In some embodiments, the sur-binding protein is a) effective in the presence of NRG and in the absence of NRG, and b) provides a further benefit when combined with GDC-0941, lapatinib, trastuzumab, pertuzumab, panitimumab, and/or cetuximab. In some embodiments, the sur-binding protein combination can afford a superior tumor growth control and/or decreased resistance than compared to ErbB2 antibodies.

In some embodiments, one or more of the SBPs or antigen binding portions thereof, can down regulate AKT phosphorylation/ErbB3 phosphorylation. In some embodiments, the phosphorylation that is reduced is related to NRG stimulation. Thus, in some embodiments, the SBPs or antigen binding portions thereof, can down regulate AKT phosphorylation that is relevant to NRG signaling to ErbB3. In some embodiments, the phosphorylation that is reduced is unrelated to NRG stimulation. In some embodiments, one or more of the SBPs or antigen binding portions thereof, can down regulate the signaling. In some embodiments, the phosphorylation can be reduced in ErbB2 overexpressing cells even when NRG is not present. In some embodiments, the SBP can reduce ligand-induced activation of ErbB3 and of the AKT and/or ERK signaling pathways in cells that overexpress ErbB2. In some embodiments, the SBP can reduce and/or inhibit ligand-induced phosphorylation of AKT, ErbB3, and/or ERK1/2. In some embodiments, any one or more of the SBPs provided herein are more potent (in inhibiting phosphorylation) than the antibodies Ab B, Ab A, or pertuzumab. In some embodiments, the SBPs comprise at least 2716-F05 and/or 2817-C01. In some embodiments, any one or more of the SBPs presented herein can reduce proliferation and/or intracellular signaling. In some embodiments, the SBPs can reduce tumor growth in vivo in both ErbB2-overexpressing and non-overexpressing cells. In some embodiments, the SBP is at least as effective as at least one or more of: cetuximab, panitimumab, pertuzumab, trastuzumab, Ab B, or Ab A. In some embodiments, the SBP is at least as effective as one or more of cetuximab, panitimumab, pertuzumab, trastuzumab, Ab B, or Ab A and the SBP is more potent. In some embodiments, the SBP is at least 1% more potent, e.g., 1, 5, 10, 20, 30, 40, 50, 60, 70, 80, 90, 100, 200, 300, 500, 1000, 5000, 10,000, 100,000, 1,000,000, or 10,000,000 percent more potent, including any range of potencies defined between any two of the preceding values. In some embodiments, the SBP acts to reduce cell proliferation in a manner that is not limited to a NRG-stimulated growth mechanism. In some embodiments, the SBPs can work via a mechanism of action that is distinct from other ErbB approaches (e.g., independent of NRG), and still maintain an ability to augment EGFR inhibitors (e.g., any of the inhibitors provided herein). In some embodiments, the sur-binding protein decreases cell surface ErbB3. In some embodiments, the sur-binding protein decreases cell surface expression of ErbB3.

In some embodiments, any one or more of the SBPs can augment another (non-SBP and/or non-ErbB3) drug that inhibits EGFR. In some embodiments, the SBPs are administered or included in a composition without another active ingredient (and/or without a different ErbB3 inhibitor).

In some embodiments, the SBPs or antigen binding portions thereof, are effective against cells that are resistant to EGFR antibodies. In some embodiments, the SBPs or antigen binding portions thereof, are effective against cells that are resistant to inhibitors of EGFR tyrosine kinase activity. In some embodiments, the SBPs or antigen binding portions thereof, are effective against cells bearing K-ras gene variants. In some embodiments, the SBPs or antigen binding portions thereof, is effective against lung cancer. In some embodiments, the SBPs or antigen binding portions thereof, is effective for a subject having lung cancer and a mutation in a K-ras gene. In some embodiments, the SBPs or antigen binding portions thereof, is effective for a subject having pancreatic cancer and a mutation in a K-ras gene. In some embodiments, one first tests a subject for the presence or absence of a K-ras gene variation. In situations where the subject has a K-ras point mutation, the subject is administered a SBPs or antigen binding portions thereof, as disclosed herein.

In some embodiments, the SBP is effective at reducing mean tumor burden at levels at least as effectively as Ab A and/or Ab B. In some embodiments, the SBP can delay tumor growth by at least 10, 15, 20, 25, 30, 35, 40, 45, 50, 54, 55, 56, 60, 62, 65, 70, 75, 80, 84, 85, 90, 95, 98, 99, 99.9% or more (including any range above any one of the preceding values).

In some embodiments, the SBP can prolong survival in a mouse model for at least some percentage of a population of mice out past 60 days. In some embodiments, the SBP can extend survival to more than 10% of a mouse population to, and/or beyond, 70, 75, or 80 days. In some embodiments, the SBP can extend survival to more than 20% of a mouse population to, and/or beyond, 70, 75, or 80 days. In some embodiments, the SBP can extend survival to about 30% of a mouse population to, and/or beyond, 70, 75, or 80 days.

Sur-Binding Protein-Based Therapeutic/Prophylactic Composition and Administration Thereof Some embodiments provide methods of treatment, inhibition, and prophylaxis by administration to a subject of an effective amount of a SBP or antigen binding portion thereof. In some embodiments, the SBP or antigen binding portion thereof, is substantially purified (e.g., substantially free from substances that limit its effect or produce undesired side effects). The subject can be an animal, including but not limited to animals such as cows, pigs, horses, chickens, cats, and dogs, and is preferably a mammal, and in some embodiments a human.

Various delivery systems are known and can be used to administer a SBP, e.g., encapsulation in liposomes, microparticles, microcapsules, recombinant cells capable of expressing the SBPs or antigen binding portions thereof, receptor-mediated endocytosis (see, e.g., Wu and Wu, J. Biol. Chem. 262:4429-4432, 1987), construction of a nucleic acid as part of a retroviral or other vector, etc. Methods of introduction include but are not limited to intradermal, intramuscular, intraperitoneal, intravenous, subcutaneous, intranasal, epidural, and oral routes. The SBPs or antigen binding portions thereof, can be administered by any convenient route, for example by infusion or bolus injection, by absorption through epithelial or mucocutaneous linings (e.g., oral mucosa, rectal and intestinal mucosa, etc.), and can be administered together with other biologically active agents. Administration can be systemic or local. In addition, it can be desirable to introduce the SBP or antigen binding portion thereof into the central nervous system by any suitable route, including intraventricular and intrathecal injection; intraventricular injection can be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In some embodiments, it may be desirable to administer the SBPs or antigen binding portions thereof, and/or antibodies locally to the area in need of treatment; this can be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In some embodiments, when administering a SBP or antigen binding portion thereof, care can be taken to use materials to which the SBP or antigen binding portion thereof, does not absorb.

In some embodiments, the SBPs, antigen binding portions thereof, and antibodies can be delivered in a vesicle, in particular a liposome (see Langer, Science 249:1527-1533, 1990; and Treat et al., in Liposomes in the Therapy of Infectious Disease and Cancer, Lopez-Berestein and Fidler (eds.), Liss, New York, pp. 353-365, 1989).

In some embodiments, the SBP or antigen binding portion thereof, can be delivered in a controlled release system. In some embodiments, a pump can be used (see Langer, supra; Sefton, CRC Crit. Ref. Biomed. Eng. 14:201, 1987; Buchwald et al., Surgery 88:507, 1980; Saudek et al., N. Engl. J. Med. 321:574, 1989). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In some embodiments, a controlled release system can be placed in proximity of the therapeutic target, e.g., an affected organ of the body, such as the brain, lungs, kidney, liver, ovary, testes, colon, pancreas, breast, and skin, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

SBPs, antigen binding portions thereof, and/or antibodies can also be provided in a pharmaceutical composition. Such compositions can comprise a therapeutically effective amount of a SBP, antigen binding portion thereof, and/or antibody and a pharmaceutically acceptable carrier. In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington: The Science and Practice of Pharmacy," A. R. Gennaro, ed. Lippincott Williams & Wilkins, Philadelphia, Pa. (20th Ed., 2003). Such compositions will contain a therapeutically effective amount of the compound, preferably in purified form, together with a suitable amount of carrier so as to provide the form for proper administration to the patient. The formulation should suit the mode of administration.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The SBPs or antigen binding portions thereof, when formulated in pharmaceutical compositions, can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, or procaine.

The amount of SBP, antigen binding portion thereof, and/or antibody that will be effective in the treatment, inhibition and prevention of a disease or disorder associated with aberrant expression and/or activity of a cell surface receptor can be determined by standard clinical techniques, in light of the disclosure presented herein. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses can be extrapolated from dose-response curves derived from in vitro or animal model test systems.

For SBPs or antigen binding portions thereof, the dosage administered to a patient is typically 0.1 mg/kg to 100 mg/kg of the patient's body weight. Preferably, the dosage administered to a patient is between 0.1 mg/kg and 20 mg/kg of the patients body weight, more preferably 1 mg/kg to 20 mg/kg of the patient's body weight. The dosage and frequency of administration of SBPs or antigen binding portions thereof, can be reduced by enhancing uptake and tissue penetration of the SBP or antigen binding portion thereof, by modifications such as, for example, lipidation.

In some embodiments, any of the disclosed SBPs can be used for the preparation of a medicament for the treatment of any of the above disorders.

In another aspect, the present invention provides a composition, e.g., a pharmaceutical composition, containing one or a combination of a SBPs, antigen binding portions thereof, and/or antibodies thereof disclosed herein, formulated together with a pharmaceutically acceptable carrier. In some embodiments, the compositions include a combination of multiple (e.g., two or more) isolated agents, which bind different epitopes on ErbB3.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active agent, i.e., SBP or binding portion thereof, antibody or fragment, bispecific and multispecific molecule, can be coated in a material to protect the agent from the action of acids and other natural conditions that can inactivate it.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical compositions can comprise other agents. For example, the composition can include at least one or more additional therapeutic agents, such as the anti-cancer agents described infra. The pharmaceutical compositions can also be administered in conjunction with radiation therapy and/or surgery. Alternately a composition can be separately co-administered with at least one or more additional therapeutic agents, such as the anti-cancer agents described infra.

For the therapeutic compositions, formulations of the present disclosure include those suitable for oral, nasal, topical (including buccal and sublingual), transdermal, subcutaneous, intrathecal, intraspinal, rectal, vaginal and/or parenteral administration. The formulations can conveniently be presented in unit dosage form and can be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present disclosure which are suitable for vaginal administration also include pessaries, tampons, creams, gels, pastes, foams or spray formulations containing such carriers as are known in the art to be appropriate. Dosage forms for the topical or transdermal administration of compositions include powders, sprays, ointments, pastes, creams, lotions, gels, solutions, patches and inhalants. The active agent can be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which can be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Particular examples of adjuvants which are well-known in the art include, for example, inorganic adjuvants (such as aluminum salts, e.g., aluminum phosphate and aluminum hydroxide), organic adjuvants (e.g., squalene), oil-based adjuvants, virosomes (e.g., virosomes which contain a membrane-bound hemagglutinin and neuraminidase derived from the influenza virus).

Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions.

In addition, prolonged absorption of the injectable pharmaceutical form can be brought about by the inclusion of agents which delay absorption such as aluminum monostearate and gelatin.

When the SBPs of the present disclosure are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the SBPs of the present disclosure, which can be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage levels will depend upon a variety of pharmacokinetic factors including the activity of the particular compositions employed, or, for compounds co-administered with antibodies or fragments thereof provided herein, the ester, salt or amide thereof, the route of administration, the time of administration, the rate of excretion of the particular agent being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the antibodies or fragments thereof employed in the pharmaceutical composition at levels lower than that required in order to achieve the desired therapeutic effect and gradually increase the dosage until the desired effect is achieved. In general, a suitable daily dose of a composition will be that amount which provides the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition can be administered as two, three, four, five, six or more sub-doses administered separately at appropriate intervals throughout the day, optionally, in unit dosage forms. While it is possible for a SBP, antigen binding portions thereof, and/or antibody of the present disclosure to be administered alone, it is preferable to administer the SBP, antigen binding portions thereof, and/or antibody as a pharmaceutical formulation (composition).

Therapeutic compositions can be administered with medical devices known in the art. For example, in a preferred embodiment, a therapeutic composition can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art. In some embodiments, the SBPs or antigen binding portions thereof, can be administered intravenously, transdermally, subcutaneously, intraperitoneally, intrathecally, epidurally, and/or spinal.

In certain embodiments, compositions disclosed herein can be formulated to ensure proper distribution in vivo. For example, the blood-brain barrier (BBB) excludes many highly hydrophilic compounds. To ensure that therapeutic compounds in compositions cross the BBB (if desired), they can be formulated, for example, in liposomes. For methods of manufacturing liposomes, see, e.g., U.S. Pat. Nos. 4,522,811; 5,374,548; and 5,399,331. The liposomes can comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which can comprise the formulations, as well as components of the invented molecules; p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

In some embodiments, the SBP compound or composition includes more than one SBP or antigen binding portions thereof, and/or antibody. In some embodiments, the composition comprises at least one SBP or antigen binding portions thereof, that binds ErbB3. In some embodiments, the composition comprises at least one SBP or antigen binding portions thereof, that binds ErbB3 and a second SBP or antigen binding portions thereof, that binds ErbB3. In some embodiments, the two or more SBPs or antigen binding portions thereof, bind to different epitopes or do not compete with one another for binding to ErbB3. In some embodiments, the two or more SBPs or antigen binding portions thereof, bind to similar or overlapping epitopes.

In some embodiments, the composition comprises at least one SBP or antigen binding portion thereof, that binds ErbB3 and a second SBP or antigen binding portion thereof, that binds ErbB1. In some embodiments, the composition comprises at least one SBP or antigen binding portion thereof, that binds ErbB3 and a second SBP or antigen binding portion thereof, that binds ErbB2. In some embodiments, the composition comprises at least one SBP or antigen binding portion thereof, that binds ErbB3 and a second SBP or antigen binding portion thereof, that binds ErbB4. In some embodiments, the composition comprises at least one SBP or antigen binding portion thereof, that binds ErbB3 and an antibody that binds that ErbB 1. In some embodiments, the composition comprises at least one SBP or antigen binding portion thereof, that binds ErbB3 and an antibody that binds ErbB2. In some embodiments, the composition comprises at least one SBP or antigen binding portion thereof, that binds ErbB3 and an antibody that binds ErbB3. In some embodiments, the composition comprises at least one SBP or antigen binding portion thereof, that binds ErbB3 and an antibody that binds ErbB4. In some embodiments, the composition comprises at least one SBP that binds ErbB3 and an antibody that binds ErbB2. For these aforementioned embodiments, the SBPs can either be a single bispecific construct or a pair of constructs In some embodiments, one can combine a SBP or antigen binding portion thereof that binds ErbB3 and a second SBP or antigen binding portion thereof, that binds, with one or more growth factors, non-ErbB receptors, and/or immune cell recruitment specificities to increase tumor cell killing. For these embodiments, the SBPs can either be a single bispecific construct or a pair of constructs.

In some embodiments, a SBP or antigen binding portion thereof, can be combined with one or more traditional chemotherapeutic, growth factor tyrosine kinase inhibitor, protein kinase inhibitor, caspase or apoptotic activators, microtubule inhibitors (e.g. taxanes), estrogen receptor inhibitors (tamoxifin), and/or aromatase inhibitors, HSP90 inhibitors.

In some embodiments, any of the methods provided herein can employ any of the compositions, compounds, kits, SBPs, SBP combinations, etc. disclosed herein.

Kits

Some embodiments also encompass kits for use in detecting cells expressing or overexpressing target molecules in vivo, or in biological samples. In some embodiments, the kits contain SBPs or antigen binding portions thereof, targeted to ErbB3. Depending on use, the SBP or antigen binding portion thereof, can be functionalized with linkers or chelators, or both, for coupling to an effector (e.g. a radioactive moiety, a liposome, a cytotoxin, an antibody, a SBP or antigen binding portion thereof, etc.) as described herein. The kits optionally further comprise buffers and compositions to be used for detection of the SBP or antigen binding portion thereof.

The kits can also include instructional materials teaching the use of the SBPs or antigen binding portions thereof, for detecting, e.g. cancer cells, and/or teaching the combination of the SBPs or antigen binding portions thereof, with functionalizing reagents or teaching the use of functionalized SBPs or antigen binding portions thereof, for imaging and/or therapeutic applications. In some embodiments, the SBPs or antigen binding portions thereof, is provided functionalized with a linker and/or a chelator (in one container) along with one or more effectors, e.g. cytotoxins, radioactive labels (in a second container) such that the two components can be separately administered (e.g. in pre-targeting approaches) or such that the two components can be administered shortly before use.

Certain instructional materials can provide recommended dosage regimen, counter indications, and the like. While the instructional materials typically comprise written or printed materials, any medium capable of storing such instructions and communicating them to an end user is contemplated. Such media include, but are not limited to electronic storage media (e.g., magnetic discs, tapes, cartridges, chips), optical media (e.g., CD ROM), and the like, or internet locations that provide the instructions. In some embodiments, a pharmaceutical pack or kit comprising one or more containers filled with one or more of the ingredients of the pharmaceutical compositions of the SBP is also provided. Optionally associated with such container(s) can be a notice in the form prescribed by a governmental agency regulating the manufacture, use or sale of pharmaceuticals or biological products, which notice reflects approval by the agency of manufacture, use or sale for human administration.

In some embodiments, any of the disclosed SBPs can be part of a kit for the treatment of one of the above disorders. In some embodiments, the kit will include a unit dose to be administered to a subject 1, 2, 3, 4, 5, 6, 7, 8, 9, 10, 11, 12, 13, 14, 15, 16, 17, 18, 19, 20, 21, 22, 23, or 24 times a day, or as infrequently as 1, 2, 3, 4, or 5 times a month. In some embodiments, the composition is configured for subcutaneous, or IV administration.

Some embodiments provided herein provide a unique, high affinity, antigen-binding structure composed of an immunoglobulin heavy chain and an invariant surrogate light chain. Some of these SBPs are predicted to work by a previously unrecognized mechanism of action. As a consequence, they not only inhibited cell proliferation and intracellular signaling driven by stimulation with the ErbB3 ligand neuregulin (NRG), but also inhibit signaling and proliferation that was driven by overexpression of ErbB2. In addition, some of these SBPs inhibited tumor growth in vivo in both ErbB2-overexpressing and non-overexpressing cells. In ErbB2 overexpressing cells, both of the anti-ErbB3 SBPs significantly augmented the activities of agents that inhibit cell proliferation by different mechanisms. Moreover, although NRG diminished the efficacy of these agents, when they were combined with anti-ErbB3 SBPs the effect of NRG was abrogated. In this capacity, the anti-ErbB3 SBPs were more effective than an ErbB2/ErbB3 dimerization inhibitory antibodies. Despite the fact that these SBPs appear to engage ErbB3 differently than previously described anti-ErB3 antibodies currently undergoing clinical testing, in some embodiments, they can retain one or more (even all) of the beneficial characteristics of this class of agents. In some embodiments, these anti-ErbB3 agents therefore show greater therapeutic applicability than previously described anti-ErbB3 antibodies for development as single agents, in combination with other ErbB directed antibodies or small molecules.

In some embodiments, the SBP binds ErbB3 selectively over EGFR and ErbB2. In some embodiments, the SBP is amenable to all chromatography methods for antibody purification. In some embodiments, 89-154 mg/L of pure protein can be collected from transient expression in HEK293 cells, for example, 90-150 or 80-160 mg/L. In some embodiments, the SBP is stable in buffer at room temperature for at least 1 year, for example, 1.1, 1.2, 1.3, 1.4, 1.5, 2 or more years at 25, 27, or 28 degrees Celsius. In some embodiments, the SBP has protein aggregates at about less than 3%, for example, less than 3, 2, or 1%. In some embodiments, the protein aggregate can be greater than 3%.

In some embodiments, the SBP can have an $EC_{50}$ that is equal to or superior to that shown in Table 0.5. In some embodiments, the $EC_{50}$ can be lower than about 50 pM for human ErbB3. In some embodiments, the EC50 can be about 40 or about 50 pM for human ErbB3. In some embodiments the $EC_{50}$ can be less than about 140 pM for cell surface ErbB3. In some embodiments the $EC_{50}$ can be less than or equal to about 40 pM for cell surface ErbB3.

TABLE 0.5

| Target binding EC50 (pM) | ErbB3-Fc (ELISA) | | Cell surface receptor (flow cytometry) BxPC-3 cells (human pancreatic) |
|---|---|---|---|
| | human | murine | |
| 2817-C01 | 41 | 124 | 138 |
| 2716-F05 | 49 | 95 | 40 |

In some embodiments, the SBP selectively binds and inhibits ErbB3 signaling and cell growth in vitro and in vivo. In some embodiments, the SBP inhibits ErbB2 overexpressing tumor cell lines in vitro and in vivo. In some embodiments, the SBP is capable of inhibiting ErbB2 overexpressing tumor cell lines in the presence or absence of neuregulin. In some embodiments, the ErbB3 Surrobodies augment the activities of ErbB2 antibody trastuzumab to a greater extent than pertuzumab. In some embodiments, a bispecific Surrobody targeting ErbB3 and another growth factor receptor (e.g., EGFR or any of the others provided in the specification) demonstrate greater anti-proliferative activity than the combination of the two monospecific SBPs.

In some embodiments, a method for suppressing a cancerous cell is provided. The method can comprise identifying a subject having a cancerous cell, wherein the cancerous cell expresses ErbB3, and administering to the subject an ErbB3 sur-binding protein in an amount sufficient to bind to ErbB3 on the cancerous cell and thereby block the Ras/Raf/MEK pathway.

In some embodiments, a method for suppressing a cancerous cell is provided. The method can comprise identifying a subject having a cancerous cell, wherein said cancerous cell expresses ErbB3, and administering to the subject an ErbB3 sur-binding protein in an amount sufficient to bind to ErbB3 on the cancerous cell and thereby block the PI3K, AKT, or PI3K and AKT pathway.

Some breast cancer patients are unresponsive to anti-ErbB2 treatment, such as trastuzumab. One mechanism for trastuzumab resistance in ErbB2-positive breast cancer involves truncation of the ErbB2 such that the extracellular domain to which trastuzumab binds is absent. ErbB2 truncation can occur by several mechanisms including proteolytic shedding and alternative initiation of translation using internal methionine residues that exclude trastuzumab and other epitopes. In either of these cases expression of truncated ErbB2 ("p95 HER-2") has been shown to be a negative prognostic factor and defines a group of patients with significantly worse outcome.

As outlined in the examples below, in some embodiments, one can use anti-ErbB3 antibody and/or sur-binding protein to treat anti-ErbB2 unresponsive tumors, such as those that have truncated ErbB2. These tumors are expected to be resistant to both trastuzumab and pertuzumab therapy. To demonstrate these benefits experimentally, one can use a human tumor cell line bearing ErbB3 and truncated ErbB2 (p95 Her-2) and test the ErbB3 Sur-binding proteins for inhibition of proliferation or ErbB3 mediated signaling, similar to in vitro assays described previously. Alternatively, cultured tumor cells that bear ErbB3, can be transiently or stably transfected or transduced to overexpress truncated Her-2. Different deleted forms of Her-2 could be introduced to recapitulate proteolytically cleaved or the alternatively translated forms and the resulting cell lines or pools could be tested to demonstrate their responsiveness to anti-ErbB3. Since the binding of anti-ErbB3 sur-binding proteins is independent of the presence of ErbB2, and since they inhibit the growth of ErbB2 driven tumors, they are expected inhibit growth of tumors expressing truncated ErbB2 and benefit this patient population.

As the binding of anti-ErbB3 sur-binding proteins is independent of the presence of ErbB2, and since they inhibit the growth of ErbB2 driven tumors, they are predicted to inhibit growth of tumors expressing truncated ErbB2 and benefit this patient population.

In some embodiments, the SBPs and antibodies provided herein can be used in combination with an MTOR (mammalian target of rapamycin) inhibitor. mTORC1 acts in a feedback pathway to reduce signaling through PI3K and mTORC2. Examples of mTOR inhibitors include, but are not limited to temsirolimus, everolimus, ridaforolimus and BEZ235. Inhibition of mTOR using a single agent can result in activation of upstream receptor tyrosine kinase signaling and AKT activation. In contrast, the result of the combined therapy is an improved inhibition of tumor growth that is at least greater than the use of the SgG and/or the compound alone at an equivalent dose. In some embodiments, the method can include identifying a subject at risk of developing a cancer, administering a dose of 2817-C01 and/or 2716-F05 (or other SgG) either prior to, subsequent to, or in combination with one or more inhibitors of mTOR. The dose of the SBP can be varied, for example, an amount that is effective on its own or an amount that is effective in combination with the inhibitor of mTOR.

It is hypothsized that upon binding NRG, ErbB3 adopts an extended conformation such that the canonical dimerization domain becomes available for interaction with other members of the ErbB family. In order to determine if 2817-C01 or 2716-F05 are influenced by this alteration in confirmation, ELISAs were performed to determine if the SBPs preferentially bind to either the extended (ligand bound) or closed (non-ligand bound) conformation of ErbB3. The results of this analysis are presented in FIG. 35 and support that the binding abilities of the SBPs are unaffected when NRG was pre-bound to ErbB3. Thus, in some embodiments, provided herein are SBPs and/or antibodies that can be effective even when ErbB3 is already bound to NRG. In some embodiments, the SBP's binding ability shifts by less than 50% in the presence of NRG, for example, less than 40, 30, 20, 10, 5 or 1% of a shift will occur in binding ability when NRG is present, compared to when NRG is absent. In some embodiments, the SBP and/or antibodies do not lock ErbB3 in a closed conformation.

Further details of the invention are provided in the following non-limiting Examples.

EXAMPLE 1

Isolation of Surroglobulins that Bind to ErbB3

This example outlines the construction of a SBP (Sabs in particular) library and the identification of SBPs (Sabs in particular) that bind ErbB3.

Phage displayed Sab libraries were composed of CDR diversified Sabs displayed as pIII fusions on the surface of M13 bacteriophage. Specifically, the Sabs are comprised of heavy chains (in particular VH1 or VH3 variable domain family members diversified in CDRs 1, 2, and 3) and the CH1 region of the IgG1 heavy chain fused to pIII protein of m13 filamentous phage, complexed with the surrogate light chain fusion 1. (Xu, Yee et al. 2008). The design and construction of diversified heavy chains for use in phage display is essentially as described in U.S. Pat. App. No. 20090082213 CONSTRUCTION OF DIVERSE SYNTHETIC PEPTIDE AND POLYPEPTIDE LIBRARIES. The sequence of the mature form of the surrogate light chain fusion 1 protein is noted in FIG. 25, SEQ ID NO: 276.

Phagemid expression of Sab libraries was accomplished by standard methods. TG-1 cells transformed with expression plasmids were grown to mid log (O.D. 600 ~0.3) in 2-YT media supplemented with 100 mcg/ml ampicillin and 2% glucose repression and then infected with m13K07 helper phage and grown overnight in 2-YT media supplemented with 100 mcg ampicillin, 70 mcg/ml kanamycin, and 200 micromolar IPTG. Phage containing supernatants were precipitated using polyethylene glycol and PBS resuspended phage were used to pan on immobilized ErbB3.

Panning of the libraries was performed by using either ErbB3-Fc (R&D Systems) immobilized on the wells of a microtiter dish or on biotinylated ErbB3-Fc immobilized on streptavidin derivatized magnetic beads (Invitrogen—Dynal).

In the plated based format, Immulon 4HBX ELISA plates were coated with ErbB3-Fc. Plates were then blocked in PBS, 0.05% Tween 20, 4% non-fat dried milk for 1 hour. Approximately $10^{12}$-$10^{13+}$ CFU of phage were blocked as above and applied to the target coated wells. To help reduce retrieval of phage that specifically bind to the Fc region of the target, 15 ug/ml of an unrelated Fc containing protein was added to the phage solution. In some instances, the phage population was additionally depleted of Fc binding clones by incubation with magnetic beads coated with an unrelated Fc containing protein. Following a two hour incubation, the wells were washed using PBS, 0.05% Tween 20. Phage were then eluted 0.2M Glycine-HCl, pH 2.2, 1 mg/ml BSA. Eluted phage were neutralized using 2M Tris base. The eluted phage were subjected to additional rounds of amplification and panning until the titer of the phage eluted from the ErbB3 coated wells exceeded the titer eluted from the wells coated with an unrelated Fc containing protein, typically 2-4 rounds.

In bead based panning, ErbB3-Fc was biotinylated using a NHS-PEO$_4$-biotinylation kit (Pierce). The biotinlyated protein was then immobilized on magnetic streptavidin beads (Dynal). Panning was carried out essentially as described above for plate based panning except that PBS, 0.05% Tween 20, 1% BSA was used as the blocking agent. Beads were collected magnetically following the initial phage binding and after each wash step.

To identify phage clones that encoded ErbB3-binding Sabs, a portion of the eluted phage were used to infect *E. coli* HB2151 allowing expression of periplasmic phage-encoded Sabs. Individual clones were picked into deep-well plates and grown overnight in 2YT containing ampicillin and 0.2 mM IPTG. Bacteria were lysed in BPERII and the lysates were applied to ErbB3-Fc coated plates. Following washing, binding of SBPs was detected using an HRP-conjugated anti-E tag antibody (Abcam).

The Sabs were sequenced and examples of the resulting sequences for the specific heavy chains are shown in FIGS. 2A and 2B.

EXAMPLE 2

Identification of Inhibitors Using a Functional Reporter Assay

To identify Sabs from the library screening that inhibit ErbB3 function, a reporter assay was employed. Bacterial clones harboring phagemids encoding ErbB3-binding Sabs were grown under inducing conditions and lysates were prepared using BPERII. The His-tagged Sabs were batch purified from the lysates using Ni-NTA beads (Qiagen) according to the manufacturer's instructions. The batch purified SBPs were functionally tested using the PathHunter™ ErbB2/ErbB3 functional assay (DiscoveRx, Fremont, Calif.). For 2815-B08, inhibition was tested using an SgG formatted molecule (see example 3) expressed in mammalian cells.

The activities of the active molecules are shown in FIGS. 3A-3D. For comparison, the activity of Pertuzumab, a monoclonal antibody that inhibits ErbB2/ErbB3 dimerization (Franklin, Carey et al. 2004) is also shown. The sequence of rhuMab pertuzumab (2C4) was obtained from (Adams, Allison et al. 2006). The data show that all of the Sabs shown interfere with the ability of NRG-1 to induce ErbB2 and ErbB3 to form heterodimers and recruit the signal transduction adaptor protein GRB.

EXAMPLE 3

Modification of Sabs to Human Surroglobulins

This example outlines one way to reformat *E. coli* expressed monovalent Sabs into mammalian expressed bivalent SgGs. In this example, SgGs are comprised of a full length heavy chain framework complexed with the surrogate light chain fusion 1. (Xu, Yee et al. 2008). The heavy chain in this example contains a human Fc gamma I. The sequences of the heavy chains were optimized for expression in mammalian cells by DNA 2.0 (Menlo Park, Calif.). Following synthesis, they were subcloned into a mammalian expression vector such that variable regions were fused to a full length IgG1 Fc. These constructs were co-transfected along with a surrogate light chain expression vector that was similarly optimized for expression in mammalian cells. SgGs were transiently produced in HEK293-based systems essentially as described (Xu, Yee et al. 2008) "Combinatorial surrobody libraries." *Proc Natl Acad Sci USA* 105(31): 10756-61). The resulting SgGs described in the examples were FPLC purified via Protein A chromatography.

EXAMPLE 4

Surroglobulins Bind to Human Erbb3 and Murine Erbb3

This example demonstrates that SgGs bind to human ErbB3 and Murine ErbB3.

Serial dilutions of anti-ErbB3 SgGs (as described in example 3) were bound to ELISA plates coated with human ErbB3-Fc (R&D Systems). Binding was detected using a biotinylated antibody that specifically recognizes VpreB, followed by streptavidin HRP. Detection used a colorimetric HRP substrate. Data was analyzed via using GraphPad Prism. The results are presented in Table 0.5 and 4.1.

TABLE 4.1

| Molecule | EC50 (nM) | $R^2$ |
|---|---|---|
| 2817-C01 | 0.04 | 0.99 |
| 2716-F05 | 0.05 | 0.99 |
| 2890-A03 | 0.36 | 0.99 |
| 2900-B11 | 4.47 | 0.99 |

Serial dilutions of anti-ErbB3 SgGs were bound to ELISA plates coated with murine ErbB3-Fc (R&D Systems). Binding was detected using a biotinylated antibody that recognizes VpreB, followed by strepatvidin HRP. Detection used a colorimetric HRP substrate. Data was analyzed via using GraphPad Prism. The results of this analysis are presented in Table 0.5 and 4.2.

TABLE 4.2

| Molecule | EC50 (nM) | $R^2$ |
|---|---|---|
| 2817-C01 | 0.12 | 0.98 |
| 2716-F05 | 0.06 | 0.97 |

EXAMPLE 5

Surroglobulins Bind to Human Tumor Cell Lines Expressing ErbB3

This example demonstrates that the SgGs bind to human tumor cells that express ErbB3.

2817-C001 or 2716-F05 binding to human BxPC-3 cells was analyzed by flow cytometry. Briefly, BxPC-3 cells were first dissociated using 0.25% trypsin, 0.2% EDTA, washed in cold PBS, 1% BSA, and then resuspended at 3–10$^6$ cells/ml. SgGs (described above) were added at the indicated concentrations in Staining Buffer (Becton Dickinson) and incubated at 4 degrees C. for 1 hour. Next the cells were washed in stain buffer and resuspended with 1:133 diluted biotinylated goat anti-human IgG (Southern Biotech #2040-08) and incubated at 4 degrees C. for 1 hour. Cells were then washed in stain buffer and resuspended with ALEXA FLUOR®488 green-fluorescent dye conjugated streptavidin (Invitrogen #S11223) and incubated at 4 degrees C. for 1 hour. One microliter of the vital stain 7AAD (Invitrogen #A1310) was added during the last 15 minutes of incubation. Cells were washed with stain buffer and analyzed on a flow cytometer.

Initially, cells that had not been stained with SgG were used to establish a gate for live cells (7AAD negative population in FIG. 4A). Thereafter only signals arising from this gated population were analyzed. Geometric mean fluorescence intensity for cells stained using the indicated concentrations of SBPs were determined using FLOWJO analysis software and EC50s were calculated using Graphpad Prism. The results are presented in Table 0.5 and 5.1 and FIGS. 4A and 4B and demonstrate that the SBPs bind to ErbB3 that is expressed on cells.

TABLE 5.1

| Molecule | EC50 (nM) | $R^2$ |
|---|---|---|
| 2817-C01 | 0.12 | 0.99 |
| 2716-F05 | 0.04 | 0.99 |

EXAMPLE 6

Surroglobulins Inhibit Binding of NRG to ErbB3

The present example demonstrates that SgGs inhibit binding of NRG to immobilized ErbB3 on plates.

ELISA plates were coated with human ErbB3-Fc. Various concentrations of the indicated anti-ErbB3 SBPs were then allowed to bind to the coated wells. Without removing the anti-ErbB3 SBPs, 0.26 ug/ml recombinant human NRG1-beta 1 extracellular domain (Ser2-Lys246) (R&D Systems) was added to the wells and allowed to further incubate for 1 hour. Bound NRG1-beta was detected using a biotinylated goat anti-NRG1-beta 1 extracellular domain (R&D Systems), followed by streptavidin HRP. Detection used a colorimetric HRP substrate.

Data was analyzed using GraphPad Prism. The results of this analysis, presented in Table 6.1 and FIG. 5, demonstrate that the SBPs inhibit the binding of NRG to ErbB3. The degree of inhibition varies among the molecules.

TABLE 6.1

| Molecule | IC50 (Nm) | $R^2$ |
|---|---|---|
| 2817-C01 | 0.99 | 0.97 |
| 2716-F05 | 0.52 | 0.97 |
| 2890-A03 | 1.39 | 0.95 |
| 2900-B11 | 2.28 | 0.61 |

EXAMPLE 7

Epitope Binning Data

Figure 6:
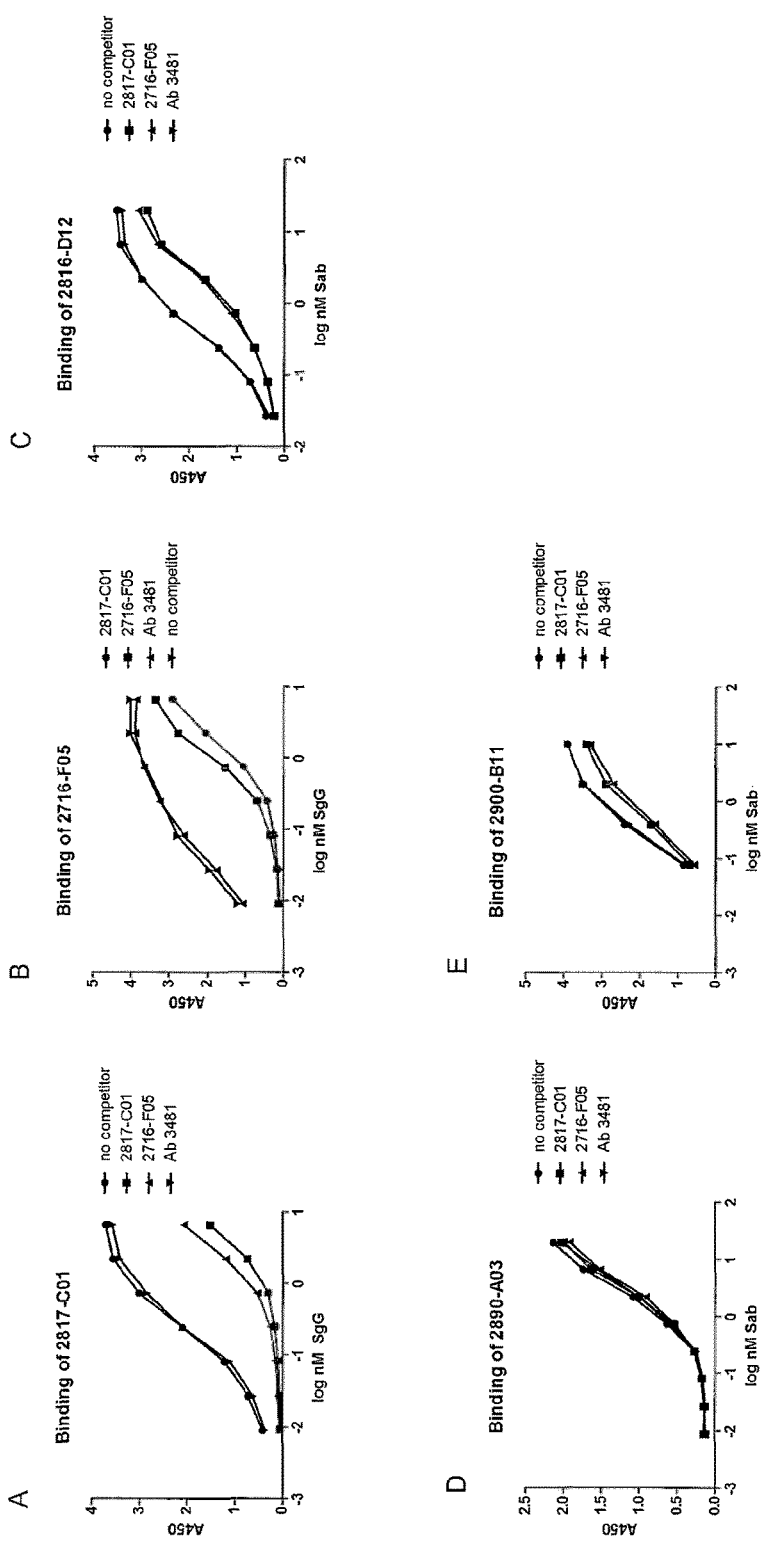
FIGS. 6A-6E are graphs depicting competition among Sabs and SgGs for binding to ErbB3. These data show that 2817-C01 and 2716-F05 Sabs and SgGs strongly compete for binding to ErbB3 indicating that they bind to identical or overlapping epitopes.

To determine whether the anti-ErbB3 SgGs or Sabs bind to overlapping or distinct portions of ErbB3, competition ELISAs were performed. ELISA plates were coated with ErbB3-Fc (R&D). After blocking, each of the competitor molecules indicated in the figure (FIG. 6) were individually added at a concentration of 1 ug/ml and allowed to bind for one hour. Test articles (indicated in the title to each graph: SgG for A, B and Sab for C, D, E) were biotinylated. The indicated concentrations of each of the test articles were then applied without removing competitor. Following 1 hour incubation, binding of the biotinylated species was detected using streptavidin HRP using colorimetric substrate.

The results are presented in FIGS. 6A-6E. These data show that 2817-C01 and 2716-F05 strongly compete with one another for binding to ErbB3 suggesting that they bind to identical or overlapping epitopes. Binding of 2816-D12 is also inhibited. The binding of 2900-B11 was affected to a far lesser extent. The binding of 2890-A03 is not affected by either 2817-C01 or 2716-F05 indicating that it binds to a different epitope. These molecules, all of which inhibit ErbB3 activity thus bind to several epitopes at least one of which is clearly distinct from the others.

EXAMPLE 8

Domains 1, 3 and 4 of ErbB3 are Involved in Surroglobulin Binding

The present example demonstrates the mapping of surroglobulin binding sites on the various ErbB3 domains.

Chimeric molecules were recombinantly constructed such that single domains derived from ErbB2 were used to replace the analogous domains in ErbB3. The chimeric proteins were expressed in HEK 293 cells as Fc fusion proteins and purified via protein A chromatography. The sequences of each of the chimeras tested are shown in FIGS. 7A, 7B, and 7C. In the sequence designations, the numbers indicate the derivation of each of the domains (I-IV) in order. For example, 2-3-3-3 comprises a chimeric protein in which domain I is from ErbB2 and the remaining domains (II-IV) are from ErbB3. 3-3-2-3 comprises a chimeric protein in which domain III is from ErbB2 and the remaining domains (I, II, and IV) are from ErbB3. 3-3-3-2 comprises a chimeric protein in which domain IV derives from ErbB2 and the remaining domains (I-III) derive from ErbB3.

ELISA plates were coated with each of these chimeric proteins along with a wild-type ErbB3-Fc fusion as a control (R&D systems). 10 nM of each of the indicated SBPs was applied to the blocked and coated wells to test for their ability to bind the chimeric proteins. After allowing the SgGs to bind, the wells were washed, and biotinylated anti-VpreB was added. To detect binding, strepataviding horseradish peroxidase was applied to the washed wells followed by detection using a colorimetric horseradish peroxidase substrate.

Figures 7D, 7E:
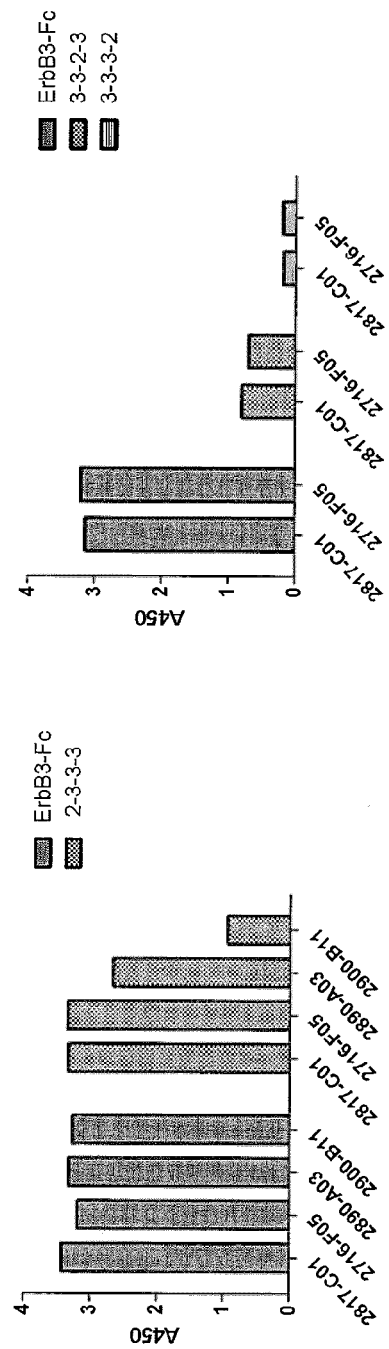
FIGS. 7D and 7E are graphs depicting binding of SgGs to various chimeras of ErbB3 and ErbB2.

The results of the binding studies for the surroglobulins to the chimeras are shown in FIGS. 7D and 7E. FIG. 7D shows that binding of 2900-B11 is markedly reduced when domain I is replaced and binding of 2890-A03 is diminished. These data suggest that domain I is important for binding of these two surroglobulins and that they bind directly to domain I. In contrast, binding of both 2817-C01 and 2716-F05 is fully retained when domain I is replaced indicating that domain I is dispensible for binding of these two SgGs. However, when domain III or IV is replaced, binding of 2817-C01 and 2716-F05 is reduced, indicating that each of them requires intact domains III and IV and that the binding epitopes for these molecules can reside within these domains (FIG. 7E).

EXAMPLE 9

Surroglobilins Inhibit Proliferation of Cancer Cell Lines

The present example demonstrates the ability of select anti-ErbB3 surroglobulins to inhibit proliferation A431 (vulval), Colo205 (colorectal) and BxPC-3 (pancreatic) human cancer cell lines.

Cells were plated at a density of $10^4$ cells/well in 96 well plates in serum-free medium. They were then treated with the indicated concentrations of SgGs for 30 minutes at 37 degrees C. NRG1β was then added to a final concentration of 10 ng/ml. Cells were allowed to grow for 96 hours and cell content was measured using Cell Titer-Glo® (Promega).

Figure 8B:
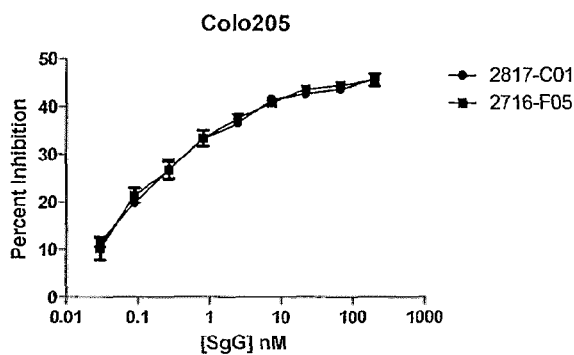
Figure 8C:
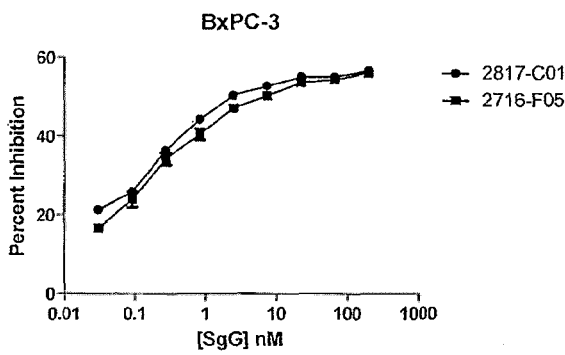

The results presented in FIGS. 8A-8C demonstrate that 2817-C01 and 2716-F05 significantly inhibit the proliferation of epithelial tumor cell lines.

EXAMPLE 10

Surroglobulins Inhibit Proliferation of Cancer Cells Bearing a Mutation in the K-RAS or B-RAF Gene The present example demonstrates that surroglobulins can inhibit the growth of cells having a mutation in the K-RAS or B-RAF gene.

A549 cells bear a point mutation in codon 12 of the ras gene. Point mutations of ras genes are among the most frequent events in human malignancies. RAS mutations are found in 30-50% of colorectal and lung cancers and an even higher percentage of pancreatic cancers. K-ras gene point mutations cause constitutive activation of signaling pathways involved in cell growth, proliferation, invasion, and metastasis, including the PI3 kinase pathway. Because the ras gene is downstream of EGFR, inhibitors of EGFR mediated activation of proliferation are unable to inhibit proliferation.

Figure 9:
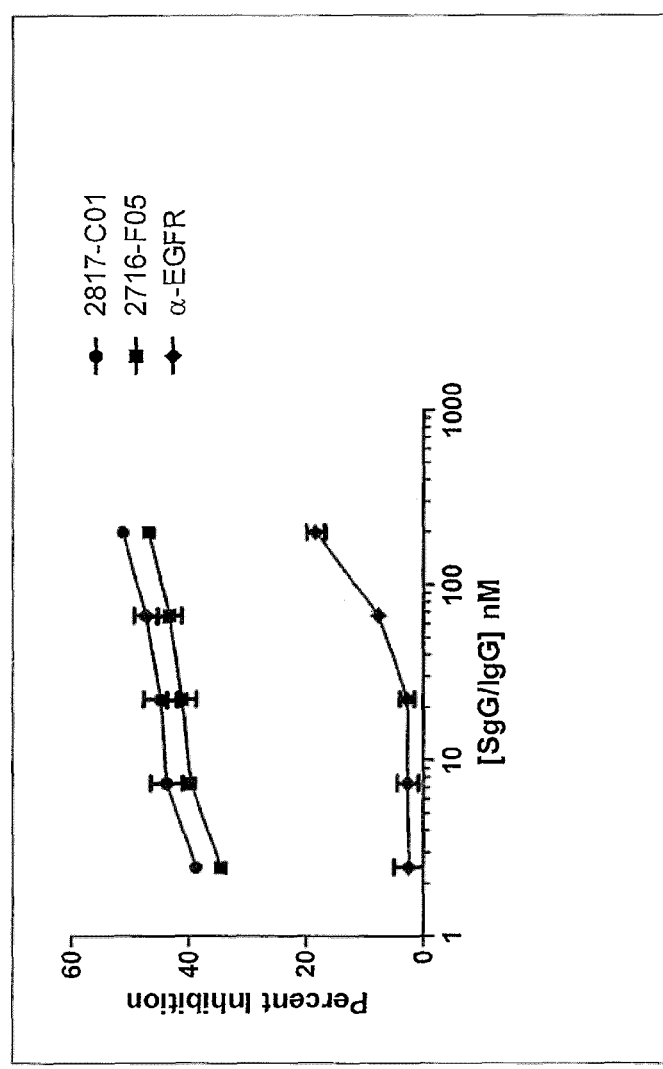
FIG. 9 is a graph depicting the ability of anti-ErbB3 SgGs to inhibit proliferation of the A549 human lung cancer cell line, compared to a control anti-EGFR antibody.

The ability of anti-ErbB3 SgGs to inhibit proliferation of the A549 human lung cancer cell line was tested. Cells were plated at a density of $10^4$ cells/well in 96 well plates in serum-free medium. They were then treated with the indicated concentrations of SgGs or with a neutralizing antibody against EGFR (Clone LA1 Millipore) for 30 minutes at 37° C. NRG1 was then added to a final concentration of 10 ng/ml. Cells were allowed to grow for 96 hours and cell content was measured using Cell Titer-Glo® (Promega). The results are shown in FIG. 9.

Activating mutations in the B-RAF gene occur in approximately 50% of melanomas as well as other tumors. The most common mutation among these is a change of valine to glutamic acid at codon 600 (V600E). Activating mutations cause constitutive downstream signaling. Colo205 cells harbor a B-RAF V600E mutation rendering them resistant to anti-EGFR antibodies. The ability of anti-ErbB3 sur-binding proteins to inhibit proliferation of Colo205 cells was tested using the same protocol as for A549 cells. FIG. 8B shows that the sur-binding proteins inhibit proliferation of Colo205 cells.

Taken together, these results demonstrate that SBPs can be effective against cells that are resistant to inhibition by antibodies to EGFR or other EGFR directed inhibitors that are resistant as a consequence of a mutation in the K-ras, B-RAF, or other downstream activated genes.

EXAMPLE 11

Surroglobulins Inhibit Proliferation of Cancer Cell Lines that Overexpress ErbB2

Approximately 25 percent of breast cancers overexpress ErbB2. Overexpression of this receptor in breast cancer is associated with increased disease recurrence and worse prognosis. Overexpression also occurs in other cancer types such as ovarian cancer, stomach cancer, and biologically aggressive forms of uterine cancer.

The ability of anti-ErbB3 SgGs to inhibit proliferation of ErbB2 overexpressing human breast cancer cell lines was tested. Cells were plated at a density of $5 \times 10^3$ cells/well in 96 well plates in complete DMEM/F12 medium. The cells were then treated with the indicated concentrations of SgGs for one hour and then either 1 ng/ml (SKBR3) or 3 ng/ml (BT474) NRG. The NRG concentrations used have been shown to optimally stimulate growth of the respective cell lines. Cells were allowed to grow for 3 days (SKBR3) or 6 days (BT474) and cell content was measured using Cell Titer-Glo® (Promega).

Figure 10B:
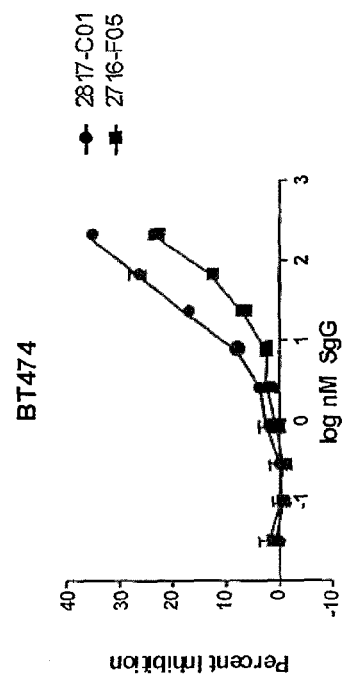
FIGS. 10A and 10B are graphs depicting results establishing that SgGs inhibit proliferation of breast cancer cell lines that overexpress ErbB2 when cells are stimulated with NRG.
Figure 10A:
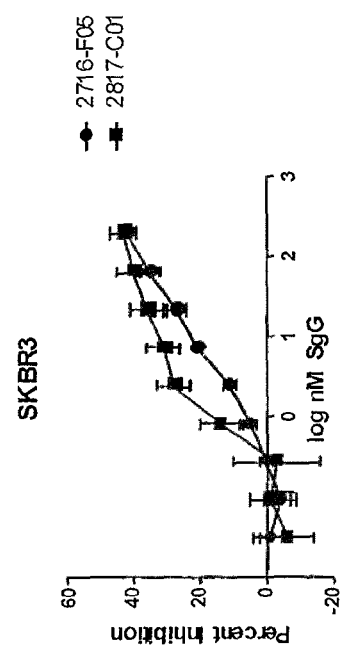

The results, shown in FIGS. 10A (SKBR3) and 10B (BT474), demonstrate that both 2817-C01 and 2716-F05 inhibit proliferation of ErbB2 overexpressing cell lines.

EXAMPLE 12

Surroglobulins Inhibit Proliferation of Cell Lines that Overexpress ErbB2 in the Absence of Exogenous NRG The ability of ErbB3 to form dimers with the other members of the ErbB family is thought to depend on stimulation with its ligand NRG. However, in cells that overexpress ErbB2, evidence has been presented that ErbB2 and ErbB3 can form heterodimers in the absence of NRG resulting in downstream AKT signaling.

Figure 11:
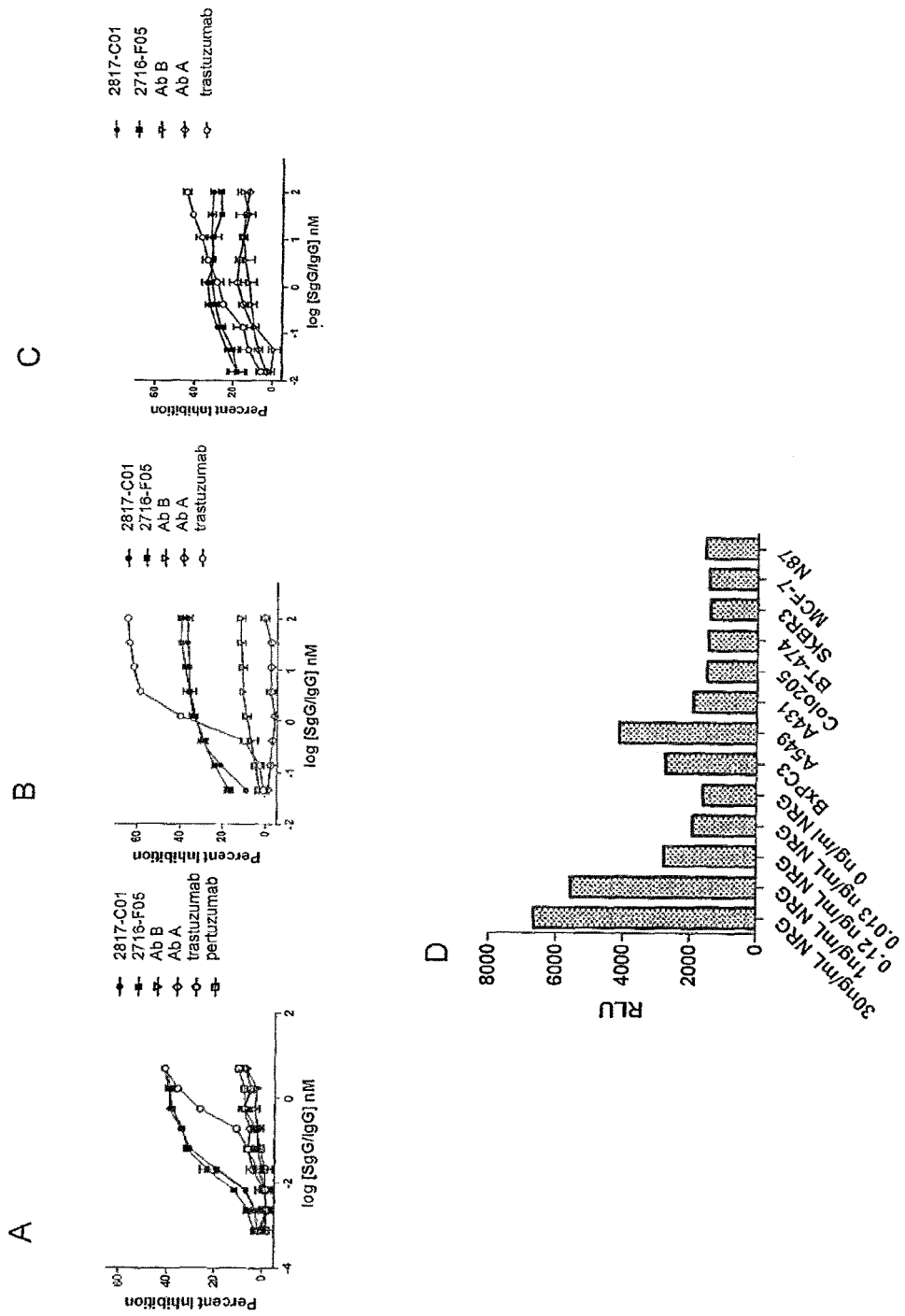
FIG. 39 11 is a graph depicting the percent inhibition of various agents in BT474 cells in the presence of NRG for SBP 2716-F05.

The ability of anti-ErbB3 sur-binding proteins to inhibit ligand-independent proliferation was tested. Cells were plated at a density of $5 \times 10^3$ cells/well in 96 well plates in complete medium. The cells were then treated with the indicated concentrations of sur-binding proteins (see FIG. 11). Cells were allowed to grow for 6 days and cell content was measured using Cell Titer-Glo® (Promega). FIGS. 11A, 11B, and 11C show the results from these experiments, which demonstrate that anti-ErbB3 sur-binding proteins potently and effectively inhibit the proliferation of the ErbB2 overexpressing breast cancer cell lines SKBR3 and BT474, as well as inhibiting ErbB2 overexpressing gastric cancer cell line NCI-N87 respectively. Antibodies Ab A, Ab B display little if any inhibition of proliferation of these cell lines in the absence of NRG.

To further ascertain whether growth in these cells is NRG-independent or whether cells might be secreting NRG and signaling in an autocrine fashion, stimulatory activity was measured using conditioned medium from the cells. Each of the cell lines indicated in FIG. 11D was grown for 3 days in complete medium to 85-90% confluence. Conditioned medium from the cells was harvested and its ability to stimulate ErbB2/ErbB3 heterodimerization was determined using the PathHunter™ ErbB2/ErbB3 functional assay (DiscoveRx, Fremont, Calif.) (see example 2). Various amounts of NRG, ranging from 0-30 ng/ml, were spiked into complete medium to establish the dynamic range of the assay. FIG. 11D shows that while several of the cell lines tested secreted measurable amounts of stimulatory factor(s) (presumed to be NRG), BT474, SKBR3, and NCI-N87 cells did not secrete measurable quantities (<0.12 ng/ml). This observation is in keeping with published reports that BT474 cells do not secrete NRG.

Since the ErbB2 overexpressing cell lines in this example did not secrete NRG and no exogenous NRG was added, the anti-ErbB3 antibodies and sur-binding proteins inhibited proliferation in the absence of this ligand in ErbB2 overexpressing cells. It is notable that Ab B and Ab A displayed minimal inhibition of proliferation in these ErbB2 overexpressing cell lines.

EXAMPLE 13

SgGs Enhance Antiproliferative Activity of Other Erb Targeted Antibodies

The ability of SgGs to enhance the anti-proliferative activity of other Erb targeted antibodies was examined. In FIG. 12A, the indicated concentrations of 2817-C01, 2716-F05 or a neutralizing anti-EGFR antibody (Millipore) were incubated with BxPC-3 cells for 96 hours in the presence of 10 ng/ml NRG1. To ascertain whether the combination of anti-EGFR and anti-ErbB3 SBPs can further inhibit BxPC-3 cell proliferation, the indicated concentrations of anti-EGFR were combined with either 200 nM 2817-C01 or 2716-F05 and incubated with cells for 96 hours in the presence of 10 ng/ml NRG1. Cell content was measured using Cell Titer-Glo® (Promega). These data demonstrate that combining inhibition of EGFR signaling using an antibody and ErbB3 signaling via these SBPs is beneficial.

The ability of SgGs to enhance the activity of Trastuzumab (an anti-ErbB2 antibody) was investigated in the ErbB2 overexpressing cell line SKBR3. FIGS. 12B and 12C show the percent inhibition of Trastuzumab alone at the indicated concentrations, or 100 nM Trastuzumab in combination with the indicated concentrations of 2817-C01 or 2716-F05. In FIG. 12B cells were then treated with 1 ng/ml NRG1 and allowed to proliferate for 3 days. In FIG. 12C no NRG was added and cells were allowed to proliferate for 6 days. Cell content was measured using Cell Titer-Glo® (Promega). The data in FIGS. 12B and C demonstrate that the anti-ErbB3 SgGs enhance the activity of Trastuzumab in the presence and absence of NRG.

Similarly to EGFR and ErbB2, ErbB4 interacts with ErbB3 and activates proliferative pathways. Combination treatment with antibodies that inhibit the activities of ErbB4 are expected to similarly enhance the activity of the anti-ErbB3 SBPs or Sabs.

EXAMPLE 14

Surroglobulins Enhance Antiproliferative Activity of Targeted Kinase Inhibitors

The ability of 2817-C01 and 2716-F05 to enhance the activity of targeted agents that inhibit proliferative signaling of other growth factor receptors or of proliferative signal transduction kinases was tested. In the first two instances the ErbB3 SBPs were tested for their ability to enhance inhibitors of other ErbB family of growth factor receptors and in the remaining four instances the ErbB3 SBPs were tested for their ability to enhance inhibitors of proliferative signal transduction kinases.

EXAMPLE 14a

Figure 13:
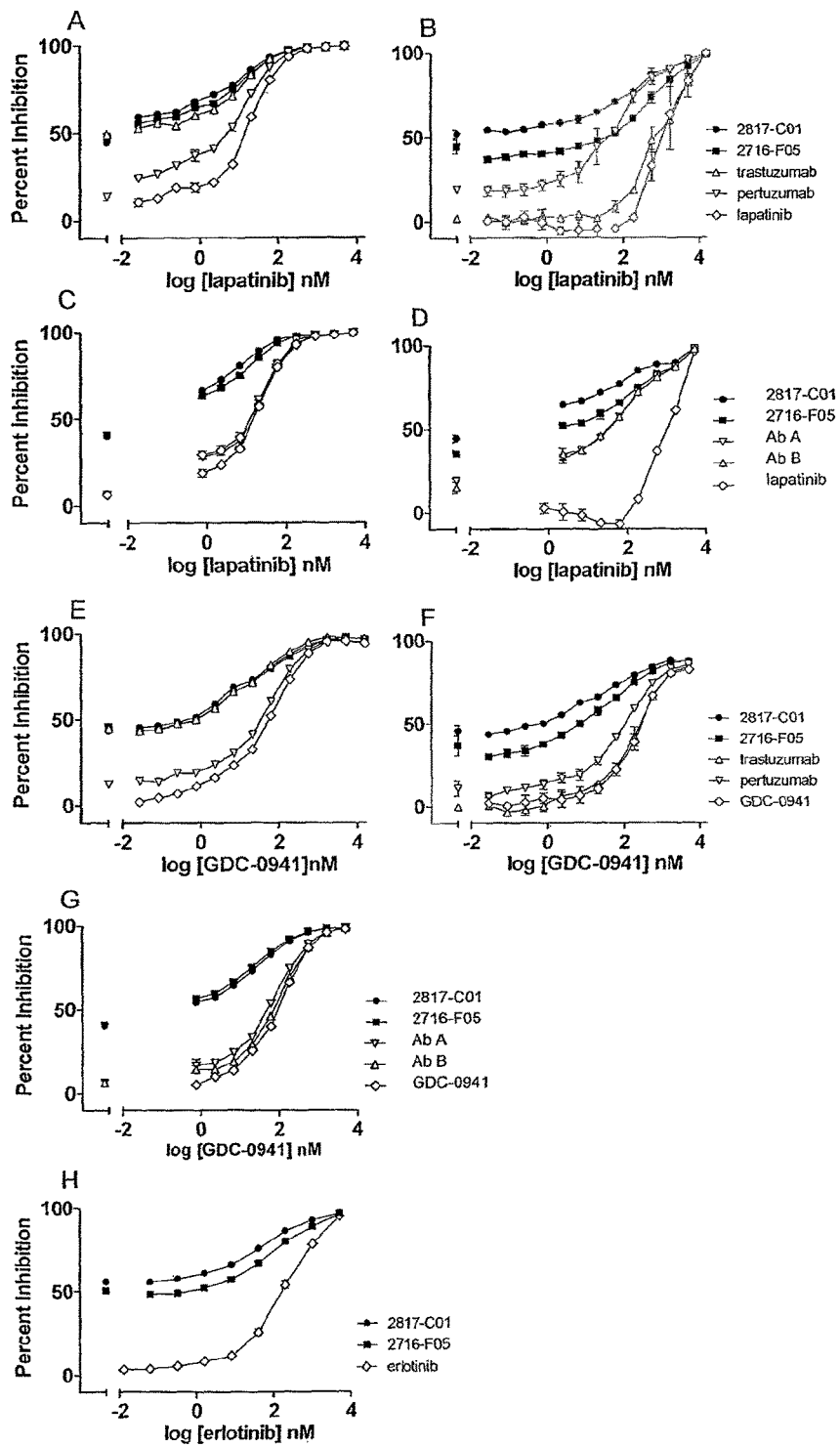
FIGS. 13A and 13B are graphs depicting the percent proliferation inhibition achieved by SgGs or anti-ErbB2 antibodies as single agents or in combination with lapatinib in the absence (FIG. 13A) or in the presence (FIG. 13B) of NRG.
FIGS. 13C and 13D are graphs displaying the results of the abilities of anti-ErbB3 antibodies (Ab A and Clone Ab B) and the SgGs to enhance various concentrations of lapatinib (on x-axis).
FIGS. 13E and 13F are graphs displaying the results of the abilities of anti-ErbB3 antibodies trastuzumab or pertuzumab, or sur-binding proteins (2817-C01 and 2716-F05) to enhance the effectiveness of various concentrations of GDC-0941(on x-axis).
FIG. 13G is a graph comparing the ability of anti-ErbB3 antibodies Ab A and Ab B with the SgGs to enhance the antiproliferative capacity of GDC-0941 in unstimulated SKBR3 cells (in the absence of NRG).
FIG. 13H is a graph demonstrating that erlotinib combined with a SgG results in a superior potency for inhibition.
FIG. 13I is a graph depicting how ErbB3 sur-binding proteins enhance the activity of the AKT inhibitor, MK-2206, in ErbB2 overexpressing cells in the absence of NRG.
FIG. 13J is a graph depicting how ErbB3 sur-binding proteins enhance the activity of the AKT inhibitor, MK-2206, in ErbB2 overexpressing cells in the presence of NRG.
FIG. 13K is a graph depicting how ErbB3 sur-binding proteins enhance the activity of the AKT inhibitor, MK-2206, in ErbB2 overexpressing cells in the absence of NRG.
FIG. 13L is a graph depicting how ErbB3 sur-binding proteins enhance the activity of the AKT inhibitor, MK-2206, in ErbB2 overexpressing cells in the presence of NRG.
FIG. 13M is a graph depicting how ErbB3 sur-binding proteins enhance the antiproliferative activity of the B-RAF inhibitor vemurafinib in B-RAF mutant Colo205 cells.
FIG. 13N is a graph depicting how anti-ErbB3 sur-binding proteins augment the activity of the MEK inhibitor selumetinib in Colo 205 NRG stimulated cells.
FIG. 13O is a graph depicting how anti-ErbB3 sur-binding proteins augment the activity of the MEK inhibitor selumetinib in A431 NRG stimulated cells.
FIG. 13P is a graph depicting how anti-ErbB3 sur-binding proteins augment the activity of the MEK inhibitor selumetinib in A549 NRG stimulated cells.
Figure 13I:
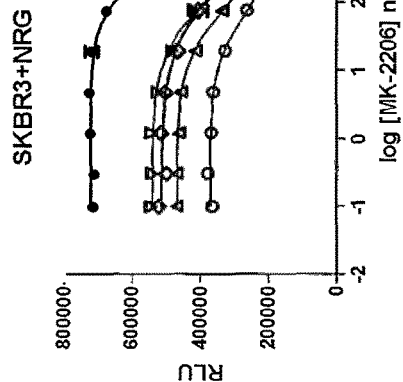
Figure 13J:
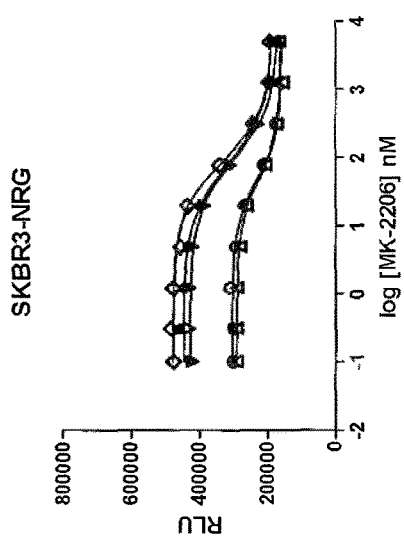
Figure 13K:
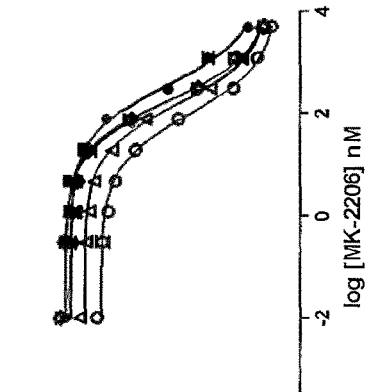
Figure 13L:
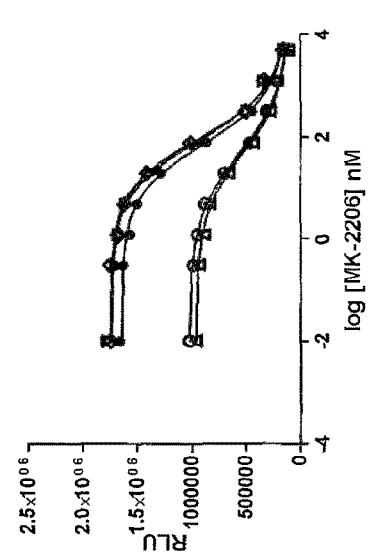

Surroglobulins Enhance Antiproliferative Activity of Targeted ErbB Kinase Inhibitor Lapatinib In this example, the results of which are shown in FIG. 13A, the ErbB3 SgGs combined with Lapatinib results in superior inhibition. Lapatinib is a dual tyrosine kinase inhibitor that inhibits the activity of ErbB2, as well as EGFR. The ability of single agent lapatinib or anti-ErbB3 SBPs to inhibit proliferation of unstimulated SKBR3 (Her2 overexpressing) cells was compared to combination treatments. Values to the left of the break in the X-axis denote the level of inhibition achieved with 10 nM of the single agents 2817-C01, 2716-F05, trastuzumab, or pertuzumab. In the combination treatments, the concentrations of lapatinib indicated to the right of the break in the x-axis were combined with 10 nM 2817-C01, 2716-F05, trastuzumab or pertuzumab. Cells were allowed to grow for 6 days and cell content was measured using Cell Titer-Glo® (Promega). The SgGs enhance the activity of lapatinib to a similar extent as trastuzumab and better than pertuzumab.

In FIG. 13B the ability of single agent lapatinib or anti-ErbB3 SBPs to inhibit proliferation of NRG stimulated SKBR3 cells was compared to combination treatments. Values to the left of the break in the X-axis denote the level of inhibition achieved with 100 nM of the single agents 2817-C01, 2716-F05, trastuzumab or pertuzumab. In the combination treatments, the concentrations of lapatinib indicated to the right of the break in the x-axis were combined with 100 nM 2817-C01, 2716-F05, trastuzumab or pertuzumab in the presence of 1 ng/ml NRG. Cells were allowed to grow for 3 days and cell content was measured using Cell Titer-Glo® (Promega). The data (FIG. 13B) showed that the SgGs enhance the activity of lapatinib in the presence or in the absence of NRG.

FIGS. 13C and 13D compare the ability of anti-ErbB3 antibodies Ab A, Ab B and the SgGs to enhance the properties of lapatinib. Values to the left of the break in the X-axis denote the level of inhibition achieved with 10 nM of the single agents 2817-C01, 2716-F05, Ab B or Ab A. In the combination treatments, the concentrations of lapatinib indicated to the right of the break in the x-axis were combined with 10 nM 2817-C01, 2716-F05, Ab A or Ab B. In the absence of NRG (FIG. 13C), Ab A and Ab B fail to impact the anti-proliferative ability of lapatinib. In the presence of NRG (FIG. 13D), Ab A and Ab B enhance lapatinib, but to a lesser extent than 2817-C01 and 2716-F05. Cells were allowed to grow for 6 days in the absence of NRG (FIG. 13C) or 3 days in the presence of 1 ng/ml NRG (FIG. 13D). Cell content was measured using Cell Titer-Glo® (Promega).

EXAMPLE 14B

Surroglobulins Enhance Antiproliferative Activity of Targeted EGFR Kinase Inhibitor Erlotinib In this example, the results of which are shown in FIG. 13H the ErbB3 SgGs combined with erlotinib resulted in a superior inhibition. Erlotinib is a tyrosine kinase inhibitor that inhibits the activity of EGFR. The ability of single agent erlotinib or anti-ErbB3 SgGs to inhibit proliferation of A431 cells was compared to combination treatments. Values to the left of the break in the X-axis indicate the level of inhibition achieved with single agents 2817-C01 or 2716-F05. In the combination treatments, the indicated concentrations of erlotinib were combined with 100 nM 2817-C01 or 2716-F05. NRG1β was added to a final concentration of 10 ng/ml. Cells were then allowed to grow for 96 hours and cell content was measured using Cell Titer-Glo® (Promega).

EXAMPLE 14C

Surroglobulins Enhance Antiproliferative Activity of the Targeted PI3 Kinase Inhibitor GDC-0941

In this example, the results of which are shown in FIG. 13E the ErbB3 SgGs combined with GDC-0941 resulted in a superior inhibition. GDC-0941 is a selective, orally bioavailable inhibitor of class I PI3 kinase (PI3K). The ability of single agent GDC-0941 or anti-ErbB3 SgGs to inhibit proliferation of unstimulated SKBR3 (Her2 overexpressing) cells was compared to combination treatments. Values to the left of the break in the X-axis denote the level of inhibition achieved with 10 nM of the single agents 2817-C01, 2716-F05, trastuzumab or pertuzumab. In the combination treatments, concentrations of GDC-0941 indicated to the right of the break in the x-axis were combined with 10 nM 2817-C01 or 2716-F05, trastuzumab or pertuzumab. Cells were allowed to grow for 6 days and cell content was measured using Cell Titer-Glo® (Promega).

FIG. 13F presents data regarding the ability of the SgGs to enhance GDC-0941 in NRG-stimulated SKBR3 cells. Values to the left of the break in the X-axis denote the level of inhibition achieved with 100 nM of the single agents 2817-C01, 2716-F05, trastuzumab or pertuzumab. To the right of the break, the indicated concentrations of GDC-0941 were combined with 100 nM 2817-C01 or 2716-F05 in the presence of 1 ng/ml NRG. Cells were allowed to grow for 3 days and cell content was measured using Cell Titer-Glo® (Promega). The data in FIGS. 13E and 13F show that the SgGs enhance the activity of GDC-0941 in the presence or in the absence of NRG.

FIG. 13G presents data that compared the ability of anti-ErbB3 antibodies Ab A and Ab B and the SgGs to enhance the antiproliferative capacity of GDC-0941 in unstimulated SKBR3 cells. Values to the left of the break in the X-axis denote the level of inhibition achieved with 10 nM of the single agents 2817-C01, 2716-F05, Ab A or Ab B. In the combination treatments, concentrations of GDC-0941 indicated to the right of the break in the x-axis were combined with 10 nM 2817-C01, 2716-F05, Ab A or Ab B. In the absence of NRG, Ab A and Ab B fail to impact the anti-proliferative ability of GDC-0941. Cells were allowed to grow for 6 days in the absence of NRG. Cell content was measured using Cell Titer-Glo® (Promega).

EXAMPLE 14D

Surroglobulins Enhance Antiproliferative Activity of the Targeted AKT Kinase Inhibitor Mk-2206

In this example, the results of which are shown in FIGS. 13I-13L the ErbB3 SgGs were combined with MK-2206 and resulted in a superior inhibition. The ability of the SgGs to enhance AKT inhibition in unstimulated or NRG-stimulated SKBR3 cells was compared. An AKT inhibitor, MK-2206, was tested against the ErbB2 overexpressing cell lines SKBR3 (13I, 13J) and BT474 (13K, 13L). The indicated amounts of MK-2206 were applied to the cells and they were allowed to proliferate in complete medium containing 10% fetal bovine serum for 6 days (13I, 13K, 13L) or 3 days (13J). Cell content was measured using Cell Titer-Glo® (Promega). When these cells were stimulated with 0.125 (13J) or 0.375 (13L) nM NRG, the ability of MK-2206 to inhibit cell proliferation was dramatically reduced. Combined treatment with MK-2206 and 10 nM of either of the sur-binding protein significantly enhanced the antiproliferative activity of MK-2206, and in NRG stimulated cells, restored activity to a level similar to that observed in unstimulated cells. The SgGs also augmented the activity of MK-2206 in non-ligand stimulated cells whereas Ab A and Ab B did not augment MK-2206.

EXAMPLE 14E

Figure 13M:
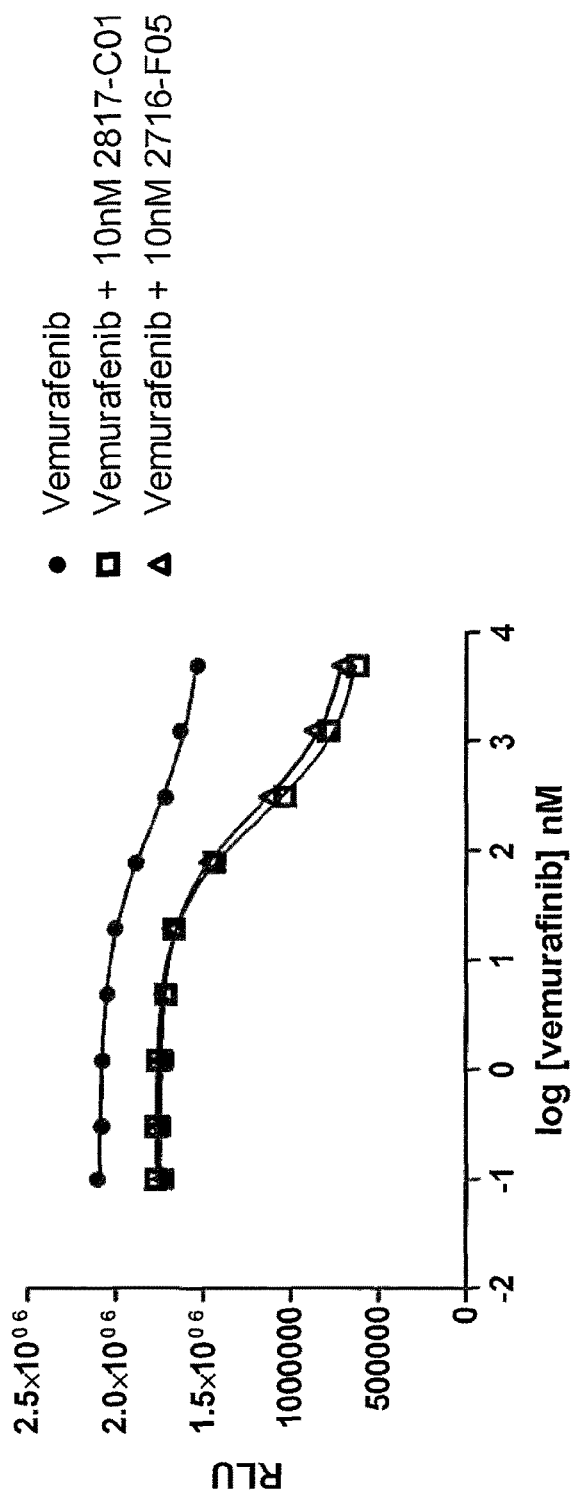

Surroglobulins Enhance Antiproliferative Activity of the Targeted B-Raf Kinase Inhibitor Vemurafinib In this example, the results of which are shown in FIG. 13M the ErbB3 SgGs were combined with vemurafinib, which resulted in a superior inhibition. The ability of the SgGs to enhance B-RAF inhibition in B-RAF mutated cells was determined. A B-RAF inhibitor vemurafinib, was tested using the B-RAF mutated Colo205 cells, in combination with either 2817-C01 or 2716-F05. Colo205 cells were treated with the indicated concentrations of vemurafinib (and the indicated amount of the SgGs) for 4 days in the presence of 10% fetal bovine serum and 10 ng/ml NRG. Cell content was measured using Cell Titer-Glo® (Promega).

Combined treatment with the anti ErbB3 sur-binding proteins and vemurafinib exhibited superior growth inhibition to treatment with vemurafinib alone (see FIG. 13M).

EXAMPLE 14F

Figure 13N:
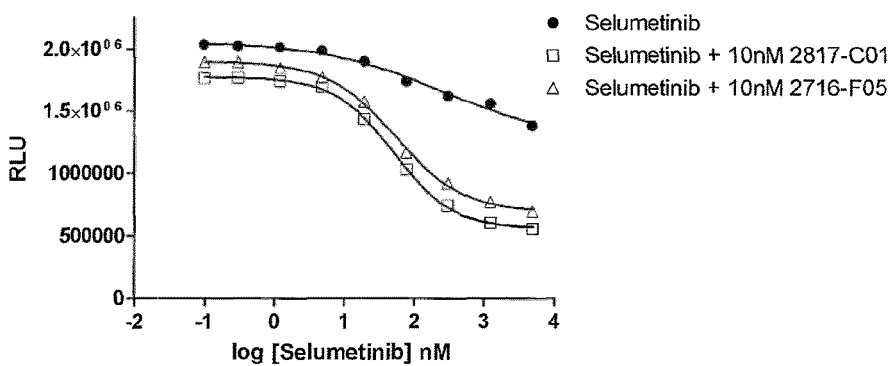
Figure 13O:
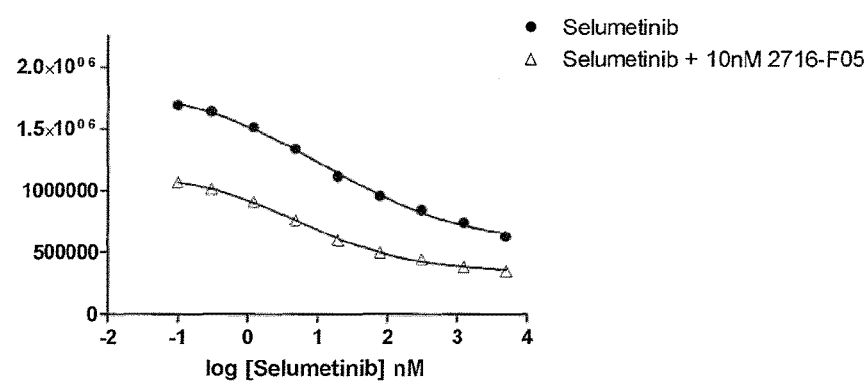
Figure 13P:
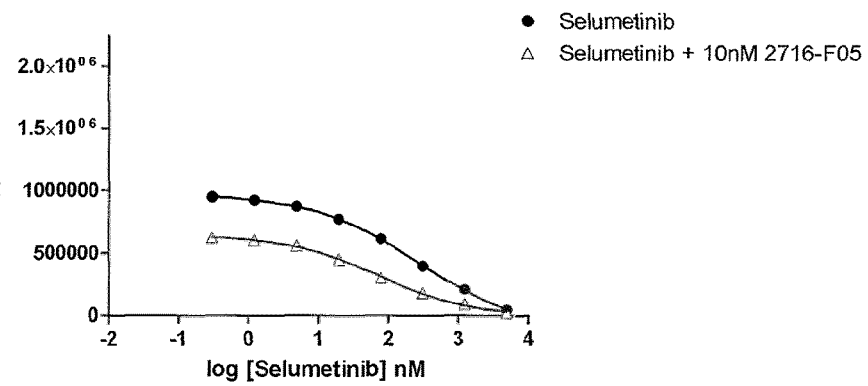

Surroglobulins Enhance Antiproliferative Activity of the Targeted Ekkinase Inhibitor Selumetinib In this example, the results of which are shown in FIGS. 13N-13P, the ErbB3 SgGs were combined with selumetinib and resulted in a superior inhibition.

The ability of anti-ErbB3 SgGs to augment the activity of the MEK inhibitor selumetinib were compared and demonstrated. Colo205 cells (B-RAF mutant) (FIG. 13N), A431 cells (overexpress EGFR) (FIG. 13O) or A549 cells (k-RAS mutant cells) (FIG. 13P) were stimulated with 10 ng/ml NRG and allowed to proliferate for 96 hours in the presence of the indicated concentrations of selumetinib. Cell content was measured using Cell Titer-Glo® (Promega).

In each of the cell lines, combined treatment with 10 nM SgG and selumetinib inhibited cell growth markedly better than selumetinib alone.

As will be appreciated by those skilled in the art, in light of the present disclosure, combining various drugs with anti-ErbB3 SgGs allows them to be efficacious over a wider range of concentrations. The clinical consequence can be that enhanced efficacy can enable patients to be more effectively treated, and, in some embodiments, as effectively treated, but with lower doses of the drugs thereby reducing toxic side effects. Moreover, combined treatment with these agents can overcome inherent or acquired mechanisms that render cells resistant to treatment with single agents.

It will also be appreciated that numerous agents are capable of inhibiting the kinase activities of ErbB 1 and ErbB2 as well as PI3K. In addition, numerous agents are capable of inhibiting members of the AKT and MAPK signaling pathways, and that in light of the present disclosure, all of the above mentioned agents can have enhanced or superior activity when used in combination with anti-ErbB3 SBPs. In some embodiments, the clinical consequence can be that enhanced efficacy can enable patients to be more effectively treated, and possibly be as effectively treated with lower doses of the drugs thereby reducing toxic side effects.

EXAMPLE 15

SBPs Inhibit Tumor Growth In Vivo

2817-C01 and 2716-F05 were tested for their ability to inhibit tumor growth in vivo. 5×10⁶ human BxPC-3 pancreatic tumor cells in 50% matrigel were injected subcutaneously into nude mice (Charles River Laboratories). Seven days after injection, mice were divided into groups of 10. Each group was dosed via intraperitoneal injection with one of the test articles indicated in FIG. 14A. Animals received a loading dose of 25 mg/kg and were dosed twice weekly thereafter with 12.5 mg/kg.

These data show that both SgGs reduced the growth of tumors in vivo and that 2716-F05 can cause tumor shrinkage. Notably, both agents performed as well as, or better than, the EGFR targeted therapeutic antibody Cetuximab.

Figure 14:
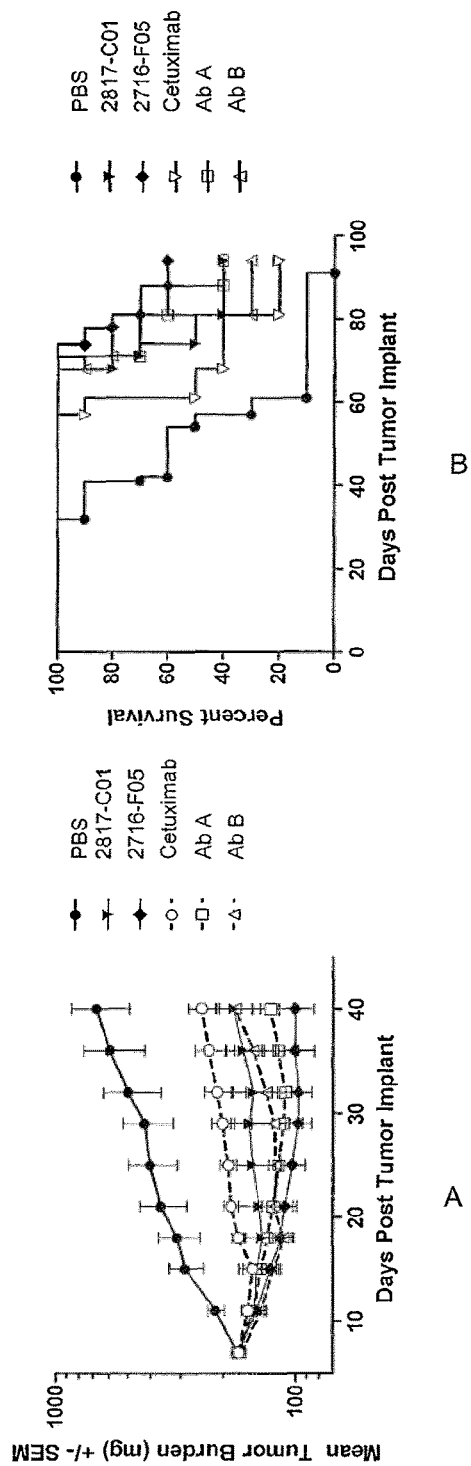
FIG. 14A is a graph depicting mean tumor burden as a function of time post tumor implant separated by treatment group.
FIG. 14B is a graph depicting the percent survival, post tumor implant, separated over time by treatment group.

FIG. 14B shows animal survival in the study. Among the animals treated with 2716-F05, 2 sustained complete remissions of the tumors and 4 sustained partial remissions.

EXAMPLE 16

Surroglobulins Inhibit Ligand-Induced ErbB3 Phosphorylation, AKT Phosphorylation and Erk Phosphorylation This example examines the impact of anti-ErbB3 SgGs on ligand-induced activation ErbB3 and of the AKT and ERK signaling pathways. Ligand induced activation was measured by increased phosphorylation of ErbB3, AKT and ERK1/2.

500,000 BxPC-3 cells were plated into each well of a 12 well tissue culture dish in serum free medium. The cells were incubated for 1 hour with the indicated amounts of SgG. They were then stimulated with 10 ng/ml NRG for 12 minutes. Cells were then washed in ice cold PBS, and lysed. Phosphorylated AKT, phosphorylated ErbB3 and phosphorylated ERK1/2 were measured in the lysates using ELISA kits from Cell Signaling Technologies®.

Figure 15A:
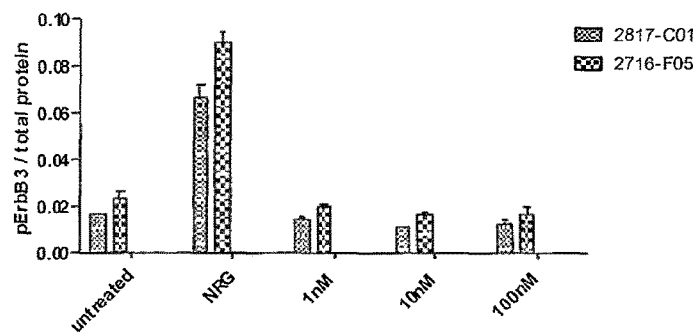
FIG. 15A is a graph depicting that SgGs potently inhibit phosphorylation of ErbB3.
Figure 15B:
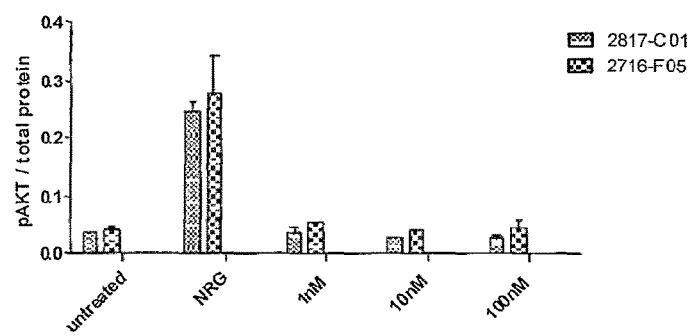
FIG. 15B is a graph depicting that SgGs potently inhibit phosphorylation of AKT.
Figure 15C:
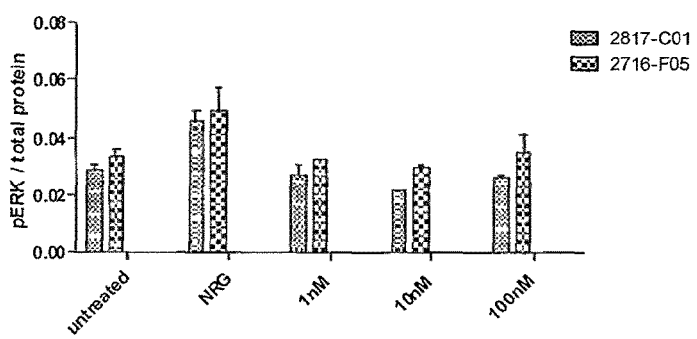
FIG. 15C is a graph depicting that SgGs potently inhibit phosphorylation of ERK1/2.

The data show that the anti-ErbB3 SgGs potently inhibit ligand-induced phosphorylation of ErbB3 (FIG. 15A), AKT (FIG. 15B) and ERK1/2 (FIG. 15C).

EXAMPLE 17

Surroglobulins Inhibit ErbB3 Phosphorylation and AKT Phosphorylation in Cells that Overexpress ErbB2

This example examines the impact of anti-ErbB3 SgGs on basal activation of ErbB3 and of the AKT signaling pathways in cells that overexpress ErbB2. Activation was measured by increased phosphorylation of ErbB3, AKT.

500,000 cells were plated into each well of a 12 well tissue culture. The cells were incubated for 1 hour with the indicated amounts of SgG. Cells were then washed in ice cold PBS, and lysed. Phosphorylated AKT and phosphorylated ErbB3 were measured in the lysates using ELISA kits from Cell Signaling Technologies®.

Figure 16:
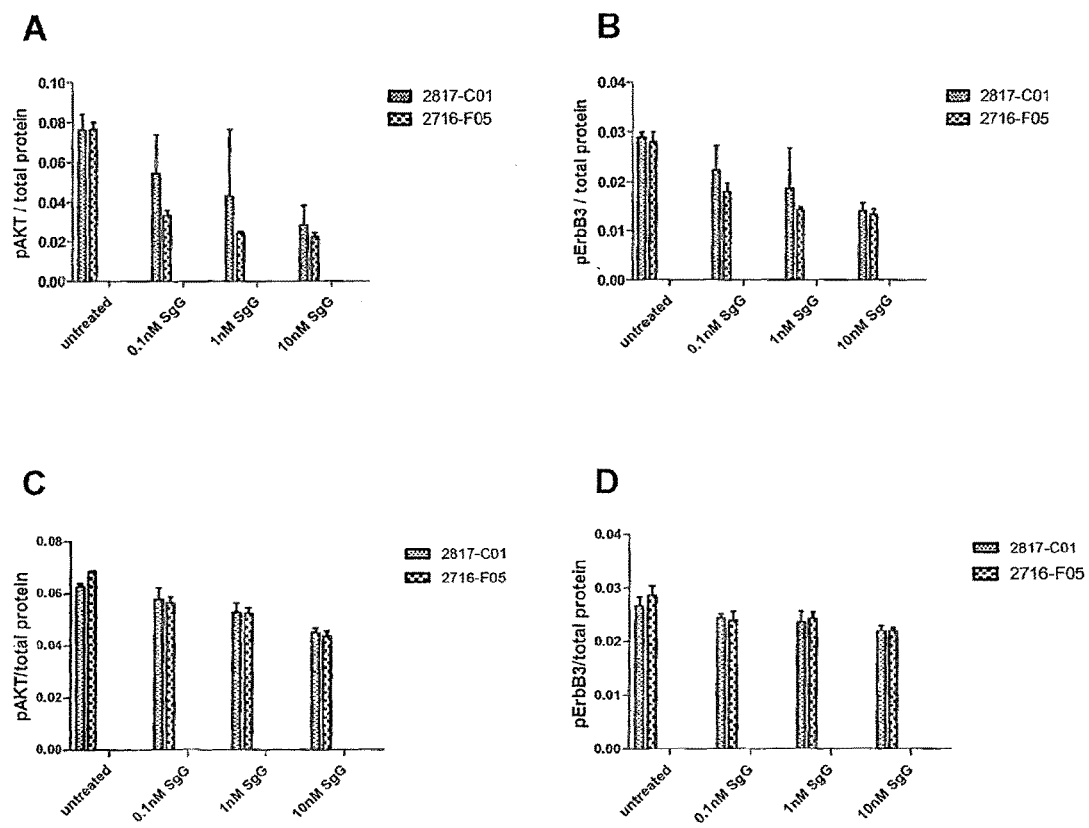
FIGS. 16A and 16B are graphs depicting that anti-ErbB3 SgGs potently inhibit phosphorylation of AKT and ErbB3 in the ErbB2 overexpressing cell line SKBR3.
FIGS. 16C and 16D are graphs depicting that anti-ErbB3 SgGs potently inhibit phosphorylation of AKT and ErbB3 in the ErbB2 overexpressing cell line BT474.

The data show that the anti-ErbB3 SgGs potently inhibit phosphorylation of AKT and ErbB3 in the ErbB2 overexpressing cell lines SKBR3 (FIGS. 16A and B) and BT474 (FIGS. 16C and 16D).

EXAMPLE 18

Surroglobulins Increase Apoptosis in Cultured Tumor Cells

The ERK and AKT pathways are pivotal regulators of cellular proliferation and apoptosis. In cancer cells, the balance between these two pathways is perturbed such that proliferation proceeds in an unregulated fashion. Since SgGs alter the phosphorylation state of AKT and ERK, the impact of the SgGs on apoptosis was investigated.

Figure 17:
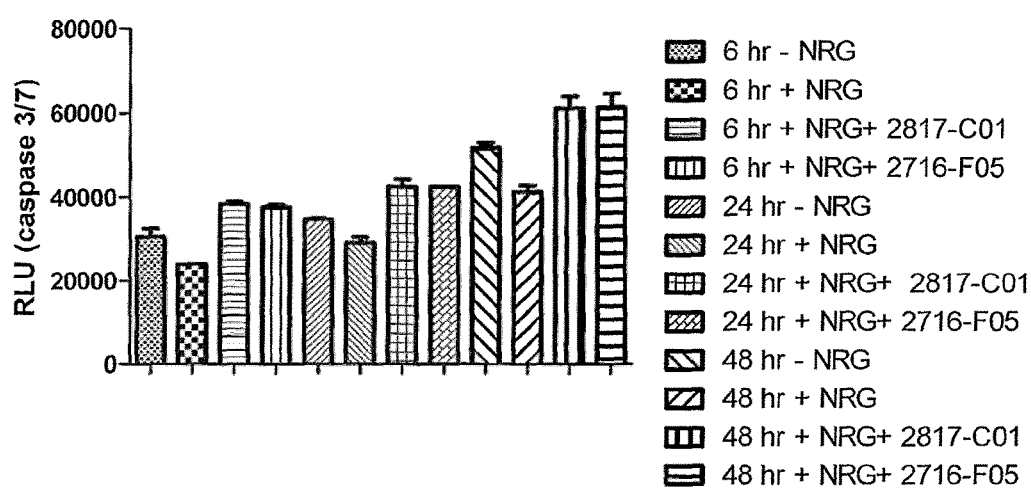
FIG. 17 is a graph depicting caspase activity and demonstrates that SgGs can counteract the antiapoptotic effects of growth factors, particularly NRG, in the tumor environment and can restore more regulated programmed cell death to transformed cells

BxPC-3 cells were plated at a density of $10^4$ cells/well in a 96 well dish in serum-free medium. On the following day SgGs (as indicated in FIG. 17) were added to a final concentration of 100 nM and incubated for 1 hr. NRG was then added to a final concentration of 10 ng/ml. Six hours, 24 hours and 48 hours after SgG addition, an equal volume of Caspase-Glo® 3/7 (Promega) detection reagent was added to the cells. Caspase-Glo® 3/7 is a specific substrate for caspases 3 and 7 and provides chemiluminescent readout when it is cleaved by one of these enzymes.

Caspase-3 is activated in the apoptotic cell both by extrinsic (death ligand) and intrinsic (mitochondrial) pathways. FIG. 17 shows that the activity of this enzyme, and by inference the number of cells undergoing apoptosis, increases over time from 6 to 48 hours in serum-free medium. Addition of NRG partially ameliorates this effect. However, if SBPs are added to the cells, not only is NRG unable to diminish apoptosis, the number of cells undergoing apoptosis increases beyond the basal level seen in cells maintained in serum-free medium. These results show that SBPs can counteract the antiapoptotic effects of growth factors, particularly NRG, in the tumor environment and can restore more regulated programmed cell death to transformed cells.

EXAMPLE 19

SBPs Inhibit Cell Migration/Invasion

Cell migration/invasion is thought to be an early step in cancer metastasis. To investigate whether SgGs can inhibit cell migration, MCF-7 cells or other cells prone to migration will be tested for their ability to migrate through a collagen coated membrane, essentially as described in (Albini, Iwamoto et al. 1987). MCF-7 cells are plated at a density of 50,000 cells per well in serum free medium containing various concentrations of SgGs in the top of a collagen coated transwell (Trevigen Inc). The bottom chamber of the transwell contains serum free medium supplemented with 10 ng/ml NRG. Migration is allowed to proceed for various lengths of time from 6 hours to 10 hours. After this period of time the upper chamber is immersed in dissociation solution (Trevigen 3455-096-05) and the number of cells dissociated from the lower face of the membrane (migrated cells) is quantitated using Calcein AM.

The metastatic potential of different cells types has been shown to coorelate with migration in this type of assay. Reduced migration as a consequence of SgG treatment will demonstrate that the SgGs can reduce the metastatic potential of tumors.

EXAMPLE 20

Treatment of Cancer Using an SgG to ErbB3

This example outlines the treatment of a cancer using a SgG to ErbB3.

A subject at risk of developing a cancer in which ErbB3 plays a role is administered a dose of 2817-C01 and/or 2716-F05. The SgG is administered at an amount sufficient to reduce to ErbB3 responsive or dependent activity. The treatment results in the reduction of ErbB3 mediated signaling, thereby slowing, reducing, or eliminating the cancer in which ErbB3 plays a role.

EXAMPLE 21

Treatment of an ErbB3 Disorder Using a SgG to ErbB3

This example outlines the treatment of a cancer using a SgG to ErbB3. A subject at risk of developing a cancer in which ErbB3 plays a role is administered a first SgG or antibody that binds to ErbB3. The first SBP or antibody includes a detection moiety, by which the amount and/or activity of ErbB3 in the subject is monitored. A dose of a SgG is administered to the subject in light of the amount and/or activity of ErbB3 detected in the subject. The administration is repeated, optionally with further monitoring of the activity of ErbB3 until the treatment results in the reduction of ErbB3 mediated signaling.

EXAMPLE 22

Treatment of Cancer Using a SgG Combination Therapy Using Targeted Tyrosine Kinase Inhibitors of the Erb Signalling Pathways This example outlines the treatment of a cancer using an SgG to ErbB3 and a compound that reduces the tyrosine kinase activity of ErbB1 or ErbB2. A subject at risk of developing a cancer in which ErbB3 plays a role is administered a dose of 2817-C01 and/or 2716-F05 (or other SgG) either prior to, subsequent to, or in combination with a compound that inhibits tyrosine kinase activity. Examples of tyrosine kinase inhibitors that can be used in this capacity are Erlotitinib, Gefitinib, Lapatinib, Neratinib, Afatinib. The SgG is administered in an amount sufficient to reduce ErbB3 mediated signaling. The tyrosine kinase inhibitor is administered in an amount sufficient to reduce ErbB 1 or ErbB2 activity. The treatment results in the reduction of ErbB3 mediated signaling, thereby slowing or reducing the cancer in which ErbB3 plays a role. The result of the combined therapy is an increase in duration or magnitude of inhibition of signaling that is at least greater than the use of the SgG and/or the compound alone at an equivalent dose.

EXAMPLE 23

Treatment of Cancer Using an SgG Combination Therapy and a Targeted Inhibitor of Cellular Translation, Protein Folding, Proliferation or Survival This example outlines the treatment of a cancer using an SgG to ErbB3 and a targeted compound that inhibits cancer growth. A subject at risk of developing a cancer in which ErbB3 plays a role is administered a dose of 2817-C01 and/or 2716-F05 (or other SgG) either prior to, subsequent to, or in combination with a compound that inhibits properly regulated cellular proliferation or survival. Inhibitors that can be used in this capacity are PI3K inhibitors, Protein kinase C inhibitors, RAF inhibitors, MAPK inhibitors, MEK inhibitors, AKT inhibitors, mTOR inhibitors, BCR/ABL and Src family tyrosine kinase inhibitors, aurora kinase inhibitors, and HSP90 inhibitors. Examples of such inhibitors can include, but are not limited to BAY43-9006, PLX4032, SB590885, PLX4720, XL281, RAF265, XL518, CI-1040, PD035901, AZD6244, GSK1120212, Sorafenib, Dasatinib, nilotinib, and imatinib, Geldanamycin.

The SgG is administered in an amount sufficient to reduce ErbB3 mediated signaling. The treatment results in the reduction of ErbB3 mediated signaling, thereby slowing or reducing the cancer in which ErbB3 plays a role. The result of the combined therapy is an improved inhibition of tumor growth that is at least greater than the use of the SgG and/or the compound alone at an equivalent dose.

EXAMPLE 24

Treatment of Cancer Using an SgG Combination Therapy with a Cytotoxic Chemotherapeutic Agent This example outlines the treatment of a cancer using an SgG to ErbB3 and a chemotherapeutic agent that inhibits cancer growth. A subject at risk of developing a cancer in which ErbB3 plays a role is administered a dose of 2817-C01 and/or 2716-F05 (or other SgG) either prior to, subsequent to, or in combination with one or more chemotherapeutic compounds. Compounds that can be used in this capacity are topoisomerase inhibitors, alkylating agents, nucleoside analogs, microtubule inhibitors, DNA crosslinking agents and DNA intercalating agents. Examples of such inhibitors can include, but are not limited Cisplatin, Etoposide, Carboplatin, Paclitaxel, Docetaxel, Vinorelbine tartrate, Doxorubicin, Vincristine sulfate, Ifosfamide, Gemcitabine hydrochloride, and/or 5-FU. The SgG is administered in an amount sufficient to reduce ErbB3 mediated signaling. The treatment results in the reduction of ErbB3 mediated signaling, thereby slowing or reducing the cancer in which ErbB3 plays a role. The result of the combined therapy is an improved inhibition of tumor growth that is at least greater than the use of the SgG and/or the compound alone at an equivalent dose.

EXAMPLE 25

Treatment of Cancer Using an SgG Combination Therapy with a Targeted Inhibitor of Angiogenesis This example outlines the treatment of a cancer using a SgG to ErbB3 and a targeted inhibitor of angiogenesis that inhibits cancer growth. A subject at risk of developing a cancer in which ErbB3 plays a role is administered a dose of 2817-C01 and/or 2716-F05 (or other SgG) either prior to, subsequent to, or in combination an inhibitor of angiogenesis. Compounds that can be used in this capacity are antibodies or surroglobulins to VEGF, PLGF, Angiopoietin, DLL-4 or receptors to any of these factors. Additional compounds that can be used in this capacity are decoy receptors, such as Aflibercept and inhibitors of signaling elicited by binding of proangiogenic compounds to their receptors including, but not limited to Axitinib, Cediranib, Regorafenib, Sunitinib, Vandetanib, Vatalanib. The SgG is administered in an amount sufficient to reduce ErbB3 mediated signaling. The treatment results in the reduction of ErbB3 mediated signaling, thereby slowing or reducing the cancer in which ErbB3 plays a role. The result of the combined therapy is an improved inhibition of tumor growth that is at least greater than the use of the SgG and/or the compound alone at an equivalent dose.

EXAMPLE 26

Treatment of Cancer Using a SgG Combination Therapy with a Therapeutic Antibody or SgG Targeting Another Member of the Erb Family This example outlines the treatment of a cancer using an SgG to ErbB3 and an antibody or surroglobulin to another member of the ErbB family. A subject at risk of developing a cancer in which ErbB3 plays a role is administered a dose of 2817-C01 and/or 2716-F05 (or other SgG) either prior to, subsequent to, or in combination with one or more antibodies or surroglobulins targeting ErbB 1, ErbB2 or ErbB4 or one of their ligands. Compounds that can be used in this capacity can include, but are not limited Cetuximab, Panitumumab, Trastuzumab, or Pertuzumab. The SgG is administered in an amount sufficient to reduce ErbB3 mediated signaling. The treatment results in the reduction of ErbB3 mediated signaling, thereby slowing or reducing the cancer in which ErbB3 plays a role. The result of the combined therapy is an improved inhibition of tumor growth that is at least greater than the use of the SgG and/or the additional antibody or SgG alone at an equivalent dose.

EXAMPLE 27

Treatment of Cancer Using a SgG Combination Therapy with a Therapeutic Antibody or SgG Targeting Another Growth Factor Receptor or its Ligand This example outlines the treatment of a cancer using a SgG to ErbB3 and an antibody or surroglobulin to another growth factor receptor or its ligand. A subject at risk of developing a cancer in which ErbB3 plays a role is administered a dose of 2817-C01 and/or 2716-F05 (or other SgG) either prior to, subsequent to, or in combination with one or more antibodies or surroglobulins targeting another growth factor receptor or its ligand. Compounds that can be used in this capacity can include, but are not limited to antibodies or surroglobulins targeting Insulin like growth factor receptors (IGF1R or IGF2R), fibroblast growth factor receptors (FGFR1, FGFR2, FGFR3, FGFR4), MET, RON, and Platelet-derived growth factor receptor (PDGFR). They can also include antibodies or surroglobulins targeting the ligands insulin like growth factor, fibroblast growth factor, HGF or MSP. The SgG is administered in an amount sufficient to reduce ErbB3 mediated signaling. The treatment results in the reduction of ErbB3 mediated signaling, thereby slowing or reducing the cancer in which ErbB3 plays a role. The result of the combined therapy is an improved inhibition of tumor growth that is at least greater than the use of the SgG and/or the additional antibody or SBP alone at an equivalent dose.

EXAMPLE 28

Uses of a Bispecific ErB3 SgG

This example outlines potential bispecific treatments of a cancer using a combination of an ErbB3 SgG and another distinctly targeted specific SgG or antibody. As mentioned previously, coadministration of complimentary agents can have significant benefits compared to the use of single agents alone. However, bispecific entities, containing two or more specificities of these types of combinations, within a single molecular entity can yield even greater benefit compared either agent alone, as well as that of coadministered combinations.

A bispecific SgG is constructed so that it comprises a variable domain that recognizes ErbB3 as well as one or more additional distinct variable domains. The additional variable domain(s) can be directed against a ligand, associated factor, receptor, or even a different epitope to ErbB3. The ErbB3 specific variable domain derives from one of the variable domains of SgGs or Sabs as shown in FIG. 2. The variable domain of additional specificity is derived by panning a Sab phage displayed library as outlined in example 1. The variable domains can be joined by numerous methods. An example of such bispecific joining has been disclosed in (Xu, et. al, JMB 2010) Further strategies to generate bispecifics can adapt novel technologies or adapt techniques previously described for bispecific assembly.

As a specific example, inhibition of both ErbB3 and another ErbB family member, as a bispecific can work synergistically through several mechanisms. For example, a bispecific ErbB3/EGFR can have greater potency/efficacy and therefore be administered at lower doses that maintain efficacy, but have superior adverse effect profiles to those typically seen with EGFR antibodies. Secondly, it can be possible to have greater potency as a result of selectively inhibiting oncologic ErbB3/EGFR dimers and networks while sparing normal EGFR homodimer physiological signaling. Since activation of ErbB3 has been implicated in generating resistance to other targeted agents, simultaneously targeting two oncological targets via a bispecific SgG or IgG can help reduce or delay the incidence of resistance to single agents.

To test an ErbB3/EGFR bispecific combination the EGFR specific SBP is generated in a manner described previously and then recombinantly express the protein, for example by using the formats as previously published (Xu, JMB 2010). The recombinant ErbB3/EGFR bispecific can be tested in vitro for growth inhibition of A431 cells or in vivo against A431 xenograft tumor growth inhibition. Furthermore, the use of ErbB3/EGFR in ras mutated tumors can reveal susceptibilities normally not addressed by EGFR inhibition alone.

Benefits similar to those possible with ErbB3/EGFR combinations can be achieved with ErbB3/ErbB2 bispecific SgGs as well. Furthermore, bispecific ErbB3 SgGs, composed of the distinct variable domains that recognize different epitopes of ErbB3, can have greater benefits to that of ErbB3 monospecific SgGs. Possible mechanisms for increased activity can be due to increased cellular internalization and receptor destruction, novel inhibitory physical engagement, or even greater ErbB3 heterodimer inhibition.

In addition ErbB3 bispecific SgGs can be made as combinations with anti-angiogenic factors such as anti-VEGF, anti-DLL4, or anti-Angiopoietin-2. In these combinations specifically concentrating the neutralization of angiogenic factors at an ErbB3 bearing tumor site can increase the efficacy of the anti-angiogenic inhibition at the site of tumor neovasculature. Similarly, ErbB3 bispecifics that are combined with other receptor tyrosine kinase growth factors or their cognate receptors can have benefits similar to those described above.

EXAMPLE 29

Inhibiting Non-ErbB3 Networks with Anti-ErbB3 SgGs

This example outlines potential treatments of a cancer that uses an ErbB3 SBP to quell an associated cancer promoting network. As ErbB signal transduction uses elements common to other signal transduction cascades it is possible that ErbB3 can contribute to the signaling or inhibition of non-ErbB3 receptor-linked pathways. ErbB3 SgGs can therefore directly reduce the non-ErbB3 signaling directly or possibly through a "bystander effect" to reduce the establishment or progression of cancers.

For example, HGF and its cognate receptor, c-met, are known mitogens and have established linkages to poor cancer prognosis. To test the consequence of ErbB3 inhibitors one can test the effects, in vitro, on HGF-stimulated proliferation. By extension, one can also test the effects of ErbB3 SgG inhibition on PDGFs, FGFs, IGFs, or other receptor kinase growth factor stimulation.

EXAMPLE 30

A subject at risk of developing a cancer in which ErbB3 plays a role is administered a dose of SBP 2817-C01 and/or SBP 2716-F05. In combination with the SBP, the subject is also administered at least one compound that binds to and/or reduces binding of ErbB2 to ErbB3 The SBP is administered in an amount sufficient to reduce ErbB3 mediated signaling. The compound is administered in an amount sufficient to reduce ErbB2 dimerization with ErbB3. The treatment results in the reduction of ErbB3 mediated signaling, thereby slowing or reducing the cancer in which ErbB3 plays a role. The result of the combined therapy is an increase in inhibition of signaling that is at least greater than the use of the SBP and/or the compound alone.

EXAMPLE 31

Treatment of Cancer Using a SBP Combination Therapy

This example outlines the treatment of a cancer using two SBPs to ErbB3. A subject at risk of developing a cancer in which ErbB3 plays a role is administered a dose of SBP 2817-C01 and/or SBP 2716-F05 or in combination with at least a second SBP that also binds ErbB3. The SBPs could be administered in an amount equal to or less than an amount sufficient to reduce ErbB3 mediated signaling for either of the SBPs individually. The treatment results in the reduction of ErbB3 mediated signaling, thereby slowing or reducing the cancer in which ErbB3 plays a role.

EXAMPLE 32

Identification of an ErbB3 Positive Cancer

A sample is taken from a subject. A SBP and/or an antibody that binds to ErbB3 is applied to the sample at a level sufficient to detect a relevant level of any ErbB3 that may be present in the sample. Binding of the SBP is detected either via a direct label or by use of a secondary antibody or agent. If the level of ErbB3 in the sample is greater than normal, the subject can have an ErbB3 related disorder.

In the alternative, the subject can be one who is known to have a cancer, but the particular cancer and/or source of the cancer may be unknown. In this arrangement, the test for ErbB3 can be used by subjects with cancer to identify that they have an ErbB3 related cancer.

EXAMPLE 33

Subsequent Treatment of an ErbB3 Positive Cancer

The subject in Example 32 who has elevated levels of ErbB3 is administered a NRG inhibiting SBP. The administration of the SBP is repeated until the growth and/or any symptoms of the cancer are reduced.

EXAMPLE 34

Identification of a Subject at Risk of Developing an ErbB3 Related Disorder

A sample is taken from a subject who wants to know if they are at risk of developing an ErbB3 related disorder. A labeled SBP that binds to ErbB3 is applied to the sample. Excess/unbound SBP/label is washed away from the sample. The sample is examined for remaining label. Samples having elevated levels (compared to the level of label remaining for subjects that are not at risk of an ErbB3 related disorder) of the remaining label will indicate the presence of higher levels of ErbB3, and thus an elevated risk of an ErbB3 related disorder.

EXAMPLE 35

Sur-Binding Proteins Inhibit Proliferation of Cancer Cell Lines

The present example demonstrated the ability of anti-ErbB3 sur-binding proteins to inhibit proliferation of NCI-N87 (gastric) and MCF-7 (breast) human cancer cell lines.

Target cells were plated at a density of 0.75-1×10$^4$ cells/well in 96 well plates in serum-free medium. They were then treated with the indicated concentrations of SgGs or anti-ErB3 antibodies (Ab A or Ab B) for 30 minutes at 37 degrees C. NRG1β was then added to a final concentration of 10 ng/ml. Cells were allowed to grow for 96 hours and cell content was measured using Cell Titer-Glo® (Promega).

The results are presented in FIGS. 28A (for NCI-N87) and 28B (for MCF-7) and demonstrate that 2817-C01 and 2716-F05 significantly inhibit the proliferation of these epithelial tumor cell lines. Indeed, the results demonstrate that 2817-C01 and 2716-F05 both inhibit more effectively than either Ab A or Ab B. Furthermore, both are also more effective in inhibiting breast cancer than Pertuzumab. The sequences of the variable regions for Ab A and Ab B are provided in FIG. 28C and FIG. 28D respectively.

EXAMPLE 36

Surroglobulins Inhibit Ligand-Induced ErbB3 Phosphorylation, AKT Phosphorylation and Erk Phosphorylation in Cells that Overexpress ErbB2

This example examined the impact of anti-ErbB3 SgGs on ligand-induced activation of ErbB3 and of the AKT and ERK signaling pathways in cells that overexpress ErbB2.

Ligand induced activation was measured by increased phosphorylation of ErbB3, AKT and ERK1/2. 500,000 SKBR3 cells were plated into wells of a 12 well tissue culture dish in serum free medium. The cells were incubated for 1 hour with the indicated amounts of SgG (see FIG. 29A, FIG. 29B, and FIG. 29C). They were then stimulated with 1 ng/ml NRG for 12 minutes. Cells were then washed in ice cold PBS, and lysed. Phosphorylated AKT, phosphorylated ErbB3 and phosphorylated ERK1/2 were measured in the lysates using ELISA kits from Cell Signaling Technologies®.

Figure 29:
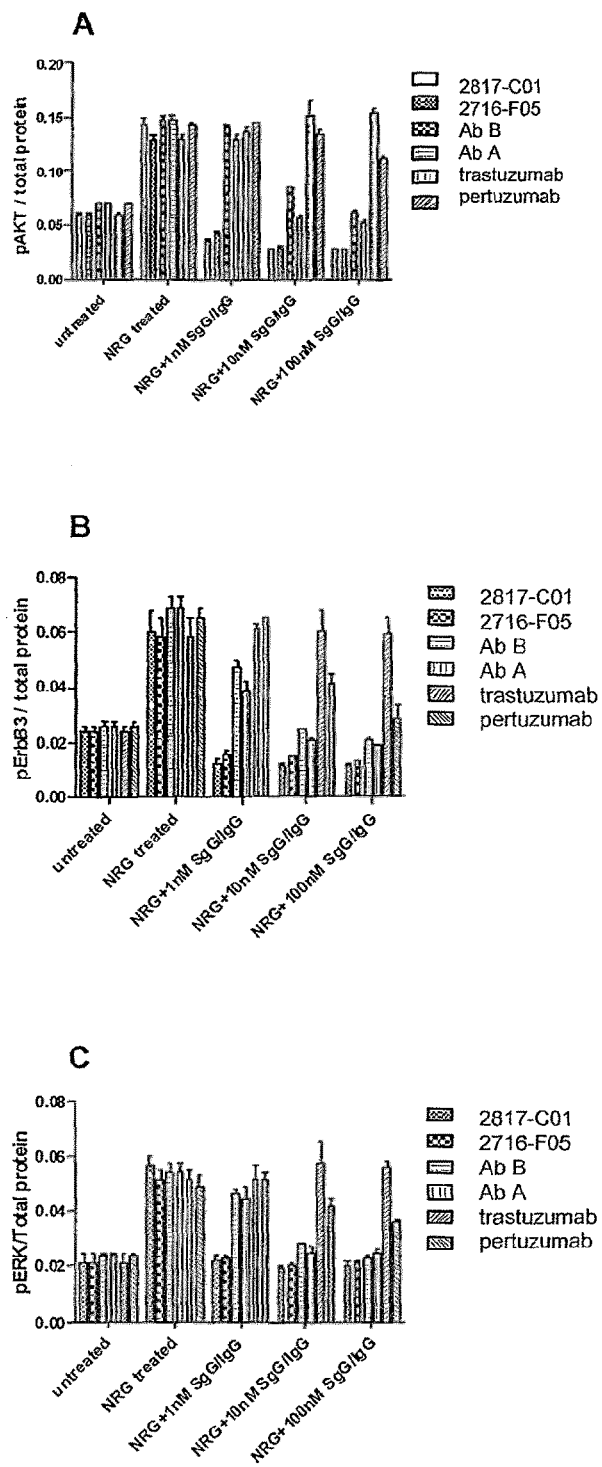
FIG. 29A-29C are graphs depicting that 2817-C01 and 2716-F05 significantly inhibit ligand-induced phophorylation of AKT (FIG. 29A), ErbB3 (FIG. 29B), and ERK1/2 (FIG. 29C).

The data show that the anti-ErbB3 SgGs potently inhibit ligand-induced phosphorylation of AKT (FIG. 29A), ErbB3 (FIG. 29B) and ERK1/2 (FIG. 29C). The SgGs 2817-C01 and 2716-F05 were more potent in inhibiting phosphorylation than the antibodies Ab B, Ab A or pertuzumab. Trastuzumab did not inhibit phosphorylation under this ligand stimulated condition.

EXAMPLE 37

SBPs Inhibit ErbB2 Overexpres Sing Tumor Growth In Vivo

Figure 30:
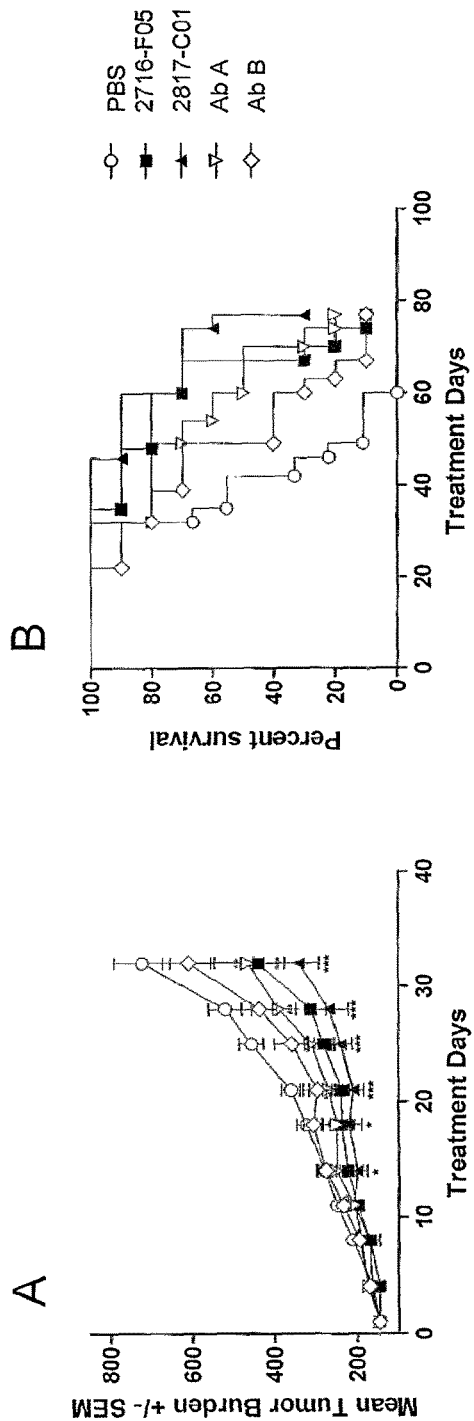
FIG. 30A is a graph depicting mean tumor growth for in vivo experiments comparing the effectiveness of various sur-binding proteins and various antibodies.
FIG. 30B is a graph depicting the percent survival as a function of time for in vivo experiments comparing the effectiveness of various sur-binding proteins and various antibodies.

2817-C01 and 2716-F05 were tested for their effectiveness in inhibiting the growth of an ErbB2 overexpressing tumor in vivo. NCI-N87 gastric cancer cells were injected subcutaneously as a matrigel suspension into CB.17 SCID mice. When tumors reached 120-170 mg, animals received a loading dose of 25 mg/kg and were dosed twice weekly thereafter with 12.5 mg/kg. 10 mice were evaluated per treatment group. The sur-binding proteins significantly delayed tumor growth by 84% and 62% respectively, and conferred a survival advantage, whereas Ab A and Ab B delayed tumor growth by 54% and 19%, respectively. The comparative results are presented in FIG. 30A (for mean tumor burden) and FIG. 30B (for the in vivo survival data).

EXAMPLE 38

SgGs Enhance Antiproliferative Activity of ErB2 Targeted Antibodies

The ability of sur-binding proteins to enhance the antiproliferative activity of Erb targeted antibodies was examined.

Figure 31:
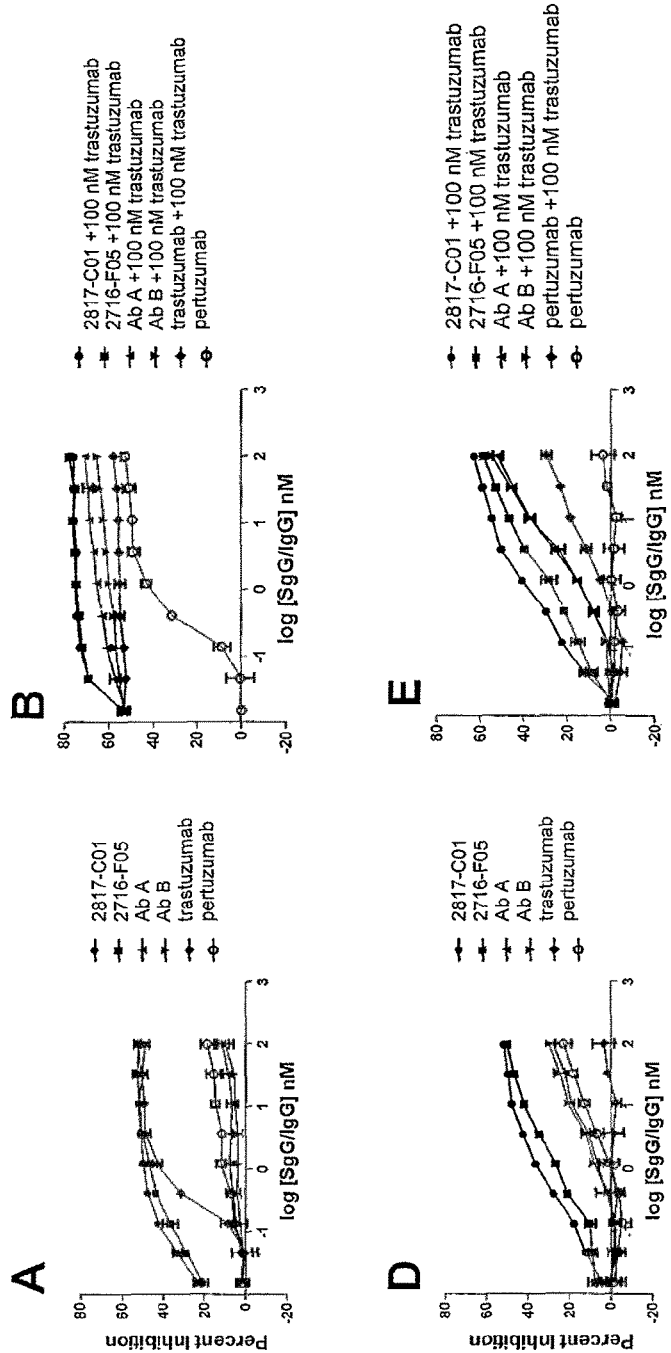
FIGS. 31A-31C depict the results of the anti-proliferative capacity of anti-ErbB2 and anti-ErbB3 agents in the absence of NRG.
FIGS. 31D-31F depict the results of the anti-proliferative capacity of anti-ErbB2 and anti-ErbB3 agents in the presence of NRG.
Figure 31:
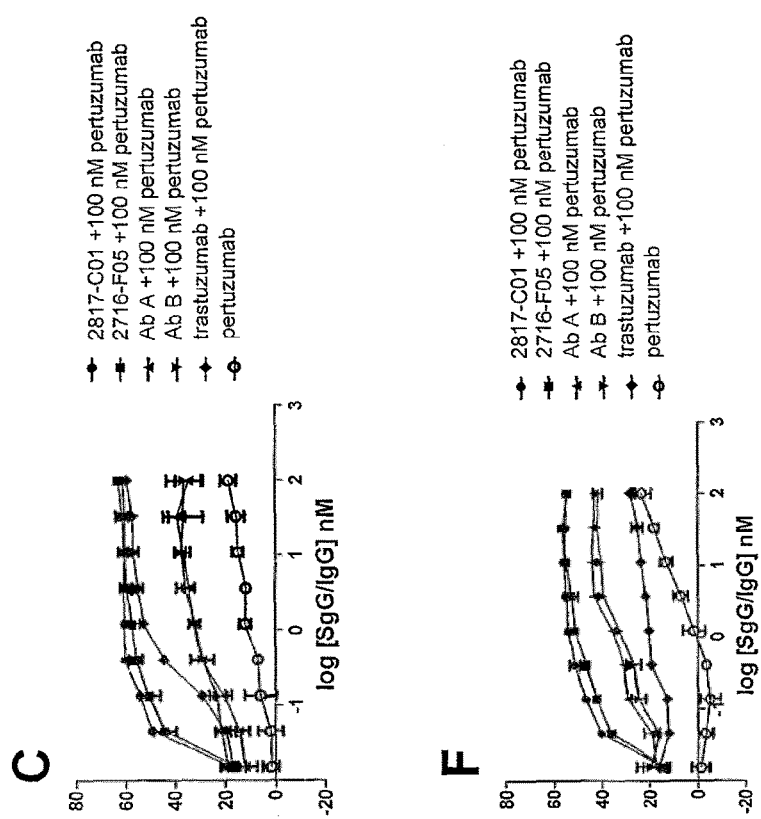

The ability of sur-binding proteins to enhance the activity of trastuzumab and pertuzumab (anti-ErbB2 antibodies) was investigated in the ErbB2 overexpressing cell line SKBR3. ErbB2 overexpressing tumors were heterogeneous with respect to the amount of ligand in the tumor microenvironment. The anti-proliferative capacity of anti-ErbB2 and anti-ErbB3 agents in the absence (FIGS. 31 A, B, and C) and in the presence (FIGS. 31 D, E, and F) of NRG was examined.

FIG. 31A shows the percent inhibition conferred by the anti-ErbB2 antibodies pertuzumab and trastuzumab, the anti-ErbB3 antibodies Ab B and Ab A and the anti-ErbB3 SgGs when the cells were not stimulated with NRG. Agents were applied to cells in complete medium and proliferation was determined after 6 days using Cell Titer-Glo® (Promega). As shown, the anti-ErbB3 sur-binding proteins inhibited growth in the absence of NRG whereas Ab B and Ab A did not appreciably affect growth. In addition, the sur-binding proteins showed superior potency to trastuzumab.

FIG. 31B shows the percent inhibition when increased amounts of the indicated agents were combined with 100 nM trastuzumab. The anti-ErbB3 sur-binding proteins showed superior enhancement to pertuzumab and to the anti-ErbB3 Ab A and Ab B. Indeed, the results demonstrate superior effectiveness of the sur-binding proteins with trastuzmab in comparison to trastuzmab and pertuzumab.

FIG. 31C shows the percent inhibition when increasing amounts of the indicated agents are combined with 100 nM pertuzumab. The sur-binding proteins showed markedly superior enhancement compared to the anti-ErbB3 antibodies, and superior potency compared to trastuzumab. Indeed, the results demonstrate superior effectiveness of the sur-binding proteins with pertuzumab in comparison to trastuzmab and pertuzumab.

FIG. 31D shows the percent inhibition of the anti-ErbB2 antibodies pertuzumab and trastuzumab, the anti-ErbB3 antibodies Ab B and Ab A and the anti-ErbB3 sur-binding proteins when the cells were stimulated with NRG. Agents were applied to cells in complete medium for 1 hour followed by stimulation with 1 ng/ml NRG. Proliferation was determined after 3 days using Cell Titer-Glo® (Promega). The anti-ErbB3 sur-binding proteins were more potent and more effective at inhibiting ligand stimulated growth than pertuzumab or the anti-ErB3 antibodies. Trastuzumab did not appreciably inhibit growth in NRG stimulated cells.

FIG. 31E shows the percent inhibition when increasing amounts of the indicated agents were combined with 100 nM trastuzumab in the presence of NRG. The anti-ErbB3 sur-binding proteins showed superior enhancement to pertuzumab and the anti-ErbB3 antibodies (Ab A and Ab B). It is notable that although trastuzumab had little detectable activity as a single agent in the presence of NRG, the combined treatment with trastuzumab and the anti-ErbB3 directed agents was superior to single agent treatments.

FIG. 31F shows the percent inhibition achieved when increasing amounts of the indicated agents were combined with 100 nM pertuzumab in the presence of NRG. The sur-binding proteins showed markedly superior enhancement compared to the anti-ErbB3 antibodies and to trastuzumab.

EXAMPLE 39

SgGs Enhance the Antiproliferative Activity of EGFR Targeted Antibodies

Figure 32:
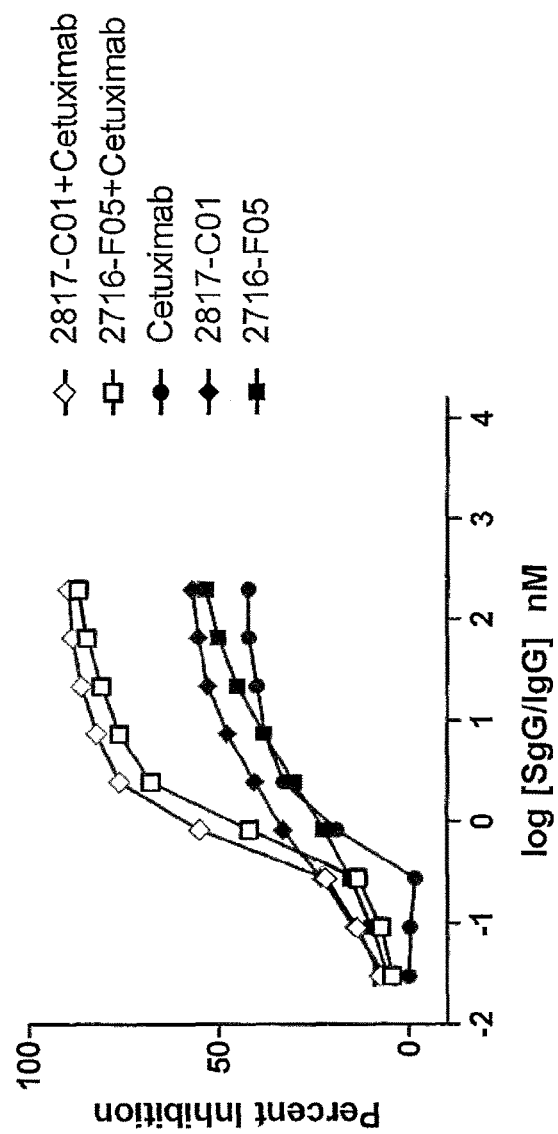
FIG. 32 is a graph depicting the anti-proliferative activity of cetuximab in combination with various options (including 2817-C01 and 2716-F05).

The ability of sur-binding proteins to enhance the antiproliferative activity of EGFR targeted antibodies was examined. The results are shown in FIG. 32. Equimolar quantities of cetuximab and either 2817-C01 or 2716-F05 were combined and were incubated with BxPC-3 cells for 96 hours in the presence of 10 ng/ml NRG1. Cell content was measured using Cell Titer-Glo® (Promega). Combined treatment with anti-ErbB3 sur-binding proteins and cetuximab resulted in markedly superior growth inhibition compared to treatment with cetuximab alone and to treatment with sur-binding proteins as single agents. These data demonstrate that combining inhibition of EGFR signaling and ErbB3 signaling (via these sur-binding proteins) is highly beneficial, and allows one to approach near complete inhibition.

EXAMPLE 40

2817-C01 and 2716-F05 Reduce Cell Surface ErbB3

Figure 33:
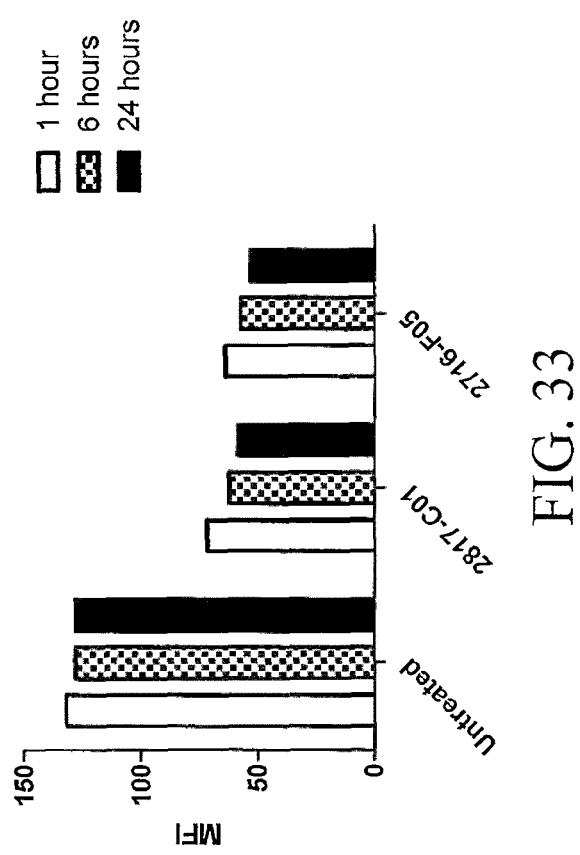
FIG. 33 is a graph demonstrating that 2817-C01 and 2716-F05 reduce cell surface ErbB3.

BxPC-3 cells were treated for the indicated lengths of time with 2817-C01 or 2716-F 05 at 37° C. Cells were then stained using a noncompeting biotinylated anti-ErbB3 polyclonal antibody followed by ALEXA FLUOR® 488 green-fluorescent dye labeled streptavidin. The mean fluorescence intensity (MFI) was determined by flow cytometry. FIG. 33 shows that the amount of ErbB3 on the cell surface that was detectable using the polyclonal antibody was reduced after exposing the cells to the anti-ErbB3 SgGs.

EXAMPLE 41

Treatment of Cancer Using Combination Therapy

This example outlines the treatment of a cancer using a SgG to ErbB3 and a small molecule (kinase inhibitor). A subject at risk of developing a cancer in which ErbB3 plays a role is administered a dose of 2817-C01 and/or 2716-F05 (or other SgG) either prior to, subsequent to, or in combination with one or more small molecule (kinase inhibitor). The SgG is administered in an amount sufficient to reduce ErbB3 mediated signaling.

The treatment results in the reduction of ErbB3 mediated signaling, thereby slowing or reducing the cancer in which ErbB3 plays a role. The result of the combined therapy is an improved inhibition of tumor growth that is at least greater than the use of the SgG and/or the small molecule (kinase) inhibitor alone at an equivalent dose.

EXAMPLE 42

Sur-Binding Protein Variants

Sabs that differed from 2817-C01 and 2716-F05 at various positions of CDR1 and CDR2 were expressed as phage and panned on ErbB3-Fc.

32 variants of 2817-C01 were identified and expressed as soluble monovalent Sabs. Their affinities for ErbB3 were determined by ELISA. FIG. 34A shows the sequences of the variants and their EC50s as determined by ELISA. Shaded amino acids differ from the corresponding amino acids in 2817-C01. All variants shared identical germ line VH3-23 frameworks with 2817-C01. They differed from 2817-C01 by 40-60% in CDR1 and 7.7-30.7% in CDR2. Despite these large variations, they all bound to ErbB3-Fc. The heavy chain variable region sequences for the 2817-C01 variants are shown in FIG. 34E.

22 variants of 2716-F05 were identified and expressed as soluble monovalent Sabs. Their affinities for ErbB3 were determined by ELISA. FIG. 34B shows the sequences of the variants and their EC50s as determined by ELISA. Shaded amino acids differ from the corresponding amino acids in 2716-F05. All variants share identical germ line VH3-23 frameworks with 2716-F05. They differ from 2716-F05 by 17-40% in CDR1 and 7.7-46.1% in CDR2. Despite these large variations, they all exhibited impressive EC50 values. FIGS. 34C and 34D provide a consensus sequence of the various residues within the CDRs that were altered and to what amino acid they were altered. The heavy chain variable region sequences for the 2716-F05 variants are shown in FIG. 34F.

In some embodiments, the consensus sequences provided in Example 42 can be used to provide variants of SBPs with the desired properties. In some embodiments, any variant of 2716-F05 and/or 2817-C01 that includes CDRs (1 or 2) within the consensus sequence in FIG. 34C or 34D is contemplated. In some embodiments, provided herein are SBPs and/or antibodies with HCDR1 and HCDR2 according to any of the consensus sequences provided herein. In some embodiments, the HCDRs fall within the consensus sequence of all of the variants of 2716-F05 or 2817-C01 (including those in FIGS. 34E and 34F). Such consensus sequences are shown below in Table 34.1 (HCDR1 for 2817-C01), Table 34.2 (HCDR2 for 2817-C01), Table 34.3 (HCDR1 for 2716-F05), Table 34.4 (HCDR2 for 2716-F05).

TABLE 34.1

| S | N | Y | G | M | H | SEQ ID NO: 291 |
|---|---|---|---|---|---|---|
|   | D |   | W |   | N | SEQ ID NO: 292 |
|   | S |   | A |   | S | SEQ ID NO: 293 |

TABLE 34.1-continued

| | | | | | | | |
|---|---|---|---|---|---|---|---|
| | | | E | | | | SEQ ID NO: 294 |
| | | | S | | | | SEQ ID NO: 295 |
| S | $X_{332}$ | Y | $X_{333}$ | M | $X_{334}$ | | SEQ ID NO: 277 |

TABLE 34.2

| W | V | A | L | I | S | S | G | G | A | Y | T | Y | SEQ ID NO: 296 |
|---|---|---|---|---|---|---|---|---|---|---|---|---|---|
| | | | S | N | | G | N | S | G | I | I | S | SEQ ID NO: 297 |
| | | | | | A | N | S | | S | T | K | | SEQ ID NO: 298 |
| | | | | | V | D | | R | N | | | | SEQ ID NO: 299 |
| | | | | | G | A | | T | | | | | SEQ ID NO: 300 |
| | | | | | S | Y | | | | | | | SEQ ID NO: 301 |
| | | | | | T | W | | | | | | | SEQ ID NO: 302 |
| W | V | $X_{335}$ | $X_{336}$ | I | S | $X_{337}$ | $X_{338}$ | $X_{339}$ | $X_{340}$ | $X_{341}$ | $X_{342}$ | $X_{343}$ | SEQ ID NO: 278 |

TABLE 34.3

| S | D | Y | W | M | H | SEQ ID NO: 303 |
|---|---|---|---|---|---|---|
| | S | | A | | N | SEQ ID NO: 304 |
| | N | | | | S | SEQ ID NO: 305 |
| S | $X_{344}$ | Y | $X_{345}$ | M | $X_{346}$ | SEQ ID NO: 279 |

TABLE 34.4

| W | V | A | L | I | S | S | G | G | Y | K | Y | SEQ ID NO: 306 |
|---|---|---|---|---|---|---|---|---|---|---|---|---|
| | | | S | V | | N | N | S | T | I | I | SEQ ID NO: 307 |
| | | | | | N | A | S | | S | N | T | SEQ ID NO: 308 |
| | | | | | A | G | | A | S | | | SEQ ID NO: 309 |
| | | | | | T | W | | N | | | | SEQ ID NO: 310 |
| | | | | | Y | R | | | | | | SEQ ID NO: 311 |
| W | V | $X_{347}$ | $X_{348}$ | I | S | $X_{349}$ | $X_{350}$ | $X_{351}$ | $X_{352}$ | $X_{353}$ | $X_{354}$ Y | SEQ ID NO: 280 |

Thus, SBPs and/or antibodies that include one or more of the above CDRs in the heavy chain are contemplated. In some embodiments, the SBP and/or antibody can include an HCDR1 of SEQ ID NO: 277 or 279. In some embodiments, the SBP and/or antibody can include an HCDR2 of SEQ ID NO: 278 or 280.

EXAMPLE 43

Sur-Binding Proteins Bind to ErbB3 in the Presence of NRG

The present example investigates if some of the present SBPs preferentially bind to different conformations of ErbB3. ELISAs were performed to determine if the sur-binding proteins preferentially bind to either the extended (ligand bound) or closed (non-ligand bound) conformation of ErbB3.

ELISA plates were coated with human ErbB3-Fc, and after washing and blocking 1.85 nM (approximately 2× the EC90 under these conditions) NRG1-beta 1 extracellular domain (Ser2-Lys246) (R&D Systems) was added to the wells. Next various concentrations of the indicated anti-ErbB3 SBPs (FIG. 35) were applied and allowed to further incubate for 1 hour, either in the continued presence of NRG or in its' absence. The resulting bound SgGs were detected using a biotinylated anti-VpreB, followed by streptavidin HRP colorimetric detection.

Figure 35:
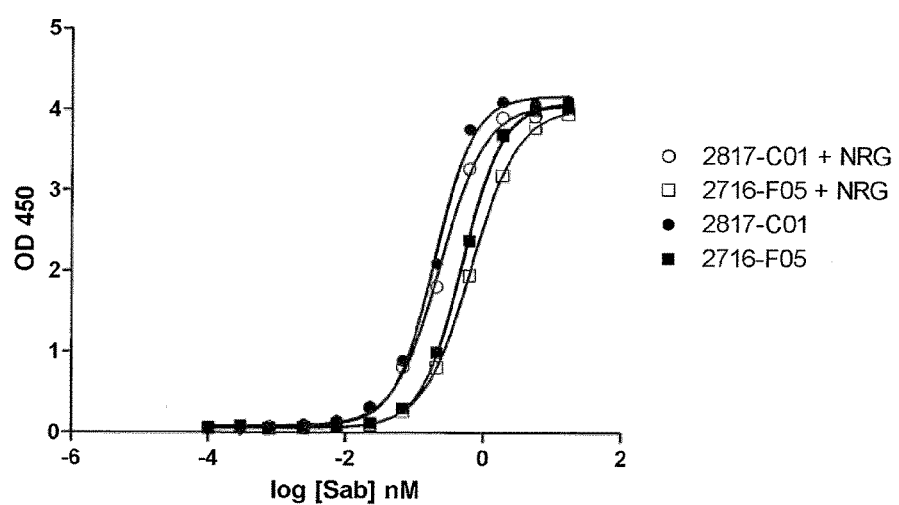
FIG. 35 is a graph demonstrating that ErbB3 sur-binding proteins bind approximately equivalently to ErbB3-Fc in the presence or absence of NRG.

The results of this analysis, presented in FIG. 35, demonstrate that the binding of SBPs was virtually unaffected when NRG was pre-bound to ErbB3.

As demonstrated in the above example, some embodiments of the SBPs can bind to and be effective against ErbB3 even in the presence of NRG. Thus, in some embodiments, the SBPs and/or antibodies provided herein can be administered or applied in situations where NRG is already or will be present, without having to worry about the impact that NRG may have. In such embodiments, such SBPs can be administered in lower amounts and/or less frequently than molecules that are adversely impacted by the presence of NRG. In some embodiments, such SBPs can be immediately active, unlike conventional competitive antagonists that require competitive dissociation of the ligand prior to demonstrating inhibitory activity. In some embodiments, the SBP is one that, as shown above, can be effective, even though it does not bind to and lock ErbB3 in a closed conformation. Thus, in some embodiments, the SBP can be effective even though it does not lock ErbB3 in a closed conformation.

EXAMPLE 44

Identification of Responsive NRG Positive Cancer

A tumor sample is taken from a subject for whom treatment with an anti-ErbB3 agent is contemplated. The level of NRG or NRG encoding mRNA in the sample is determined using immunohistochemistry.

If NRG is present the patient is considered to be a responsive candidate for treatment with the anti-ErbB3 agent provided herein. The tumor is also considered to be potentially can sensitized to additional agents when treated in combination with an anti-ErbB3 agent.

EXAMPLE 45

Use of ErbB3 Sur-Binding Proteins to Treat Anti-ErbB2 Unresponsive Tumors

This example outlines the use of an anti-ErbB3 antibody and/or sur-binding protein to treat anti-ErbB2 unresponsive tumors, such as those that have truncated ErbB2. These tumors are expected to be resistant to both trastuzumab and pertuzumab therapy.

One obtains a human tumor cell line bearing ErbB3 and truncated ErbB2 (p95 Her-2) and tests the ErbB3 Sur-binding proteins for inhibition of proliferation or ErbB3 mediated signaling, similar to in vitro assays described previously.

Furthermore, cultured tumor cells that bear ErbB3, are transiently and/or stably transfected or transduced to over-express truncated Her-2. Different deleted forms of Her-2 are introduced to recapitulate proteolytically cleaved or the alternatively translated forms and the resulting cell lines or pools are tested to demonstrate their responsiveness to anti-ErbB3. Since the binding of anti-ErbB3 sur-binding proteins is independent of the presence of ErbB2, and since they inhibit the growth of ErbB2 driven tumors, they will inhibit growth of tumors expressing truncated ErbB2.

EXAMPLE 46

Identifying Anti-ErbB2 Unresponsive Tumors

This example outlines a method of screening for subjects that are anti-ERBB2 unresponsive.

A tumor sample is obtained from a patient. The tumor is subjected to testing to detect the presence of truncated ErbB2. Detection involves the use of 1 or more antibodies that selectively recognize the intracellular domain or the extracellular domain of ErbB2 [for example, Clin Cancer Res. 2010 Aug. 15; 16(16):4226-35. Quantitation of p95HER2 in paraffin sections by using a p95-specific antibody and correlation with outcome in a cohort of trastuzumab-treated breast cancer patients. Sperinde J, Jin X, Banerjee J, Penuel E, Saha A, Diedrich G, Huang W, Leitzel K, Weidler J, Ali S M, Fuchs E M, Singer C F, Köstler W J, Bates M, Parry G, Winslow J, Lipton A.]. Preferential binding to the intracellular domain indicates the presence of the truncated form.

In addition or alternatively, the presence of circulating proteolytically cleaved ErbB2 extracellular domain is detected by commercially available ELISA (Siemens Healthcare Diagnostics, Erlagen, Germany). A positive result indicates truncated ErbB2 expression. Patients expressing a truncated form are treated with 2817-C01 and/or 2716-F05 either as a single sur-binding agent or, in the alternative, in combination with other treatments.

As the binding of anti-ErbB3 sur-binding proteins is independent of the presence of ErbB2, and as they inhibit the growth of ErbB2 driven tumors, they are predicted to inhibit growth of tumors expressing truncated ErbB2 and benefit the subject.

As outlined in the above examples, in some embodiments, the antibodies and/or sur-binding proteins provided herein can be useful in treating ErbB2 related disorders, especially where the disorder involves a variant of ErbB2. In some embodiments, this can include a method of treating cancer or other disorder in which a variant of ErbB2 is produced. The method can include identifying a subject to receive a treatment for cancer. The cancer can involve the expression of a variant form of an ErbB2 protein. The method can further comprise administering to the subject any of the SBPs or antigen binding portions thereof, as described herein. In some embodiments, this can be administered without a compound that targets ErbB2 or variants thereof. In some embodiments, this can be administered with another ErbB3 therapeutic. In some embodiments, the variant ErbB2 protein is a proteolytically cleaved ErbB2 protein. In some embodiments, the variant ErbB2 protein is an alternatively translated truncated ErbB2 protein. In some embodiments, the cancer comprises a cancerous cell that expresses p95 Her2. In some embodiments, the SBP can be used to treat a herceptin unresponsive tumor. In some embodiments, the SBP can also be used to treat gastric cancer, lung cancer, and/or other epithelial cancers. In some embodiments, the variant ErbB2 protein is selected from one or more of the group consisting of 611-HER2-CTF, A648-HER2-CTF, K676-HER2-CTF, and 687-HER2-CTF.

EXAMPLE 47

Treatment of Cancer Using an SgG Combination Therapy with an Inhibitor of mTOR

This example outlines the treatment of a cancer using an SgG to ErbB3 and an inhibitor of mTOR (mammalian target of rapamycin). A subject at risk of developing a cancer is administered a dose of 2817-C01 and/or 2716-F05 prior to, subsequent to, or in the alternative, in combination with everolimus, an inhibitor of mTOR.

The result of the combined therapy is an improved inhibition of tumor growth that is at least greater than the use of the SgG and/or the compound alone at an equivalent dose.

As demonstrated in the example above, the SGG can be combined with an inhibitor of mTOR. Thus, in some embodiments, a method for a cancer therapy can include administering to a subject an effective amount of an inhibitor of mTOR and an effective amount of a SGG. The compounds can be administered at different times and/or at the same time. In some embodiments, a pharmaceutical composition comprising an mTOR inhibitor and an SGG is provided. Each ingredient can be provided in an amount that is effective for the molecule in isolation and/or in an amount that is effective when one part is co-administered with the other.

EXAMPLE 48

Antibody Versions of Sur-Binding Proteins

This example illustrates that when the heavy chains of the sur-binding proteins are complexed with conventional mature germ line immunoglobulin light chains, their binding to ErbB3 can be significantly lower compared to when the heavy chains are complexed with surrogate light chain.

The heavy chains of 2817-C01 (FIG. 37A) and 2716-F05 (FIG. 37B) were co-expressed in HEK293 cells with with 10 germline antibody kappa or lambda light chains essentially as described in EXAMPLE 3. The listing of these light chains is provide in FIG. 37A and FIG. 37B.

Figure 37A:
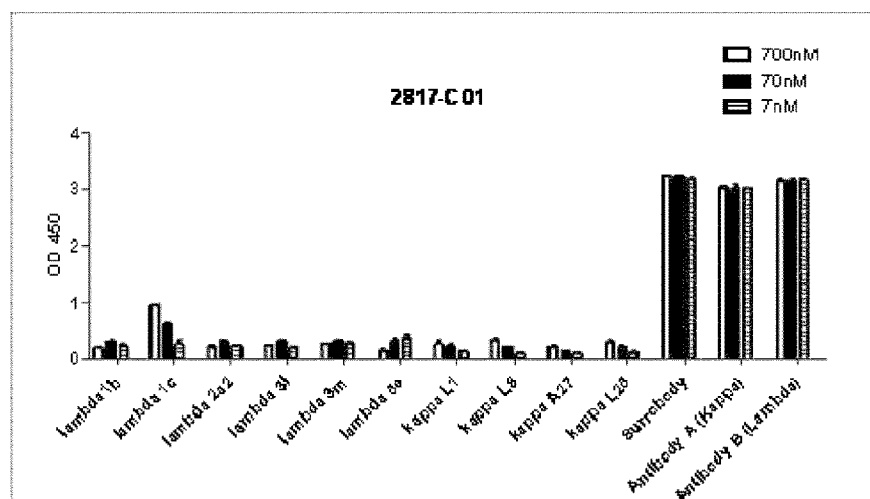
FIG. 37A and FIG. 37B are graphs depicting the binding ability of SBP 2817-C01 and SBP 2716-F05 respectively.
Figure 37B:
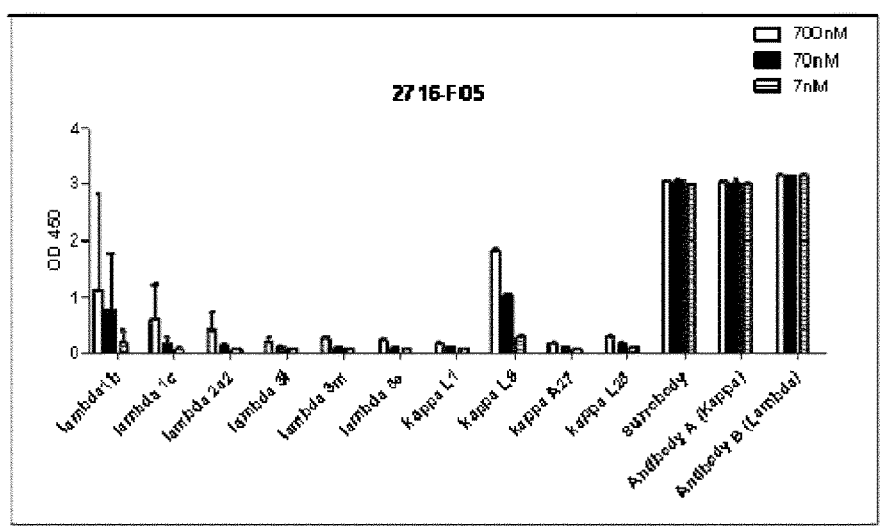

Binding of the resulting proteins was evaluated by ELISA. Various concentrations, as shown in FIGS. 37A and 37B, were allowed to bind to plates coated with human ErbB3-Fc (R&D Systems). Binding was detected using biotinylated antibodies that specifically recognize immunoglobulin kappa, immunoglobulin lambda or VpreB, followed by streptavidin HRP. Detection used a colorimetric HRP substrate.

The results are shown in FIGS. 37A and 37B. The results demonstrate that the surrogate light chain provided markedly superior properties to the sur-binding proteins, demonstrating that surrogate light chain provides superior aspects for binding.

EXAMPLE 49

Inhibition of ErbB2-Overexpres Sing Cell Proliferation

Figure 38:
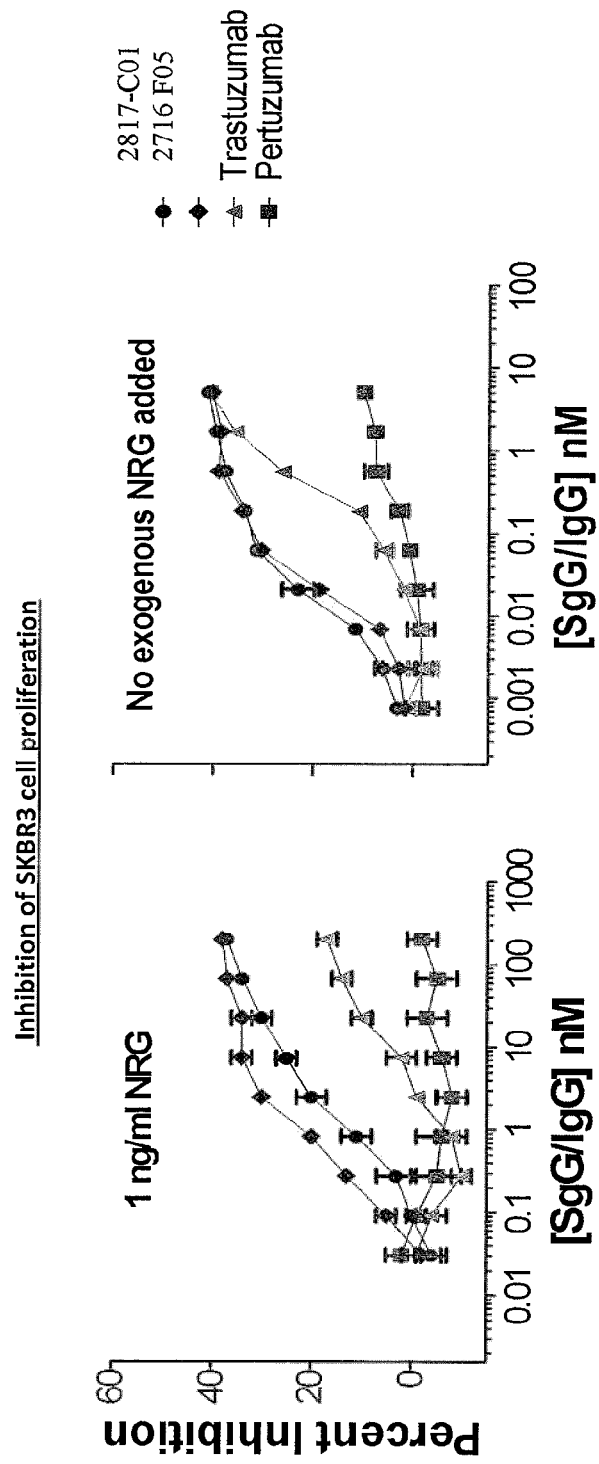
FIG. 38 is a pair of graphs depicting the percent inhibition of various agents in SKBR3 cells in the presence and absence of NRG.
Figure 39A:
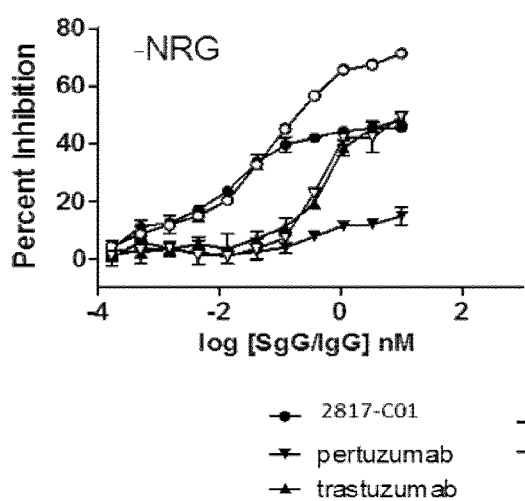
FIG. 39A is a graph depicting the percent inhibition of various agents in SKBR3 cells in the absence of NRG for SBP 2817-C01.
Figure 39B:
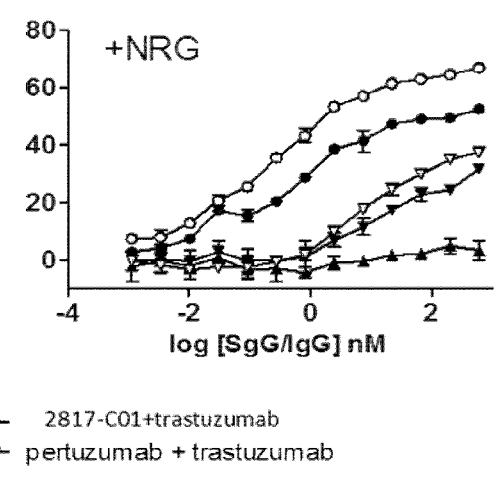
FIG. 39B is a graph depicting the percent inhibition of various agents in SKBR3 cells in the presence of NRG for SBP 2817-C01.
Figure 39C:
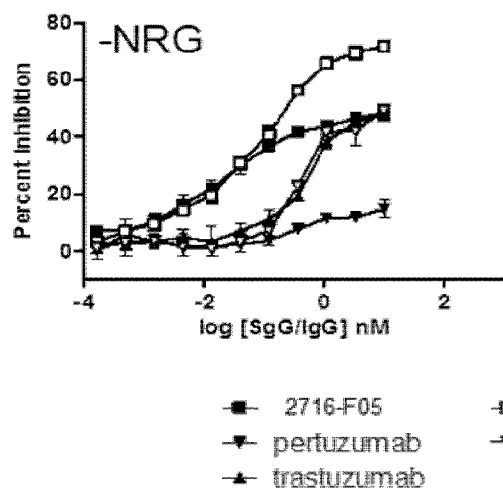
FIG. 39C is a graph depicting the percent inhibition of various agents in SKBR3 cells in the absence of NRG for SBP 2716-F05.
Figure 39D:
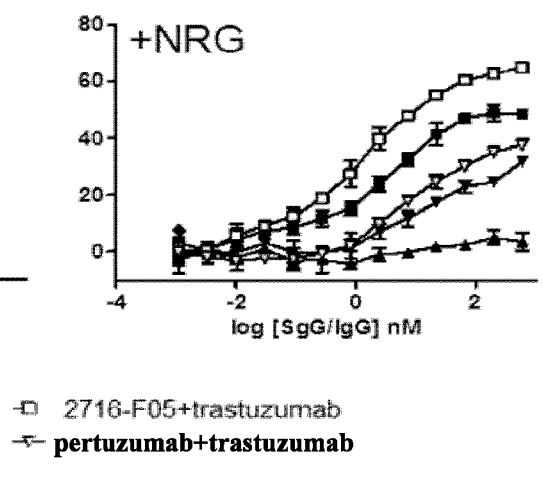
FIG. 39D is a graph depicting the percent inhibition of various agents in SKBR3 cells in the presence of NRG for SBP 2716-F05.
Figure 39E:
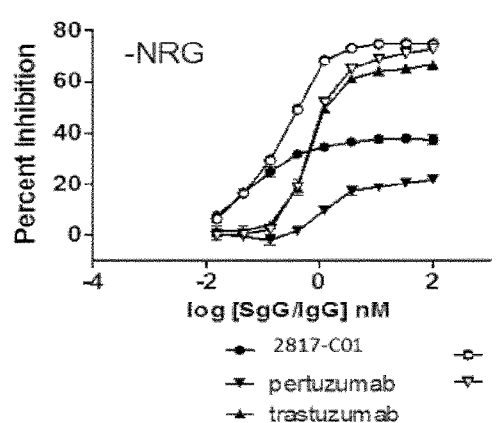
FIG. 39E is a graph depicting the percent inhibition of various agents in BT474 cells in the absence of NRG for SBP 2817-C01.
Figure 39F:
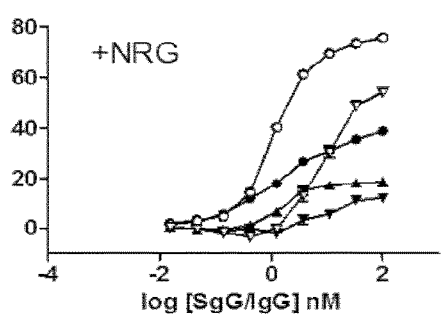
FIG. 39F is a graph depicting the percent inhibition of various agents in BT474 cells in the presence of NRG for SBP 2817-C01.
Figure 39G:
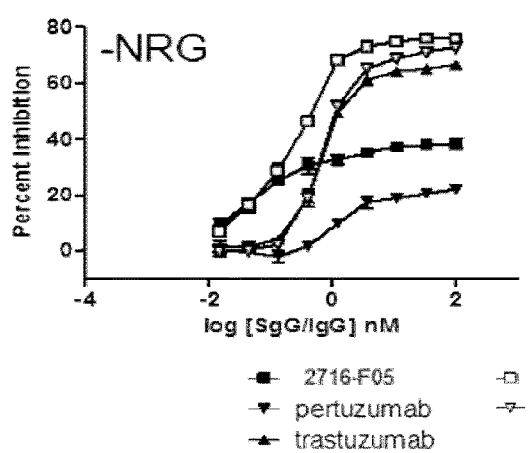
FIG. 39G is a graph depicting the percent inhibition of various agents in BT474 cells in the absence of NRG for SBP 2716-F05.
Figure 39H:
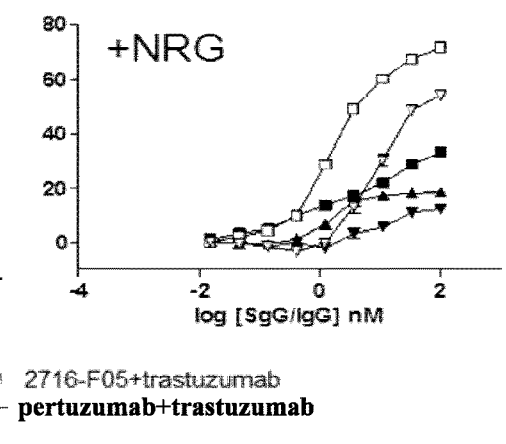

SKBR3 and NCI-N87 cells were incubated in complete media in the absence of NRG for 6 days or for 3 days with 1 ng/ml NRG, as indicated. All experiments were performed in triplicate. FIG. 38 depicts a comparison of the inhibition in SKBR3 cell proliferation in the presence and absence of NRG. FIG. 11C depicts a graph demonstrating the ability of the SBPs to inhibit NCI-N87 cell growth.

EXAMPLE 50

SBP Based Augmentation of Trastuzumab is Greater than Augmentation by Pertuzumab The present example outlines data comparing the effectiveness of 2817-C01 and 2716-F05 with trastuzumab and the combination of trastuzumab and pertuzumab or trastuzumab and 2810-C01 and 2716-F05. SKBR3 cells were incubated in complete media in the absence or presence of NRG for 6 or 3 days, respectively. BT474 cells were incubated in complete media for 6 days under both conditions. All experiments were performed in triplicate. As shown in FIGS. 39A-39D, 2817-C01 and 2716-F05 were just as, if not more (especially in the presence of NRG), effective as the combination of pertuzumab and trastuzumab, and the combination of 2817-C01 or 2716-F05 and trastuzumab was more effective than the antibody combinations in SKBR3 cells. Similarly, as shown in FIGS. 39E-39H, 2817-C01 and 2716-F05 were more effective than any single antibody tested (in the presence of NRG), and the combination of 2817-C01 or 2716-F05 and trastuzumab was more effective than any antibody combination in BT474 cells, both in the presence and absence of NRG. The results in FIGS. 39A-39H in regard to the combinations noted are co-titration values. The value on the x-axis is the concentration of both a) the SBP and trastuzumab or b) pertuzumab and trastuzumab.

In some embodiments, the SBP has the ability to induce the noted percent inhibition shown in FIGS. 39A-39D (SKBR3 cells) and/or FIGS. 39E-39H (BT474 cells) in the presence or absence of NRG. In some embodiments, the SBP can be combined with trastuzumab in an amount equal to that noted in FIGS. 39A-39H and/or in an amount sufficient to achieve the level of inhibition present in FIGS. 39A-39H.

EXAMPLE 51

Bispecific SBPs

The present example presents evidence that bispecific SBPs for ErbB3 and EGFR provide superior properties over the SBPs individually, as well as the combination of the SBPs.

Figure 40:
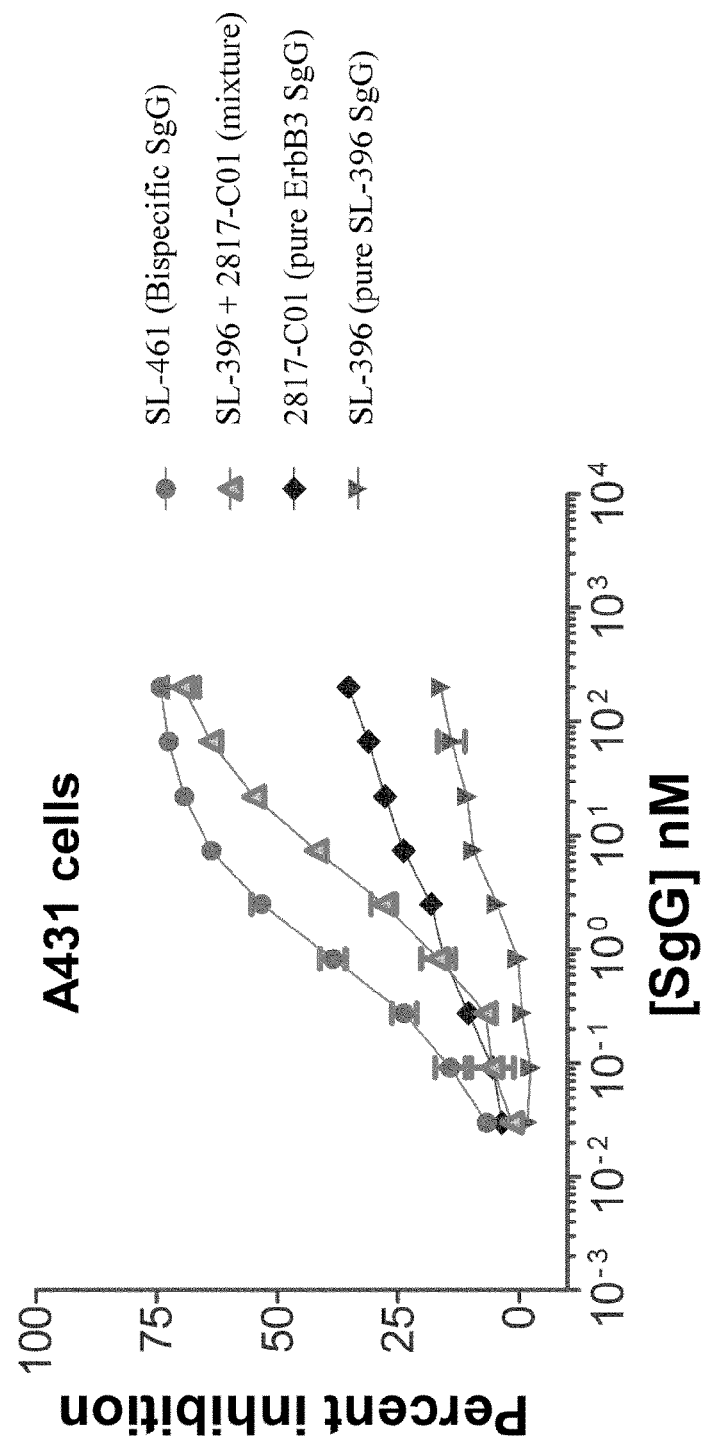
FIG. 40 is a graph displaying the effectiveness of combinations over individual SBPs and bispecifics over combinations.
Figure 42:
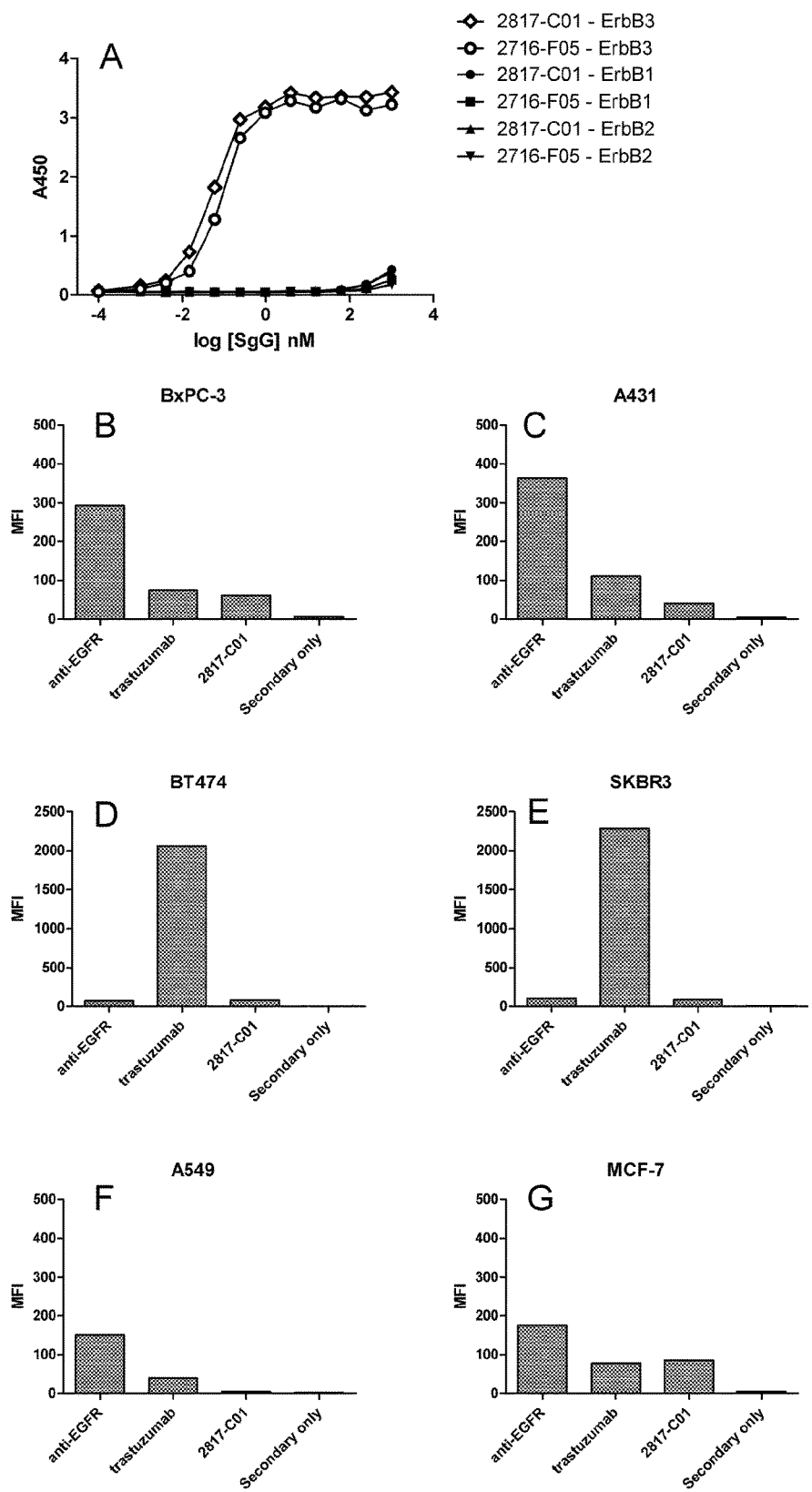
FIGS. 42A-42G are graphs depicting data that demonstrate that the anti-ErbB3 SBPs can be selective over other proteins.

A431 cells were incubated in serum-free media for 4 days. When tested in combination, the monospecific SBP 2716-F05 (SBP to ErbB3) and SBP SL-396 (SBP to EGFR) were present at equal concentration as indicated in FIG. 40. The nucleic and amino acid heavy chain sequences of the SBP to EGFR (SL-396) are provided in FIG. 41A. The nucleic acid for the ErbB3 heavy chain is provided in FIG. 41B. The amino acid sequence of 2716-F05 is provided in FIG. 41C. The surrogate light chain employed in this case was the fusion 1 arrangement.

As can be seen in the results shown in FIG. 40, while the combination of the two SBPs provided a superior benefit over the individual SBPs, the bispecific SBP (SL-461), which bound to both ErbB3 and EGFR, provided an even greater benefit over the combination.

EXAMPLE 52

Selectivity of Anti-ErbB3 SBPs

The present example demonstrates the selectivity of the SBPs for ErbB3 over other ErbB family members. ELISA plates were coated with human ErbB3-Fc, EGFR-Fc (ErbB1) or ErbB2-Fc. Various concentrations of the indicated anti-ErbB3 SBPs were then allowed to bind to the coated wells. Binding was detected using a biotinylated antibody that specifically recognizes VpreB, followed by streptavidin HRP. Detection used a colorimetric HRP substrate. The results, shown in FIG. 42A, indicate that the sur-binding proteins selectively bind ErbB3 and not EGFR or ErbB2 in an ELISA format. In FIGS. 42B-G, the indicated cell lines were stained with anti-EGFR (R&D systems), trastuzumab or 2817-C01 and analyzed by flow cytometry. The results demonstrated that variations in the abundance of EGFR and ErbB2 among different cell lines do not impact the staining with the sur-binding protein and additionally indicate that the sur-binding protein does not appreciably bind these members of the ErbB family.

All references cited throughout the specification, and the references cited therein, are hereby expressly incorporated by reference in their entirety.

---

What is claimed is:

1. A sur-binding protein comprising:
   (i) a surrogate light chain (SLC) sequence comprising, from N-terminus to C-terminus, a VpreB1 sequence covalently fused to a λ5 sequence, wherein the SLC sequence comprises the amino acid sequence of SEQ ID NO: 276; and
   (ii) a heavy chain variable region amino acid sequence comprising:
      (a) a heavy chain complementarity determining region (CDR) 1 sequence comprising SEQ ID NO: 39, a heavy chain CDR2 sequence comprising SEQ ID NO: 40, and a heavy chain CDR3 sequence comprising SEQ ID NO: 41; or
      (b) a heavy chain CDR1 sequence comprising SEQ ID NO: 43, a heavy chain CDR2 sequence comprising SEQ ID NO: 44, and a heavy chain CDR3 sequence comprising SEQ ID NO: 45;
   wherein the heavy chain variable region amino acid sequence is conjugated to the SLC sequence to form a sur-binding protein, and wherein said sur-binding protein specifically binds to an ErbB3 protein.

2. The sur-binding protein of claim 1, wherein the ErbB3 protein comprises the sequence of SEQ ID NO: 36.

3. The sur-binding protein of claim 1, wherein the SLC sequence is covalently conjugated to the heavy chain variable region amino acid sequence.

4. The sur-binding protein of claim 1, wherein the SLC sequence is non-covalently conjugated to the heavy chain variable region amino acid sequence to form a dimeric complex.

5. A bispecific sur-binding protein comprising:
   (i) a first surrogate light chain (SLC) sequence comprising, from N-terminus to C-terminus, a VpreB1 sequence covalently fused to a λ5 sequence, wherein the first SLC sequence comprises the amino acid sequence of SEQ ID NO: 276;
   (ii) a first heavy chain variable region amino acid sequence comprising:
      (a) a heavy chain complementarity determining region (CDR) 1 sequence comprising SEQ ID NO: 39, a heavy chain CDR2 sequence comprising SEQ ID NO: 40, and a heavy chain CDR3 sequence comprising SEQ ID NO: 41; or
      (b) a heavy chain CDR1 sequence comprising SEQ ID NO: 43, a heavy chain CDR2 sequence comprising SEQ ID NO: 44, and a heavy chain CDR3 sequence comprising SEQ ID NO: 45,
   wherein the first heavy chain variable region amino acid sequence is paired with the first SLC sequence to form a first sur-binding protein binding site, wherein the first sur-binding protein binding site binds to an ErbB3 protein; and
   (iii) a second SLC sequence comprising, from N-terminus to C-terminus, a VpreB1 sequence covalently fused to a λ5 sequence, wherein the second SLC sequence comprises the amino acid sequence of SEQ ID NO: 276; and
   (iv) a second heavy chain variable region amino acid sequence that is paired with the second SLC sequence to form a second sur-binding protein site, wherein the second sur-binding protein site binds to a second target.

6. A method for suppressing tumor growth in a subject comprising providing an ErbB3 sur-binding protein to a tumor in the subject, wherein the tumor comprises a cell that expresses ErbB3, thereby suppressing tumor growth, wherein the ErbB3 sur-binding protein comprises:
   (i) a surrogate light chain (SLC) sequence comprising, from N-terminus to C-terminus, a VpreB1 sequence covalently fused to a λ5 sequence, wherein the SLC sequence comprises the amino acid sequence of SEQ ID NO: 276; and
   (ii) a heavy chain variable region amino acid sequence comprising:
      (a) a heavy chain complementarity determining region (CDR) 1 sequence comprising SEQ ID NO: 39, a heavy chain CDR2 sequence comprising SEQ ID NO: 40, and a heavy chain CDR3 sequence comprising SEQ ID NO: 41; or
      (b) a heavy chain CDR1 sequence comprising SEQ ID NO: 43, a heavy chain CDR2 sequence comprising SEQ ID NO: 44, and a heavy chain CDR3 sequence comprising SEQ ID NO: 45;
   wherein the heavy chain variable region amino acid sequence is conjugated to the SLC sequence to form the ErbB3 sur-binding protein.

7. The method of claim 6, wherein the tumor cell is selected from the group consisting of squamous cell cancer, small-cell lung cancer, non-small cell lung cancer, gastric cancer, pancreatic cancer, glial cell tumors, glioblastoma, cervical cancer, ovarian cancer, liver cancer, bladder cancer, hepatoma, breast cancer, colon cancer, melanoma, colorectal cancer, endometrial carcinoma, salivary gland carcinoma, renal cancer, prostate cancer, vulval cancer, thyroid cancer, hepatic carcinoma and of head and neck cancer.

* * * * *